(12) United States Patent
Zhu et al.

(10) Patent No.: US 7,521,470 B2
(45) Date of Patent: Apr. 21, 2009

(54) FACTOR XA INHIBITORS

(75) Inventors: Bing-Yan Zhu, Palo Alto, CA (US);
Shawn M. Bauer, Pacifica, CA (US);
Zhaozhong J. Jia, San Mateo, CA (US);
Gary D. Probst, San Francisco, CA (US);
Yanchen Zhang, Kensington, CA (US);
Robert M. Scarborough, Half Moon Bay, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 297 days.

(21) Appl. No.: 11/158,274

(22) Filed: Jun. 20, 2005

(65) Prior Publication Data

US 2006/0100193 A1    May 11, 2006

Related U.S. Application Data

(60) Provisional application No. 60/580,899, filed on Jun. 18, 2004.

(51) Int. Cl.
| | |
|---|---|
| *A61K 31/415* | (2006.01) |
| *A61K 31/4164* | (2006.01) |
| *A61K 31/4192* | (2006.01) |
| *C07D 249/04* | (2006.01) |
| *C07D 233/66* | (2006.01) |
| *C07D 207/34* | (2006.01) |

(52) U.S. Cl. ................ 514/381; 548/266.2; 548/311.1; 548/517; 514/383; 514/385; 514/397; 514/422

(58) Field of Classification Search ............. 548/266.2, 548/311.1, 517; 514/381, 383, 385, 397, 514/422

See application file for complete search history.

(56) References Cited

U.S. PATENT DOCUMENTS 6,423,713 B1    7/2002  Anantanarayan et al.
7,157,456 B2    1/2007  Straub et al.
2005/0171358 A1    8/2005  Shimozono et al.
2007/0066615 A1    3/2007  Gerdes et al.

FOREIGN PATENT DOCUMENTS

| CA | 2453846 A1 | 1/2003 |
|---|---|---|
| DE | 10322469.6 * | 5/2003 |
| WO | WO 99/28317 | 6/1999 |
| WO | WO 01/21160 A2 | 3/2001 |
| WO | WO 01/47919 A1 | 7/2001 |
| WO | WO 01/91558 A1 | 12/2001 |
| WO | WO 02/00651 A2 | 1/2002 |
| WO | WO 03/008395 A1 | 1/2003 |
| WO | WO 03/059894 | 7/2003 |
| WO | WO 2004/101531 | 11/2004 |
| WO | WO 2004/101557 A1 | 11/2004 |
| WO | WO 2004/106329 | 12/2004 |
| WO | WO 2005/032468 A2 | 4/2005 |
| WO | WO 2005/035528 | 4/2005 |
| WO | WO 2005/082892 | 9/2005 |

OTHER PUBLICATIONS

Ostrovsky, et al., "Analyses of Activity for Factory Xa Inhibitors Based on Monte Carlo Simulations", *J. Med. Chem.* 2003, 46, 5691-5699.

* cited by examiner

*Primary Examiner*—Rei-Tsang Shiao
*Assistant Examiner*—Janet L Coppins
(74) *Attorney, Agent, or Firm*—Foley & Lardner LLP

(57) ABSTRACT

The present invention is directed to compounds represented by Formula I and pharmaceutically acceptable salts, solvates, hydrates, and prodrugs thereof which are inhibitors of Factor Xa. The present invention is also directed to and intermediates used in making such compounds, pharmaceutical compositions containing such compounds, methods to prevent or treat a number of conditions characterized by undesired thrombosis and methods of inhibiting the coagulation of a blood sample.

29 Claims, No Drawings

FACTOR XA INHIBITORS

CROSS-REFERENCES TO RELATED APPLICATIONS

This application claims the benefit of U.S. Patent Application No. 60/580,899, filed Jun. 18, 2004, the content of which is incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Hemostasis, the control of bleeding, occurs by surgical means, or by the physiological properties of vasoconstriction and coagulation. This invention is particularly concerned with blood coagulation and ways in which it assists in maintaining the integrity of mammalian circulation after injury, inflammation, disease, congenital defect, dysfunction or other disruption. Although platelets and blood coagulation are both involved in thrombus formation, certain components of the coagulation cascade are primarily responsible for the amplification or acceleration of the processes involved in platelet aggregation and fibrin deposition.

Thrombin is a key enzyme in the coagulation cascade as well as in hemostasis. Thrombin plays a central role in thrombosis through its ability to catalyze the conversion of fibrinogen into fibrin and through its potent platelet activation activity. Direct or indirect inhibition of thrombin activity has been the focus of a variety of recent anticoagulant strategies as reviewed by Claeson, G., "Synthetic Peptides and Peptidomimetics as Substrates and Inhibitors of Thrombin and Other Proteases in the Blood Coagulation System", *Blood Coag. Fibrinol.*, 5:411-436 (1994). Several classes of anticoagulants currently used in the clinic directly or indirectly affect thrombin (i.e. heparins, low-molecular weight heparins, heparin-like compounds and coumarins).

A prothrombinase complex, including Factor Xa (a serine protease, the activated form of its Factor X precursor and a member of the calcium ion binding, gamma carboxyglutamyl (Gla)-containing, vitamin K dependent, blood coagulation glycoprotein family), converts the zymogen prothrombin into the active procoagulant thrombin. Unlike thrombin, which acts on a variety of protein substrates as well as at a specific receptor, factor Xa appears to have a single physiologic substrate, namely prothrombin. Since one molecule of factor Xa may be able to generate up to 138 molecules of thrombin (Elodi et al., *Thromb. Res.* 15:617-619 (1979)), direct inhibition of factor Xa as a way of indirectly inhibiting the formation of thrombin may be an efficient anticoagulant strategy. Therefore, it has been suggested that compounds which selectively inhibit factor Xa may be useful as in vitro diagnostic agents, or for therapeutic administration in certain thrombotic disorders, see e.g., WO 94/13693.

Polypeptides derived from hematophagous organisms have been reported which are highly potent and specific inhibitors of factor Xa. U.S. Pat. No. 4,588,587 describes anticoagulant activity in the saliva of the Mexican leech, *Haementeria officinalis*. A principal component of this saliva was shown to be the polypeptide factor Xa inhibitor, antistasin (ATS), by Nutt, E. et al., "The Amino Acid Sequence of Antistasin, a Potent Inhibitor of Factor Xa Reveals a Repeated Internal Structure", *J. Biol. Chem.*, 263:10162-10167 (1988). Another potent and highly specific inhibitor of Factor Xa, called tick anticoagulant peptide (TAP), has been isolated from the whole body extract of the soft tick *Ornithidoros moubata*, as reported by Waxman, L., et al., "Tick Anticoagulant Peptide (TAP) is a Novel Inhibitor of Blood Coagulation Factor Xa", *Science*, 248:593-596 (1990).

Factor Xa inhibitory compounds which are not large polypeptide-type inhibitors have also been reported (see e.g. Tidwell, R. R. et al., "Strategies for Anticoagulation With Synthetic Protease Inhibitors. Xa Inhibitors Versus Thrombin Inhibitors", *Thromb. Res.*, 19:339-349 (1980); Turner, A. D. et al., "p-Amidino Esters as Irreversible Inhibitors of Factor IXa and Xa and Thrombin", *Biochemistry*, 25:4929-4935 (1986); Hitomi, Y. et al., "Inhibitory Effect of New Synthetic Protease Inhibitor (FUT-175) on the Coagulation System", *Haemostasis*, 15:164-168 (1985); Sturzebecher, J. et al., "Synthetic Inhibitors of Bovine Factor Xa and Thrombin. Comparison of Their Anticoagulant Efficiency", *Thromb. Res.*, 54:245-252 (1989); Kam, C. M. et al., "Mechanism Based Isocoumarin Inhibitors for Trypsin and Blood Coagulation Serine Proteases: New Anticoagulants", *Biochemistry*, 27:2547-2557 (1988); Hauptmann, J. et al., "Comparison of the Anticoagulant and Antithrombotic Effects of Synthetic Thrombin and Factor Xa Inhibitors", *Thromb. Haemost.*, 63:220-223 (1990)).

Others have reported Factor Xa inhibitors which are small molecule organic compounds, such as nitrogen containing heterocyclic compounds which have amidino substituent groups, wherein two functional groups of the compounds can bind to Factor Xa at two of its active sites. For example, WO 98/28269 describes pyrazole compounds having a terminal $C(=NH)-NH_2$ group; WO 97/21437 describes benzimidazole compounds substituted by a basic radical which are connected to a naphthyl group via a straight or branched chain alkylene, $C(=O)$ or $S(=O)_2$ bridging group; WO 99/10316 describes compounds having a 4-phenyl-N-alkylamidino-piperidine and 4-phenoxy-N-alkylamidino-piperidine group connected to a 3-amidinophenyl group via a carboxamidealkyleneamino bridge; and EP 798295 describes compounds having a 4-phenoxy-N-alkylamidino-piperidine group connected to an amidinonaphthyl group via a substituted or unsubstituted sulfonamide or carboxamide bridging group.

There exists a need for effective therapeutic agents for the regulation of hemostasis, and for the prevention and treatment of thrombus formation and other pathological processes in the vasculature induced by thrombin such as restenosis and inflammation. In particular, there continues to be a need for compounds which selectively inhibit factor Xa or its precursors. Compounds that have different combinations of bridging groups and functional groups than compounds previously discovered are needed, particularly compounds which selectively or preferentially bind to Factor Xa. Compounds with a higher degree of binding to Factor Xa than to thrombin are desired, especially those compounds having good bioavailability and/or solubility.

BRIEF SUMMARY OF THE INVENTION

The present invention provides in one aspect, compounds having the formula:

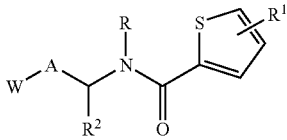

and pharmaceutically acceptable salts thereof. In formula (I), A represents benzene, a six-membered heterocyle containing 1-3 nitrogen atoms or a five-membered heterocycle containing 1-4 nitrogen, oxygen or sulfur atoms; with 0-4 substituents selected from halogen, oxo, $R^A$, —$OR^A$, $N(R^A)_2$, $CO_2R^A$, $CON(R^A)_2$, $S(O)_2R^A$, $S(O)_2N(R^A)_2$, $X^1OR^A$, $X^1CO_2R^A$, $X^1CON(R^A)_2$, $X^1N(R^A)_2$, wherein each $R^A$ is independently selected from H, $C_{1-8}$alkyl, $C_{2-8}$ alkenyl, $C_{2-8}$alkynyl, or optionally two $R^A$ attached to the same atom are combined to form a 3-, 4-, 5-, 6- or 7-membered ring; R represents a member selected from the group consisting of H and $C_{1-4}$alkyl; $R^1$ represents a member selected from the group consisting of halogen, $C_{1-8}$alkyl, $C_{2-8}$alkenyl and $C_{2-8}$alkynyl; $R^2$ represents a member selected from the group consisting of H, $C_{1-8}$alkyl, —X—$OR^{2a}$, —X—$SR^{2a}$, —X—$COR^{2a}$, —X—$CO_2R^{2a}$ and —X—$N(R^{2a})_2$, wherein X is $C_{1-8}$alkylene and each $R^{2a}$ is independently selected from H and $C_{1-8}$alkyl, or optionally two $R^{2a}$ groups attached to the same nitrogen atom are combined to form a 4-, 5-, 6- or 7-membered ring.

The letter W represent a moiety having a formula selected from (a), (b), and (c):

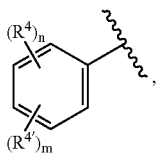

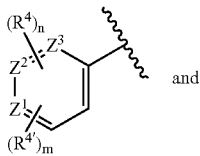

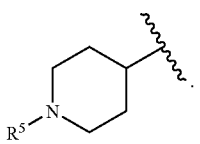

With reference to formula (b), the symbols $Z^1$, $Z^2$, and $Z^3$ each independently represent N, C or CH with the proviso that two of $Z^1$, $Z^2$, and $Z^3$ are other than N.

With reference to formulas (a) and (b), the subscript n is an integer of from 0 to 3 and the subscript m is an integer of from 0 to 1. The symbol $R^4$ represents, in each occurrence, a member selected from the group consisting of halogen, —$OR^{4a}$, —$OC(O)R^{4a}$, —$NR^{4a}R^{4b}$, —$SR^{4a}$, $S(O)R^{4a}$, $S(O)_2R^{4a}$, $S(O)_2$ $NR^{4a}R^{4b}$, —$R^{4c}$, —CN, —$NO_2$, —$CO_2R^{4a}$, —$CONR^{4a}R^{4b}$, —$C(O)R^{4a}$, —$OC(O)NR^{4a}R^{4b}$, —$NR^{4b}C(O)R^{4a}$, —$NR^{4b}C(O)_2R^{4c}$, —$NR^{4a}$—$C(O)NR^{4a}R^{4b}$, —$X^1OR^{4a}$, —$X^1OC(O)R^{4a}$, —$X^1NR^{4a}R^{4b}$, —$X^1SR^{4a}$, —$X^1S(O)R^{4a}$, —$X^1S(O)_2R^{4a}$, —$X^1CN$, —$X^1NO_2$, —$X^1CO_2R^{4a}$, —$X^1CONR^{4a}R^{4b}$, —O—$X^1CO_2R^{4a}$, —$X^1CONR^{4a}R^{4b}$, —O—$X^1CONR^{4a}R^{4b}$, —$X^1C(O)R^{4a}$, —O—$X^1NR^{4a}R^{4b}$, —$S(O)X^1NR^{4a}R^{4b}$, —$S(O)_2X^1NR^{4a}R^{4b}$, —$X^1OC(O)$ $NR^{4a}R^{4b}$, —$X^1NR^{4a}C(O)R^{4a}$, —$X^1NR^{4b}C(O)_2R^{1c}$, —$X^1NR^{4a}C(O)NR^{4a}R^{4b}$, —Y, —$X^1$—Y, —O—Y, —$NR^{4a}$Y, —SY, —S(O)Y and —$S(O)_2$Y. Similarly, $R^{4'}$ represents a member selected from the group consisting of —C(=NH)$R^{4a}$, —C(=$NR^{4c}$)$R^{4a}$, —C(=NH)$NR^{4a}R^{4b}$, —C(=$NR^{4c}$)$NR^{4a}R^{4b}$, —C(=$N^+R^{4c}R^{4c}$)$NR^{4a}R^{4b}$, —$X^2$—C(=NH)$NR^{4a}R^{4b}$, —$X^2$—C(=$NR^{4c}$)$NR^{4a}R^{4b}$, —$X^2$—C(=$N^+R^{4c}R^{4c}$)$NR^{4a}R^{4b}$ and —C(=$NR^{4a}$)$NR^{4a}$—Y, wherein Y is a five or six-membered aryl, heterocyclyl or aryl-$C_{1-2}$alkyl, optionally substituted with from one to three substitutents selected from the group consisting of halogen, oxo, —$OR^{4a}$, —$OC(O)R^{4a}$, —$NR^{4a}R^{4b}$, —$R^{4c}$, —$SR^{4a}$, S(O)$R^{4a}$, $S(O)_2R^{4a}$, $S(O)_2NR^{4a}R^{4b}$, —CN, —$NO_2$, —$CO_2R^{4a}$, —$CONR^{4a}R^{4b}$, —$C(O)R^{4a}$, —$NR^{4b}C(O)R^{4a}$, —$NR^{4b}C(O)_2R^{4c}$, —$X^1R^{4a}$, —$X^1OR^{4a}$, —$X^1SR^{4a}$, —$X^1S(O)R^{4a}$, —$X^1S(O)_2R^{4a}$, —$X^1CN$, —$X^1NO_2$, —$X^1CO_2R^{4a}$, —$X^1CONR^{4a}R^{4b}$, —$X^1C(O)R^{4a}$, —O—$X^1NR^{4a}R^{4b}$, —$S(O)X^1NR^{4a}R^{4b}$, —$S(O)_2X^1NR^{4a}R^{4b}$, —$X^1OC(O)$ $NR^{4a}R^{4b}$, —$X^1NR^{4b}C(O)R^{4a}$, —$X^1NR^{4b}C(O)_2R^{4c}$, —$X^1NR^{4a}$—$C(O)NR^{4a}R^{4b}$, —$X^1OC(O)R^{4a}$, —$X^1NR^{4a}R^{4b}b$, —O—$X^1OR^{4a}$, —O—$X^1NR^{4a}R^{4b}$, —O—$X^1CO_2R^{4a}$, —O—$X^1CONR^{4a}R^{4b}$, —$NR^{4b}$—$X^1OR^{4a}$, —$NR^{4b}$—$X^1NR^{4a}R^{4b}$, —$NR^{4b}$—$X^1CO_2R^{4a}$, and —$NR^{4b}$—$X^1CONR^{4a}R^{4b}$; each $X^1$ and $X^2$ are members independently selected from the group consisting of $C_{1-4}$alkylene, $C_{2-4}$alkenylene and $C_{2-4}$alkynylene; each $R^{4a}$ and $R^{4b}$ are independently selected from the group consisting of hydrogen, $C_{1-8}$alkyl, $C_{1-8}$haloalkyl, $C_{3-6}$cycloalkyl, $C_{3-6}$heterocycloalkyl, $C_{2-8}$alkenyl, $C_{2-8}$alkynyl, aryl, heteroaryl, aryl-$C_{1-4}$ alkyl, and aryloxy-$C_{1-4}$alkyl; each $R^{4c}$ is independently selected from the group consisting of $C_{1-8}$alkyl, $C_{1-8}$haloalkyl, $C_{3-6}$cycloalkyl, $C_{3-6}$heterocycloalkyl, $C_{2-8}$alkenyl, $C_{2-8}$alkynyl, aryl, heteroaryl, aryl-$C_{1-4}$alkyl, and aryloxy-$C_{1-4}$ alkyl, and optionally any two of $R^{4a}$, $R^{4b}$ and $R^{4c}$ when part of a common $R^4$ or $R^{4'}$ substituent can be combined with the atoms to which each is attached to form a saturated or unsaturated, four to nine-membered mono- or bicyclic ring having from 0 to 2 additional heteroatoms as ring members. Additionally, each of $R^{4a}$, $R^{4b}$ and $R^{4c}$ is optionally further substituted with from one to three members selected from the group consisting of —OH, oxo, —$R^m$, —$OR^m$, —$OC(O)$ $NHR^m$, —$OC(O)N(R^m)_2$, —SH, —$SR^m$, —$S(O)R^m$, —$S(O)_2$ $R^m$, —$SO_2NH_2$, —$S(O)_2NHR^m$, —$S(O)_2N(R^m)_2$, —$NHS(O)_2R^m$, —$NR^mS(O)_2R^m$, —$C(O)NH_2$, —$C(O)$ $NHR^m$, —$C(O)N(R^m)_2$, —$C(O)R^m$, —$NHC(O)R^m$, —$NR^mC$ $(O)R^m$, —$NHC(O)NH_2$, —$NR^mC(O)NH_2$, —$NR^mC(O)$ $NHR^m$, —$NHC(O)NHR^m$, —$NR^mC(O)N(R^m)_2$, —$NHC(O)$ $N(R^m)_2$, —$CO_2H$, —$CO_2R^m$, —$NHCO_2R^m$, —$NR^mCO_2R^m$, —CN, —$NO_2$, —$NH_2$, —$NHR^m$, —$N(R^m)_2$, —$NR^mS(O)$ $NH_2$ and —$NR^mS(O)_2NHR^m$, wherein each $R^m$ is independently an unsubstituted $C_{1-6}$alkyl, benzyl or combined with the atoms to which each is attached to form a saturated four-, five-, six- or seven-membered ring having from 0 to 2 additional heteroatoms as ring members.

Turning next to formula (c), the symbol $R^5$ represents a member selected from the group consisting of $R^{5a}$, —$CO_2R^{5c}$, —$CONR^{5a}R^{5b}$, —$C(O)R^{5a}$, —C(=$NR^{5a}$) $NR^{5a}R^{5b}$, —C(=$NR^{5c}R^{5c}$)$NR^{5a}R^{5b}$, —C(=$NR^{5a}$)$R^{5a}$, —C(=$NR^{5a}$)$Y^1$, —$X^3OR^{5a}$, —$X^3OC(O)R^{5a}$, —$X^3NR^{5a}R^{5b}$, —$X^3SR^{5a}$, —$X^3CN$, —$X^3NO_2$, —$X^3CO_2R^{5a}$, —$X^3CONR^{5a}R^{5b}$, —$X^3C(O)R^{5a}$, —$X^3OC$ $(O)NR^{5a}R^{5b}$, —$X^3NR^{5a}C(O)R^{5a}$, —$X^3NR^{5b}C(O)_2R^{5c}$, —$X^3NR^{5a}C(O)NR^{5a}R^{5b}$, —$X^3C(=NR^{5a})NR^{5a}R^{5b}$, —$Y^1$, and —$X^3$—$Y^1$, wherein $Y^1$ is a five or six-membered aryl or heteroaryl ring or aryl-$C_{1-2}$ alkyl, optionally substituted with from one to three substituents selected from the group consisting of halogen, —$OR^{5a}$, —$OC(O)R^{5a}$, —$NR^{5a}R^{5b}R^{5c}$, —$SR^{5a}$, —CN, —$NO_2$, —$CO_2R^{5a}$, —$CONR^{5a}R^{5b}$, —$C(O)R^{5a}$, —$NR^{5b}C(O)R^{5a}$, —$NR^{5b}C(O)_2R^{5c}$, —$X^3OR^{5a}$, —$X^3SR^{5a}$, —$X^3CN$, —$X^3NO_2$, —$X^3CO_2R^{5a}$, —$X^3CONR^{5a}R^{5b}$, —$X^3C(O)R^{5a}$, —$X^3OC(O)NR^{5a}R^{5b}$, —$X^3NR^{5b}C(O)R^{5a}$, —$X^3NR^{5b}C(O)_2R^{5c}$, —$X^3NR^{5a}C(O)NR^{5a}R^{5b}$, —$X^3OC(O)R^{5a}$, —$X^3NR^{5a}R^{5b}$, —O—$X^3OR^{5a}$, —O—$X^3NR^{5a}R^{5b}$, —O—$X^3CO_2R^{5a}$, —O—$X^3CONR^{5a}R^{5b}$, —$NR^{5b}$—$X^3OR^{5a}$, —$NR^{5b}$—$X^3NR^{5a}R^{5b}$, —$NR^{5b}$—$X^3CO_2R^{5a}$, and —$NR^{5b}$—$X^3CONR^{5a}R^{5b}$, wherein each $X^3$ is a member independently selected from the group consisting of $C_{1-4}$alkylene, $C_{2-4}$alkenylene and $C_{2-4}$alkynylene; each $R^{5a}$ and $R^{5b}$ are independently selected from the group consisting of hydrogen, $C_{1-8}$alkyl, $C_{1-8}$haloalkyl, $C_{3-6}$ cycloalkyl, $C_{3-6}$heterocycloalkyl, $C_{2-8}$alkenyl, $C_{2-8}$alkynyl, aryl, heteroaryl, aryl-$C_{1-4}$ alkyl, and aryloxy-$C_{1-4}$alkyl; each $R^{5c}$ is independently selected from the group consisting of $C_{1-8}$ alkyl, $C_{1-8}$haloalkyl, $C_{3-6}$cycloalkyl, $C_{3-6}$heterocycloalkyl, $C_{2-8}$alkenyl, $C_{2-8}$alkynyl, aryl, heteroaryl, aryl-$C_{1-4}$alkyl, and aryloxy-$C_{1-4}$ alkyl; and optionally any two of $R^{5a}$, $R^{5b}$ and $R^{5c}$ when part of a common $R^5$ substituent can be combined with the atoms to which each is attached to form a saturated four-, five-, six- or seven-membered ring having from 0 to 1 additional heteroatoms as ring members. Additionally, each of $R^{5a}$, $R^{5b}$ and $R^{5c}$ is optionally further substituted with from one to three members selected from the group consisting of —OH, —$OR''$, —$OC(O)NHR''$, —$OC(O)N(R'')_2$, —SH, —$SR''$, —$S(O)R''$, —$S(O)_2R''$, —$SO_2NH_2$, —$S(O)_2NHR''$, —$S(O)_2N(R'')_2$, —$NHS(O)_2R''$, —$NR''S(O)_2R''$, —$C(O)NH_2$, —$C(O)NHR''$, —$C(O)N(R'')_2$, —$C(O)R''$, —$NHC(O)R''$, —$NR''C(O)R''$, —$NHC(O)NH_2$, —$NR''C(O)NH_2$, —$NR''C(O)NHR''$, —$NHC(O)NHR''$, —$NR''C(O)N(R'')_2$, —$NHC(O)N(R'')_2$, —$CO_2H$, —$CO_2R''$, —$NHCO_2R''$, —$NR''CO_2R''$, —CN, —$NO_2$, —$NH_2$, —$NHR''$, —$N(R'')_2$, —$NR''S(O)NH_2$ and —$NR''S(O)_2NHR''$, wherein each $R''$ is independently an unsubstituted $C_{1-6}$alkyl or benzyl.

The present invention further provides chemical intermediates, pharmaceutical compositions and methods for preventing or treating a condition in a mammal characterized by undesired thrombosis comprising the step of administering to said mammal a therapeutically effective amount of a compound of the present invention. Such conditions include but are not limited to acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like.

The present invention further provides methods for inhibiting the coagulation of a blood sample comprising contacting said sample with a compound of the present invention.

BRIEF DESCRIPTION OF THE DRAWINGS

Not applicable

DETAILED DESCRIPTION OF THE INVENTION

Abbreviations and Definitions

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group is one having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. When "cycloalkyl" is used in combination with "alkyl", as in $C_{3-5}$cycloalkyl-alkyl, the cycloalkyl portion is meant to have from three to five carbon atoms, while the alkyl portion is an alkylene moiety having from one to three carbon atoms (e.g., —$CH_2$—, —$CH_2CH_2$— or —$CH_2CH_2CH_2$—).

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups (typically provided as —$NR^aR^b$ or a variant thereof), the alkyl portions can be the same or different and can also be combined to form a 3-7 membered ring with the nitrogen atom to which each is attached. Accordingly, a group represented as —$NR^aR^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom or through a carbon atom. Non-limiting examples of aryl groups include phenyl, naphthyl and biphenyl, while non-limiting examples of heteroaryl groups include 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, benzopyrazolyl, 5-indolyl, 1-isoquinolyl, 5-isoquinolyl, 2-quinoxalinyl, 5-quinoxalinyl, 3-quinolyl, and 6-quinolyl. If not specifically stated, substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like).

The term "heterocycle" or "heterocyclic" refers to a saturated or unsaturated non-aromatic cyclic group containing at least one sulfur, nitrogen or oxygen heteroatom. Each heterocycle can be attached at any available ring carbon or heteroatom. Each heterocycle may have one or more rings. When multiple rings are present, they can be fused together or linked covalently. Each heterocycle must contain at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Non-limiting examples of heterocycle groups include benzene, pyridine, pyridimidine, pyrazine, morpholin-3-one, piperazine-2-one, pyridine-2-one, piperidine, morpholine, piperazine, isoxazole, isothiazole, pyrazole, imidazole, oxazole, thiazole, isoxazoline, pyrazoline, imidazoline, 1,2,3-triazole, 1,2,4-triazole, 1,3,4-oxadiazole, 1,3,4-thiadiazole, 1,2,4-oxadiazole, 1,2,4-thiadiazole, pyrazol-5-one, pyrrolidine-2,5-dione, imidazolidine-2,4-dione, pyrrolidine, pyrrole, furan, thiophene, and the like.

The above terms (e.g., "aryl" and "heteroaryl"), in some embodiments, will include both substituted and unsubstituted forms of the indicated radical. Preferred substituents for each type of radical are provided below. For brevity, the terms aryl and heteroaryl will refer to substituted or unsubstituted versions as provided below.

Substituents for the aryl and heteroaryl groups are varied and are generally selected from: -halogen, -oxo, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro(C$_1$-C$_4$)alkoxy, and perfluoro(C$_1$-C$_4$)alkyl, in a number ranging from zero to the total number of open valences on the aromatic ring system; and where R', R" and R''' are independently selected from hydrogen, C$_{1-8}$alkyl, C$_{3-6}$cycloalkyl, C$_{2-8}$alkenyl, C$_{2-8}$alkynyl, unsubstituted aryl and heteroaryl, (unsubstituted aryl)-C$_{1-4}$alkyl, and unsubstituted aryloxy-C$_{1-4}$alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. one of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occuring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

General

Embodiments of the Invention

Compounds

In one aspect, the present invention provides compounds having the formula:

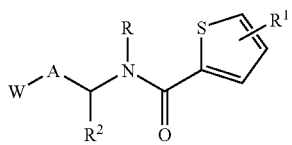

(I)

and pharmaceutically acceptable salts thereof. In formula (I), A represents benzene, a six-membered heterocycle containing 1-3 nitrogen atoms or a five-membered heterocycle containing 1-4 nitrogen, oxygen or sulfur atoms; with 0-4 substituents selected from halogen, oxo, $R^4$, —$OR^4$, $N(R^4)_2$, $CO_2R^4$, $CON(R^4)_2$, $S(O)_2R^4$, $S(O)_2N(R^4)_2$, $X^1OR^4$, $X^1CO_2R^4$, $X^1CON(R^4)_2$, $X^1N(R^4)_2$, wherein each $R^4$ is independently selected from H, $C_{1-8}$ alkyl, $C_{2-8}$alkenyl, $C_{2-8}$alkynyl, or optionally two $R^4$ attached to the same atom are combined to form a 3-, 4-, 5-, 6- or 7-membered ring; R represents a member selected from the group consisting of H and $C_{1-4}$alkyl; $R^1$ represents a member selected from the group consisting of halogen, $C_{1-8}$alkyl, $C_{2-8}$alkenyl and $C_{2-8}$alkynyl; $R^2$ represents a member selected from the group consisting of H, $C_{1-8}$alkyl, —X—$OR^{2a}$, —X—$SR^{2a}$, —X—$COR^{2a}$, —X—$CO_2R^{2a}$ and —X—$N(R^{2a})_2$; wherein X is $C_{1-8}$alkylene and each $R^{2a}$ is independently selected from the group consisting of H and $C_{1-8}$alkyl, or optionally two $R^{2a}$ groups attached to the same nitrogen atom are combined to form a 4-, 5-, 6- or 7-membered ring. For the embodiments in which $R^2$ is present and other than H, a preferred group of embodiments are those in which the carbon to which $R^2$ is attached has the (R)-stereochemical configuration.

The letter W represent a moiety having a formula selected from (a), (b), and (c):

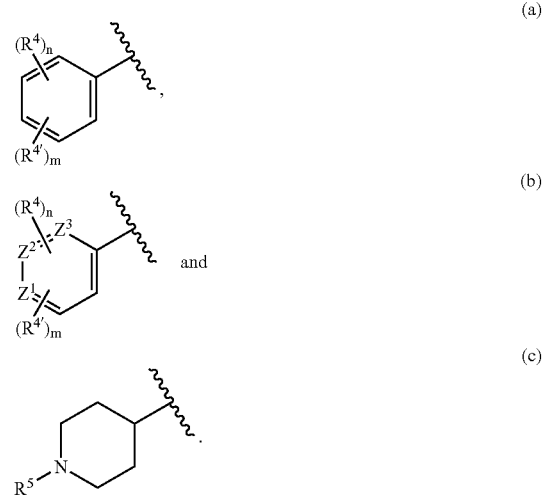

wherein the wavy line indicates the point of attachment to the rest of the molecule.

With reference to formula (b), the symbols $Z^1$, $Z^2$, and $Z^3$ each independently represent N, C or CH with the proviso that two of $Z^1$, $Z^2$, and $Z^3$ are other than N. The pyridyl nitrogen can be in a position para to the attachment of the A ring($Z^1$(4-pyridyl)), meta($Z^2$ (3-pyridyl)) or ortho($Z^3$(2-pyridyl)).

With reference to formulas (a) and (b), the subscript n is an integer of from 0 to 3and the subscript m is an integer of from 0 to 1. The symbol $R^4$ represents, in each occurrence, a member selected from the group consisting of halogen, —$OR^{4a}$, —$OC(O)R^{4a}$, —$NR^{4a}R^{4b}$, —$SR^{4a}$, $S(O)R^{4a}$, $S(O)_2R^{4a}$, $S(O)_2$ $NR^{4a}R^{4b}$, —$R^{4c}$, —CN, —$NO_2$, —$CO_2R^{4a}$, —$CONR^{4a}R^{4b}$, —$C(O)R^{4a}$, —$OC(O)NR^{4a}R^{4b}$, —$NR^{4b}C(O)R^{4a}$, —$NR^{4b}C(O)_2R^{4c}$, —$NR^{4a}$—$C(O)NR^{4a}R^{4b}$, —$X^1OR^{4a}$, —$X^1OC(O)R^{4a}$, —$X^1NR^{4a}R^{4b}$, —$X^1SR^{4a}$, —$X^1S(O)R^{4a}$, —$X^1S(O)_2R^{4a}$, —$X^1CN$, —$X^1NO_2$, —$X^1CO_2R^{4a}$, —O—$X^1CO_2R^{4a}$, —$X^1CONR^{4a}R^{4b}$, —O—$X^1CONR^{4a}R^{4b}$, —$X^1C(O)R^{4a}$, —O—$X^1NR^{4a}R^{4b}$, —$S(O)X^1NR^{4a}R^{4b}$, —$S(O)_2X^1NR^{4a}R^{4b}$, —$X^1OC(O)$ $NR^{4a}R^{4b}$, —$X^1NR^{4a}C(O)R^{4a}$, —$X^1NR^{4b}C(O)_2R^{4c}$, —$X^1NR^{4a}C(O)NR^{4a}R^{4b}$, —Y, —$X^1$—Y, —O—Y, —$NR^{4a}$Y, —SY, —S(O)Y and —S(O)$_2$Y. Similarly, $R^{4'}$ represents a member selected from the group consisting of —C(=NH)$R^{4a}$, —C(=$NR^{4c}$)$R^{4a}$, —C(=NH)$NR^{4a}R^{4b}$, —C(=$NR^{4c}$)$NR^{4a}R^{4b}$, —C(=$N^+R^{4c}R^{4c}$)$NR^{4a}R^{4b}$, —$X^2$—C(=NH)$NR^{4a}R^{4b}$, —$X^2$—C(=$NR^{4c}$)$NR^{4a}R^{4b}$, —$X^2$C(=$N^+R^{4c}R^{4c}$)$NR^{4a}R^{4b}$ and —C(=$NR^{4a}$)$NR^{4a}$—Y; wherein Y is a five or six-membered aryl, heterocyclyl or aryl-$C_{1-2}$alkyl, optionally substituted with from one to three substituents selected from the group consisting of halogen, oxo, —OR$^{4a}$, —OC(O)R$^{4a}$, —NR$^{4a}$R$^{4b}$, R$^{4c}$, —SR$^{4a}$, S(O)R$^{4a}$, S(O)$_2$R$^{4a}$, S(O)$_2$NR$^{4a}$R$^{4b}$, —CN, —NO$_2$, —CO$_2$R$^{4a}$, —CONR$^{4a}$R$^{4b}$, —C(O)R$^{4a}$, NR$^{4b}$C(O)R$^{4a}$, —NR$^{4b}$C(O)$_2$R$^{4c}$, —X$^1$R$^{4a}$, —X$^1$OR$^{4a}$, —X$^1$SR$^{4a}$, —X$^1$S(O)R$^{4a}$, —X$^1$S(O)$_2$R$^{4a}$, —X$^1$CN, —X$^1$NO$_2$, —X$^1$CO$_2$R$^{4a}$, —X$^1$CONR$^{4a}$R$^{4b}$, —X$^1$C(O)R$^{4a}$, —O—X$^1$NR$^{4a}$R$^{4b}$, —S(O)X$^1$NR$^{4a}$R$^{4b}$, —S(O)$_2$X$^1$NR$^{4a}$R$^{4b}$, —X$^1$OC(O)NR$^{4a}$R$^{4b}$, —X$^1$NR$^{4b}$C(O)R$^{4a}$, —X$^1$NR$^{4b}$C(O)$_2$R$^{4c}$, —X$^1$NR$^{4a}$—C(O)NR$^{4a}$R$^{4b}$, —X$^1$OC(O)R$^{4a}$, —X$^1$NR$^{4a}$R$^{4b}$, —O—X$^1$OR$^{4a}$, —O—X$^1$NR$^{4a}$R$^{4b}$, —O—X$^1$CO$_2$R$^{4a}$, —O—X$^1$CONR$^{4a}$R$^{4b}$, —NR$^{4b}$—X$^1$OR$^{4a}$, —NR$^{4b}$—X$^1$NR$^{4a}$R$^{4b}$, —NR$^{4b}$—X$^1$CO$_2$R$^{4a}$, and —NR$^{4b}$—X$^1$CONR$^{4a}$R$^{4b}$; each X$^1$ and X$^2$ are members independently selected from the group consisting of C$_{1-4}$alkylene, C$_{2-4}$alkenylene and C$_{2-4}$alkynylene; each R$^{4a}$ and R$^{4b}$ are independently selected from the group consisting of hydrogen, C$_{1-8}$alkyl, C$_{1-8}$ haloalkyl, C$_{3-6}$cycloalkyl, C$_{3-6}$heterocycloalkyl, C$_{2-8}$alkenyl, C$_{2-8}$alkynyl, aryl, heteroaryl, aryl-C$_{1-4}$ alkyl, and aryloxy-C$_{1-4}$alkyl; each R$^{4c}$ is independently selected from the group consisting of C$_{1-8}$alkyl, C$_{1-8}$haloalkyl, C$_{3-6}$cycloalkyl, C$_{3-6}$heterocycloalkyl, C$_{2-8}$alkenyl, C$_{2-8}$alkynyl, aryl, heteroaryl, aryl-C$_{1-4}$alkyl, and aryloxy-C$_{1-4}$ alkyl, and optionally any two of R$^{4a}$, R$^{4b}$ and R$^{4c}$ when part of a common R$^4$ or R$^{4'}$ substituent can be combined with the atoms to which each is attached to form a saturated or unsaturated, four to nine-membered mono- or bicyclic ring having from 0 to 2 additional heteroatoms as ring members. Additionally, each of R$^{4a}$, R$^{4b}$ and R$^{4c}$ is optionally further substituted with from one to three members selected from the group consisting of —OH, oxo, —R$^m$, —OR$^m$, —OC(O) NHR$^m$, —OC(O)N(R$^m$)$_2$, —SH, —SR$^m$, —S(O)R$^m$, —S(O)$_2$ R$^m$, —SO$_2$NH$_2$, —S(O)$^2$NHR$^m$, —S(O)$_2$N(R$^m$)$_2$, —NHS(O)$_2$ R$^m$, —NR$^m$S(O)$_2$R$^m$, —C(O)NH$_2$, —C(O) NHR$^m$, —C(O)N(R$^m$)$_2$, —C(O)R$^m$, —NHC(O)R$^m$, —NR$^m$C (O)R$^m$, —NHC(O)NH$_2$, —NR$^m$C(O)NH$_2$, —NR$^m$C(O) NHR$^m$, —NHC(O)NHR$^m$, —NR$^m$C(O)N(R$^m$)$_2$, —NHC(O) N(R$^m$)$_2$, —CO$_2$H, —CO$_2$R$^m$, —NHCO$_2$R$^m$, —NR$^m$CO$_2$R$^m$, —CN, —NO$_2$, —NH$_2$, —NHR$^m$, —N(R$^m$)$_2$, —NR$^m$S(O) NH$_2$ and —NR$^m$S(O)$_2$NHR$^m$, wherein each R$^m$ is independently an unsubstituted C$_{1-6}$alkyl, benzyl or combined with the atoms to which each is attached to form a saturated four-, five-, six- or seven-membered ring having from 0 to 2 additional heteroatoms as ring members.

Turning next to formula (c), the symbol R$^5$ represents a member selected from the group consisting of —R$^{5a}$, —CO$_2$R$^{5c}$, —CONR$^{5a}$R$^{5b}$, —C(O)R$^{5a}$, —C(=NR$^{5a}$) NR$^{5a}$R$^{5b}$, —C(=N$^+$R$^{5c}$R$^{5c}$)NR$^{5a}$R$^{5b}$, —C(=NR$^{5a}$)R$^{5a}$, —C(=NR$^{5a}$)Y$^1$, —X$^3$OR$^{5a}$, —X$^3$OC(O)R$^{5a}$, —X$^3$NR$^{5a}$R$^{5b}$, —X$^3$SR$^{5a}$, —X$^3$CN, —X$^3$NO$_2$, —X$^3$CO$_2$R$^{5a}$, —X$^3$CONR$^{5a}$R$^{5b}$, —X$^3$C(O)R$^{5a}$, —X$^3$OC (O)NR$^{5a}$R$^{5b}$, —X$^3$NR$^{5a}$C(O)R$^{5a}$, —X$^3$NR$^{5b}$C(O)$_2$R$^{5c}$, —X$^3$NR$^{5a}$C(O)NR$^{5a}$R$^{5b}$, —X$^3$—C(=NR$^{5a}$)NR$^{5a}$R$^{5b}$, —Y$^1$, and —X$^3$—Y$^1$, wherein Y$^1$ is a five or six-membered aryl or heteroaryl ring or aryl-C$_{1-2}$alkyl, optionally substituted with from one to three substituents selected from the group consisting of halogen, —OR$^{5a}$, —OC(O)R$^{5a}$, —NR$^{5a}$R$^{5b}$, —R$^{5c}$, —SR$^{5a}$, —CN, —NO$_2$, —CO$_2$R$^{5a}$, —CONR$^{5a}$R$^{5b}$, —C(O)R$^{5a}$, —NR$^{5b}$C(O)R$^{5a}$, —NR$^{5b}$C(O)$_2$ R$^{5c}$, —X$^3$OR$^{5a}$, —X$^3$SR$^{5a}$, —X$^3$CN, —X$^3$NO$_2$, —X$^3$CO$_2$R$^{5a}$, —X$^3$CONR$^{5a}$R$^{5b}$, —X$^3$C(O)R$^{5a}$, —X$^3$OC (O)NR$^{5a}$R$^{5b}$, —X$^3$NR$^{5b}$C(O)R$^{5a}$, —X$^3$NR$^{5b}$C(O)$_2$R$^{5c}$, —X$^3$NR$^{5a}$—C(O)NR$^{5a}$R$^{5b}$, —X$^3$OC(O)R$^{5a}$, —X$^3$NR$^{5a}$R$^{5b}$, —O—X$^3$OR$^{5a}$, —O—X$^3$NR$^{5a}$R$^{5b}$, —O—X$^3$CO$_2$R$^{5a}$, —O—X$^3$CONR$^{5a}$R$^{5b}$, —NR$^{5b}$—X$^3$OR$^{5a}$, —NR$^{5b}$—X$^3$NR$^{5a}$R$^{5b}$, —NR$^{5b}$—X$^3$CO$_2$R$^{5a}$, and —NR$^{5b}$—X$^3$CONR$^{5a}$R$^{5b}$, wherein each X$^3$ is a member independently selected from the group consisting of C$^{1-4}$alkylene, C$_{2-4}$alkenylene and C$_{2-4}$alkynylene; each R$^{5a}$ and R$^{5b}$ are independently selected from the group consisting of hydrogen, C$_{1-8}$alkyl, C$_{1-8}$haloalkyl, C$_{3-6}$ cycloalkyl, C$_{3-6}$heterocycloalkyl, C$_{2-8}$alkenyl, C$_{2-8}$alkynyl, aryl, heteroaryl, aryl-C$_{1-4}$alkyl, and aryloxy-C$_{1-4}$alkyl; each R$^{5c}$ is independently selected from the group consisting of C$_{1-8}$ alkyl, C$_{1-8}$haloalkyl, C$_{3-6}$cycloalkyl, C$_{3-6}$heterocycloalkyl, C$_{2-8}$alkenyl, C$_{2-8}$alkynyl, aryl, heteroaryl, aryl-C$_{1-4}$alkyl, and aryloxy-C$_{1-4}$alkyl; and optionally any two of R$^{5a}$, R$^{5b}$ and R$^{5c}$ when part of a common R$^5$ substituent can be combined with the atoms to which each is attached to form a saturated four-, five-, six- or seven-membered ring having from 0 to 1 additional heteroatoms as ring members. Additionally, each of R$^{5a}$, R$^{5b}$ and R$^{5c}$ is optionally further substituted with from one to three members selected from the group consisting of —OH, —OR″, —OC(O)NHR″, —OC(O)N(R″)$_2$, —SH, —SR″, —S(O)R″, —S(O)$_2$R″, —SO$_2$NH$_2$, —S(O)$_2$NHR″, —S(O)$_2$N(R″)$_2$, —NHS(O)$_2$R″, —NR″S(O)$_2$R″, —C(O) NH$_2$, —C(O)NHR″, —C(O)N(R″)$_2$, —C(O)R″, —NHC(O) R″, —NR″C(O)R″, —NHC(O)NH$_2$, —NR″C(O)NH$_2$, —NR″C(O)NHR″, —NHC(O)NHR″, —NR″C(O)N(R″)$_2$, —NHC(O)N(R″)$_2$, —CO$_2$H, —CO$_2$R″, —NHCO$_2$R″, —NR″CO$_2$R″, —CN, —NO$_2$, —NH$_2$, —NHR″, —N(R″)$_2$, —NR″S(O)NH$_2$ and —NR″S(O)$_2$NHR″, wherein each R″ is independently an unsubstituted C$_{1-6}$alkyl or benzyl.

With the above formula are a number of specific embodiments of the invention. In one group of embodiments, W has a formula selected from the group consisting of (a), (d), (e) and (c):

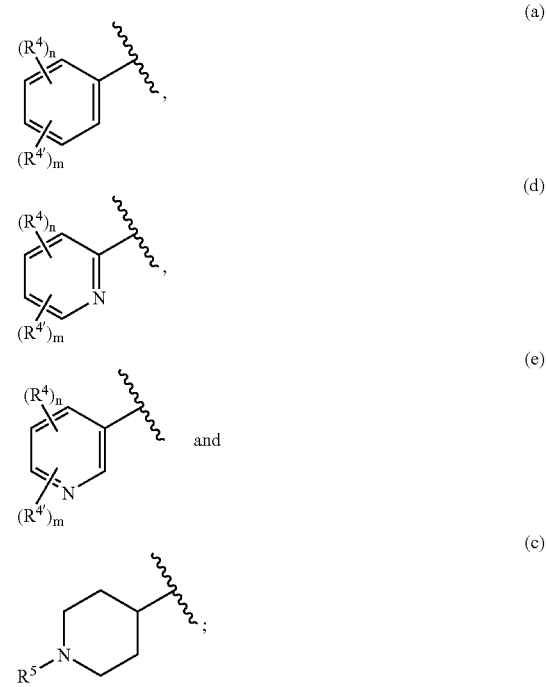

In another group of embodiments, W has the formula (a), (d) or (e). In another group of embodiments, W has the formula (c). In a specific group of embodiments, at least one of n and m is 1 and each R$^4$ and R$^{4'}$ can be any of the substituents provided with reference to the full scope of the invention. In one group of embodiments, R$^{4'}$ is selected from

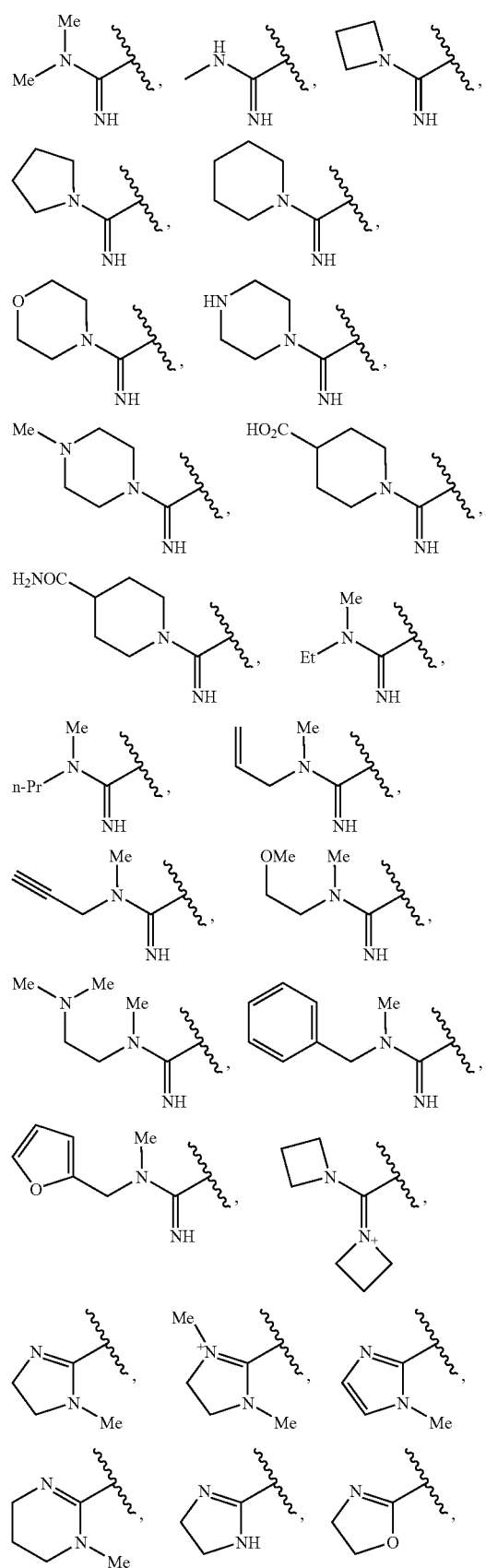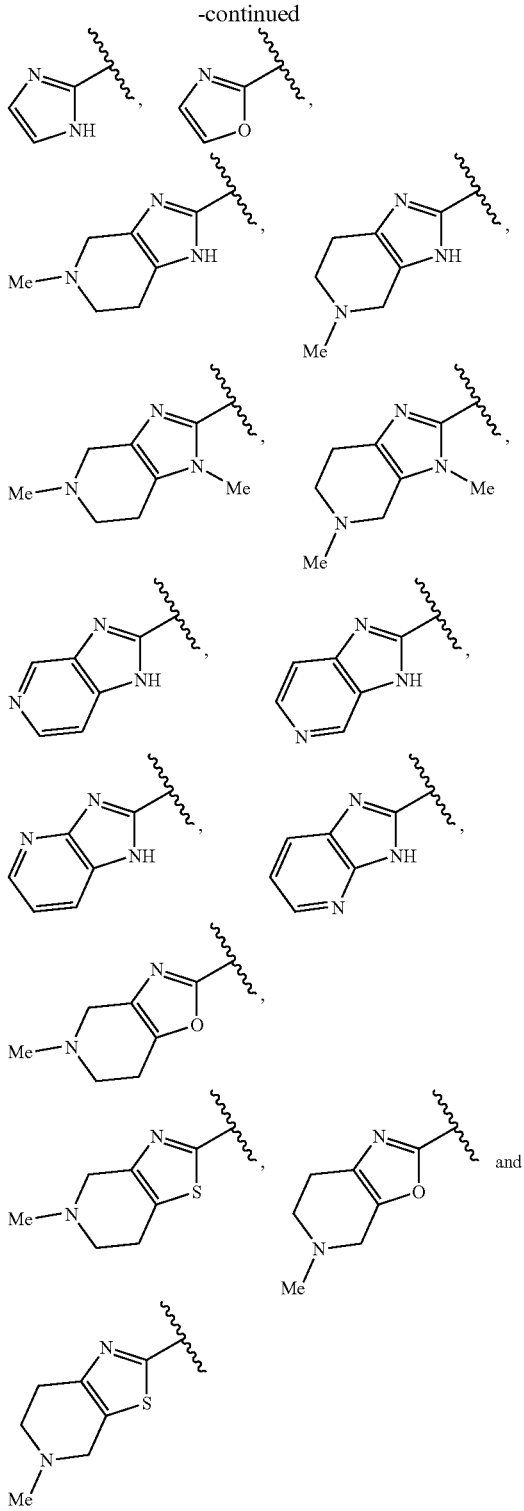

wherein the wavy line indicates the point of attachment to the remainder of the compound.

In another group of embodiments, at least one of n and m is 1 and each $R^4$ and $R^{4'}$ is independently selected from the group consisting of H, halogen, $OR^{4a}$, $C_{1-4}$alkyl, $SR^{4a}$, $S(O)R^{4a}$, $S(O)_2R^{4a}$, $S(O)_2N(R^{4a}R^{4b})$, $NR^{4a}R^{4b}$, $C_{1-4}$alkyl$OR^{4a}$, $C_{1-4}$alkl$NR^{4a}R^{4b}$, $C_{1-4}$alkyl$CO_2R^{4a}$, $OC_{1-4}$alkyl$OR^{4a}$, $OC_{1-4}alkylN(R^{4a}N^{4b})$, $N(R^{4a})C_{1-4}alkylOR^{4b}$, $N(R^{4a})C_{1-4}alkylN(R^{4a}R^{4b})$, $S(O)_2C_{1-4}alkylN(R^{4a}R^{4b})$,
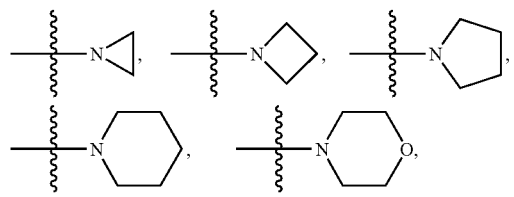
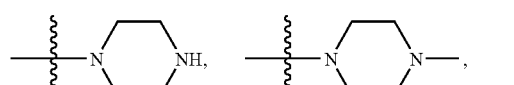
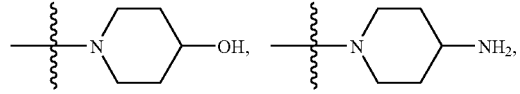
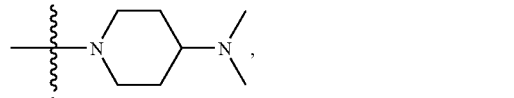
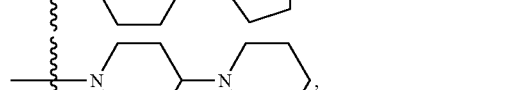
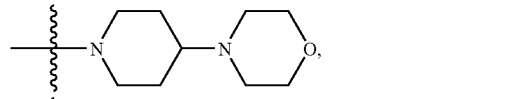
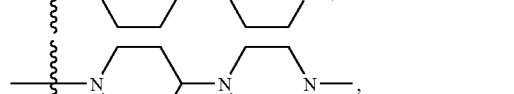
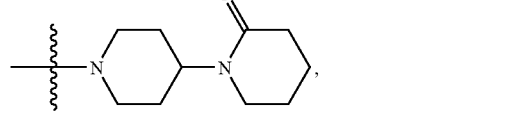
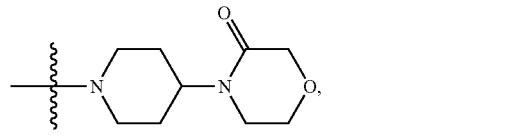
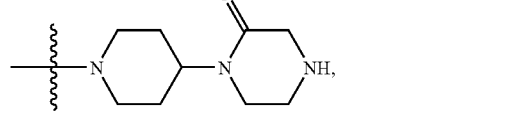
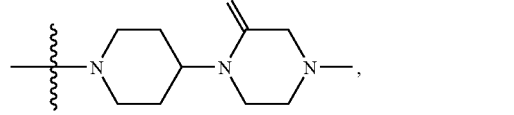
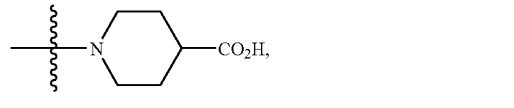
-continued
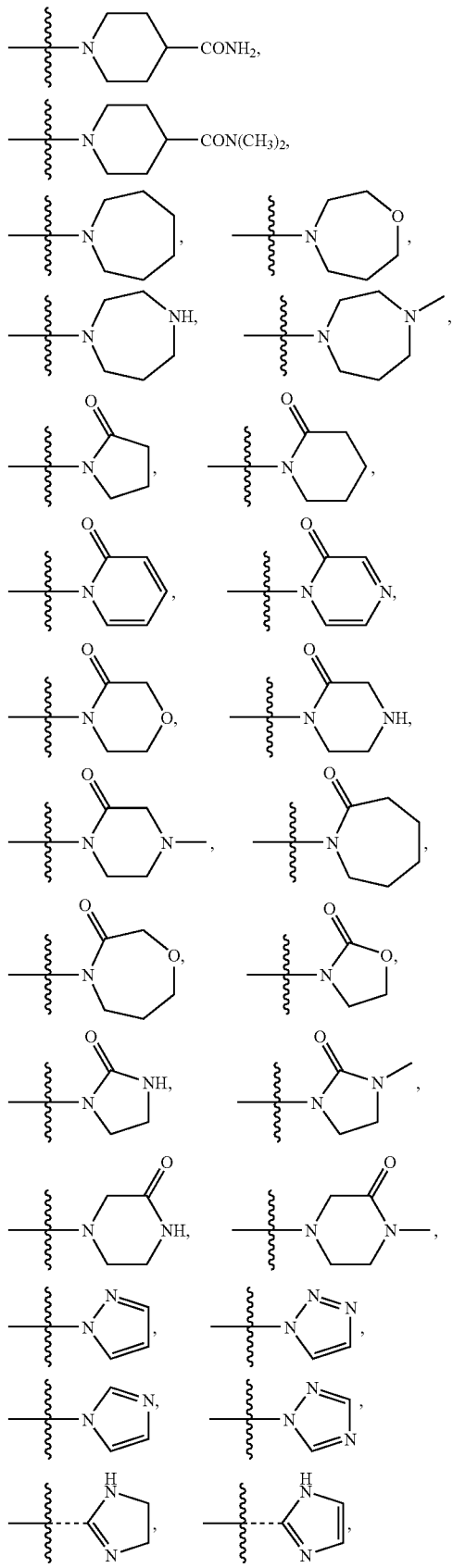

-continued
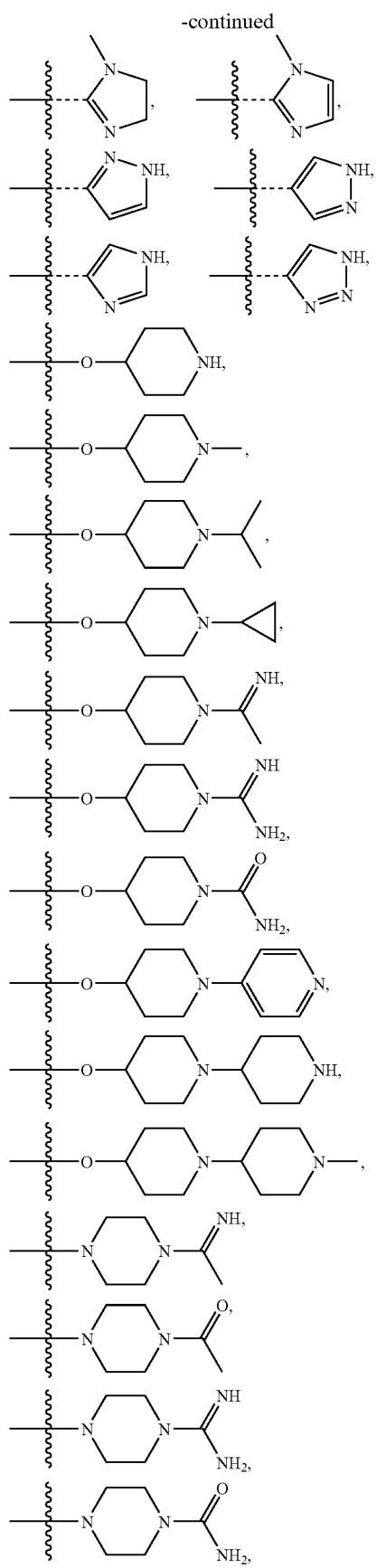
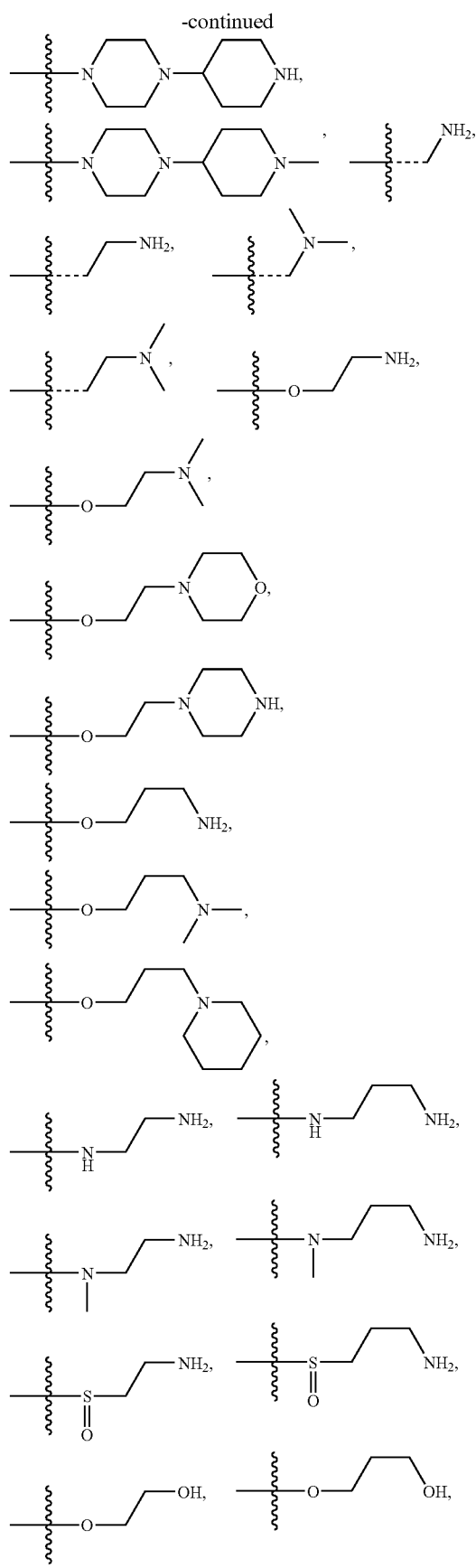

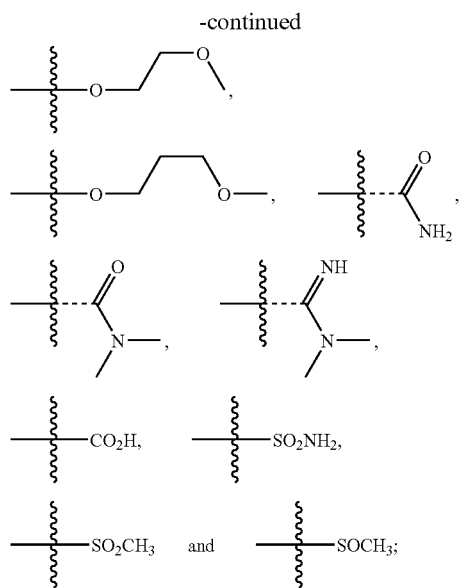
each $R^{4a}$ is independently H or $C_{1-4}$alkyl; each $R^{4d}$ is independently selected from the group consisting of H, OH, $NH_2$, $N(CH_3)_2$, $CONH_2$ and $CON(CH_3)_2$; and the wavy line indicates the point of attachment to the rest of the molecule.
In another group of embodiments, at least one of n and m is 1 and each $R^4$ and $R^{4'}$ is selected from the group consisting of:
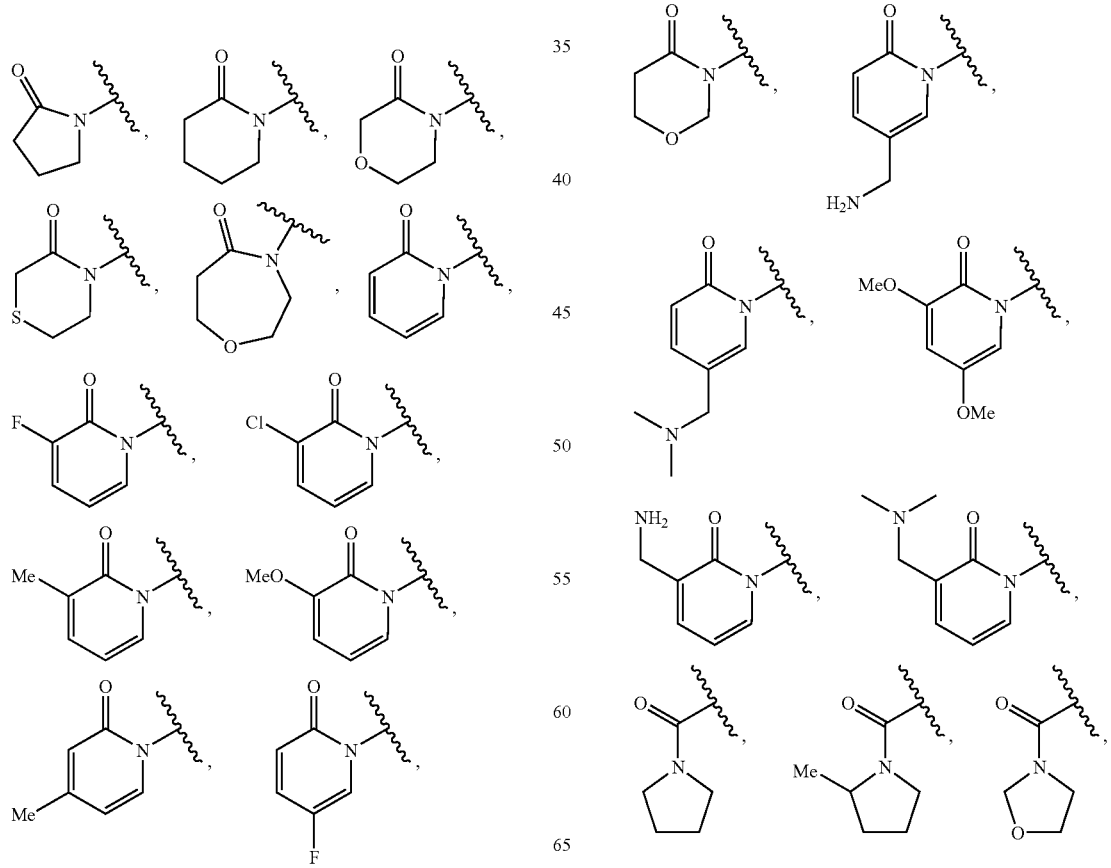

-continued

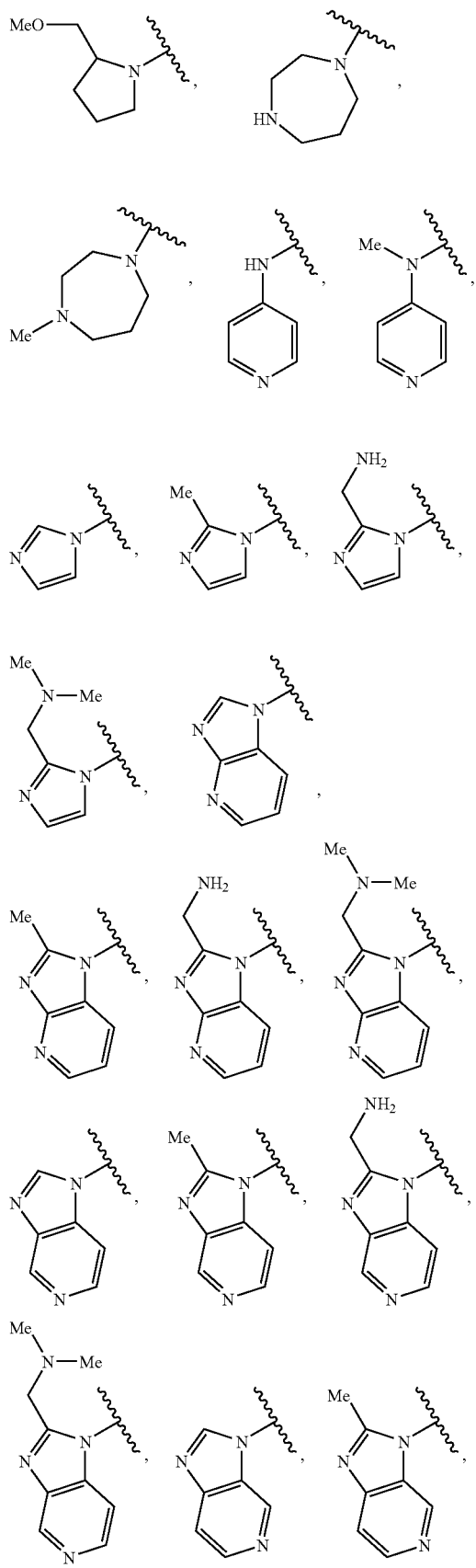

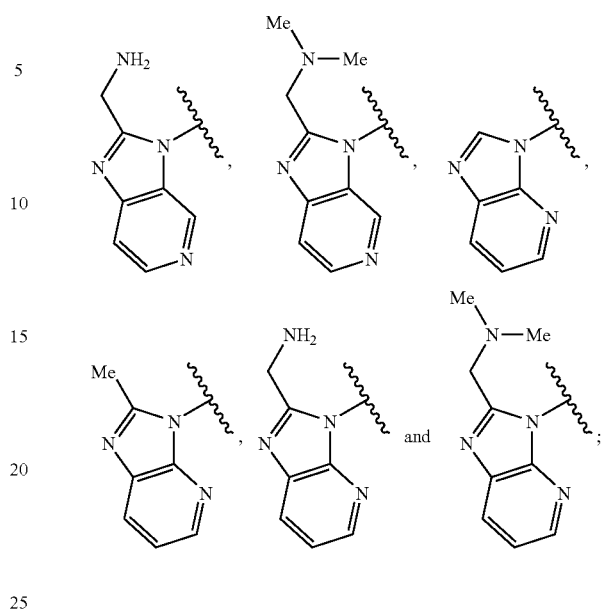

and the wavy line indicates the point of attachment to the rest of the molecule.

In other embodiments, compounds of formula I are provided in which $R^{4'}$ is attached to the ring at a position para to A. In other embodiments, compounds of formula I are provided in which $R^4$ is attached to the ring at a position ortho to A. Within these embodiments, specific embodiments are provided in which Y is an optionally substituted member selected from the group consisting of phenyl, benzyl, pyridyl, pyridylmethyl, pyrimidinyl, pyrazolyl, triazolyl and imidazolyl. Preferably, A represents benzene or a six-membered heterocyle containing 1-3 nitrogen atoms. One group of embodiments are those in which A is selected from the group consisting of: benzene, pyridine, pyridimidine, pyrazine, morpholin-3-one, piperazine-2-one, pyridine-2-one, piperidine, morpholine and piperazine. Yet another group of embodiments are those in which A is selected from the group consisting of:

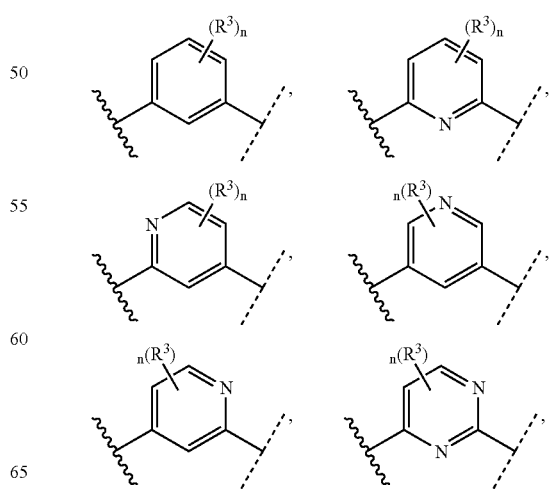

-continued

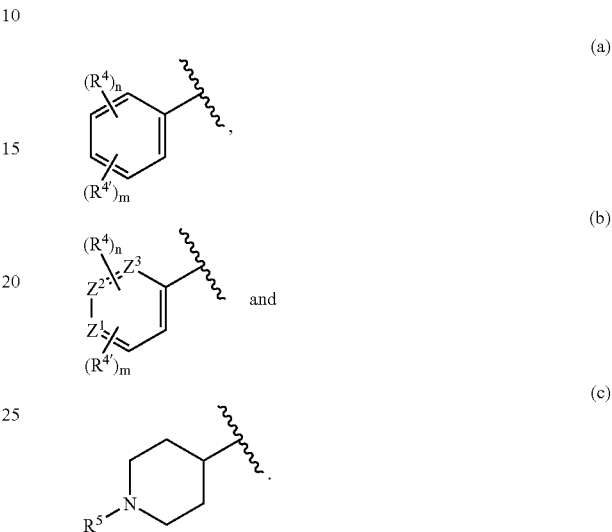

n is and integer from 0 to 3; each $R^3$ is independently selected from the group consisting of halogen, $C_{1-8}$alkyl, $C_{2-8}$alkenyl, $C_{2-8}$alkynyl, $OR^{3a}$, $N(R^{3a})_2$, $X^0CO_2R^{3a}$, $X^0CON(R^{3a})_2$, $SO_2C_{1-4}$, $SO_2N(R^{3a})_2$; each $R^{3a}$ is independently selected from the group consisting of H, $C_{1-8}$alkyl, $C_{2-8}$alkenyl and $C_{2-8}$alkynyl; and $X^0$ is a bond or $C_{1-8}$alkylene; and the dashed line indicates the point of attachment to A and the wavy line indicates the point of attachment to the rest of the molecule.

In one aspect, the present invention provides compounds having the formula:

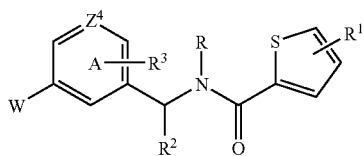

and pharmaceutically acceptable salts thereof. In formula (I), R represents a member selected from the group consisting of H and $C_{1-4}$alkyl; $R^1$ represents a member selected from the group consisting of halogen, $C_{1-8}$alkyl, $C_{2-8}$alkenyl and $C_{2-8}$alkynyl; $R^2$ represents a member selected from the group consisting of H, $C_{1-8}$alkyl, —X—$OR^{2a}$, —X—$SR^{2a}$, —X—$COR^{2a}$, —X—$CO_2R^{2a}$ and —X—$N(R^{2a})_2$; wherein X is $C_{1-8}$alkylene and each $R^{2a}$ is independently selected from the group consisting of H and $C_{1-8}$alkyl, or optionally two $R^{2a}$ groups attached to the same nitrogen atom are combined to form a 4-, 5-, 6- or 7-membered ring. The symbol $R^3$ represents a member selected from the group consisting of H and halogen.

The letter W represent a moiety having a formula selected from (a), (b), and (c):

(a)

(b)

(c)

With reference to formula (b), the symbols $Z^1$, $Z^2$, and $Z^3$ each independently represent N, C or CH with the proviso that two of $Z^1$, $Z^2$, and $Z^3$ are other than N.

With reference to formulas (a) and (b), the subscript n is an integer of from 0 to 3 and the subscript m is an integer of from 0 to 1. The symbol $R^4$ represents, in each occurrence, a member selected from the group consisting of halogen, —$OR^{4a}$, —$OC(O)R^{4a}$, —$NR^{4a}R^{4b}$, —$SR^{4a}$, $S(O)R^{4a}$, $S(O)_2R^{4a}$, $S(O)_2$ $NR^{4a}R^{4b}$, —$R^{4c}$, —CN, —$NO_2$, —$CO_2R^{4a}$, —$CONR^{4a}R^{4b}$, —$C(O)R^{4a}$, —$OC(O)NR^{4a}R^{4b}$, —$NR^{4b}C(O)R^{4a}$, —$NR^{4b}C(O)_2R^{4c}$, —$NR^{4a}$—$C(O)NR^{4a}R^{4b}$, —$X^1OR^{4a}$, —$X^1OC(O)R^{4a}$, —$X^1NR^{4a}R^{4b}$, —$X^1SR^{4a}$, —$X^1S(O)R^{4a}$, —$X^1S(O)_2R^{4a}$, —$X^1CN$, —$X^1NO_2$, —$X^1CO_2R^{4a}$, —O—$X^1CO_2R^{4a}$, —$X^1CONR^{4a}R^{4b}$, —O—$X^1CONR^{4a}R^{4b}$, —$X^1C(O)R^{4a}$, —O—$X^1NR^{4a}R^{4b}$, —$S(O)X^1NR^{4a}R^{4b}$, —$S(O)_2X^1NR^{4a}R^{4b}$, —$X^1OC(O)$ $NR^{4a}R^{4b}$, —$X^1NR^{4a}C(O)R^{4a}$, —$X^1NR^{4b}C(O)_2R^{4c}$, —$X^1NR^{4a}C(O)NR^{4a}R^{4b}$, —Y, —$X^1$—Y, —O—Y, —$NR^{4a}$Y, —SY, —S(O)Y and —$S(O)_2$Y. Similarly, $R^{4'}$ represents a member selected from the group consisting of —C(=NH)$R^{4a}$, —C(=$NR^{4c}$)$R^{4a}$, —C(=NH)$NR^{4a}R^{4b}$, —C(=$NR^{4c}$)$NR^{4a}R^{4b}$, —C(=$N^+R^{4c}R^{4c}$)$NR^{4a}R^{4b}$, —$X^2$—C(=NH)$NR^{4a}R^{4b}$, —$X^2$—C(=$NR^{4c}$)$NR^{4a}R^{4b}$, —$X^2$—C(=$N^+R^{4c}R^{4c}$)$NR^{4a}R^{4b}$ and —C(=$NR^{4a}$)$NR^{4a}$—Y, wherein Y is a five or six-membered aryl, heterocyclyl or aryl-$C_{1-2}$alkyl, optionally substituted with from one to three substitutents selected from the group consisting of halogen, oxo, —$OR^{4a}$, —$OC(O)R^{4a}$, —$NR^{4a}R^{4b}$, —$R^{4c}$, —$SR^{4a}$, $S(O)$ $R^{4a}$, $S(O)_2R^{4a}$, $S(O)_2NR^{4a}R^{4b}$, —CN, —$NO_2$, —$CO_2R^{4a}$, —$CONR^{4a}R^{4b}$, —$C(O)R^{4a}$, —$NR^{4b}C(O)R^{4a}$, —$NR^{4b}C(O)_2$ $R^{4c}$, —$X^1R^{4a}$, —$X^1OR^{4a}$, —$X^1SR^{4a}$, —$X^1S(O)R^{4a}$, —$X^1S(O)_2R^{4a}$, —$X^1CN$, —$X^1NO_2$, —$X^1CO_2R^{4a}$, —$X^1CONR^{4a}R^{4b}$, —$X^1C(O)R^{4a}$, —O—$X^1NR^{4a}R^{4b}$, —$S(O)X^1NR^{4a}R^{4b}$, —$S(O)_2X^1NR^{4a}R^{4b}$, —$X^1OC(O)$ $NR^{4a}R^{4b}$, —$X^1NR^{4b}C(O)R^{4a}$, —$X^1NR^{4b}C(O)_2R^{4c}$, —$X^1NR^{4a}$—$C(O)NR^{4a}R^{4b}$, —$X^1OC(O)R^{4a}$, —X$^1$NR$^{4a}$R$^{4b}$, —O—X$^1$OR$^{4a}$, —O—X$^1$NR$^{4a}$R$^{4b}$, —O—X$^1$CO$_2$R$^{4a}$, —O—X$^1$CONR$^{4a}$R$^{4b}$, —NR$^{4b}$—X$^1$OR$^{4a}$, —NR$^{4b}$—X$^1$NR$^{4a}$R$^{4b}$, —NR$^{4b}$—X$^1$CO$_2$R$^{4a}$, and —NR$^{4b}$—X$^1$CONR$^{4a}$R$^{4b}$; each X$^1$ and X$^2$ are members independently selected from the group consisting of C$_{1-4}$alkylene, C$_{2-4}$alkenylene and C$_{2-4}$alkynylene; each R$^{4a}$ and R$^{4b}$ are independently selected from the group consisting of hydrogen, C$_{1-8}$alkyl, C$_{1-8}$ haloalkyl, C$_{3-6}$cycloalkyl, C$_{3-6}$heterocycloalkyl, C$_{2-8}$alkenyl, C$_{2-8}$alkynyl, aryl, heteroaryl, aryl-C$_{1-4}$alkyl, and aryloxy-C$_{1-4}$alkyl; each R$^{4c}$ is independently selected from the group consisting of C$_{1-8}$alkyl, C$_{1-8}$haloalkyl, C$_{3-6}$cycloalkyl, C$_{3-6}$heterocycloalkyl, C$_{2-8}$alkenyl, C$_{2-8}$ alkynyl, aryl, heteroaryl, aryl-C$_{1-4}$alkyl, and aryloxy-C$_{1-4}$alkyl, and optionally any two of R$^{4a}$, R$^{4b}$ and R$^{4c}$ when part of a common R$^4$ or R$^{4'}$ substituent can be combined with the atoms to which each is attached to form a saturated or unsaturated, four to nine-membered mono- or bicyclic ring having from 0 to 2 additional heteroatoms as ring members. Additionally, each of R$^{4a}$, and R$^{4b}$ and R$^{4c}$ is optionally further substituted with from one to three members selected from the group consisting of —OH, oxo, —R$^m$, —OR$^m$, —OC(O)NHR$^m$, —OC(O)N(R$^m$)$_2$, —SH, —SR$^m$, —S(O)R$^m$, —S(O)$_2$R$^m$, —SO$_2$NH$_2$, —S(O)$_2$NHR$^m$, —S(O)$_2$N(R$^m$)$_2$, —NHS(O)$_2$R$^m$, —NR$^m$S(O)$_2$R$^m$, —C(O)NH$_2$, —C(O)NHR$^m$, —C(O)N(R$^m$)$_2$, —C(O)R$^m$, —NHC(O)R$^m$, —NR$^m$C(O)R$^m$, —NHC(O)NH$_2$, —NR$^m$C(O)NH$_2$, —NR$^m$C(O)NHR$^m$, —NHC(O)NHR$^m$, —NR$^m$C(O)N(R$^m$)$_2$, —NHC(O)N(R$^m$)$_2$, —CO$_2$H, —CO$_2$R$^m$, —NHCO$_2$R$^m$, —NR$^m$CO$_2$R$^m$, —CN, —NO$_2$, —NH$_2$, —NHR$^m$, —N(R$^m$)$_2$, —NR$^m$S(O)NH$_2$ and —NR$^m$S(O)$_2$NHR$^m$, wherein each R$^m$ is independently an unsubstituted C$_{1-6}$alkyl, benzyl or combined with the atoms to which each is attached to form a saturated four-, five-, six- or seven-membered ring having from 0 to 2 additional heteroatoms as ring members.

Turning next to formula (c), the symbol R$^5$ represents a member selected from the group consisting of —R$^{5a}$, —CO$_2$R$^{5c}$, —CONR$^{5a}$R$^{5b}$, —C(O)R$^{5a}$, —C(=NH)NR$^{5a}$R$^{5b}$, —C(=NR$^{5c}$)NR$^{5a}$R$^{5b}$, —C(=N$^+$R$^{5c}$R$^{5c}$)NR$^{5a}$R$^{5b}$, —C(=NR$^{5a}$)R$^{5a}$, —C(=NR$^{5a}$)Y$^1$, —X$^3$OR$^{5a}$, —X$^3$OC(O)R$^{5a}$, —X$^3$NR$^{5a}$R$^{5b}$, —X$^3$SR$^{5a}$, —X$^3$CN, —X$^3$NO$_2$, —X$^3$CO$_2$R$^{5a}$, —X$^3$CONR$^{5a}$R$^{5b}$, —X$^3$C(O)R$^{5a}$, —X$^3$OC(O)NR$^{5a}$R$^{5b}$, —X$^3$NR$^{5a}$C(O)R$^{5a}$, —X$^3$NR$^{5b}$C(O)$_2$R$^{5c}$, —X$^3$NR$^{5a}$C(O)NR$^{5a}$R$^{5b}$, —X$^3$—C(=NR$^{5a}$)NR$^{5a}$R$^{5b}$, —Y$^1$, and —X$^3$—Y$^1$, wherein Y$^1$ is a five or six-membered aryl or heteroaryl ring or aryl-C$_{1-2}$alkyl, optionally substituted with from one to three substitutents selected from the group consisting of halogen, —OR$^{5a}$, —OC(O)R$^{5a}$, —NR$^{5a}$R$^{5b}$, —R$^{5c}$, —SR$^{5a}$, —CN, —NO$_2$, —CO$_2$R$^{5a}$, —CONR$^{5a}$R$^{5b}$, —C(O)R$^{5a}$, —NR$^{5b}$C(O)R$^{5a}$, —NR$^{5b}$C(O)$_2$R$^{5c}$, —X$^3$OR$^{5a}$, —X$^3$SR$^{5a}$, —X$^3$CN, —X$^3$NO$_2$, —X$^3$CO$_2$R$^{5a}$, —X$^3$CONR$^{5a}$R$^{5b}$, —X$^3$C(O)R$^{5a}$, —X$^3$OC(O)NR$^{5a}$R$^{5b}$, —X$^3$NR$^{5b}$C(O)R$^{5a}$, —X$^3$NR$^{5b}$C(O)$_2$R$^{5c}$, —X$^3$NR$^{5a}$—C(O)NR$^{5a}$R$^{5b}$, —X$^3$OC(O)R$^{5a}$, —X$^3$NR$^{5a}$R$^{5b}$, —O—X$^3$OR$^{5a}$, —O—X$^3$NR$^{5a}$R$^{5b}$, —O—X$^3$CO$_2$R$^{5a}$, —O—X$^3$CONR$^{5a}$R$^{5b}$, —NR$^{5b}$—X$^3$OR$^{5a}$, —NR$^{5b}$—X$^3$NR$^{5a}$R$^{5b}$, —NR$^{5b}$—X$^3$CO$_2$R$^{5a}$, and —NR$^{5b}$—X$^3$CONR$^{5a}$R$^{5b}$, wherein each X$^3$ is a member independently selected from the group consisting of C$_{1-4}$alkylene, C$_{2-4}$alkenylene and C$_{2-4}$ alkynylene; each R$^{5a}$ and R$^{5b}$ are independently selected from the group consisting of hydrogen, C$_{1-8}$alkyl, C$_{1-8}$haloalkyl, C$_{3-6}$cycloalkyl, C$_{3-6}$heterocycloalkyl, C$_{2-8}$alkenyl, C$_{2-8}$ alkynyl, aryl, heteroaryl, aryl-C$_{1-4}$alkyl, and aryloxy-C$_{1-4}$alkyl; each R$^{5c}$ is independently selected from the group consisting of C$_{1-8}$alkyl, C$_{1-8}$haloalkyl, C$_{3-6}$cycloalkyl, C$_{3-6}$ heterocycloalkyl, C$_{2-8}$alkenyl, C$_{2-8}$alkynyl, aryl, heteroaryl, aryl-C$_{1-4}$alkyl, and aryloxy-C$_{1-4}$ alkyl; and optionally any two of R$^{5a}$, R$^{5b}$ and R$^{5c}$ when part of a common R$^5$ substituent can be combined with the atoms to which each is attached to form a saturated four-, five-, six- or seven-membered ring having from 0 to 1 additional heteroatoms as ring members. Additionally, each of R$^{5a}$, R$^{5b}$ and R$^{5c}$ is optionally further substituted with from one to three members selected from the group consisting of —OH, —OR'', —OC(O)NHR'', —OC(O)N(R'')$_2$, —SH, —SR'', —S(O)R'', —S(O)$_2$R'', —SO$_2$NH$_2$, —S(O)$_2$NHR'', —S(O)$_2$N(R'')$_2$, —NHS(O)$_2$R'', —NR''S(O)$_2$R'', —C(O)NH$_2$, —C(O)NHR'', —C(O)N(R'')$_2$, —C(O)R'', —NHC(O)R'', —NR''C(O)R'', —NHC(O)NH$_2$, —NR''C(O)NH$_2$, —NR''C(O)NHR'', —NHC(O)NHR'', —NR''C(O)N(R'')$_2$, —NHC(O)N(R'')$_2$, —CO$_2$H, —CO$_2$R'', —NHCO$_2$R'', —NR''CO$_2$R'', —CN, —NO$_2$, —NH$_2$, —NHR'', —N(R'')$_2$, —NR''S(O)NH$_2$ and —NR''S(O)$_2$NHR'', wherein each R'' is independently an unsubstituted C$_{1-6}$alkyl or benzyl.

With the above formulas are a number of other embodiments of the invention. In one group of embodiments, W has formula (a). In another group of embodiments, the subscript m is 1. In another group of embodiments R$^{4'}$ can be any of the substituents provided with reference to the full scope of the invention. In one group of embodiments, R$^{4'}$ is selected from

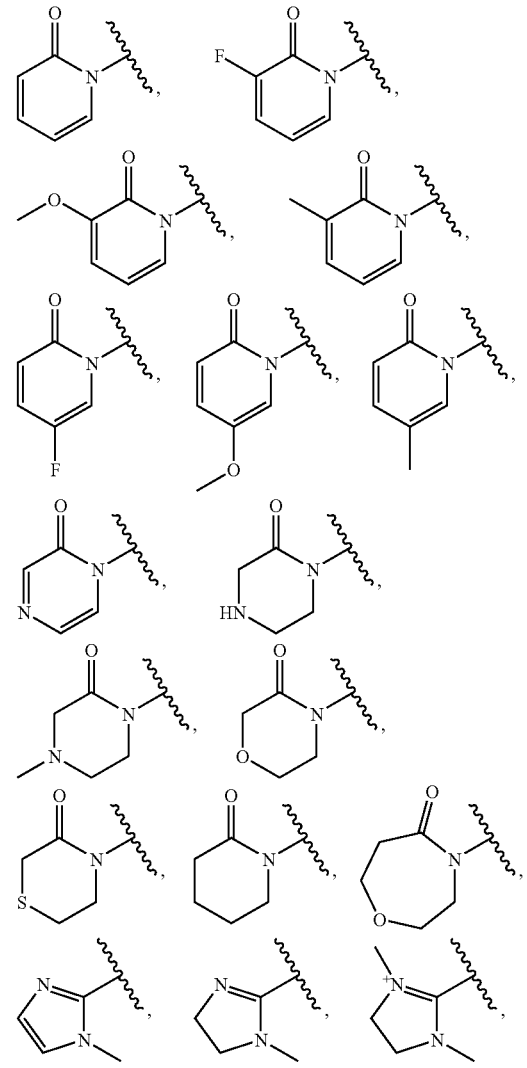

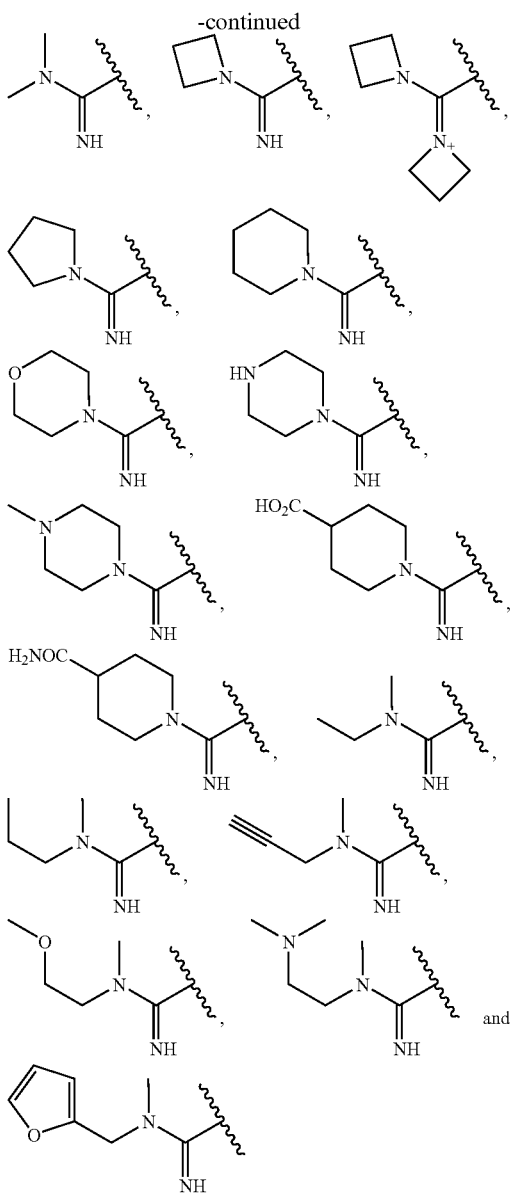

wherein the wavy line indicates the point of attachment to the remainder of the compound. More preferably, $R^{4'}$ is attached to the phenyl ring at a position para to the attachment of the ring A.

In one aspect, the present invention provides compounds having the formula:

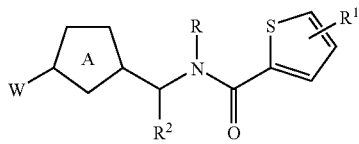

and pharmaceutically acceptable salts thereof. In formula (I), A represents a five-membered heterocycle containing 1-4 nitrogen, oxygen or sulfur atoms; with 0-4 substituents selected from halogen, oxo, $R^4$, —$OR^4$, $N(R^4)_2$, $CO_2R^4$, $CON(R^4)_2$, $S(O)_2R^4$, $S(O)_2N(R^4)_2$, $X^1OR^4$, $X^1CO_2R^4$, $X^1CON(R^4)_2$, $X^1N(R^4)_2$, wherein each $R^4$ is independently selected from H, $C_{1-8}$ alkyl, $C_{2-8}$ alkenyl, $C_{2-8}$ alkynyl, or optionally two $R^4$ attached to the same atom are combined to form a 3-, 4-, 5-, 6- or 7-membered ring. In one group of embodiments A is selected from the group consisting of: isoxazole, isothiazole, pyrazole, imidazole, oxazole, thiazole, isoxazoline, pyrazoline, imidazoline, 1,2,3-triazole, 1,2,4-triazole, 1,3,4-oxadiazole, 1,3,4-thiadiazole, 1,2,4-oxadiazole, 1,2,4-thiadiazole, pyrazol-5-one, pyrrolidine-2,5-dione, imidazolidine-2,4-dione, pyrrolidine, pyrrole, furan and thiophene. R represents a member selected from the group consisting of H and $C_{1-4}$ alkyl; $R^1$ represents a member selected from the group consisting of halogen, $C_{1-8}$ alkyl, $C_{2-8}$ alkenyl and $C_{2-8}$ alkynyl; $R^2$ represents a member selected from the group consisting of H, $C_{1-8}$ alkyl, —X—$OR^{2a}$, —X—$SR^{2a}$, —X—$COR^{2a}$, —X—$CO_2R^{2a}$ and —X—$N(R^{2a})_2$; wherein X is $C_{1-8}$ alkylene and each $R^{2a}$ is independently selected from the group consisting of H and $C_{1-8}$ alkyl, or optionally two $R^{2a}$ groups attached to the same nitrogen atom are combined to form a 4-, 5-, 6- or 7-membered ring.

The letter W represent a moiety having a formula selected from (a), (b), and (c):

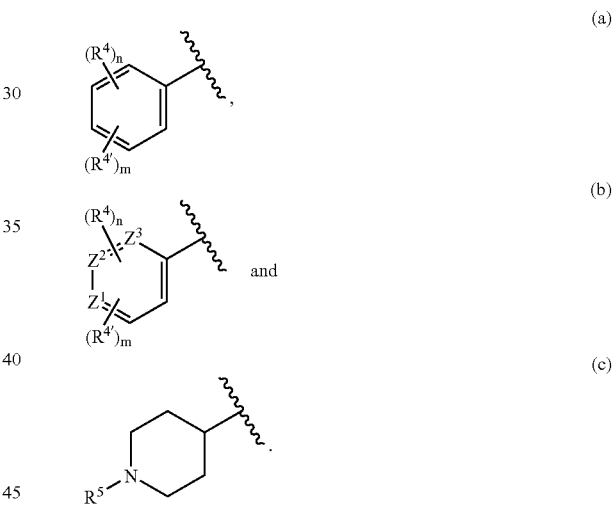

With reference to formula (b), the symbols $Z^1$, $Z^2$, and $Z^3$ each independently represent N, C or CH with the proviso that two of $Z^1$, $Z^2$, and $Z^3$ are other than N.

With reference to formulas (a) and (b), the subscript n is an integer of from 0 to 3 and the subscript m is an integer of from 0 to 1. The symbol $R^4$ represents, in each occurrence, a member selected from the group consisting of halogen, —$OR^{4a}$, —$OC(O)R^{4a}$, —$NR^{4a}R^{4b}$, —$SR^{4a}$, $S(O)R^{4a}$, $S(O)_2R^{4a}$, $S(O)_2NR^{4a}R^{4b}$, —$R^{4c}$, —CN, —$NO_2$, —$CO_2R^{4a}$, —$CONR^{4a}R^{4b}$, —$C(O)R^{4a}$, —$OC(O)NR^{4a}R^{4b}$, —$NR^{4b}C(O)R^{4a}$, —$NR^{4b}C(O)_2R^{4c}$, —$NR^{4a}$—$C(O)NR^{4a}R^{4b}$, —$X^1OR^{4a}$, —$X^1OC(O)R^{4a}$, —$X^1NR^{4a}R^{4b}$, —$X^1SR^{4a}$, —$X^1S(O)R^{4a}$, —$X^1S(O)_2R^{4a}$, —$X^1CN$, —$X^1NO_2$, —$X^1CO_2R^{4a}$, —O—$X^1CO_2R^{4a}$, —$X^1CONR^{4a}R^{4b}$, —O—$X^1CONR^{4a}R^{4b}$, —$X^1C(O)R^{4a}$, —O—$X^1NR^{4a}R^{4b}$, —$S(O)X^1R^{4a}R^{4b}$, —$S(O)_2X^1NR^{4a}R^{4b}$, —$X^1OC(O)NR^{4a}R^{4b}$, —$X^1NR^{4a}C(O)R^{4a}$, —$X^1NR^{4b}C(O)R^{4c}$, represents a member selected from the group consisting of —C(=NH)$R^{4a}$, —C(=$NR^{4c}$)$R^{4a}$, —C(=NH)$NR^{4a}R^{4b}$, —C(=$NR^{4c}$)$NR^{4a}R^{4b}$, —C(=$N^+R^{4c}R^{4c}$)$NR^{4a}R^{4b}$, —$X^2$—

C(=NH)NR⁴ᵃR⁴ᵇ, —X²—C(=NR⁴ᶜ)NR⁴ᵃR⁴ᵇ, —X²—C(=N⁺R⁴ᶜR⁴ᶜ)NR⁴ᵃR⁴ᵇ and —C(=NR⁴ᵃ)NR⁴ᵃ—Y, wherein Y is a five or six-membered aryl, heterocyclyl or aryl-$C_{1-2}$ alkyl, optionally substituted with from one to three substitutents selected from the group consisting of halogen, oxo, —OR⁴ᵃ, —OC(O)R⁴ᵃ, —NR⁴ᵃR⁴ᵇ, R⁴ᶜ, —SR⁴ᵃ, S(O)R⁴ᵃ, S(O)₂R⁴ᵃ, S(O)₂NR⁴ᵃR⁴ᵇ, —CN, —NO₂, —CO₂R⁴ᵃ, —CONR⁴ᵃR⁴ᵇ, —C(O)R⁴ᵃ, —NR⁴ᵇC(O)R⁴ᵃ, —NR⁴ᵇC(O)₂R⁴ᶜ, —X¹R⁴ᵃ, —X¹OR⁴ᵃ, —X¹SR⁴ᵃ, —X¹S(O)R⁴ᵃ, —X¹S(O)₂R⁴ᵃ, —X¹CN, —X¹NO₂, —X¹CO₂R⁴ᵃ, —X¹CONR⁴ᵃR⁴ᵇ, —X¹C(O)R⁴ᵃ, —O—X¹NR⁴ᵃR⁴ᵇ, —S(O)X¹NR⁴ᵃR⁴ᵇ, —S(O)₂X¹NR⁴ᵃR⁴ᵇ, —X¹OC(O)NR⁴ᵃR⁴ᵇ, —X¹NR⁴ᵇC(O)R⁴ᵃ, —X¹NR⁴ᵇC(O)₂R⁴ᶜ, —X¹NR⁴ᵃ—C(O)NR⁴ᵃR⁴ᵇ, —X¹OC(O)R⁴ᵃ, —X¹NR⁴ᵃR⁴ᵇ, —O—X¹OR⁴ᵃ, —O—¹NR⁴ᵃR⁴ᵇ, —O—X¹CO₂R⁴ᵃ, —O—X¹CONR⁴ᵃR⁴ᵇ, —NR⁴ᵇ—X¹OR⁴ᵃ, —NR⁴ᵇ—X¹NR⁴ᵃR⁴ᵇ, —NR⁴ᵇ—X¹CO₂R⁴ᵃ, and —NR⁴ᵇ—X¹CONR⁴ᵃR⁴ᵇᵇ; each X¹ and X² are members independently selected from the group consisting of $C_{1-4}$alkylene, $C_{2-4}$alkenylene and $C_{2-4}$alkynylene; each R⁴ᵃ and R⁴ᵇ are independently selected from the group consisting of hydrogen, $C_{1-8}$alkyl, $C_{1-8}$ haloalkyl, $C_{3-6}$cycloalkyl, $C_{3-6}$heterocycloalkyl, $C_{2-8}$alkenyl, $C_{2-8}$alkynyl, aryl, heteroaryl, aryl-$C_{1-4}$alkyl, and aryloxy-$C_{1-4}$alkyl; each R⁴ᶜ is independently selected from the group consisting of $C_{1-8}$alkyl, $C_{1-8}$haloalkyl, $C_{3-6}$cycloalkyl, $C_{3-6}$heterocycloalkyl, $C_{2-8}$ alkynyl, aryl, heteroaryl, aryl-$C_{1-4}$alkyl, and aryloxy-$C_{1-4}$alkyl, and optionally any two of R⁴ᵃ, R⁴ᵇ and R⁴ᶜ when part of a common R⁴ or R⁴' substituent can be combined with the atoms to which each is attached to form a saturated or unsaturated, four to nine-membered mono- or bicyclic ring having from 0 to 2 additional heteroatoms as ring members. Additionally, each of R⁴ᵃ, R⁴ᵇ and R⁴ᶜ is optionally further substituted with from one to three members selected from the group consisting of —OH, oxo, —R′″, —OR′″, —OC(O)NHR′″, —OC(O)N(R′″)₂, —SH, —SR′″, —S(O)R′″, —S(O)₂ R′″, —SO₂NH₂, —S(O)₂NHR′″, —S(O)₂N(R′″)₂, —NHS(O)₂R′″, —NR′″S(O)₂R′″, —C(O)NH₂, —C(O)NHR′″, —C(O)N(R′″)₂, —C(O)R′″, —NHC(O)R′″, —NR′″C(O)R′″, —NHC(O)NH₂, —NR′″C(O)NH₂, —NR′″C(O)NHR′″, —NHC(O)NHR′″, —NR′″C(O)N(R′″)₂, —NHC(O)N(R′″)₂, —CO₂H, —CO₂R′″, —NHCO₂R′″, —NR′″CO₂R′″, —CN, —NO₂, —NH₂, —NHR′″, —N(R′″)₂, —NR′″S(O)NH₂ and —NR′″S(O)₂NHR′″, wherein each R′″ is independently an unsubstituted $C_{1-6}$alkyl, benzyl or combined with the atoms to which each is attached to form a saturated four-, five-, six- or seven-membered ring having from 0 to 2 additional heteroatoms as ring members.

Turning next to formula (c), the symbol R⁵ represents a member selected from the group consisting of —R⁵ᵃ, —CO₂R⁵ᶜ, —CONR⁵ᵃR⁵ᵇ, —C(O)R⁵ᵃ, —C(=NH)NR⁵ᵃR⁵ᵇ, —C(=NR⁵ᶜ)NR⁵ᵃR⁵ᵇ, —C(=N⁺R⁵ᶜR⁵ᶜ)NR⁵ᵃR⁵ᵇ, —C(=NR⁵ᵃ)R⁵ᵃ, —C(=NR⁵ᵃ)Y¹, —X³OR⁵ᵃ, —X³OC(O)R⁵ᵃ, —X³NR⁵ᵃR⁵ᵇ, —X³SR⁵ᵃ, —X³CN, —X³NO₂, —X³CO₂R⁵ᵃ, —X³CONR⁵ᵃR⁵ᵇ, —X³C(O)R⁵ᵃ, —X³OC(O)NR⁵ᵃR⁵ᵇ, —X³NR⁵ᵃC(O)R⁵ᵃ, —X³NR⁵ᵇC(O)₂R⁵ᶜ, —X³NR⁵ᵃC(O)NR⁵ᵃR⁵ᵇ, —X³—C(=NR⁵ᵃ)NR⁵ᵃR⁵ᵇ, —Y¹, and —X³—Y¹, wherein Y¹ is a five or six-membered aryl or heteroaryl ring or aryl-$C_{1-2}$alkyl, optionally substituted with from one to three substituents selected from the group consisting of halogen, —OR⁵ᵃ, —OC(O)R⁵ᵃ, —NR⁵ᵃR⁵ᵇ, —R⁵ᶜ, —SR⁵ᵃ, —CN, —NO₂, —CO₂R⁵ᵃ, —CONR⁵ᵃR⁵ᵇ, —C(O)R⁵ᵃ, —NR⁵ᵇC(O)R⁵ᵃ, —NR⁵ᵇC(O)₂R⁵ᶜ, —X³OR⁵ᵃ, —X³SR⁵ᵃ, —X³CN, —X³NO₂, —X³CO₂R⁵ᵃ, —X³CONR⁵ᵃR⁵ᵇ, —X³C(O)R⁵ᵃ, —X³OC(O)NR⁵ᵃR⁵ᵇ, —X³NR⁵ᵇC(O)R⁵ᵃ, —X³NR⁵ᵇC(O)₂R⁵ᶜ, —X³NR⁵ᵃC(O)NR⁵ᵃR⁵ᵇ, —X³OC(O)R⁵ᵃ, —X³NR⁵ᵃR⁵ᵇ, —O—X³OR⁵ᵃ, —O—X³NR⁵ᵃR⁵ᵇ, —O—X³CO₂R⁵ᵃ, —O—X³CONR⁵ᵃR⁵ᵇ, NR⁵ᵇ—X³OR⁵ᵃ, —NR⁵ᵇ—X³NR⁵ᵃR⁵ᵇ, —NR⁵ᵇ—X³CO₂R⁵ᵃ, and —NR⁵ᵇ—X³CONR⁵ᵃR⁵ᵇ, wherein each X³ is a member independently selected from the group consisting of $C_{1-4}$alkylene, $C_{2-4}$alkenylene and $C_{2-4}$ alkynylene; each R⁵ᵃ and R⁵ᵇ are independently selected from the group consisting of hydrogen, $C_{1-8}$alkyl, $C_{1-8}$haloalkyl, $C_{3-6}$cycloalkyl, $C_{3-6}$heterocycloalkyl, $C_{2-8}$alkenyl, $C_{2-8}$ alkynyl, aryl, heteroaryl, aryl-$C_{1-4}$alkyl, and aryloxy-$C_{1-4}$alkyl; each R⁵ᶜ is independently selected from the group consisting of $C_{1-8}$alkyl, $C_{1-8}$haloalkyl, $C_{3-6}$cycloalkyl, $C_{3-6}$ heterocycloalkyl, $C_{2-8}$alkenyl, $C_{2-8}$alkynyl, aryl, heteroaryl, aryl-$C_{1-4}$alkyl, and aryloxy-$C_{1-4}$ alkyl; and optionally any two of R⁵ᵃ, R⁵ᵇ and R⁵ᶜ when part of a common R⁵ substituent can be combined with the atoms to which each is attached to form a saturated four-, five-, six- or seven-membered ring having from 0 to 1 additional heteroatoms as ring members. Additionally, each of R⁵ᵃ, R⁵ᵇ and R⁵ᶜ is optionally further substituted with from one to three members selected from the group consisting of —OH, —OR′′, —OC(O)NHR′′, —OC(O)N(R′′)₂, —SH, —SR′′, —S(O)R′′, —S(O)₂R′′, —SO₂NH₂, —S(O)₂NHR′′, —S(O)₂N(R′′)₂, —NHS(O)₂R′′, —NR′′S(O)₂R′′, —C(O)NH₂, —C(O)NHR′′, —C(O)N(R′′)₂, —C(O)R′′, —NHC(O)R′′, —NR′′C(O)R′′, —NHC(O)NH₂, —NR′′C(O)NH₂, —NR′′C(O)NHR′′, —NHC(O)NHR′′, —NR′′C(O)N(R′′)₂, —NHC(O)N(R′′)₂, —CO₂H, —CO₂R′′, —NHCO₂R′′, —NR′′CO₂R′′, —CN, —NO₂, —NH₂, —NHR′′, —N(R′′)₂, —NR′′S(O)NH₂ and —NR′′S(O)₂NHR′′, wherein each R′′ is independently an unsubstituted $C_{1-6}$alkyl or benzyl.

With the above formulas are a number of other embodiments of the invention. In one group of embodiments, A is selected from the group consisting of:

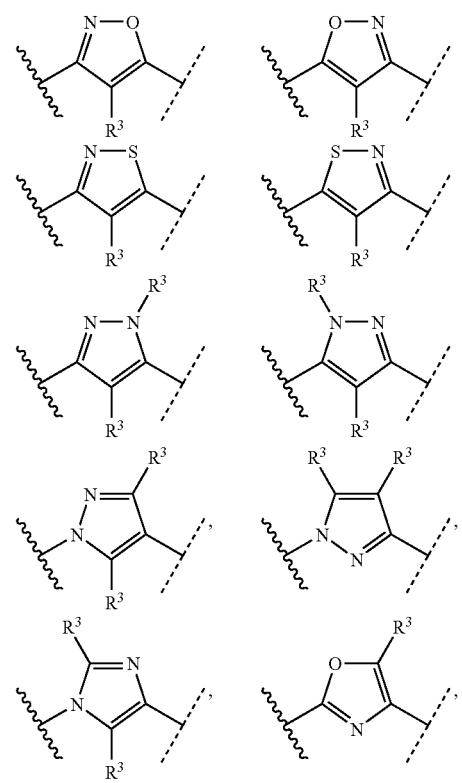

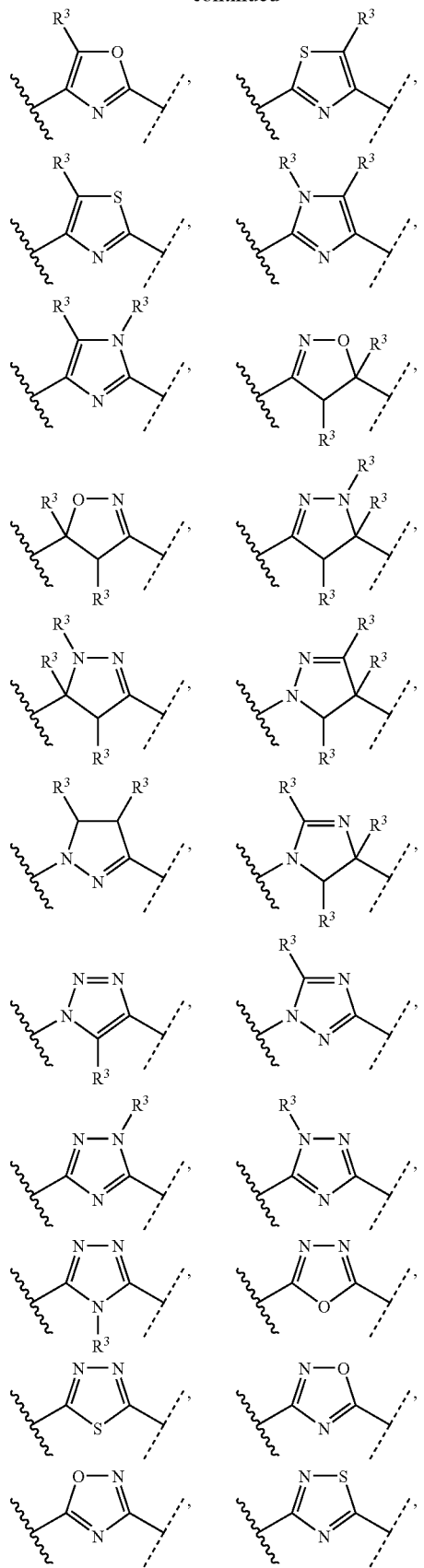
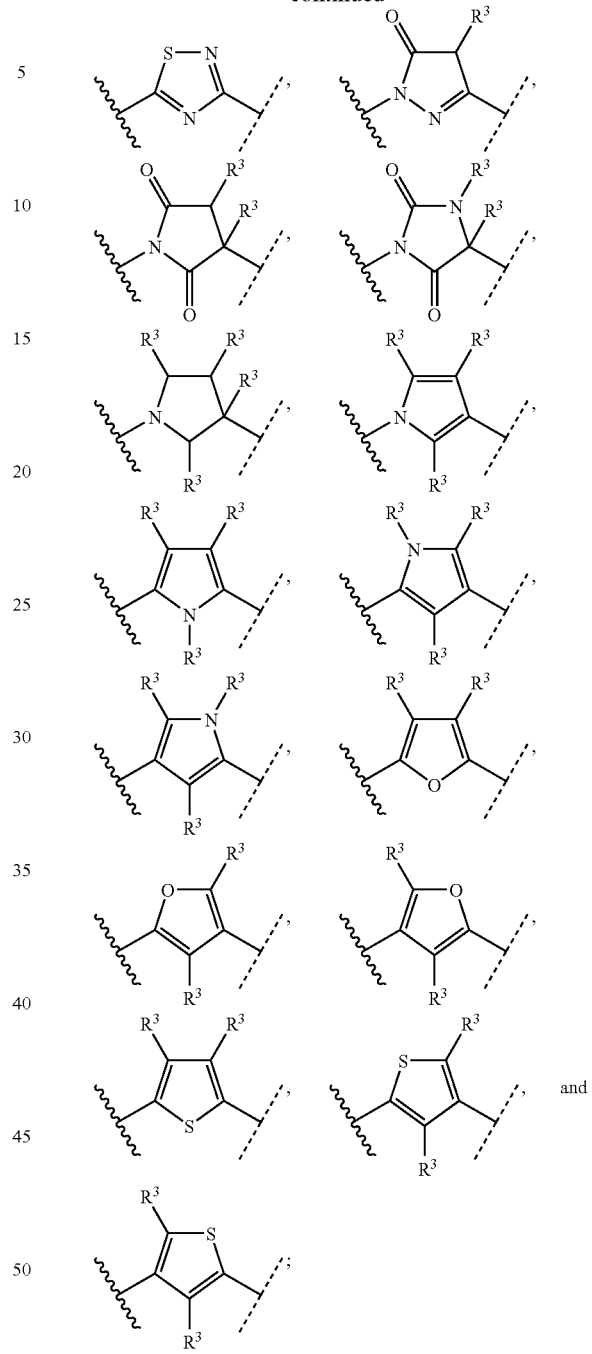

each $R^3$ is independently selected from the group consisting of halogen, $C_{1-8}$alkyl, $C_{2-8}$alkenyl, $C_{2-8}$alkynyl, $OR^{3a}$, $N(R^{3a})_2$, $X^0CO_2R^{3a}$, $X^0CON(R^{3a})_2$, $SO_2C_{1-4}$, $SO_2N(R^{3a})_2$; each $R^{3a}$ is independently selected from the group consisting of H, $C_{1-8}$alkyl, $C_{2-8}$alkenyl and $C_{2-8}$alkynyl; and $X^0$ is a bond or $C_{1-8}$alkylene; and the dashed line indicates the point of attachment to A and the wavy line indicates the point of attachment to the rest of the molecule. In another group of embodiments, W has formula (a). In another group of embodiments, the subscript m is 1. In another group of embodiments $R^{4'}$ can be any of the substituents provided with reference to the full scope of the invention. In one group of embodiments, $R^{4'}$ is selected from

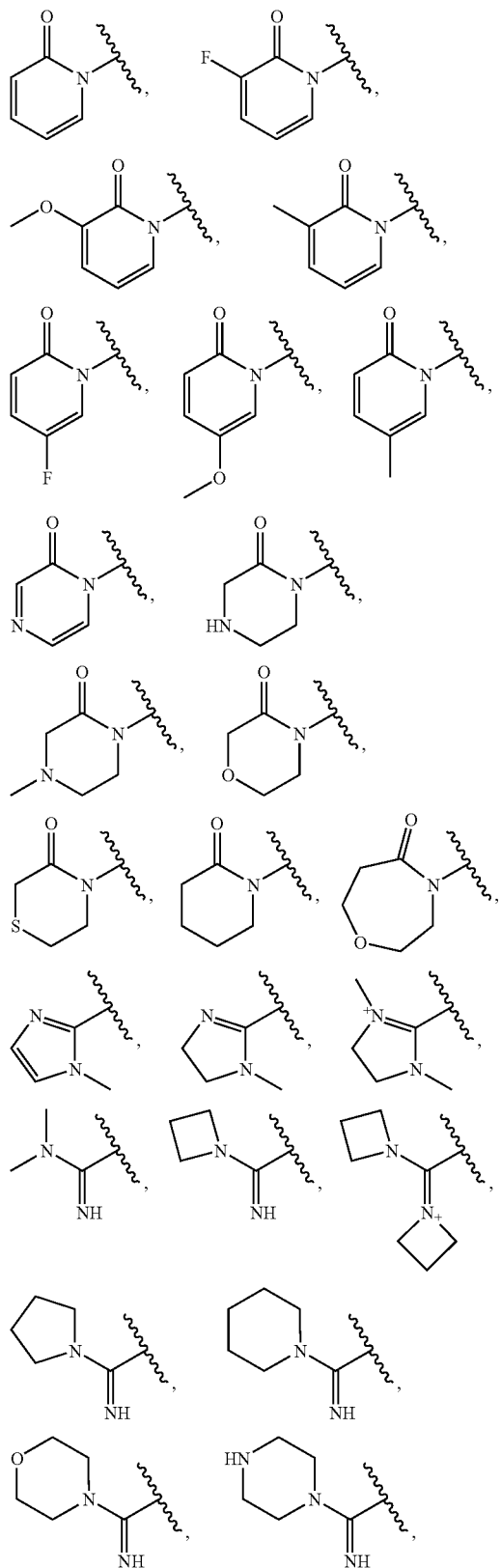

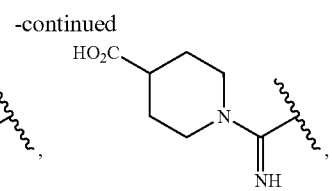

-continued

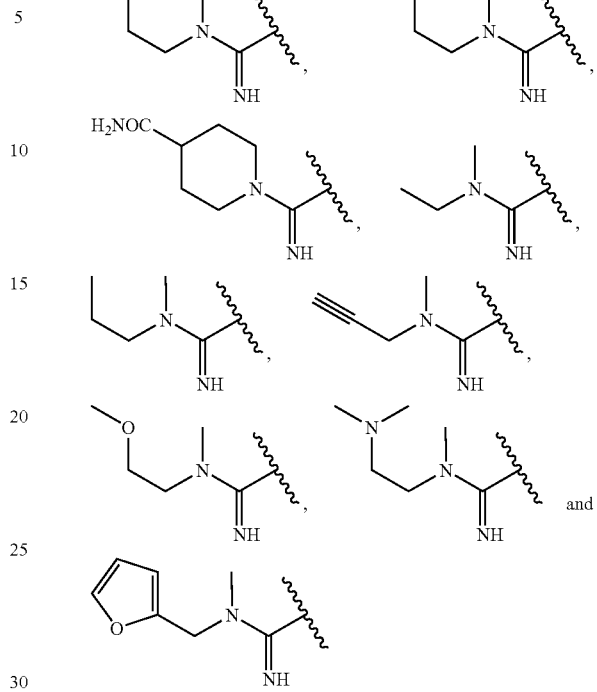

wherein the wavy line indicates the point of attachment to the remainder of the compound. More preferably, $R^{4'}$ is attached to the phenyl ring at a position para to the attachment of the ring A. In another group of embodiments, the subscript n is an integer of from 0 to 1. In another group of embodiments n is 1; $R^4$ is attached to the phenyl ring at a position ortho to A and $R^{4'}$ is attached to the phenyl ring at a position para to A. In one group of embodiments, $R^4$ is selected from the group consisting of halogen, —$OR^{4a}$, —$NR^{4a}R^{4b}$, —$SR^{4a}$, —Y, —$X^1$—Y, —O—Y, —$NR^{4a}$Y and —SY.

In another group of embodiments, m is 0 or 1, n is 0, 1 or 2 and at least one $R^4$ is selected from the group consisting of

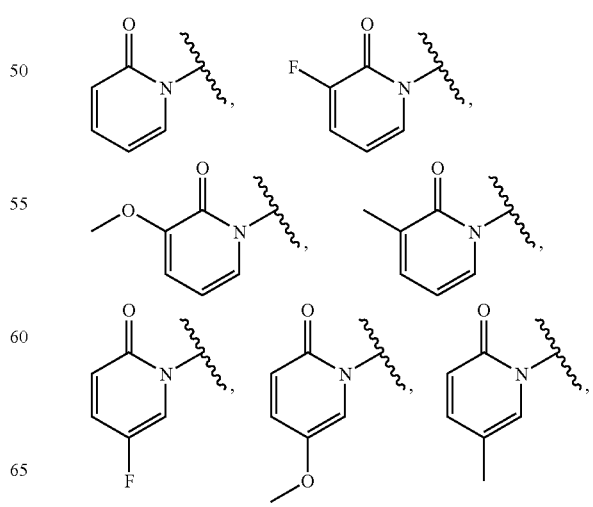

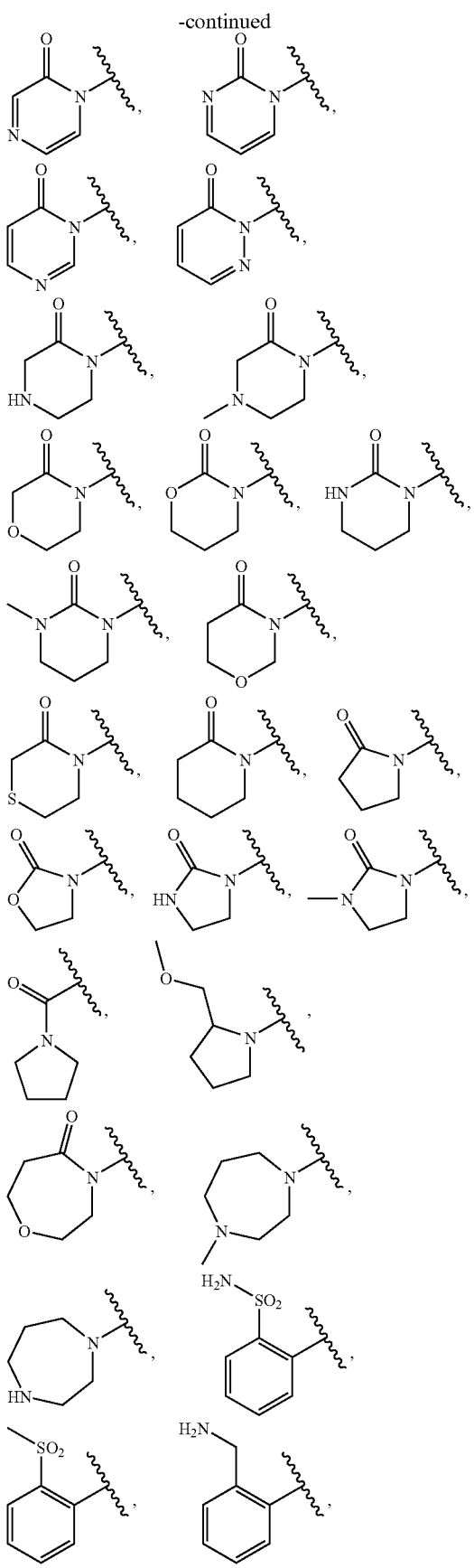
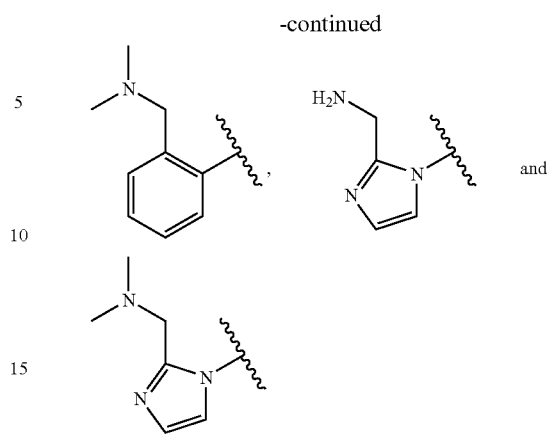

wherein the wavy line indicates the point of attachment to the remainder of the compound.

In another group of embodiments, m is 0 or 1; n is 0, 1 or 2; and at least one $R^4$ is selected from the group consisting of —Y, —$X^1$—Y, —O—Y, —$NR^{4a}$Y, —SY, —S(O)Y and —$S(O)_2$Y, wherein Y is an optionally substituted member selected from the group consisting of phenyl, benzyl, pyridyl, pyridylmethyl, pyrimidinyl and pyrazolyl. More preferably, $R^4$ is selected from the group consisting of —Y, —$X^1$—Y, —O—Y and —$NR^{4a}$Y, wherein Y is an optionally substituted member selected from the group consisting of phenyl, benzyl, pyridyl and pyridylmethyl. Still further preferred are those embodiments in which the optional substituents are selected from the group consisting of halogen, —$OR^{4a}$, —$NR^{4a}R^{4b}$, —$R^{4c}$, —$SR^{4a}$, —$CO_2R^{4a}$, —$CONR^{4a}R^{4b}$, —$C(O)R^{4a}$, —$X^1OR^{4a}$ and —$X^1NR^{4a}R^{4b}$.

In other embodiments, compounds of formula I are provided in which $R^2$ is present the carbon attached to $R^2$ has the R-configuration. Other embodiments are provided in which $R^3$ is other than H the carbon attached to $R^3$ has the R-configuration.

In other embodiments, compounds of formula I are provided in which W has the formula (b). Within this group, specific embodiments are provided in which $Z^1$ is N. Other embodiments are provided in which $Z^2$ is N. Other embodiments are provided in which $Z^3$ is N.

In another group of embodiments, the subscript m is 1. In another group of embodiments $R^{4'}$ can be any of the substituents provided with reference to the full scope of the invention. In one group of embodiments, $R^{4'}$ is selected from

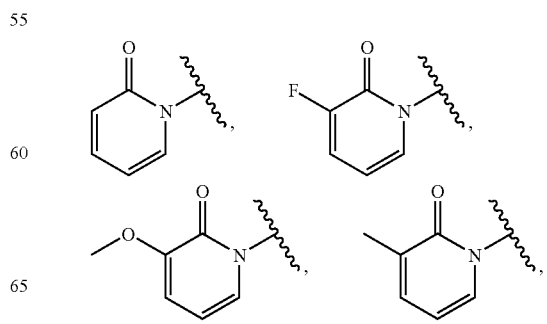

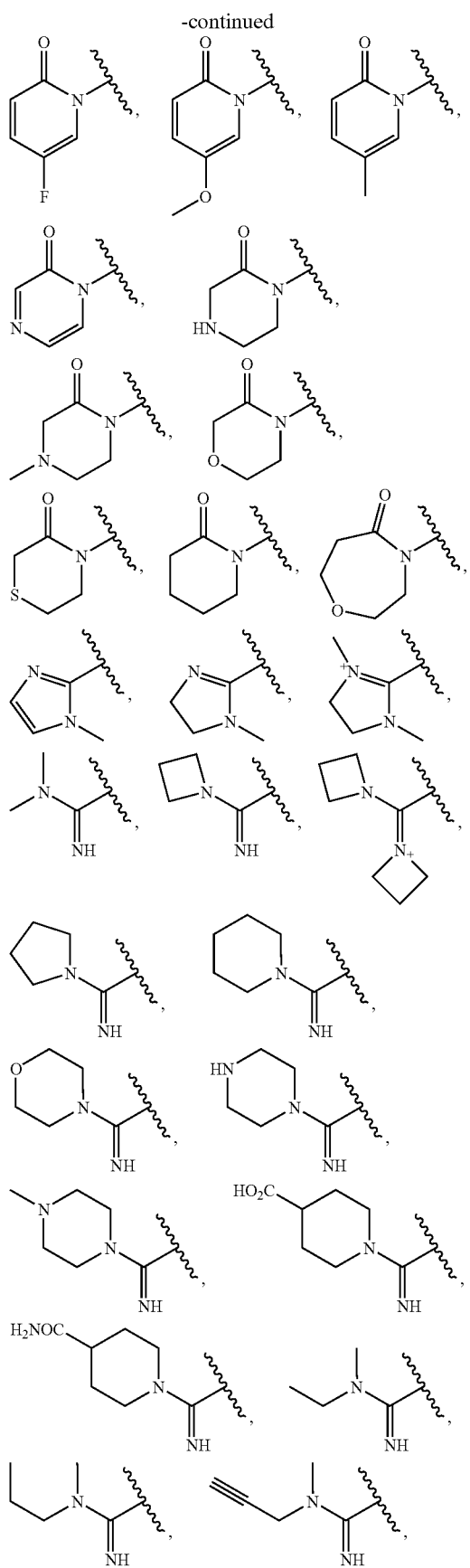

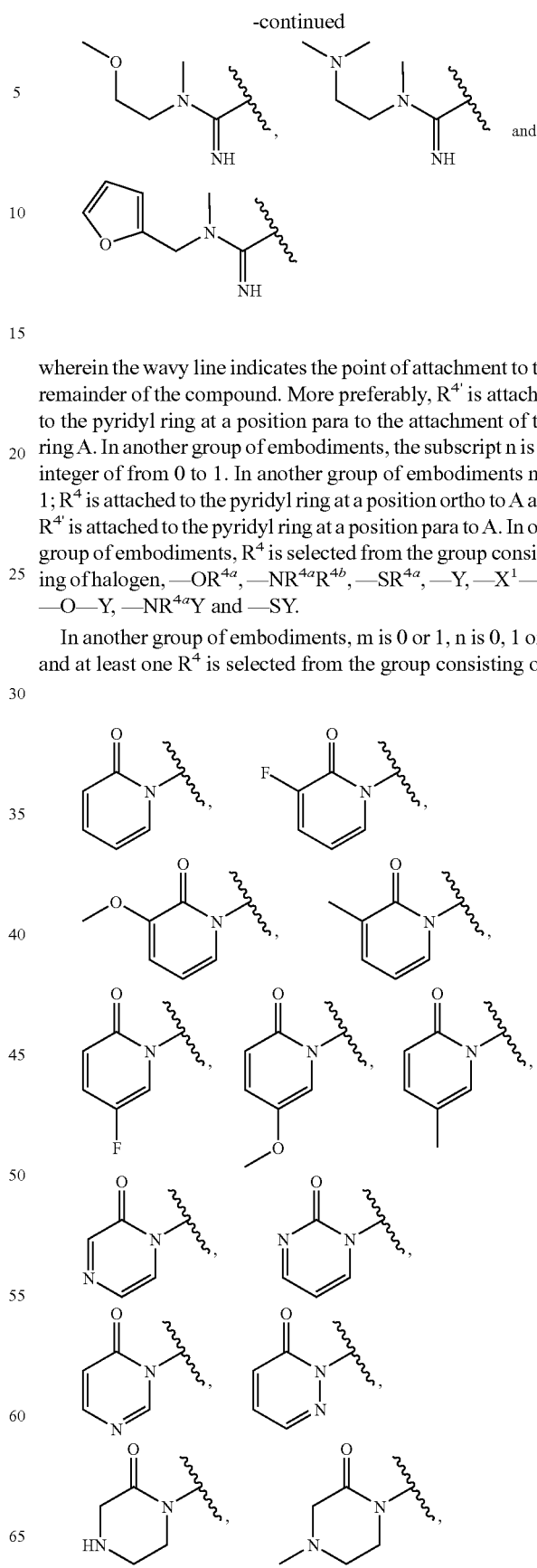

wherein the wavy line indicates the point of attachment to the remainder of the compound. More preferably, $R^{4'}$ is attached to the pyridyl ring at a position para to the attachment of the ring A. In another group of embodiments, the subscript n is an integer of from 0 to 1. In another group of embodiments n is 1; $R^4$ is attached to the pyridyl ring at a position ortho to A and $R^{4'}$ is attached to the pyridyl ring at a position para to A. In one group of embodiments, $R^4$ is selected from the group consisting of halogen, $-OR^{4a}$, $-NR^{4a}R^{4b}$, $-SR^{4a}$, $-Y$, $-X^1-Y$, $-O-Y$, $-NR^{4a}Y$ and $-SY$.

In another group of embodiments, m is 0 or 1, n is 0, 1 or 2 and at least one $R^4$ is selected from the group consisting of -continued

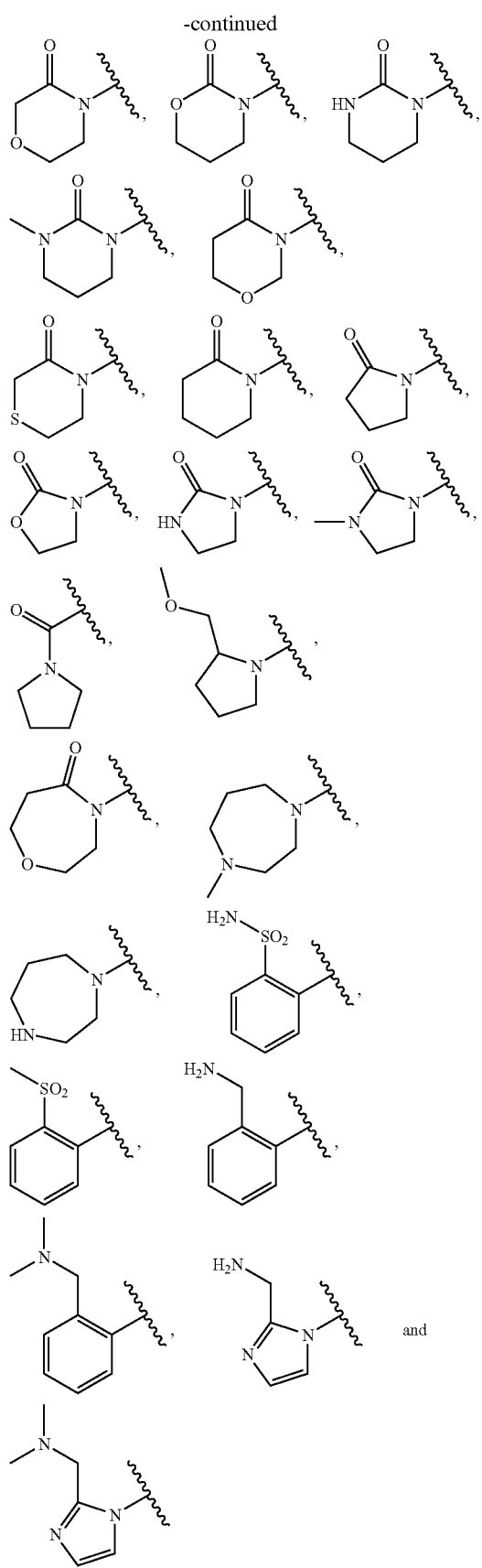

wherein the wavy line indicates the point of attachment to the remainder of the compound.

In another group of embodiments, m is 0 or 1; n is 0, 1 or 2; and at least one $R^4$ is selected from the group consisting of —Y, —$X^1$—Y, —O—Y, —$NR^{4a}$Y, —SY, —S(O)Y and —$S(O)_2$Y, wherein Y is an optionally substituted member selected from the group consisting of phenyl, benzyl, pyridyl, pyridylmethyl, pyrimidinyl and pyrazolyl. More preferably, $R^4$ is selected from the group consisting of —Y, —$X^1$—Y, —O—Y and —$NR^{4a}$Y, wherein Y is an optionally substituted member selected from the group consisting of phenyl, benzyl, pyridyl and pyridylmethyl. Still further preferred are those embodiments in which the optional substituents are selected from the group consisting of halogen, —$OR^{4a}$, —$NR^{4a}R^{4b}$, —$R^{4c}$, —$SR^{4a}$, —$CO_2R^{4a}$, —$CONR^{4a}R^{4b}$, —$C(O)R^{4a}$, —$X^1OR^{4a}$ and —$X^1NR^{4a}R^{4b}$.

In other embodiments, compounds of formula I are provided in which W has the formula (c). Other embodiments are provided in which $Y^1$ is selected from the group consisting of optionally substituted phenyl and optionally substituted pyridyl. Other embodiments are provided in which $R^5$ is selected from the group consisting of —$R^{5a}$, —C(=NH)$NR^{5a}R^{5b}$, —C(=NH)$R^{5a}$, —C(=NH)$Y^1$ and —$X^3$—$Y^1$.

In one aspect, the present invention provides compounds having the formula:

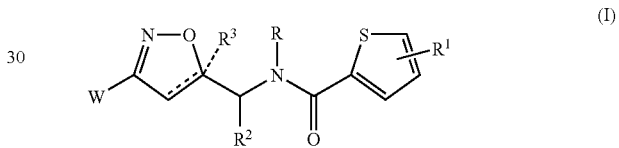

(I)

and pharmaceutically acceptable salts thereof. In formula (I), R represents a member selected from the group consisting of H and $C_{1-4}$alkyl; $R^1$ represents a member selected from the group consisting of halogen, $C_{1-8}$alkyl, $C_{2-8}$alkenyl and $C_{2-8}$alkynyl; $R^2$ represents a member selected from the group consisting of H, $C_{1-8}$alkyl, —X—$OR^{2a}$, —X—$SR^{2a}$, —X—$COR^{2a}$, —X—$CO_2R^{2a}$, and —X—$N(R^{2a})_2$; wherein X is $C_{1-8}$alkylene and each $R^{2a}$ is independently selected from the group consisting of H and $C_{1-8}$alkyl, or optionally two $R^{2a}$ groups attached to the same nitrogen atom are combined to form a 4-, 5-, 6- or 7-membered ring. Each dashed line in formula (I) independently represents an optional bond, with the understanding that only one optional bond is present. The symbol $R^3$ represents a member selected from the group consisting of H and $C_{1-4}$alkyl; or is absent when a carbon-carbon double bond is present in the ring to which $R^3$ would otherwise be attached. For the embodiments in which $R^2$ is present or $R^3$ is present and other than H, a preferred group of embodiments are those in which the carbon to which $R^2$ or $R^3$ is attached has the (R)-stereochemical configuration.

The letter W represent a moiety having a formula selected from (a), (b), and (c):

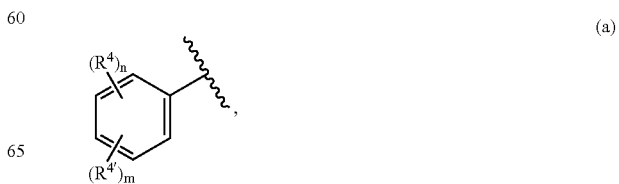

(a)

-continued

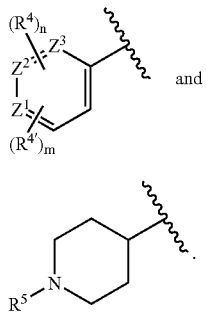

(b)

and (c)

With reference to formula (b), the symbols $Z^1$, $Z^2$, and $Z^3$ each independently represent N, C or CH with the proviso that two of $Z^1$, $Z^2$, and $Z^3$ are other than N. The pyridyl nitrogen can be in a position para to the attachment of the isoxazole or isoxazoline ring($Z^1$(4-pyridyl)), meta($Z^2$(3-pyridyl)) or ortho($Z^3$(2-pyridyl)).

With reference to formulas (a) and (b), the subscript n is an integer of from 0 to 3 and the subscript m is an integer of from 0 to 1. The symbol $R^4$ represents, in each occurrence, a member selected from the group consisting of halogen, —$OR^{4a}$, —$OC(O)R^{4a}$, —$NR^{4a}R^{4b}$, —$SR^{4a}$, $S(O)R^{4a}$, $S(O)_2R^{4a}$, $S(O)_2 NR^{4a}R^{4b}$, —$R^{4c}$, —CN, —$NO_2$, —$CO_2R^{4a}$, —$CONR^{4a}R^{4b}$, —$C(O)R^{4a}$, —$OC(O)NR^{4a}R^{4b}$, —$NR^{4b}C(O)R^{4a}$, —$NR^{4b}C(O)_2R^{4c}$, —$NR^{4a}$—$C(O)NR^{4a}R^{4b}$, —$X^1OR^{4a}$, —$X^1OC(O)R^{4a}$, —$X^1NR^{4a}R^{4b}$, —$X^1SR^{4a}$, —$X^1S(O)R^{4a}$, —$X^1S(O)_2R^{4a}$, —$X^1CN$, —$X^1NO_2$, —$X^1CO_2R^{4a}$, —O—$X^1CO_2R^{4a}$, —$X^1CONR^{4a}R^{4b}$, —O—$X^1CONR^{4a}R^{4b}$, —$X^1C(O)R^{4a}$, —O—$X^1NR^{4a}R^{4b}$, —$S(O)X^1NR^{4a}R^{4b}$, —$S(O)_2X^1NR^{4a}R^{4b}$, —$X^1OC(O)NR^{4a}R^{4b}$, —$X^1NR^{4a}C(O)R^{4a}$, —$X^1NR^{4b}C(O)_2R^{4c}$, —$X^1NR^{4a}C(O)NR^{4a}R^{4b}$, —Y, —$X^1$—Y, —O—Y, —$NR^{4a}$Y, —SY, —S(O)Y and —$S(O)_2$Y. Similarly, $R^{4'}$ represents a member selected from the group consisting of —C(=NH)$R^{4a}$, —C(=$NR^{4c}$)$R^{4a}$, —C(=NH)$NR^{4a}R^{4b}$, —C(=$NR^{4c}$)$NR^{4a}R^{4b}$, —C(=$N^+R^{4c}R^{4c}$)$NR^{4a}R^{4b}$, —$X^2$—C(=NH)$NR^{4a}R^{4b}$, —$X^2$—C(=$NR^{4c}$)$NR^{4a}R^{4b}$, —$X^2$—C(=$N^+R^{4c}R^{4c}$)$NR^{4a}R^{4b}$ and —C(=$NR^{4a}$)$NR^{4a}$—Y, wherein Y is a five or six-membered aryl, heterocyclyl or aryl-$C_{1-2}$alkyl, optionally substituted with from one to three substitutents selected from the group consisting of halogen, oxo, —$OR^{4a}$, —$OC(O)R^{4a}$, —$NR^{4a}R^{4b}$, —$R^{4c}$, —$SR^{4a}$, $S(O)R^{4a}$, $S(O)_2R^{4a}$, $S(O)_2NR^{4a}R^{4b}$, —CN, —$NO_2$, —$CO_2R^{4a}$, —$CONR^{4a}R^{4b}$, —$C(O)R^{4a}$, —$NR^{4b}C(O)R^{4a}$, —$NR^{4b}C(O)_2R^{4c}$, —$X^1R^{4a}$, —$X^1OR^{4a}$, —$X^1SR^{4a}$, —$X^1S(O)R^{4a}$, —$X^1S(O)_2R^{4a}$, —$X^1CN$, —$X^1NO_2$, —$X^1CO_2R^{4a}$, —$X^1CONR^{4a}R^{4b}$, —$X^1C(O)R^{4a}$, —O—$X^1NR^{4a}R^{4b}$, —$S(O)X^1NR^{4a}R^{4b}$, —$S(O)_2X^1NR^{4a}R^{4b}$, —$X^1OC(O)NR^{4a}R^{4b}$, —$X^1NR^{4b}C(O)R^{4a}$, —$X^1NR^{4b}C(O)_2R^{4c}$, —$X^1NR^{4a}$—$C(O)NR^{4a}R^{4b}$, —$X^1OC(O)R^{4a}$, —$X^1NR^{4a}R^{4b}$, —O—$X^1OR^{4a}$, —O—$X^1NR^{4a}R^{4b}$, —O—$X^1CO_2R^{4a}$, —O—$X^1CONR^{4a}R^{4b}$, —$NR^{4b}$—$X^1OR^{4a}$, —$NR^{4b}$—$X^1NR^{4a}R^{4b}$, —$NR^{4b}$—$X^1CO_2R^{4a}$, and —$NR^{4b}$—$X^1CONR^{4a}R^{4b}$; each $X^1$ and $X^2$ are members independently selected from the group consisting of $C_{1-4}$alkylene, $C_{2-4}$alkenylene and $C_{2-4}$alkynylene; each $R^{4a}$ and $R^{4b}$ are independently selected from the group consisting of hydrogen, $C_{1-8}$alkyl, $C_{1-8}$ haloalkyl, $C_{3-6}$cycloalkyl, $C_{3-6}$heterocycloalkyl, $C_{2-8}$alkenyl, $C_{2-8}$alkynyl, aryl, heteroaryl, aryl-$C_{1-4}$alkyl, and aryloxy-$C_{1-4}$alkyl; each $R^{4c}$ is independently selected from the group consisting of $C_{1-8}$alkyl, $C_{1-8}$haloalkyl, $C_{3-6}$cycloalkyl, $C_{3-6}$heterocycloalkyl, $C_{2-8}$alkenyl, $C_{2-8}$alkynyl, aryl, heteroaryl, aryl-$C_{1-4}$alkyl, and aryloxy-$C_{1-4}$alkyl, and optionally any two of $R^{4a}$, $R^{4b}$ and $R^{4c}$ when part of a common $R^4$ or $R^{4'}$ substituent can be combined with the atoms to which each is attached to form a saturated or unsaturated, four to nine-membered mono- or bicyclic ring having from 0 to 2 additional heteroatoms as ring members. Additionally, each of $R^{4a}$, $R^{4b}$ and $R^{4c}$ is optionally further substituted with from one to three members selected from the group consisting of —OH, oxo, —$R'''$, —$OR'''$, —OC(O) NH$R'''$, —OC(O)N($R'''$)$_2$, —SH, —$SR'''$, —S(O)$R'''$, —S(O)$_2$ $R'''$, —$SO_2NH_2$, —S(O)$_2$NH$R'''$, —S(O)$_2$N($R'''$)$_2$, NHS(O)$_2R'''$, —$NR'''S(O)_2R'''$, —C(O)NH$_2$, —C(O)NH$R'''$, —C(O)N($R'''$)$_2$, —C(O)$R'''$, —NHC(O)$R'''$, —$NR'''C(O)R'''$, —NHC(O)NH$_2$, —$NR'''C(O)NH_2$, —$NR'''C(O)$NH$R'''$, —NHC(O)NH$R'''$, —$NR'''C(O)N(R''')_2$, —NHC(O)N($R'''$)$_2$, —$CO_2H$, —$CO_2R'''$, —NHCO$_2R'''$, —$NR'''CO_2R'''$, —CN, —$NO_2$, —NH$_2$, —NH$R'''$, —N($R'''$)$_2$, —$NR'''S(O)NH_2$ and —$NR'''S(O)_2NHR'''$, wherein each $R'''$ is independently an unsubstituted $C_{1-6}$alkyl, benzyl or combined with the atoms to which each is attached to form a saturated four-, five-, six- or seven-membered ring having from 0 to 2 additional heteroatoms as ring members.

Turning next to formula (c), the symbol $R^5$ represents a member selected from the group consisting of —$R^{5a}$, —$CO_2R^{5c}$, —$CONR^{5a}R^{5b}$, —$C(O)R^{5a}$, $C(=NR^{5a})NR^{5a}R^{5b}$, —$C(=N^+R^{5c}R^{5c})NR^{5a}R^{5b}$, —$C(=NR^{5a})R^{5a}$, —$C(=NR^{5a})Y^1$, —$X^3OR^{5a}$, —$X^3OC(O)R^{5a}$, —$X^3NR^{5a}R^{5b}$, —$X^3SR^{5a}$, —$X^3CN$, —$X^3NO_2$, —$X^3CO_2R^{5a}$, —$X^3CONR^{5a}R^{5b}$, —$X^3C(O)R^{5a}$, —$X^3OC(O)NR^{5a}R^{5b}$, —$X^3NR^{5a}C(O)R^{5a}$, —$X^3NR^{5b}C(O)_2R^{5c}$, —$X^3NR^{5a}C(O)NR^{5a}R^{5b}$, —$X^3$—$C(=NR^{5a})NR^{5a}R^{5b}$, —$Y^1$, and —$X^3$—$Y^1$, wherein $Y^1$ is a five or six-membered aryl or heteroaryl ring or aryl-$C_{1-2}$alkyl, optionally substituted with from one to three substitutents selected from the group consisting of halogen, —$OR^{5a}$, —$OC(O)R^{5a}$, —$NR^{5a}R^{5b}$, —$R^{5c}$, —$SR^{5a}$, —CN, —$NO_2$, —$CO_2R^{5a}$, —$CONR^{5a}R^{5b}$, —$C(O)R^{5a}$, —$NR^{5b}C(O)R^{5a}$, —$NR^{5b}C(O)_2R^{5c}$, —$X^3OR^{5a}$, —$X^3SR^{5a}$, —$X^3CN$, —$X^3NO_2$, —$X^3CO_2R^{5a}$, —$X^3CONR^{5a}R^{5b}$, —$X^3C(O)R^{5a}$, —$X^3OC(O)NR^{5a}R^{5b}$, —$X^3NR^{5b}C(O)R^{5a}$, —$X^3NR^{5b}C(O)_2R^{5c}$, —$X^3NR^{5a}$—$C(O)NR^{5a}R^{5b}$, —$X^3OC(O)R^{5a}$, —$X^3NR^{5b}R^{5b}$, —O—$X^3OR^{5a}$, —O—$X^3NR^{5a}R^{5b}$, —O—$X^3CO_2R^{5a}$, —O—$X^3CONR^{5a}R^{5b}$, —$NR^{5b}$—$X^3OR^{5a}$, —$NR^{5b}$—$X^3NR^{5a}R^{5b}$, —$NR^{5b}$—$X^3CO_2R^{5a}$, and —$NR^{5b}$—$X^3CONR^{5a}R^{5b}$, wherein each $X^3$ is a member independently selected from the group consisting of $C_{1-4}$alkylene, $C_{2-4}$alkenylene and $C_{2-4}$alkynylene; each $R^{5a}$ and $R^{5b}$ are independently selected from the group consisting of hydrogen, $C_{1-8}$alkyl, $C_{1-8}$haloalkyl, $C_{3-6}$ cycloalkyl, $C_{3-6}$heterocycloalkyl, $C_{2-8}$alkenyl, $C_{2-8}$alkynyl, aryl, heteroaryl, aryl-$C_{1-4}$alkyl, and aryloxy-$C_{1-4}$alkyl; each $R^{5c}$ is independently selected from the group consisting of $C_{1-8}$ alkyl, $C_{1-8}$haloalkyl, $C_{3-6}$cycloalkyl, $C_{3-6}$heterocycloalkyl, $C_{2-8}$alkenyl, $C_{2-8}$alkynyl, aryl, heteroaryl, aryl-$C_{1-4}$alkyl, and aryloxy-$C_{1-4}$alkyl; and optionally any two of $R^{5a}$, $R^{5b}$ and $R^{5c}$ when part of a common $R^5$ substituent can be combined with the atoms to which each is attached to form a saturated four-, five-, six- or seven-membered ring having from 0 to 1 additional heteroatoms as ring members. Additionally, each of $R^{5a}$, $R^{5b}$ and $R^{5c}$ is optionally further substituted with from one to three members selected from the group consisting of —OH, —$OR''$, —OC(O)NH$R''$, —OC(O)N($R''$)$_2$, —SH, —$SR''$, —S(O)$R''$, —S(O)$_2R''$, —$SO_2NH_2$, —S(O)$_2$NH$R''$, —S(O)$_2$N($R''$)$_2$, —NHS(O)$_2R''$, —$NR''S(O)_2R''$, —C(O) NH$_2$, —C(O)NH$R''$, —C(O)N($R''$)$_2$, —C(O)$R''$, —NHC(O) $R''$, —$NR''C(O)R''$, —NHC(O)NH$_2$, —$NR''C(O)NH_2$, —$NR''C(O)NHR''$, —NHC(O)NH$R''$, —$NR''C(O)N(R'')_2$, —NHC(O)N(R")$_2$, —CO$_2$H, —CO$_2$R", —NHCO$_2$R", —NR"CO$_2$R", —CN, —NO$_2$, —NH$_2$, —NHR", —N(R")$_2$, —NR"S(O)NH$_2$ and —NR"S(O)$_2$NHR", wherein each R" is independently an unsubstituted C$_{1-6}$alkyl or benzyl.

With the above formula are a number of specific embodiments of the invention. In one group of embodiments, W has formula (a). In another group of embodiments, the subscript m is 1. In another group of embodiments R$^{4'}$ can be any of the substituents provided with reference to the full scope of the invention. In one group of embodiments, R$^{4'}$ is selected from

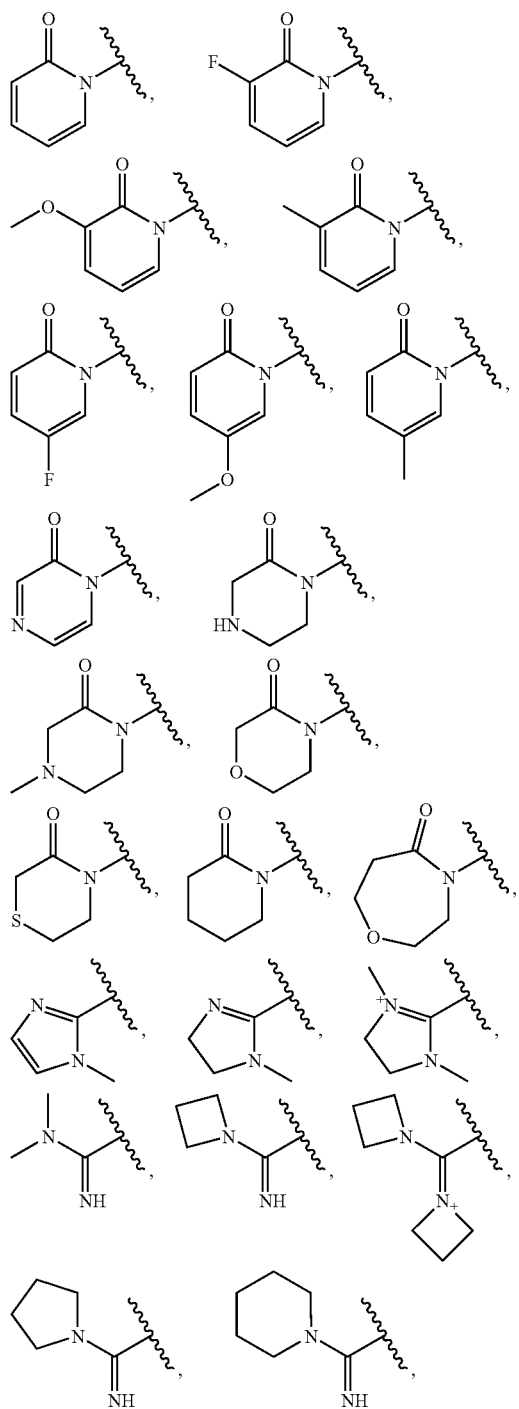

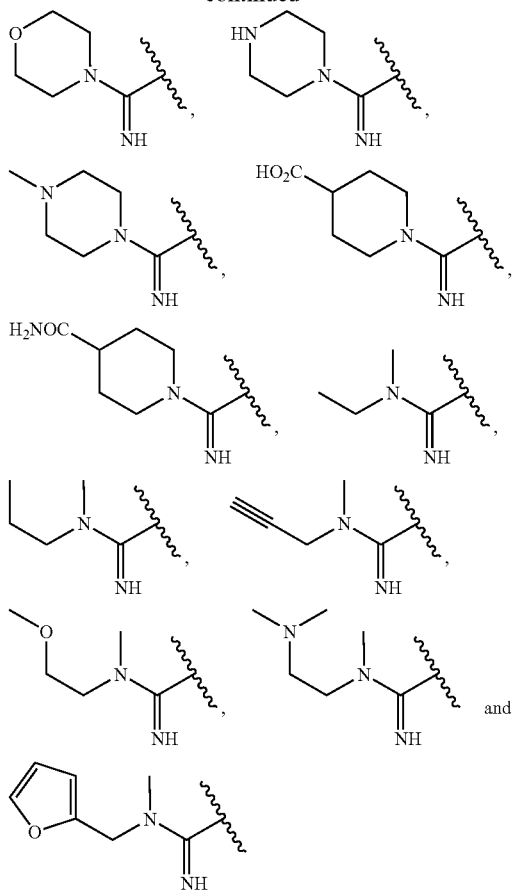

wherein the wavy line indicates the point of attachment to the remainder of the compound. More preferably, R$^{4'}$ is attached to the phenyl ring at a position para to the attachment of the the isoxazole or isoxazoline ring. In another group of embodiments, the subscript n is an integer of from 0 to 1. In another group of embodiments n is 1; R$^4$ is attached to the phenyl ring at a position ortho to the isoxazole or isoxazoline ring and R$^{4'}$ is attached to the phenyl ring at a position para to the isoxazole or isoxazoline ring. In one group of embodiments, R$^4$ is selected from the group consisting of halogen, —OR$^{4a}$, —NR$^{4a}$R$^{4b}$, —SR$^{4a}$, —Y, —X$^1$—Y, —O—Y, —NR$^{4a}$Y and —SY.

In another group of embodiments, m is 0 or 1, n is 0, 1 or 2 and at least one R$^4$ is selected from the group consisting of

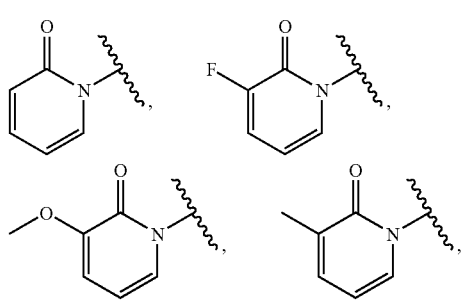

-continued

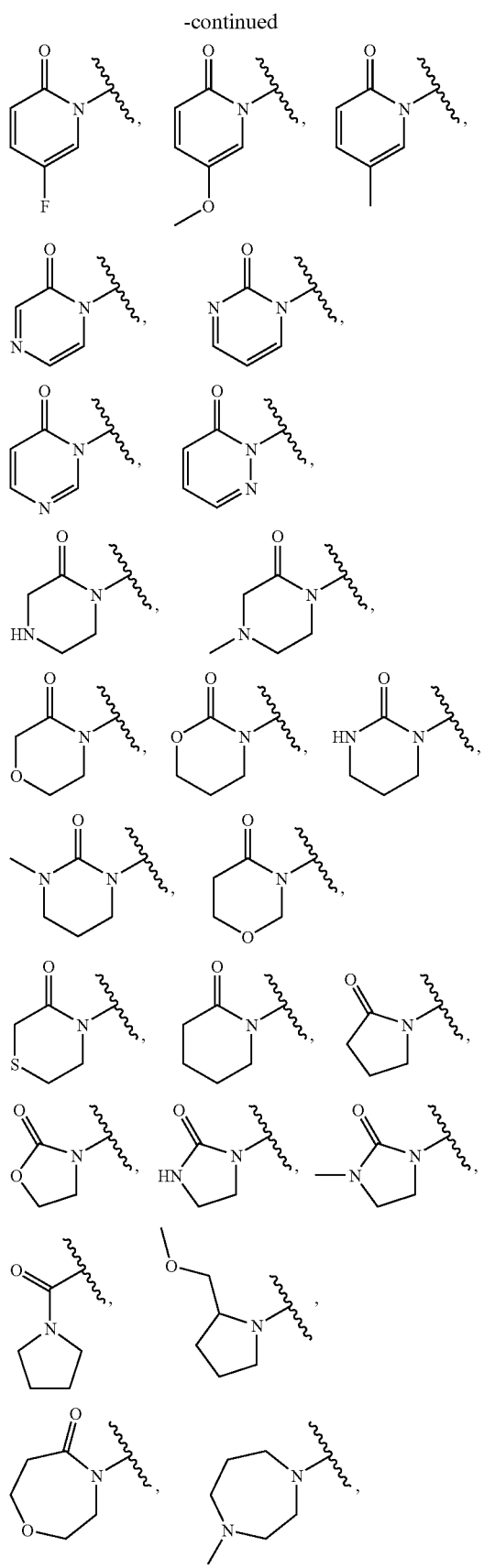

-continued

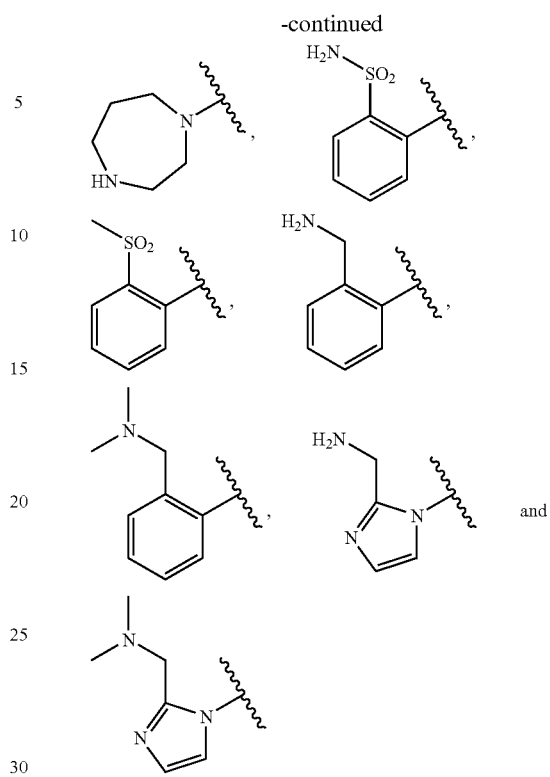

wherein the wavy line indicates the point of attachment to the remainder of the compound.

In another group of embodiments, m is 0 or 1; n is 0, 1, or 2; and at least one $R^4$ is selected from the group consisting of —Y, —$X^1$—Y, —O—Y, —$NR^{4a}$Y, —SY, —S(O)Y and —S(O)$_2$Y, wherein Y is an optionally substituted member selected from the group consisting of phenyl, benzyl, pyridyl, pyridylmethyl, pyrimidinyl and pyrazolyl. More preferably, $R^4$ is selected from the group consisting of —Y, —$X^1$—Y, —O—Y and —$NR^{4a}$Y, wherein Y is an optionally substituted member selected from the group consisting of phenyl, benzyl, pyridyl and pyridylmethyl. Still further preferred are those embodiments in which the optional substituents are selected from the group consisting of halogen, —$OR^{4a}$, —$NR^{4a}R^{4b}$, —$R^{4c}$, —$SR^{4a}$, —$CO_2R^{4a}$, —$CONR^{4a}R^{4b}$, —$C(O)R^{4a}$, —$X^1OR^{4a}$ and —$X^1NR^{4a}R^{4b}$.

In other embodiments, compounds of formula I are provided in which $R^2$ is present the carbon attached to $R^2$ has the R-configuration. Other embodiments are provided in which $R^3$ is other than H the carbon attached to $R^3$ has the R-configuration.

In other embodiments, compounds of formula I are provided in which W has the formula (b). Within this group, specific embodiments are provided in which $Z^1$ is N. Other embodiments are provided in which $Z^2$ is N. Other embodiments are provided in which $Z^3$ is N.

In another group of embodiments, the subscript m is 1. In another group of embodiments $R^{4'}$ can be any of the substituents provided with reference to the full scope of the invention. In one group of embodiments, $R^{4'}$ is selected from

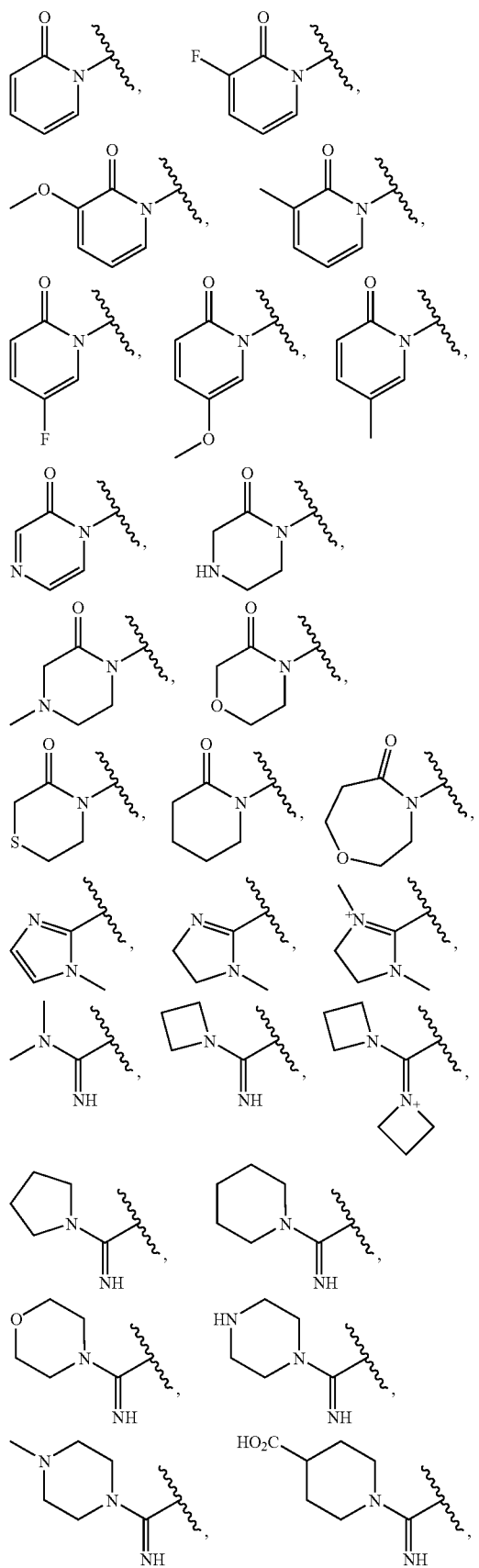
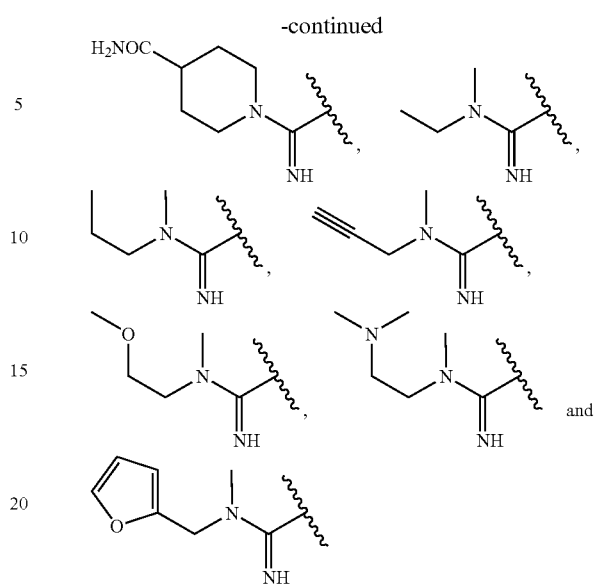
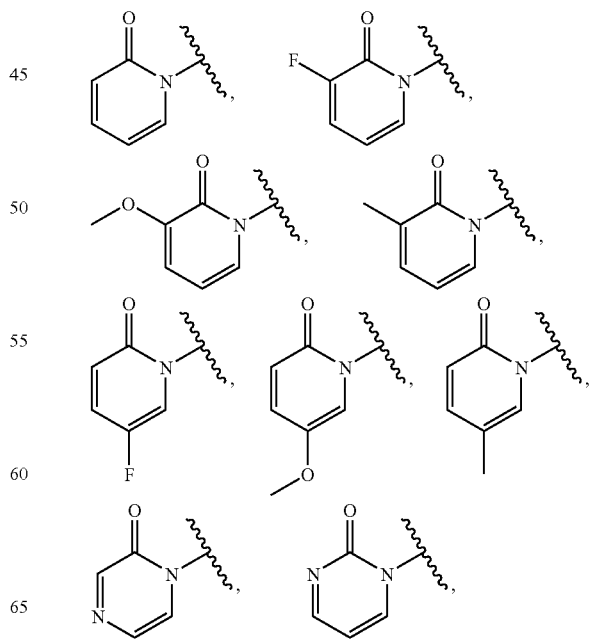

wherein the wavy line indicates the point of attachment to the remainder of the compound. More preferably, $R^{4'}$ is attached to the pyridyl ring at a position para to the attachment of the isoxazole or isoxazoline ring. In another group of embodiments, the subscript n is an integer of from 0 to 1. In another group of embodiments n is 1; $R^4$ is attached to the pyridyl ring at a position ortho to the isoxazole or isoxazoline ring and $R^{4'}$ is attached to the pyridyl ring at a position para to the isoxazole or isoxazoline ring. In one group of embodiments, $R^4$ is selected from the group consisting of halogen, —$OR^{4a}$, —$NR^{4a}R^{4b}$, —$SR^{4a}$, —Y, —$X^1$—Y, —O—Y, —$NR^{4a}$Y and —SY.

In another group of embodiments, m is 0 or 1, n is 0, 1 or 2 and at least one $R^4$ is selected from the group consisting of

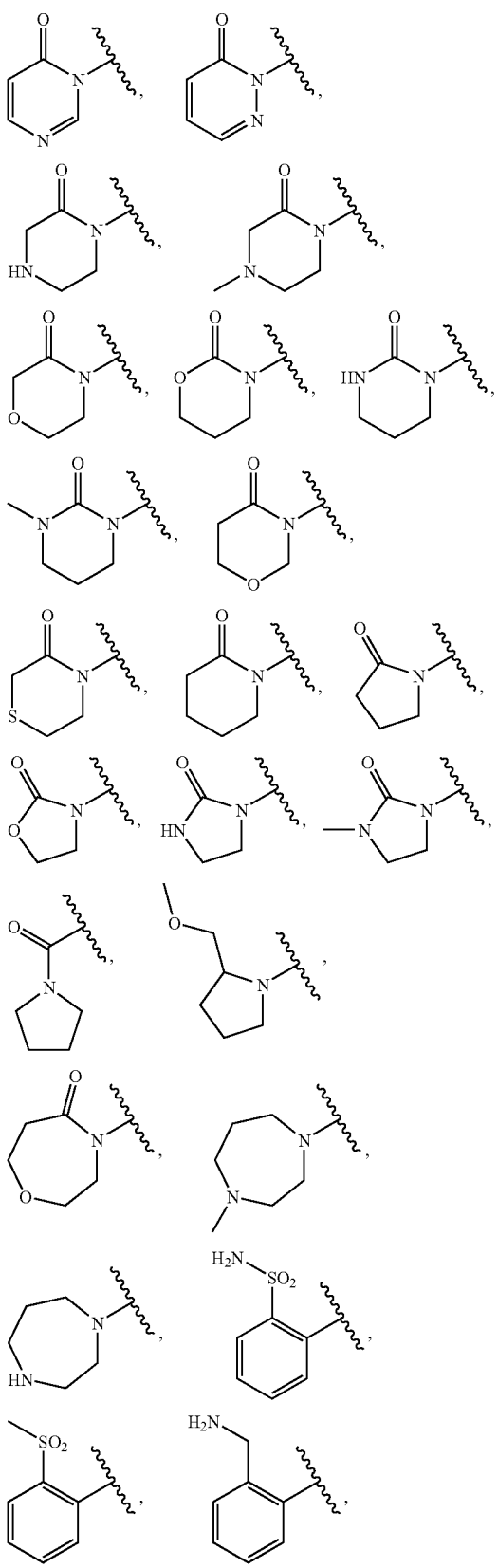
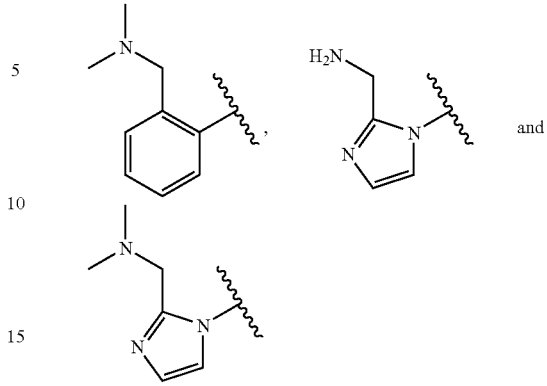

wherein the wavy line indicates the point of attachment to the remainder of the compound.

In another group of embodiments, m is 0 or 1; n is 1, 2, or 3; and at least one $R^4$ is selected from the group consisting of —Y, —$X^1$—Y, —O—Y, —$NR^{4a}$Y, —SY, —S(O)Y and —S(O)$_2$Y, wherein Y is an optionally substituted member selected from the group consisting of phenyl, benzyl, pyridyl, pyridylmethyl, pyrimidinyl and pyrazolyl. More preferably, $R^4$ is selected from the group consisting of —Y, —$X^1$—Y, —O—Y and —$NR^{4a}$Y, wherein Y is an optionally substituted member selected from the group consisting of phenyl, benzyl, pyridyl and pyridylmethyl. Still further preferred are those embodiments in which the optional substituents are selected from the group consisting of halogen, —$OR^{4a}$, —$NR^{4a}R^{4b}$, —$R^{4c}$, —$SR^{4a}$, —$CO_2R^{4a}$, —$CONR^{4a}R^{4b}$, —$C(O)R^{4a}$, —$X^1OR^{4a}$ and —$X^1NR^{4a}R^{4b}$.

In other embodiments, compounds of formula I are provided in which W has the formula (c). Other embodiments are provided in which $Y^1$ is selected from the group consisting of optionally substituted phenyl and optionally substituted pyridyl. Other embodiments are provided in which $R^5$ is selected from the group consisting of —$R^{5a}$, —C(=NH)$NR^{5a}R^{5b}$, —C(=NH)$R^{5a}$, —C(=NH)$Y^1$ and —$X^3$—$Y^1$.

Within the present invention, the compounds provided in the examples below are each preferred embodiments, along with their pharmaceutically acceptable salts. Preferred examples of compounds of formula (I) include:

5-Chloro-thiophene-2-carboxylic acid [3-(4-bromo-phenyl)-4,5-dihydro-isoxazol-5-ylmethyl]-amide;

5-Chloro-thiophene-2-carboxylic acid [3-(3-bromo-phenyl)-isoxazol-5-ylmethyl]-amide;

5-Chloro-thiophene-2-carboxylic acid [3-(4-phenoxy-phenyl)-4,5-dihydro-isoxazol-5-ylmethyl]-amide;

5-Chloro-thiophene-2-carboxylic acid {3-[4-(N-methyl-carbamimidoyl)-phenyl]-isoxazol-5-ylmethyl}-amide;

5-Chloro-thiophene-2-carboxylic acid {3-[4-(N,N-dimethyl-carbamimidoyl)-phenyl]-isoxazol-5-ylmethyl}-methyl-amide;

5-Chloro-thiophene-2-carboxylic acid methyl-{3-[4-(1-methyl-4,5-dihydro-1H-imidazol-2-yl)-phenyl]-isoxazol-5-ylmethyl}-amide;

5-Chloro-thiophene-2-carboxylic acid {3-[4-(imino-pyrrolidin-1-yl-methyl)-phenyl]-isoxazol-5-ylmethyl}-methyl-amide;

5-Chloro-thiophene-2-carboxylic acid {3-[4-(imino-piperidin-1-yl-methyl)-phenyl]-isoxazol-5-ylmethyl}-methyl-amide;

1-{[4-(5-{[(5-Chloro-thiophene-2-carbonyl)-methyl-amino]-methyl}-isoxazol-3-yl)-phenyl]-imino-methyl}-piperidine-4-carboxylic acid ethyl ester;

5-Chloro-thiophene-2-carboxylic acid {3-[4-(azetidin-1-yl-imino-methyl)-phenyl]-isoxazol-5-ylmethyl}-methyl-amide;

5-Chloro-thiophene-2-carboxylic acid {3-[4-(azetidin-1-yl-azetidin-1-ylidene-methyl)-phenyl]-isoxazol-5-ylmethyl}-methyl-amide;

5-Chloro-thiophene-2-carboxylic acid {3-[4-(N-ethyl-N-methyl-carbamimidoyl)-phenyl]-isoxazol-5-ylmethyl}-methyl-amide;

5-Chloro-thiophene-2-carboxylic acid methyl-{3-[4-(N-methyl-N-propyl-carbamimidoyl)-phenyl]-isoxazol-5-ylmethyl}-amide;

5-Chloro-thiophene-2-carboxylic acid (3-{4-[N-(2-dimethylamino-ethyl)-N-methyl-carbamimidoyl]-phenyl}-isoxazol-5-ylmethyl)-methyl-amide;

1-{[4-(5-{[(5-Chloro-thiophene-2-carbonyl)-methyl-amino]-methyl}-isoxazol-3-yl)-phenyl]-imino-methyl}-piperidine-4-carboxylic acid amide;

5-Chloro-thiophene-2-carboxylic acid (3-{4-[N-(2-methoxy-ethyl)-N-methyl-carbamimidoyl]-phenyl}-isoxazol-5-ylmethyl)-methyl-amide;

5-Chloro-thiophene-2-carboxylic acid methyl-{3-[4-(N-methyl-N-prop-2-ynyl-carbamimidoyl)-phenyl]-isoxazol-5-ylmethyl}-amide;

(R)-5-Chloro-thiophene-2-carboxylic acid (1-{3-[4-(imino-piperidin-1-yl-methyl)-phenyl]-isoxazol-5-yl}-ethyl)-amide;

(R)-5-Chloro-thiophene-2-carboxylic acid (1-{3-[4-(N,N-dimethyl-carbamimidoyl)-phenyl]-isoxazol-5-yl}-ethyl)-amide;

(S)-5-Chloro-thiophene-2-carboxylic acid (1-{3-[4-(1-methyl-4,5-dihydro-1H-imidazol-2-yl)-phenyl]-isoxazol-5-yl}-ethyl)-amide;

(S)-5-Chloro-thiophene-2-carboxylic acid (1-{3-[4-(imino-pyrrolidin-1-yl-methyl)-phenyl]-isoxazol-5-yl}-ethyl)-amide;

5-Chloro-thiophene-2-carboxylic acid {3-[4-(imino-piperidin-1-yl-methyl)-2-pyrrolidin-1-yl-phenyl]-4,5-dihydro-isoxazol-5-ylmethyl}-amide;

5-Chloro-thiophene-2-carboxylic acid {3-[4-(imino-piperidin-1-yl-methyl)-2-methylsulfanyl-phenyl]-isoxazol-5-ylmethyl}-amide;

5-Chloro-thiophene-2-carboxylic acid (3-phenyl-4,5-dihydro-isoxazol-5-ylmethyl)-amide;

5-Chloro-thiophene-2-carboxylic acid (5-methyl-3-phenyl-4,5-dihydro-isoxazol-5-ylmethyl)-amide;

5-Chloro-thiophene-2-carboxylic acid (3-phenyl-isoxazol-5-ylmethyl)-amide;

5-Chloro-thiophene-2-carboxylic acid (3-p-tolyl-4,5-dihydro-isoxazol-5-ylmethyl)-amide;

5-Chloro-thiophene-2-carboxylic acid (5-methyl-3-p-tolyl-4,5-dihydro-isoxazol-5-ylmethyl)-amide;

5-Chloro-thiophene-2-carboxylic acid (3-p-tolyl-isoxazol-5-ylmethyl)-amide;

5-Chloro-thiophene-2-carboxylic acid [3-(4-methoxy-phenyl)-4,5-dihydro-isoxazol-5-ylmethyl]-amide;

5-Chloro-thiophene-2-carboxylic acid [3-(4-methoxy-phenyl)-5-methyl-4,5-dihydro-isoxazol-5-ylmethyl]-amide;

5-Chloro-thiophene-2-carboxylic acid [3-(4-methoxy-phenyl)-isoxazol-5-ylmethyl]-amide;

5-Chloro-thiophene-2-carboxylic acid [3-(4-chloro-phenyl)-4,5-dihydro-isoxazol-5-ylmethyl]-amide;

5-Chloro-thiophene-2-carboxylic acid [3-(4-chloro-phenyl)-5-methyl-4,5-dihydro-isoxazol-5-ylmethyl]-amide;

5-Chloro-thiophene-2-carboxylic acid [3-(4-chloro-phenyl)-isoxazol-5-ylmethyl]-amide;

4-(5-{[(5-Chloro-thiophene-2-carbonyl)-amino]-methyl}-4,5-dihydro-isoxazol-3-yl)-benzoic acid methyl ester;

4-(5-{[(5-Chloro-thiophene-2-carbonyl)-amino]-methyl}-isoxazol-3-yl)-benzoic acid methyl ester;

4-(5-{[(5-Chloro-thiophene-2-carbonyl)-amino]-methyl}-4,5-dihydro-isoxazol-3-yl)-benzoic acid;

4-(5-{[(5-Chloro-thiophene-2-carbonyl)-amino]-methyl}-isoxazol-3-yl)-benzoic acid;

5-Chloro-thiophene-2-carboxylic acid [3-(4-amino-phenyl)-4,5-dihydro-isoxazol-5-ylmethyl]-amide;

5-Chloro-thiophene-2-carboxylic acid (3-{4-[(2-diethylamino-ethyl)-methyl-carbamoyl]-phenyl}-isoxazol-5-ylmethyl)-amide;

5-Chloro-thiophene-2-carboxylic acid [3-(1-ethyl-piperidin-4-yl)-4,5-dihydro-isoxazol-5-ylmethyl]-amide;

5-Chloro-thiophene-2-carboxylic acid [3-(1-benzyl-piperidin-4-yl)-4,5-dihydro-isoxazol-5-ylmethyl]-amide;

5-Chloro-thiophene-2-carboxylic acid [3-(1-isopropyl-piperidin-4-yl)-4,5-dihydro-isoxazol-5-ylmethyl]-amide;

5-Chloro-thiophene-2-carboxylic acid [3-(1-carbamimidoyl-piperidin-4-yl)-4,5-dihydro-isoxazol-5-ylmethyl]-amide;

5-Chloro-thiophene-2-carboxylic acid {3-[1-(1-imino-ethyl)-piperidin-4-yl]-4,5-dihydro-isoxazol-5-ylmethyl}-amide;

5-Chloro-thiophene-2-carboxylic acid {3-[1-(imino-phenyl-methyl)-piperidin-4-yl]-4,5-dihydro-isoxazol-5-ylmethyl}-amide;

5-Chloro-thiophene-2-carboxylic acid {3-[1-(imino-pyridin-2-yl-methyl)-piperidin-4-yl]-4,5-dihydro-isoxazol-5-ylmethyl}-amide;

5-Chloro-thiophene-2-carboxylic acid (3-piperidin-4-yl-isoxazol-5-ylmethyl)-amide;

5-Chloro-thiophene-2-carboxylic acid [3-(1-ethyl-piperidin-4-yl)-isoxazol-5-ylmethyl]-amide;

5-Chloro-thiophene-2-carboxylic acid [3-(1-benzyl-piperidin-4-yl)-isoxazol-5-ylmethyl]-amide;

5-Chloro-thiophene-2-carboxylic acid [3-(1-carbamimidoyl-piperidin-4-yl)-isoxazol-5-ylmethyl]-amide;

5-Chloro-thiophene-2-carboxylic acid {3-[1-(1-imino-ethyl)-piperidin-4-yl]-isoxazol-5-ylmethyl}-amide;

5-Chloro-thiophene-2-carboxylic acid {3-[1-(imino-phenyl-methyl)-piperidin-4-yl]-isoxazol-5-ylmethyl}-amide;

5-Chloro-thiophene-2-carboxylic acid [3-(2'-formyl-biphenyl-4-yl)-4,5-dihydro-isoxazol-5-ylmethyl]-amide;

5-Chloro-thiophene-2-carboxylic acid [3-(2'-chloro-biphenyl-4-yl)-4,5-dihydro-isoxazol-5-ylmethyl]-amide;

5-Chloro-thiophene-2-carboxylic acid [3-(2'-methylsulfanyl-biphenyl-4-yl)-4,5-dihydro-isoxazol-5-ylmethyl]-amide;

5-Chloro-thiophene-2-carboxylic acid [3-(4-pyridin-4-yl-phenyl)-4,5-dihydro-isoxazol-5-ylmethyl]-amide;

5-Chloro-thiophene-2-carboxylic acid [3-(4-pyridin-3-yl-phenyl)-isoxazol-5-ylmethyl]-amide;

5-Chloro-thiophene-2-carboxylic acid [3-(2'-azepan-1-yl-methyl-biphenyl-4-yl)-4,5-dihydro-isoxazol-5-ylmethyl]-amide;

5-Chloro-thiophene-2-carboxylic acid [3-(2'-dimethylaminomethyl-5'-methoxy-biphenyl-4-yl)-4,5-dihydro-isoxazol-5-ylmethyl]-amide;

5-Chloro-thiophene-2-carboxylic acid [3-(2'-hydroxymethyl-4'-methoxy-biphenyl-4-yl)-4,5-dihydro-isoxazol-5-ylmethyl]-amide;

5-Chloro-thiophene-2-carboxylic acid [3-(3'-pyrrolidin-1-ylmethyl-biphenyl-4-yl)-isoxazol-5-ylmethyl]-amide;

5-Chloro-thiophene-2-carboxylic acid [3-(4'-dimethylaminomethyl-biphenyl-4-yl)-isoxazol-5-ylmethyl]-amide;

5-Chloro-thiophene-2-carboxylic acid [3-(4'-pyrrolidin-1-ylmethyl-biphenyl-4-yl)-isoxazol-5-ylmethyl]-amide;

5-Chloro-thiophene-2-carboxylic acid [3-(2'-dimethylaminomethyl-5'-methoxy-biphenyl-4-yl)-isoxazol-5-ylmethyl]-amide;

5-Chloro-thiophene-2-carboxylic acid [3-(4-pyridin-2-yl-phenyl)-isoxazol-5-ylmethyl]-amide;

5-Chloro-thiophene-2-carboxylic acid [3-(4-benzylamino-phenyl)-4,5-dihydro-isoxazol-5-ylmethyl]-amide;

5-Chloro-thiophene-2-carboxylic acid [3-(4-phenylamino-phenyl)-4,5-dihydro-isoxazol-5-ylmethyl]-amide;

5-Chloro-thiophene-2-carboxylic acid {3-[4-(4-fluoro-phenylamino)-phenyl]-4,5-dihydro-isoxazol-5-ylmethyl}-amide;

5-Chloro-thiophene-2-carboxylic acid {3-[4-(pyridin-2-ylamino)-phenyl]-4,5-dihydro-isoxazol-5-ylmethyl}-amide;

5-Chloro-thiophene-2-carboxylic acid {3-[4-(2-methyl-pyridin-4-ylamino)-phenyl]-4,5-dihydro-isoxazol-5-ylmethyl}-amide;

5-Chloro-thiophene-2-carboxylic acid (3-{4-[(2-amino-pyrimidin-4-yl)-methyl-amino]-phenyl}-4,5-dihydro-isoxazol-5-ylmethyl)-amide;

5-Chloro-thiophene-2-carboxylic acid {3-[4-(2-ethyl-2H-pyrazol-3-ylamino)-phenyl]-4,5-dihydro-isoxazol-5-ylmethyl}-amide;

5-Chloro-thiophene-2-carboxylic acid [3-(4-morpholin-4-yl-phenyl)-4,5-dihydro-isoxazol-5-ylmethyl]-amide;

5-Chloro-thiophene-2-carboxylic acid {3-[4-(2-methoxymethyl-pyrrolidin-1-yl)-phenyl]-4,5-dihydro-isoxazol-5-ylmethyl}-amide;

5-Chloro-thiophene-2-carboxylic acid {3-[2-fluoro-4-(5-oxo-[1,4]oxazepan-4-yl)-phenyl]-4,5-dihydro-isoxazol-5-ylmethyl}-amide;

5-Chloro-thiophene-2-carboxylic acid [3-(4-phenylamino-phenyl)-isoxazol-5-ylmethyl]-amide;

5-Chloro-thiophene-2-carboxylic acid {3-[4-(4-methoxyphenylamino)-phenyl]-isoxazol-5-ylmethyl}-amide;

5-Chloro-thiophene-2-carboxylic acid {3-[4-(pyridin-2-ylamino)-phenyl]-isoxazol-5-ylmethyl}-amide;

5-Chloro-thiophene-2-carboxylic acid {3-[4-(methyl-pyridin-4-yl-amino)-phenyl]-isoxazol-5-ylmethyl}-amide;

5-Chloro-thiophene-2-carboxylic acid [3-(4-pyrrolidin-1-yl-phenyl)-isoxazol-5-ylmethyl]-amide;

5-Chloro-thiophene-2-carboxylic acid [3-(4-morpholin-4-yl-phenyl)-isoxazol-5-ylmethyl]-amide;

5-Chloro-thiophene-2-carboxylic acid [3-(4-benzylamino-phenyl)-isoxazol-5-ylmethyl]-amide;

5-Chloro-thiophene-2-carboxylic acid {3-[4-(1-methyl-piperidin-4-ylamino)-phenyl]-isoxazol-5-ylmethyl}-amide;

2-[4-(5-{[(5-Chloro-thiophene-2-carbonyl)-amino]-methyl}-4,5-dihydro-isoxazol-3-yl)-phenylamino]-benzoic acid methyl ester;

3-[4-(5-{[(5-Chloro-thiophene-2-carbonyl)-amino]-methyl}-4,5-dihydro-isoxazol-3-yl)-phenylamino]-benzoic acid methyl ester;

4-[4-(5-{[(5-Chloro-thiophene-2-carbonyl)-amino]-methyl}-4,5-dihydro-isoxazol-3-yl)-phenylamino]-benzoic acid methyl ester;

5-Chloro-thiophene-2-carboxylic acid [3-(2'-pyrrolidin-1-ylmethyl-biphenyl-3-yl)-4,5-dihydro-isoxazol-5-ylmethyl]-amide;

5-Chloro-thiophene-2-carboxylic acid [3-(3'-dimethylaminomethyl-biphenyl-3-yl)-4,5-dihydro-isoxazol-5-ylmethyl]-amide;

5-Chloro-thiophene-2-carboxylic acid [3-(3'-pyrrolidin-1-ylmethyl-biphenyl-3-yl)-4,5-dihydro-isoxazol-5-ylmethyl]-amide;

5-Chloro-thiophene-2-carboxylic acid [3-(4'-dimethylaminomethyl-biphenyl-3-yl)-4,5-dihydro-isoxazol-5-ylmethyl]-amide;

5-Chloro-thiophene-2-carboxylic acid [3-(4'-pyrrolidin-1-ylmethyl-biphenyl-3-yl)-4,5-dihydro-isoxazol-5-ylmethyl]-amide;

5-Chloro-thiophene-2-carboxylic acid [3-(2'-dimethylaminomethyl-biphenyl-3-yl)-isoxazol-5-ylmethyl]-amide;

5-Chloro-thiophene-2-carboxylic acid [3-(3'-dimethylaminomethyl-biphenyl-3-yl)-isoxazol-5-ylmethyl]-amide;

5-Chloro-thiophene-2-carboxylic acid [3-(3'-pyrrolidin-1-ylmethyl-biphenyl-3-yl)-isoxazol-5-ylmethyl]-amide;

5-Chloro-thiophene-2-carboxylic acid [3-(4'-dimethylaminomethyl-biphenyl-3-yl)-isoxazol-5-ylmethyl]-amide;

5-Chloro-thiophene-2-carboxylic acid [3-(4'-pyrrolidin-1-ylmethyl-biphenyl-3-yl)-isoxazol-5-ylmethyl]-amide;

5-Chloro-thiophene-2-carboxylic acid [3-(3-pyridin-3-yl-phenyl)-4,5-dihydro-isoxazol-5-ylmethyl]-amide;

5-Chloro-thiophene-2-carboxylic acid [3-(3-pyridin-4-yl-phenyl)-4,5-dihydro-isoxazol-5-ylmethyl]-amide; and 5-Chloro-thiophene-2-carboxylic acid [3-(3-pyridin-3-yl-phenyl)-isoxazol-5-ylmethyl]-amide.

More preferred examples of the compounds of formula (I) include:

5-Chloro-thiophene-2-carboxylic acid {3-[4-(imino-piperidin-1-yl-methyl)-phenyl]-4,5-dihydro-isoxazol-5-ylmethyl}-amide;

1-{[4-(5-{[(5-Chloro-thiophene-2-carbonyl)-amino]-methyl}-4,5-dihydro-isoxazol-3-yl)-phenyl]-imino-methyl}-piperidine-4-carboxylic acid ethyl ester;

5-Chloro-thiophene-2-carboxylic acid {3-[4-(N-methyl-N-prop-2-ynyl-carbamimidoyl)-phenyl]-4,5-dihydro-isoxazol-5-ylmethyl}-amide;

5-Chloro-thiophene-2-carboxylic acid (3-{4-[N-(2-methoxy-ethyl)-N-methyl-carbamimidoyl]-phenyl}-4,5-dihydro-isoxazol-5-ylmethyl)-amide;

5-Chloro-thiophene-2-carboxylic acid {3-[4-(N-furan-2-ylmethyl-N-methyl-carbamimidoyl)-phenyl]-4,5-dihydro-isoxazol-5-ylmethyl}-amide;

5-Chloro-thiophene-2-carboxylic acid {3-[4-(N-methyl-N-prop-2-ynyl-carbamimidoyl)-phenyl]-isoxazol-5-ylmethyl}-amide;

5-Chloro-thiophene-2-carboxylic acid (3-{4-[N-(2-methoxy-ethyl)-N-methyl-carbamimidoyl]-phenyl}-5-methyl-4,5-dihydro-isoxazol-5-ylmethyl)-amide;

1-{[4-(5-{[(5-Chloro-thiophene-2-carbonyl)-amino]-methyl}-5-methyl-4,5-dihydro-isoxazol-3-yl)-phenyl]-imino-methyl}-piperidine-4-carboxylic acid amide;

5-Chloro-thiophene-2-carboxylic acid {3-[4-(N,N-dimethyl-carbamimidoyl)-2-fluoro-phenyl]-dihydro-isoxazol-5-ylmethyl}-amide;

5-Chloro-thiophene-2-carboxylic acid {3-[2-dimethylamino-4-(N,N-dimethyl-carbamimidoyl)-phenyl]-4,5-dihydro-isoxazol-5-ylmethyl}-amide;

5-Chloro-thiophene-2-carboxylic acid {3-[2-dimethylamino-4-(1-methyl-4,5-dihydro-1H-imidazol-2-yl)-phenyl]-4,5-dihydro-isoxazol-5-ylmethyl}-amide;

5-Chloro-thiophene-2-carboxylic acid {3-[2-dimethylamino-4-(imino-pyrrolidin-1-yl-methyl)-phenyl]-4,5-dihydro-isoxazol-5-ylmethyl}-amide;

5-Chloro-thiophene-2-carboxylic acid {3-[4-(N,N-dimethyl-carbamimidoyl)-2-pyrrolidin-1-yl-phenyl]-4,5-dihydro-isoxazol-5-ylmethyl}-amide;

5-Chloro-thiophene-2-carboxylic acid {3-[4-(1-methyl-4,5-dihydro-1H-imidazol-2-yl)-2-pyrrolidin-1-yl-phenyl]-4,5-dihydro-isoxazol-5-ylmethyl}-amide;

5-Chloro-thiophene-2-carboxylic acid {3-[4-(imino-pyrrolidin-1-yl-methyl)-2-pyrrolidin-1-yl-phenyl]-4,5-dihydro-isoxazol-5-ylmethyl}-amide;

5-Chloro-thiophene-2-carboxylic acid {3-[4-(1-methyl-4,5-dihydro-1H-imidazol-2-yl)-2-morpholin-4-yl-phenyl]-4,5-dihydro-isoxazol-5-ylmethyl}-amide;

5-Chloro-thiophene-2-carboxylic acid {3-[4-(imino-pyrrolidin-1-yl-methyl)-2-morpholin-4-yl-phenyl]-4,5-dihydro-isoxazol-5-ylmethyl}-amide;

5-Chloro-thiophene-2-carboxylic acid {3-[4-(imino-piperidin-1-yl-methyl)-2-morpholin-4-yl-phenyl]-4,5-dihydro-isoxazol-5-ylmethyl}-amide;

5-Chloro-thiophene-2-carboxylic acid {3-[2-[(2-methoxy-ethyl)-methyl-amino]-4-(1-methyl-4,5-dihydro-1H-imidazol-2-yl)-phenyl]-4,5-dihydro-isoxazol-5-ylmethyl}-amide;

5-Chloro-thiophene-2-carboxylic acid (3-{4-(imino-pyrrolidin-1-yl-methyl)-2-[(2-methoxy-ethyl)-methyl-amino]-phenyl}-4,5-dihydro-isoxazol-5-ylmethyl)-amide;

5-Chloro-thiophene-2-carboxylic acid (3-{4-(imino-piperidin-1-yl-methyl)-2-[(2-methoxy-ethyl)-methyl-amino]-phenyl}-4,5-dihydro-isoxazol-5-ylmethyl)-amide;

5-Chloro-thiophene-2-carboxylic acid {3-[2-azepan-1-yl-4-(N,N-dimethyl-carbamimidoyl)-phenyl]-4,5-dihydro-isoxazol-5-ylmethyl}-amide;

5-Chloro-thiophene-2-carboxylic acid {3-[4-(2-methyl-pyrrolidine-1-carbonyl)-phenyl]-4,5-dihydro-isoxazol-5-ylmethyl}-amide;

5-Chloro-thiophene-2-carboxylic acid {3-[4-(pyrrolidine-1-carbonyl)-phenyl]-isoxazol-5-ylmethyl}-amide;

5-Chloro-thiophene-2-carboxylic acid [3-(2'-amino-biphenyl-4-yl)-4,5-dihydro-isoxazol-5-ylmethyl]-amide;

5-Chloro-thiophene-2-carboxylic acid [3-(2'-trifluoromethyl-biphenyl-4-yl)-4,5-dihydro-isoxazol-5-ylmethyl]-amide;

5-Chloro-thiophene-2-carboxylic acid [3-(2'-methoxy-biphenyl-4-yl)-4,5-dihydro-isoxazol-5-ylmethyl]-amide;

5-Chloro-thiophene-2-carboxylic acid [3-(2'-methoxymethyl-biphenyl-4-yl)-isoxazol-5-ylmethyl]-amide;

5-Chloro-thiophene-2-carboxylic acid [3-(4-pyridin-3-yl-phenyl)-4,5-dihydro-isoxazol-5-ylmethyl]-amide;

5-Chloro-thiophene-2-carboxylic acid [3-(5'-chloro-2'-{[(2-methoxy-ethyl)-methyl-amino]-methyl}-biphenyl-4-yl)-4,5-dihydro-isoxazol-5-ylmethyl]-amide;

5-Chloro-thiophene-2-carboxylic acid [3-(2'-pyrrolidin-1-ylmethyl-biphenyl-4-yl)-isoxazol-5-ylmethyl]-amide;

5-Chloro-thiophene-2-carboxylic acid [3-(3'-dimethylaminomethyl-biphenyl-4-yl)-isoxazol-5-ylmethyl]-amide;

5-Chloro-thiophene-2-carboxylic acid {3-[4-(2-chloro-pyridin-4-ylamino)-phenyl]-4,5-dihydro-isoxazol-5-ylmethyl}-amide;

5-Chloro-thiophene-2-carboxylic acid {3-[4-(pyrimidin-4-ylamino)-phenyl]-4,5-dihydro-isoxazol-5-ylmethyl}-amide;

5-Chloro-thiophene-2-carboxylic acid {3-[4-(1-methyl-1H-pyrazol-3-ylamino)-phenyl]-4,5-dihydro-isoxazol-5-ylmethyl}-amide;

5-Chloro-thiophene-2-carboxylic acid {3-[4-(4-methyl-piperazin-1-yl)-phenyl]-4,5-dihydro-isoxazol-5-ylmethyl}-amide;

5-Chloro-thiophene-2-carboxylic acid {3-[4-(1-methyl-piperidin-4-ylamino)-phenyl]-4,5-dihydro-isoxazol-5-ylmethyl}-amide;

5-Chloro-thiophene-2-carboxylic acid (3-{4-[(2-dimethylamino-ethyl)-methyl-amino]-phenyl}-4,5-dihydro-isoxazol-5-ylmethyl)-amide;

5-Chloro-thiophene-2-carboxylic acid {3-[4-(2-oxo-piperidin-1-yl)-phenyl]-4,5-dihydro-isoxazol-5-ylmethyl}-amide; and 5-Chloro-thiophene-2-carboxylic acid {3-[4-(3-oxo-thiomorpholin-4-yl)-phenyl]-4,5-dihydro-isoxazol-5-ylmethyl}-amide.

Particularly preferred examples of the compounds of formula (I) include:

5-Chloro-thiophene-2-carboxylic acid [3-(4-cyano-phenyl)-4,5-dihydro-isoxazol-5-ylmethyl]-amide;

5-Chloro-thiophene-2-carboxylic acid {3-[4-(N,N-dimethyl-carbamimidoyl)-phenyl]-4,5-dihydro-isoxazol-5-ylmethyl}-amide;

5-Chloro-thiophene-2-carboxylic acid {3-[4-(1-methyl-4,5-dihydro-1H-imidazol-2-yl)-phenyl]-4,5-dihydro-isoxazol-5-ylmethyl}-amide;

5-Chloro-thiophene-2-carboxylic acid {3-[4-(imino-pyrrolidin-1-yl-methyl)-phenyl]-4,5-dihydro-isoxazol-5-ylmethyl}-amide;

5-Chloro-thiophene-2-carboxylic acid (3-{4-[N-(2-dimethylamino-ethyl)-N-methyl-carbamimidoyl]-phenyl}-4,5-dihydro-isoxazol-5-ylmethyl)-amide;

5-Chloro-thiophene-2-carboxylic acid {3-[4-(N-methyl-N-propyl-carbamimidoyl)-phenyl]-4,5-dihydro-isoxazol-5-ylmethyl}-amide;

5-Chloro-thiophene-2-carboxylic acid {3-[4-(N-ethyl-N-methyl-carbamimidoyl)-phenyl]-4,5-dihydro-isoxazol-5-ylmethyl}-amide;

5-Chloro-thiophene-2-carboxylic acid [3-(4-cyano-phenyl)-isoxazol-5-ylmethyl]-amide;

5-Chloro-thiophene-2-carboxylic acid {3-[4-(N,N-dimethyl-carbamimidoyl)-phenyl]-isoxazol-5-ylmethyl}-amide;

5-Chloro-thiophene-2-carboxylic acid {3-[4-(1-methyl-4,5-dihydro-1H-imidazol-2-yl)-phenyl]-isoxazol-5-ylmethyl}-amide;

5-Chloro-thiophene-2-carboxylic acid {3-[4-(imino-pyrrolidin-1-yl-methyl)-phenyl]-isoxazol-5-ylmethyl}-amide;

5-Chloro-thiophene-2-carboxylic acid {3-[4-(imino-piperidin-1-yl-methyl)-phenyl]-isoxazol-5-ylmethyl}-amide;

1-{[4-(5-{[(5-Chloro-thiophene-2-carbonyl)-amino]-methyl}-isoxazol-3-yl)-phenyl]-imino-methyl}-piperidine-4-carboxylic acid ethyl ester;

5-Chloro-thiophene-2-carboxylic acid {3-[4-(azetidin-1-yl-imino-methyl)-phenyl]-isoxazol-5-ylmethyl}-amide;

5-Chloro-thiophene-2-carboxylic acid {3-[4-(azetidin-1-yl-azetidin-1-ylidene-methyl)-phenyl]-isoxazol-5-ylmethyl}-amide;

5-Chloro-thiophene-2-carboxylic acid {3-[4-(N-ethyl-N-methyl-carbamimidoyl)-phenyl]-isoxazol-5-ylmethyl}-amide;

5-Chloro-thiophene-2-carboxylic acid {3-[4-(N-methyl-N-propyl-carbamimidoyl)-phenyl]-isoxazol-5-ylmethyl}-amide;

5-Chloro-thiophene-2-carboxylic acid (3-{4-[N-(2-dimethylamino-ethyl)-N-methyl-carbamimidoyl]-phenyl}-isoxazol-5-ylmethyl)-amide;

5-Chloro-thiophene-2-carboxylic acid {3-[4-(N-furan-2-ylmethyl-N-methyl-carbamimidoyl)-phenyl]-isoxazol-5-ylmethyl}-amide;

5-Chloro-thiophene-2-carboxylic acid (3-{4-[N-(2-methoxy-ethyl)-N-methyl-carbamimidoyl]-phenyl}-isoxazol-5-ylmethyl)-amide;

5-Chloro-thiophene-2-carboxylic acid methyl-{3-[4-(N-methylcarbamimidoyl)-phenyl]-isoxazol-5-ylmethyl}-amide;

(R)-5-Chloro-thiophene-2-carboxylic acid (1-{3-[4-(N,N-dimethyl-carbamimidoyl)-phenyl]-isoxazol-5-yl}-ethyl)-amide;

(R)-5-Chloro-thiophene-2-carboxylic acid (1-{3-[4-(1-methyl-4,5-dihydro-1H-imidazol-2-yl)-phenyl]-isoxazol-5-yl}-ethyl)-amide;

(R)-5-Chloro-thiophene-2-carboxylic acid (1-{3-[4-(imino-pyrrolidin-1-yl-methyl)-phenyl]-isoxazol-5-yl}-ethyl)-amide;

(S)-5-Chloro-thiophene-2-carboxylic acid (1-{3-[4-(imino-piperidin-1-yl-methyl)-phenyl]-isoxazol-5-yl}-ethyl)-amide;

5-Chloro-thiophene-2-carboxylic acid {3-[4-(N,N-dimethyl-carbamimidoyl)-phenyl]-5-methyl-4,5-dihydro-isoxazol-5-ylmethyl}-amide;

5-Chloro-thiophene-2-carboxylic acid {5-methyl-3-[4-(1-methyl-4,5-dihydro-1H-imidazol-2-yl)-phenyl]-4,5-dihydro-isoxazol-5-ylmethyl}-amide;

5-Chloro-thiophene-2-carboxylic acid {3-[4-(imino-pyrrolidin-1-yl-methyl)-phenyl]-5-methyl-4,5-dihydro-isoxazol-5-ylmethyl}-amide;

5-Chloro-thiophene-2-carboxylic acid {3-[4-(imino-piperidin-1-yl-methyl)-phenyl]-5-methyl-4,5-dihydro-isoxazol-5-ylmethyl}-amide;

1-{[4-(5-{[(5-Chloro-thiophene-2-carbonyl)-amino]-methyl}-5-methyl-4,5-dihydro-isoxazol-3-yl)-phenyl]-imino-methyl}-piperidine-4-carboxylic acid ethyl ester;

5-Chloro-thiophene-2-carboxylic acid {3-[4-(azetidin-1-yl-imino-methyl)-phenyl]-5-methyl-4,5-dihydro-isoxazol-5-ylmethyl}-amide;

5-Chloro-thiophene-2-carboxylic acid {3-[4-(azetidin-1-yl-azetidin-1-ylidene-methyl)-phenyl]-5-methyl-4,5-dihydro-isoxazol-5-ylmethyl}-amide;

5-Chloro-thiophene-2-carboxylic acid {3-[4-(N-ethyl-N-methyl-carbamimidoyl)-phenyl]-5-methyl-4,5-dihydro-isoxazol-5-ylmethyl}-amide;

5-Chloro-thiophene-2-carboxylic acid (3-{4-[N-(2-dimethylamino-ethyl)-N-methyl-carbamimidoyl]-phenyl}-5-methyl-4,5-dihydro-isoxazol-5-ylmethyl)-amide;

5-Chloro-thiophene-2-carboxylic acid {3-[4-(N-furan-2-ylmethyl-N-methyl-carbamimidoyl)-phenyl]-5-methyl-4,5-dihydro-isoxazol-5-ylmethyl}-amide;

5-Chloro-thiophene-2-carboxylic acid {5-methyl-3-[4-(N-methylcarbamimidoyl)-phenyl]-4,5-dihydro-isoxazol-5-ylmethyl}-amide;

5-Chloro-thiophene-2-carboxylic acid {3-[2-fluoro-4-(1-methyl-4,5-dihydro-1H-imidazol-2-yl)-phenyl]-isoxazol-5-ylmethyl}-amide;

5-Chloro-thiophene-2-carboxylic acid {3-[2-fluoro-4-(imino-pyrrolidin-1-yl-methyl)-phenyl]-isoxazol-5-ylmethyl}-amide;

5-Chloro-thiophene-2-carboxylic acid {3-[2-fluoro-4-(imino-piperidin-1-yl-methyl)-phenyl]-isoxazol-5-ylmethyl}-amide;

5-Chloro-thiophene-2-carboxylic acid {3-[2-dimethylamino-4-(imino-piperidin-1-yl-methyl)-phenyl]-4,5-dihydro-isoxazol-5-ylmethyl}-amide;

5-Chloro-thiophene-2-carboxylic acid {3-[4-(N,N-dimethyl-carbamimidoyl)-2-morpholin-4-yl-phenyl]-4,5-dihydro-isoxazol-5-ylmethyl}-amide;

5-Chloro-thiophene-2-carboxylic acid (3-{4-(N,N-dimethyl-carbamimidoyl)-2-[(2-methoxy-ethyl)-methyl-amino]-phenyl}-4,5-dihydro-isoxazol-5-ylmethyl)-amide;

5-Chloro-thiophene-2-carboxylic acid {3-[2-azepan-1-yl-4-(1-methyl-4,5-dihydro-1H-imidazol-2-yl)-phenyl]-4,5-dihydro-isoxazol-5-ylmethyl}-amide;

5-Chloro-thiophene-2-carboxylic acid {3-[2-azepan-1-yl-4-(imino-pyrrolidin-1-yl-methyl)-phenyl]-4,5-dihydro-isoxazol-5-ylmethyl}-amide;

5-Chloro-thiophene-2-carboxylic acid {3-[2-azepan-1-yl-4-(imino-piperidin-1-yl-methyl)-phenyl]-4,5-dihydro-isoxazol-5-ylmethyl}-amide;

5-Chloro-thiophene-2-carboxylic acid {3-[2-dimethylamino-4-(N,N-dimethyl-carbamimidoyl)-phenyl]-isoxazol-5-ylmethyl}-amide;

5-Chloro-thiophene-2-carboxylic acid {3-[2-dimethylamino-4-(1-methyl-4,5-dihydro-1H-imidazol-2-yl)-phenyl]-isoxazol-5-ylmethyl}-amide;

5-Chloro-thiophene-2-carboxylic acid {3-[2-dimethylamino-4-(imino-pyrrolidin-1-yl-methyl)-phenyl]-isoxazol-5-ylmethyl}-amide;

5-Chloro-thiophene-2-carboxylic acid {3-[2-dimethylamino-4-(imino-piperidin-1-yl-methyl)-phenyl]-isoxazol-5-ylmethyl}-amide;

5-Chloro-thiophene-2-carboxylic acid {3-[4-(N,N-dimethyl-carbamimidoyl)-2-morpholin-4-yl-phenyl]-isoxazol-5-ylmethyl}-amide;

5-Chloro-thiophene-2-carboxylic acid {3-[4-(1-methyl-4,5-dihydro-1H-imidazol-2-yl)-2-morpholin-4-yl-phenyl]-isoxazol-5-ylmethyl}-amide;

5-Chloro-thiophene-2-carboxylic acid {3-[4-(imino-pyrrolidin-1-yl-methyl)-2-morpholin-4-yl-phenyl]-isoxazol-5-ylmethyl}-amide;

5-Chloro-thiophene-2-carboxylic acid {3-[4-(imino-piperidin-1-yl-methyl)-2-morpholin-4-yl-phenyl]-isoxazol-5-ylmethyl}-amide;

5-Chloro-thiophene-2-carboxylic acid {3-[4-(N,N-dimethyl-carbamimidoyl)-2-methoxy-phenyl]-4,5-dihydro-isoxazol-5-ylmethyl}-amide;

5-Chloro-thiophene-2-carboxylic acid {3-[2-methoxy-4-(1-methyl-4,5-dihydro-1H-imidazol-2-yl)-phenyl]-4,5-dihydro-isoxazol-5-ylmethyl}-amide;

5-Chloro-thiophene-2-carboxylic acid {3-[4-(imino-pyrrolidin-1-yl-methyl)-2-methoxy-phenyl]-4,5-dihydro-isoxazol-5-ylmethyl}-amide;

5-Chloro-thiophene-2-carboxylic acid {3-[4-(imino-piperidin-1-yl-methyl)-2-methoxy-phenyl]-4,5-dihydro-isoxazol-5-ylmethyl}-amide;

5-Chloro-thiophene-2-carboxylic acid {3-[4-(N,N-dimethyl-carbamimidoyl)-2-ethoxy-phenyl]-4,5-dihydro-isoxazol-5-ylmethyl}-amide;

5-Chloro-thiophene-2-carboxylic acid {3-[2-ethoxy-4-(1-methyl-4,5-dihydro-1H-imidazol-2-yl)-phenyl]-4,5-dihydro-isoxazol-5-ylmethyl}-amide;

5-Chloro-thiophene-2-carboxylic acid {3-[2-ethoxy-4-(imino-pyrrolidin-1-yl-methyl)-phenyl]-4,5-dihydro-isoxazol-5-ylmethyl}-amide;

5-Chloro-thiophene-2-carboxylic acid {3-[4-(N,N-dimethyl-carbamimidoyl)-2-isopropoxy-phenyl]-4,5-dihydro-isoxazol-5-ylmethyl}-amide;

5-Chloro-thiophene-2-carboxylic acid {3-[2-isopropoxy-4-(1-methyl-4,5-dihydro-1H-imidazol-2-yl)-phenyl]-4,5-dihydro-isoxazol-5-ylmethyl}-amide;

5-Chloro-thiophene-2-carboxylic acid {3-[4-(imino-pyrrolidin-1-yl-methyl)-2-isopropoxy-phenyl]-4,5-dihydro-isoxazol-5-ylmethyl}-amide;

5-Chloro-thiophene-2-carboxylic acid {3-[2-cyclopentyloxy-4-(N,N-dimethyl-carbamimidoyl)-phenyl]-4,5-dihydro-isoxazol-5-ylmethyl}-amide;

5-Chloro-thiophene-2-carboxylic acid {3-[2-cyclopentyloxy-4-(1-methyl-4,5-dihydro-1H-imidazol-2-yl)-phenyl]-4,5-dihydro-isoxazol-5-ylmethyl}-amide;

5-Chloro-thiophene-2-carboxylic acid {3-[2-cyclopentyloxy-4-(imino-pyrrolidin-1-yl-methyl)-phenyl]-4,5-dihydro-isoxazol-5-ylmethyl}-amide;

5-Chloro-thiophene-2-carboxylic acid {3-[2-cyclohexyloxy-4-(N,N-dimethyl-carbamimidoyl)-phenyl]-4,5-dihydro-isoxazol-5-ylmethyl}-amide;

5-Chloro-thiophene-2-carboxylic acid {3-[2-cyclohexyloxy-4-(1-methyl-4,5-dihydro-1H-imidazol-2-yl)-phenyl]-4,5-dihydro-isoxazol-5-ylmethyl}-amide;

5-Chloro-thiophene-2-carboxylic acid {3-[2-cyclohexyloxy-4-(imino-pyrrolidin-1-yl-methyl)-phenyl]-4,5-dihydro-isoxazol-5-ylmethyl}-amide;

5-Chloro-thiophene-2-carboxylic acid {3-[4-(N,N-dimethyl-carbamimidoyl)-2-methoxy-phenyl]-isoxazol-5-ylmethyl}-amide;

5-Chloro-thiophene-2-carboxylic acid {3-[2-methoxy-4-(1-methyl-4,5-dihydro-1H-imidazol-2-yl)-phenyl]-isoxazol-5-ylmethyl}-amide;

5-Chloro-thiophene-2-carboxylic acid {3-[4-(imino-pyrrolidin-1-yl-methyl)-2-methoxy-phenyl]-isoxazol-5-ylmethyl}-amide;

5-Chloro-thiophene-2-carboxylic acid {3-[4-(imino-piperidin-1-yl-methyl)-2-methoxy-phenyl]-isoxazol-5-ylmethyl}-amide;

5-Chloro-thiophene-2-carboxylic acid {3-[4-(N,N-dimethyl-carbamimidoyl)-2-ethoxy-phenyl]-isoxazol-5-ylmethyl}-amide;

5-Chloro-thiophene-2-carboxylic acid {3-[2-ethoxy-4-(1-methyl-4,5-dihydro-1H-imidazol-2-yl)-phenyl]-isoxazol-5-ylmethyl}-amide;

5-Chloro-thiophene-2-carboxylic acid {3-[2-ethoxy-4-(imino-pyrrolidin-1-yl-methyl)-phenyl]-isoxazol-5-ylmethyl}-amide;

5-Chloro-thiophene-2-carboxylic acid {3-[2-ethoxy-4-(imino-piperidin-1-yl-methyl)-phenyl]-isoxazol-5-ylmethyl}-amide;

5-Chloro-thiophene-2-carboxylic acid {3-[4-(N,N-dimethyl-carbamimidoyl)-2-isopropoxy-phenyl]-isoxazol-5-ylmethyl}-amide;

5-Chloro-thiophene-2-carboxylic acid {3-[2-isopropoxy-4-(1-methyl-4,5-dihydro-1H-imidazol-2-yl)-phenyl]-isoxazol-5-ylmethyl}-amide;

5-Chloro-thiophene-2-carboxylic acid {3-[4-(imino-pyrrolidin-1-yl-methyl)-2-isopropoxy-phenyl]-isoxazol-5-ylmethyl}-amide;

5-Chloro-thiophene-2-carboxylic acid {3-[4-(imino-piperidin-1-yl-methyl)-2-isopropoxy-phenyl]-isoxazol-5-ylmethyl}-amide;

5-Chloro-thiophene-2-carboxylic acid {3-[4-(N,N-dimethyl-carbamimidoyl)-2-phenoxy-phenyl]-isoxazol-5-ylmethyl}-amide;

5-Chloro-thiophene-2-carboxylic acid {3-[4-(1-methyl-4,5-dihydro-1H-imidazol-2-yl)-2-phenoxy-phenyl]-isoxazol-5-ylmethyl}-amide;

5-Chloro-thiophene-2-carboxylic acid {3-[4-(imino-pyrrolidin-1-yl-methyl)-2-phenoxy-phenyl]-isoxazol-5-ylmethyl}-amide;

5-Chloro-thiophene-2-carboxylic acid {3-[4-(N,N-dimethyl-carbamimidoyl)-2-(4-methoxy-phenoxy)-phenyl]-isoxazol-5-ylmethyl}-amide;

5-Chloro-thiophene-2-carboxylic acid {3-[2-(4-methoxy-phenoxy)-4-(1-methyl-4,5-dihydro-1H-imidazol-2-yl)-phenyl]-isoxazol-5-ylmethyl}-amide;

5-Chloro-thiophene-2-carboxylic acid {3-[4-(imino-pyrrolidin-1-yl-methyl)-2-(4-methoxy-phenoxy)-phenyl]-isoxazol-5-ylmethyl}-amide;

5-Chloro-thiophene-2-carboxylic acid {3-[4-(N,N-dimethyl-carbamimidoyl)-2-methylsulfanyl-phenyl]-4,5-dihydro-isoxazol-5-ylmethyl}-amide;

5-Chloro-thiophene-2-carboxylic acid {3-[4-(1-methyl-4,5-dihydro-1H-imidazol-2-yl)-2-methylsulfanyl-phenyl]-4,5-dihydro-isoxazol-5-ylmethyl}-amide;

5-Chloro-thiophene-2-carboxylic acid {3-[4-(imino-pyrrolidin-1-yl-methyl)-2-methylsulfanyl-phenyl]-4,5-dihydro-isoxazol-5-ylmethyl}-amide;

5-Chloro-thiophene-2-carboxylic acid {3-[4-(imino-piperidin-1-yl-methyl)-2-methylsulfanyl-phenyl]-4,5-dihydro-isoxazol-5-ylmethyl}-amide;

5-Chloro-thiophene-2-carboxylic acid {3-[4-(N,N-dimethyl-carbamimidoyl)-2-methylsulfanyl-phenyl]-isoxazol-5-ylmethyl}-amide;

5-Chloro-thiophene-2-carboxylic acid {3-[4-(1-methyl-4,5-dihydro-1H-imidazol-2-yl)-2-methylsulfanyl-phenyl]-isoxazol-5-ylmethyl}-amide;

5-Chloro-thiophene-2-carboxylic acid {3-[4-(imino-pyrrolidin-1-yl-methyl)-2-methylsulfanyl-phenyl]-isoxazol-5-ylmethyl}-amide;

5-Chloro-thiophene-2-carboxylic acid [3-(4-amino-phenyl)-isoxazol-5-ylmethyl]-amide;

5-Chloro-thiophene-2-carboxylic acid [3-(4-dimethylcarbamoyl-phenyl)-4,5-dihydro-isoxazol-5-ylmethyl]-amide;

5-Chloro-thiophene-2-carboxylic acid {3-[4-(azetidine-1-carbonyl)-phenyl]-4,5-dihydro-isoxazol-5-ylmethyl}-amide;

5-Chloro-thiophene-2-carboxylic acid {3-[4-(pyrrolidine-1-carbonyl)-phenyl]-4,5-dihydro-isoxazol-5-ylmethyl}-amide;

5-Chloro-thiophene-2-carboxylic acid (3-{4-[(2-diethylamino-ethyl)-methyl-carbamoyl]-phenyl}-4,5-dihydro-isoxazol-5-ylmethyl)-amide;

5-Chloro-thiophene-2-carboxylic acid [3-(4-pyridin-4-yl-phenyl)-isoxazol-5-ylmethyl]-amide;

5-Chloro-thiophene-2-carboxylic acid [3-(2'-dimethylaminomethyl-biphenyl-4-yl)-4,5-dihydro-isoxazol-5-ylmethyl]-amide;

5-Chloro-thiophene-2-carboxylic acid [3-(2'-pyrrolidin-1-ylmethyl-biphenyl-4-yl)-4,5-dihydro-isoxazol-5-ylmethyl]-amide;

5-Chloro-thiophene-2-carboxylic acid [3-(2'-piperidin-1-ylmethyl-biphenyl-4-yl)-4,5-dihydro-isoxazol-5-ylmethyl]-amide;

5-Chloro-thiophene-2-carboxylic acid [3-(2'-morpholin-4-ylmethyl-biphenyl-4-yl)-4,5-dihydro-isoxazol-5-ylmethyl]-amide;

5-Chloro-thiophene-2-carboxylic acid [3-(2'-{[(2-methoxy-ethyl)-methyl-amino]-methyl}-biphenyl-4-yl)-4,5-dihydro-isoxazol-5-ylmethyl]-amide;

5-Chloro-thiophene-2-carboxylic acid {3-[2'-(4-methyl-piperazin-1-ylmethyl)-biphenyl-4-yl]-4,5-dihydro-isoxazol-5-ylmethyl}-amide;

5-Chloro-thiophene-2-carboxylic acid [3-(2'-{[(2-dimethylamino-ethyl)-methyl-amino]-methyl}-biphenyl-4-yl)-4,5-dihydro-isoxazol-5-ylmethyl]-amide;

5-Chloro-thiophene-2-carboxylic acid [3-(5'-methoxy-2'-pyrrolidin-1-ylmethyl-biphenyl-4-yl)-4,5-dihydro-isoxazol-5-ylmethyl]-amide;

5-Chloro-thiophene-2-carboxylic acid [3-(5'-chloro-2'-dimethylaminomethyl-biphenyl-4-yl)-4,5-dihydro-isoxazol-5-ylmethyl]-amide;

5-Chloro-thiophene-2-carboxylic acid [3-(5'-chloro-2'-pyrrolidin-1-ylmethyl-biphenyl-4-yl)-4,5-dihydro-isoxazol-5-ylmethyl]-amide;

5-Chloro-thiophene-2-carboxylic acid [3-(2'-formyl-biphenyl-4-yl)-isoxazol-5-ylmethyl]-amide; 5-Chloro-thiophene-2-carboxylic acid [3-(2'-dimethylaminomethyl-biphenyl-4-yl)-isoxazol-5-ylmethyl]-amide;

5-Chloro-thiophene-2-carboxylic acid [3-(5'-methoxy-2'-pyrrolidin-1-ylmethyl-biphenyl-4-yl)-isoxazol-5-ylmethyl]-amide;

5-Chloro-thiophene-2-carboxylic acid [3-(2'-dimethylaminomethyl-4'-methoxy-biphenyl-4-yl)-isoxazol-5-ylmethyl]-amide;

5-Chloro-thiophene-2-carboxylic acid [3-(4'-methoxy-2'-pyrrolidin-1-ylmethyl-biphenyl-4-yl)-isoxazol-5-ylmethyl]-amide;

5-Chloro-thiophene-2-carboxylic acid [3-(4-pyridin-2-yl-phenyl)-4,5-dihydro-isoxazol-5-ylmethyl]-amide;

5-Chloro-thiophene-2-carboxylic acid {3-[4-(pyridin-3-ylamino)-phenyl]-4,5-dihydro-isoxazol-5-ylmethyl}-amide;

5-Chloro-thiophene-2-carboxylic acid {3-[4-(pyridin-4-ylamino)-phenyl]-4,5-dihydro-isoxazol-5-ylmethyl}-amide;

5-Chloro-thiophene-2-carboxylic acid {3-[4-(methyl-pyridin-4-yl-amino)-phenyl]-4,5-dihydro-isoxazol-5-ylmethyl}-amide;

5-Chloro-thiophene-2-carboxylic acid (3-{4-[(3-dimethylamino-propyl)-methyl-amino]-phenyl}-4,5-dihydro-isoxazol-5-ylmethyl)-amide;

5-Chloro-thiophene-2-carboxylic acid {3-[4-(2-oxo-pyrrolidin-1-yl)-phenyl]-4,5-dihydro-isoxazol-5-ylmethyl}-amide;

4-[4-(5-{[(5-Chloro-thiophene-2-carbonyl)-amino]-methyl}-4,5-dihydro-isoxazol-3-yl)-phenyl]-3-oxo-piperazine-1-carboxylic acid benzyl ester;

5-Chloro-thiophene-2-carboxylic acid {3-[4-(3-oxo-morpholin-4-yl)-phenyl]-4,5-dihydro-isoxazol-5-ylmethyl}-amide;

5-Chloro-thiophene-2-carboxylic acid {3-[4-(3-methyl-2-oxo-imidazolidin-1-yl)-phenyl]-4,5-dihydro-isoxazol-5-ylmethyl}-amide;

5-Chloro-thiophene-2-carboxylic acid {3-[4-(5-oxo-[1,4]oxazepan-4-yl)-phenyl]-4,5-dihydro-isoxazol-5-ylmethyl}-amide;

5-Chloro-thiophene-2-carboxylic acid {3-[2-fluoro-4-(pyridin-4-ylamino)-phenyl]-4,5-dihydro-isoxazol-5-ylmethyl}-amide;

5-Chloro-thiophene-2-carboxylic acid {3-[2-fluoro-4-(4-methyl-[1,4]diazepan-1-yl)-phenyl]-4,5-dihydro-isoxazol-5-ylmethyl}-amide;

5-Chloro-thiophene-2-carboxylic acid {3-[4-(pyridin-3-ylamino)-phenyl]-isoxazol-5-ylmethyl}-amide;

5-Chloro-thiophene-2-carboxylic acid {3-[4-(pyridin-4-ylamino)-phenyl]-isoxazol-5-ylmethyl}-amide; and 5-Chloro-thiophene-2-carboxylic acid [3-(2'-pyrrolidin-1-ylmethyl-biphenyl-3-yl)-isoxazol-5-ylmethyl]-amide.

5-Chloro-N-((3-(4-(2-oxopyridin-1(2H)-yl)phenyl)-4,5-dihydroisoxazol-5-yl)methyl)thiophene-2-carboxamide;

5-Chloro-N-((3-(4-(3-fluoro-2-oxopyridin-1(2H)-yl)phenyl)-4,5-dihydroisoxazol-5-yl)methyl)thiophene-2-carboxamide;

5-Chloro-N-((3-(4-(5-fluoro-2-oxopyridin-1(2H)-yl)phenyl)-4,5-dihydroisoxazol-5-yl)methyl)thiophene-2-carboxamide;

5-Chloro-N-((3-(4-(3-methyl-2-oxopyridin-1(2H)-yl)phenyl)-4,5-dihydroisoxazol-5-yl)methyl)thiophene-2-carboxamide;

5-Chloro-N-((3-(4-(3-methoxy-2-oxopyridin-1(2H)-yl)phenyl)-4,5-dihydroisoxazol-5-yl)methyl)thiophene-2-carboxamide;

5-Chloro-N-((3-(4-(3-chloro-2-oxopyridin-1(2H)-yl)phenyl)-4,5-dihydroisoxazol-5-yl)methyl)thiophene-2-carboxamide;

5-Chloro-N-((3-(4-(4-methyl-2-oxopyridin-1(2H)-yl)phenyl)-4,5-dihydroisoxazol-5-yl)methyl)thiophene-2-carboxamide;

5-Chloro-N-((3-(4-(5-methyl-2-oxopyridin-1(2H)-yl)phenyl)-4,5-dihydroisoxazol-5-yl)methyl)thiophene-2-carboxamide;

5-Chloro-N-((3-(4-(5-methoxy-2-oxopyridin-1(2H)-yl)phenyl)-4,5-dihydroisoxazol-5-yl)methyl)thiophene-2-carboxamide;

5-Chloro-N-((3-(4-(5-chloro-2-oxopyridin-1(2H)-yl)phenyl)-4,5-dihydroisoxazol-5-yl)methyl)thiophene-2-carboxamide;

5-Chloro-N-((3-(4-iodophenyl)isoxazol-5-yl)methyl)thiophene-2-carboxamide;

5-Chloro-N-((3-(4-(2-oxopyridin-1(2H)-yl)phenyl)isoxazol-5-yl)methyl)thiophene-2-carboxamide;

5-Chloro-N-((1-(4-(2-oxopyridin-1(2H)-yl)phenyl)-1H-1,2,3-triazol-4-yl)methyl)thiophene-2-carboxamide;

5-Chloro-N-((1-(4-(3-fluoro-2-oxopyridin-1(2H)-yl)phenyl)-1H-1,2,3-triazol-4-yl)methyl)thiophene-2-carboxamide;

5-Chloro-N-((1-(4-(3-chloro-2-oxopyridin-1(2H)-yl)phenyl)-1H-1,2,3-triazol-4-yl)methyl)thiophene-2-carboxamide;

5-Chloro-N-((1-(4-(3-methyl-2-oxopyridin-1(2H)-yl)phenyl)-1H-1,2,3-triazol-4-yl)methyl)thiophene-2-carboxamide;

5-Chloro-N-((1-(4-(3-methoxy-2-oxopyridin-1(2H)-yl)phenyl)-1H-1,2,3-triazol-4-yl)methyl)thiophene-2-carboxamide;

5-Chloro-N-((1-(4-(4-methyl-2-oxopyridin-1(2H)-yl)phenyl)-1H-1,2,3-triazol-4-yl)methyl)thiophene-2-carboxamide;

5-Chloro-N-((1-(4-(5-methyl-2-oxopyridin-1(2H)-yl)phenyl)-1H-1,2,3-triazol-4-yl)methyl)thiophene-2-carboxamide;

5-Chloro-N-((1-(4-(5-methoxy-2-oxopyridin-1(2H)-yl)phenyl)-1H-1,2,3-triazol-4-yl)methyl)thiophene-2-carboxamide;

5-Chloro-N-((1-(4-(5-fluoro-2-oxopyridin-1(2H)-yl)phenyl)-1H-1,2,3-triazol-4-yl)methyl)thiophene-2-carboxamide;

5-Chloro-N-((1-(4-(5-chloro-2-oxopyridin-1(2H)-yl)phenyl)-1H-1,2,3-triazol-4-yl)methyl)thiophene-2-carboxamide;

5-Chloro-N-((1-(4-(2-oxopiperidin-1-yl)phenyl)-1H-1,2,3-triazol-4-yl)methyl)thiophene-2-carboxamide;

5-Chloro-N-((1-(4-(3-oxomorpholino)phenyl)-1H-1,2,3-triazol-4-yl)methyl)thiophene-2-carboxamide;

5-Chloro-N-((1-(4-(3-oxothiomorpholino)phenyl)-1H-1,2,3-triazol-4-yl)methyl)thiophene-2-carboxamide;

5-Chloro-N-((1-(4-(5-oxo-1,4-oxazepan-4-yl)phenyl)-1H-1,2,3-triazol-4-yl)methyl)thiophene-2-carboxamide;

5-Chloro-N-((1-(2-fluoro-4-iodophenyl)-1H-1,2,3-triazol-4-yl)methyl)thiophene-2-carboxamide;

5-Chloro-N-((1-(2-fluoro-4-(2-oxopyridin-1(2H)-yl)phenyl)-1H-1,2,3-triazol-4-yl)methyl)thiophene-2-carboxamide;

5-Chloro-N-((1-(2-fluoro-4-(3-oxomorpholino)phenyl)-1H-1,2,3-triazol-4-yl)methyl)thiophene-2-carboxamide;

5-Chloro-N-((1-(2-hyroxy-4-(2-oxopyridin-1(2H)-yl)phenyl)-1H-1,2,3-triazol-4-yl)methyl)thiophene-2-carboxamide;

5-Chloro-N-((1-(2-(4-methylpiperazin-1-yl)-4-(2-oxopyridin-1(2H)-yl)phenyl)-1H-1,2,3-triazol-4-yl)methyl)thiophene-2-carboxamide;

5-Chloro-N-((1-(5-(2-oxopyridin-1(2H)-yl)pyridin-2-yl)-1H-1,2,3-triazol-4-yl)methyl)thiophene-2-carboxamide;

5-Chloro-N-((3-(6-(2-oxopyridin-1(2H)-yl)pyridin-3-yl)isoxazol-5-yl)methyl)thiophene-2-carboxamide;

5-Chloro-N-((3-(4-(2-oxopyridin-1(2H)-yl)phenyl)-1,2,4-oxadiazol-5-yl)methyl)thiophene-2-carboxamide;

5-Chloro-N-((1-(4-(1-methyl-4,5-dihydro-1H-imidazol-2-yl)phenyl)-1H-1,2,3-triazol-4-yl)methyl)thiophene-2-carboxamide;

N-((1-(4-(N,N-Dimethylcarbamimidoyl)phenyl)-1H-1,2,3-triazol-4-yl)methyl)-5-chlorothiophene-2-carboxamide;

N-((1-(4-(N-Ethyl-N-methylcarbamimidoyl)phenyl)-1H-1,2,3-triazol-4-yl)methyl)-5-chlorothiophene-2-carboxamide;

N-((1-(4-(N-Methyl-N-propylcarbamimidoyl)phenyl)-1H-1,2,3-triazol-4-yl)methyl)-5-chlorothiophene-2-carboxamide;

N-((1-(4-(N-(2-Methoxyethyl)-N-methylcarbamimidoyl)phenyl)-1H-1,2,3-triazol-4-yl)methyl)-5-chlorothiophene-2-carboxamide;

N-((1-(4-(Azetidin-1-yl(imino)methyl)phenyl)-1H-1,2,3-triazol-4-yl)methyl)-5-chlorothiophene-2-carboxamide;

5-Chloro-N-((1-(4-(imino(pyrrolidin-1-yl)methyl)phenyl)-1H-1,2,3-triazol-4-yl)methyl)thiophene-2-carboxamide;

5-Chloro-N-((1-(4-(imino(piperidin-1-yl)methyl)phenyl)-1H-1,2,3-triazol-4-yl)methyl)thiophene-2-carboxamide;

N-((1-(4-(N,N-Dimethylcarbamimidoyl)-2-fluorophenyl)-1H-1,2,3-triazol-4-yl)methyl)-5-chlorothiophene-2-carboxamide;

N-((1-(4-(Azetidin-1-yl(imino)methyl)-2-fluorophenyl)-1H-1,2,3-triazol-4-yl)methyl)-5-chlorothiophene-2-carboxamide;

5-Chloro-N-((1-(2-fluoro-4-(imino(pyrrolidin-1-yl)methyl)phenyl)-1H-1,2,3-triazol-4-yl)methyl)thiophene-2-carboxamide;

5-Chloro-N-((1-(2-fluoro-4-(imino(piperidin-1-yl)methyl)phenyl)-1H-1,2,3-triazol-4-yl)methyl)thiophene-2-carboxamide;

5-Chloro-N-((1-(2-fluoro-4-(1-methyl-4,5-dihydro-1H-imidazol-2-yl)phenyl)-1H-1,2,3-triazol-4-yl)methyl)thiophene-2-carboxamide;

N-((1-(4-(N,N-Dimethylcarbamimidoyl)phenyl)-1H-pyrazol-4-yl)methyl)-5-chlorothiophene-2-carboxamide;

5-Chloro-N-((1-(4-(1-methyl-4,5-dihydro-1H-imidazol-2-yl)phenyl)-1H-pyrazol-4-yl)methyl)thiophene-2-carboxamide;

N-((1-(4-(Azetidin-1-yl(imino)methyl)phenyl)-1H-pyrazol-4-yl)methyl)-5-chlorothiophene-2-carboxamide;

5-Chloro-N-((1-(4-(imino(pyrrolidin-1-yl)methyl)phenyl)-1H-pyrazol-4-yl)methyl)thiophene-2-carboxamide;

5-Chloro-N-((1-(4-(imino(piperidin-1-yl)methyl)phenyl)-1H-pyrazol-4-yl)methyl)thiophene-2-carboxamide;

N-((5-(4-(N,N-Dimethylcarbamimidoyl)phenyl)isoxazol-3-yl)methyl)-5-chlorothiophene-2-carboxamide;

5-Chloro-N-((5-(4-(1-methyl-4,5-dihydro-1H-imidazol-2-yl)phenyl)isoxazol-3-yl)methyl)thiophene-2-carboxamide;

5-Chloro-N-((5-(4-(imino(pyrrolidin-1-yl)methyl)phenyl)isoxazol-3-yl)methyl)thiophene-2-carboxamide;

5-Chloro-N-((5-(4-(imino(piperidin-1-yl)methyl)phenyl)isoxazol-3-yl)methyl)thiophene-2-carboxamide;

N-((3-(4-(N,N-Dimethylcarbamimidoyl)phenyl)-1,2,4-oxadiazol-5-yl)methyl)-5-chlorothiophene-2-carboxamide;

5-Chloro-N-((3-(4-(1-methyl-4,5-dihydro-1H-imidazol-2-yl)phenyl)-1,2,4-oxadiazol-5-yl)methyl)thiophene-2-carboxamide;

5-Chloro-N-((3-(4-(imino(pyrrolidin-1-yl)methyl)phenyl)-1,2,4-oxadiazol-5-yl)methyl)thiophene-2-carboxamide;

5-Chloro-N-((3-(4-(imino(piperidin-1-yl)methyl)phenyl)-1,2,4-oxadiazol-5-yl)methyl)thiophene-2-carboxamide;

N-((2-(4-(N,N-Dimethylcarbamimidoyl)phenyl)oxazol-4-yl)methyl)-5-chlorothiophene-2-carboxamide;

5-Chloro-N-((2-(4-(1-methyl-4,5-dihydro-1H-imidazol-2-yl)phenyl)oxazol-4-yl)methyl)thiophene-2-carboxamide;

5-Chloro-N-((2-(4-(imino(pyrrolidin-1-yl)methyl)phenyl)oxazol-4-yl)methyl)thiophene-2-carboxamide;

5-Chloro-N-((2-(4-(imino(piperidin-1-yl)methyl)phenyl)oxazol-4-yl)methyl)thiophene-2-carboxamide;

Ethyl 1-((4-(4-((2-chlorothiophene-5-carboxamido)methyl)oxazol-2-yl)phenyl)(imino)methyl)piperidine-4-carboxylate;

N-((2-(4-(N-Ethyl-N-methylcarbamimidoyl)phenyl)oxazol-4-yl)methyl)-5-chlorothiophene-2-carboxamide;

N-((2-(4-(N-Methyl-N-propylcarbamimidoyl)phenyl)oxazol-4-yl)methyl)-5-chlorothiophene-2-carboxamide;

N-((2-(4-(N-(2-(Dimethylamino)ethyl)-N-methylcarbamimidoyl)phenyl)oxazol-4-yl)methyl)-5-chlorothiophene-2-carboxamide;

N-((2-(4-(N-(2-Methoxyethyl)-N-methylcarbamimidoyl)phenyl)oxazol-4-yl)methyl)-5-chlorothiophene-2-carboxamide;

1-((4-(4-((2-Chlorothiophene-5-carboxamido)methyl)oxazol-2-yl)phenyl)(imino)methyl)piperidine-4-carboxamide;

N-((2-(4-(N-Methylcarbamimidoyl)phenyl)oxazol-4-yl)methyl)-5-chlorothiophene-2-carboxamide;

N-((2-(4-(N-(Furan-2-ylmethyl)-N-methylcarbamimidoyl)phenyl)oxazol-4-yl)methyl)-5-chlorothiophene-2-carboxamide;

N-((2-(4-(N,N-Dimethylcarbamimidoyl)phenyl)thiazol-4-yl)methyl)-5-chlorothiophene-2-carboxamide;

5-Chloro-N-((2-(4-(1-methyl-4,5-dihydro-1H-imidazol-2-yl)phenyl)thiazol-4-yl)methyl)thiophene-2-carboxamide;

5-Chloro-N-((2-(4-(imino(pyrrolidin-1-yl)methyl)phenyl)thiazol-4-yl)methyl)thiophene-2-carboxamide;

5-Chloro-N-((2-(4-(imino(piperidin-1-yl)methyl)phenyl)thiazol-4-yl)methyl)thiophene-2-carboxamide;

Ethyl 1-((4-(4-((2-chlorothiophene-5-carboxamido)methyl)thiazol-2-yl)phenyl)(imino)methyl)piperidine-4-carboxylate;

N-((2-(4-(N-(2-(Dimethylamino)ethyl)-N-methylcarbamimidoyl)phenyl)thiazol-4-yl)methyl)-5-chlorothiophene-2-carboxamide;

N-((2-(4-(N-(Furan-2-ylmethyl)-N-methylcarbamimidoyl)phenyl)thiazol-4-yl)methyl)-5-chlorothiophene-2-carboxamide;

N-((2-(4-(N-Methyl-N-(prop-2-ynyl)carbamimidoyl)phenyl)thiazol-4-yl)methyl)-5-chlorothiophene-2-carboxamide;

N-((2-(4-(N-Methylcarbamimidoyl)phenyl)thiazol-4-yl)methyl)-5-chlorothiophene-2-carboxamide;

5-Chloro-N-((4-(4-(imino(pyrrolidin-1-yl)methyl)phenyl)oxazol-2-yl)methyl)thiophene-2-carboxamide;

N-((4-(4-(N,N-Dimethylcarbamimidoyl)phenyl)thiazol-2-yl)methyl)-5-chlorothiophene-2-carboxamide;

5-Chloro-N-((4-(4-(1-methyl-4,5-dihydro-1H-imidazol-2-yl)phenyl)thiazol-2-yl)methyl)thiophene-2-carboxamide;

5-Chloro-N-((4-(4-(imino(pyrrolidin-1-yl)methyl)phenyl)thiazol-2-yl)methyl)thiophene-2-carboxamide;

5-Chloro-N-((4-(4-(imino(piperidin-1-yl)methyl)phenyl)thiazol-2-yl)methyl)thiophene-2-carboxamide;

N-((1-(4-(N,N-Dimethylcarbamimidoyl)phenyl)-1H-imidazol-4-yl)methyl)-5-chlorothiophene-2-carboxamide;

5-Chloro-N-((1-(4-(1-methyl-4,5-dihydro-1H-imidazol-2-yl)phenyl)-1H-imidazol-4-yl)methyl)thiophene-2-carboxamide;

N-((1-(4-(Azetidin-1-yl(imino)methyl)phenyl)-1H-imidazol-4-yl)methyl)-5-chlorothiophene-2-carboxamide;

5-Chloro-N-((1-(4-(imino(pyrrolidin-1-yl)methyl)phenyl)-1H-imidazol-4-yl)methyl)thiophene-2-carboxamide;

5-Chloro-N-((1-(4-(imino(piperidin-1-yl)methyl)phenyl)-1H-imidazol-4-yl)methyl)thiophene-2-carboxamide;

N-((5-(4-(N,N-Dimethylcarbamimidoyl)phenyl)pyridin-3-yl)methyl)-5-chlorothiophene-2-carboxamide;

5-Chloro-N-((5-(4-(1-methyl-4,5-dihydro-1H-imidazol-2-yl)phenyl)pyridin-3-yl)methyl)thiophene-2-carboxamide;

N-((5-(4-(Azetidin-1-yl(imino)methyl)phenyl)pyridin-3-yl)methyl)-5-chlorothiophene-2-carboxamide;

5-Chloro-N-((5-(4-(imino(pyrrolidin-1-yl)methyl)phenyl)pyridin-3-yl)methyl)thiophene-2-carboxamide;

5-Chloro-N-((5-(4-(imino(piperidin-1-yl)methyl)phenyl)pyridin-3-yl)methyl)thiophene-2-carboxamide;

N-((5-(4-(N,N-Dimethylcarbamimidoyl)phenyl)-2-fluorophenyl)methyl)-5-chlorothiophene-2-carboxamide;

5-Chloro-N-((5-(4-(1-methyl-4,5-dihydro-1H-imidazol-2-yl)phenyl)-2-fluorophenyl)methyl)thiophene-2-carboxamide;

5-Chloro-N-((5-(4-(imino(pyrrolidin-1-yl)methyl)phenyl)-2-fluorophenyl)methyl)thiophene-2-carboxamide;

N-((3-(4-(N,N-Dimethylcarbamimidoyl)phenyl)-4-fluorophenyl)methyl)-5-chlorothiophene-2-carboxamide;

5-Chloro-N-((3-(4-(1-methyl-4,5-dihydro-1H-imidazol-2-yl)phenyl)-4-fluorophenyl)methyl)thiophene-2-carboxamide;

5-Chloro-N-((3-(4-(imino(pyrrolidin-1-yl)methyl)phenyl)-4-fluorophenyl)methyl)thiophene-2-carboxamide;

N-((3-(4-(N,N-Dimethylcarbamimidoyl)phenyl)phenyl)methyl)-5-chlorothiophene-2-carboxamide;

5-Chloro-N-((3-(4-(1-methyl-4,5-dihydro-1H-imidazol-2-yl)phenyl)phenyl)methyl)thiophene-2-carboxamide;

5-Chloro-N-((3-(4-(imino(pyrrolidin-1-yl)methyl)phenyl)phenyl)methyl)thiophene-2-carboxamide;

5-Chloro-N-((1-(6-(4-methyl-1,4-diazepan-1-yl)pyridin-3-yl)-1H-1,2,3-triazol-4-yl)methyl)thiophene-2-carboxamide;

N-((1-(6-(1,4-Diazepan-1-yl)pyridin-3-yl)-1H-1,2,3-triazol-4-yl)methyl)-5-chlorothiophene-2-carboxamide;

N-((1-(6-(1,4-Oxazepan-4-yl)pyridin-3-yl)-1H-1,2,3-triazol-4-yl)methyl)-5-chlorothiophene-2-carboxamide;

5-Chloro-N-((1-(6-morpholinopyridin-3-yl)-1H-1,2,3-triazol-4-yl)methyl)thiophene-2-carboxamide;

5-Chloro-N-((1-(6-(3-oxomorpholino)pyridin-3-yl)-1H-1,2,3-triazol-4-yl)methyl)thiophene-2-carboxamide;

5-Chloro-N-((1-(6-(2-oxopiperidin-1-yl)pyridin-3-yl)-1H-1,2,3-triazol-4-yl)methyl)thiophene-2-carboxamide;

5-Chloro-N-((1-(6-(2-oxopyridin-1(2H)-yl)pyridin-3-yl)-1H-1,2,3-triazol-4-yl)methyl)thiophene-2-carboxamide;

5-Chloro-N-((1-(6-(piperazin-1-yl)pyridin-3-yl)-1H-1,2,3-triazol-4-yl)methyl)thiophene-2-carboxamide;

5-Chloro-N-((1-(6-(4-methylpiperazin-1-yl)pyridin-3-yl)-1H-1,2,3-triazol-4-yl)methyl)thiophene-2-carboxamide;

5-Chloro-N-((1-(6-(piperidin-1-yl)pyridin-3-yl)-1H-1,2,3-triazol-4-yl)methyl)thiophene-2-carboxamide;

5-Chloro-N-((3-(4-(8-(trifluoromethyl)quinolin-4-ylamino)phenyl)-4,5-dihydroisoxazol-5-yl)methyl)thiophene-2-carboxamide;

5-Chloro-N-((3-(4-(7-(trifluoromethyl)quinolin-4-ylamino)phenyl)-4,5-dihydroisoxazol-5-yl)methyl)thiophene-2-carboxamide;

5-Chloro-N-((3-(4-(6-(trifluoromethyl)quinolin-4-ylamino)phenyl)-4,5-dihydroisoxazol-5-yl)methyl)thiophene-2-carboxamide;

5-Chloro-N-((3-(4-(quinolin-6-ylamino)phenyl)-4,5-dihydroisoxazol-5-yl)methyl)thiophene-2-carboxamide;

5-Chloro-N-((3-(4-(2,5-dihydro-1H-pyrrole-1-carbonyl)phenyl)-4,5-dihydroisoxazol-5-yl)methyl)thiophene-2-carboxamide;

5-Chloro-N-((3-(4-(2,5-dihydro-1H-pyrrole-1-carbonyl)phenyl)-4,5-dihydroisoxazol-5-yl)methyl)thiophene-2-carboxamide;

N-((3-(4-((2-Hydroxypropyl)carbamoyl)phenyl)-4,5-dihydroisoxazol-5-yl)methyl)-5-chlorothiophene-2-carboxamide;

5-Chloro-N-((3-(4-(3-methylpyridin-4-ylamino)phenyl)-4,5-dihydroisoxazol-5-yl)methyl)thiophene-2-carboxamide;

5-Chloro-N-((3-(4-(2-ethoxypyridin-4-ylamino)phenyl)-4,5-dihydroisoxazol-5-yl)methyl)thiophene-2-carboxamide;

5-Chloro-N-((3-(4-(3,5-dichloropyridin-4-ylamino)phenyl)-4,5-dihydroisoxazol-5-yl)methyl)thiophene-2-carboxamide; and 5-Chloro-N-((3-(4-(3-(trifluoromethyl)pyridin-4-ylamino)phenyl)-4,5-dihydroisoxazol-5-yl)methyl)thiophene-2-carboxamide All the preferred, more preferred, and most preferred compounds listed above are selective inhibitors of Factor Xa.

Compositions

The present invention further provides compositions comprising one or more compounds of formula (I) or a tautomer or a pharmaceutically acceptable salt thereof, and a pharmaceutically acceptable carrier. It will be appreciated that the compounds of formula (I) in this invention may be derivatized at functional groups to provide prodrug derivatives which are capable of conversion back to the parent compounds in vivo. Examples of such prodrugs include the physiologically acceptable and metabolically labile ester derivatives, such as methoxymethyl esters, methylthiomethyl esters, or pivaloyloxymethyl esters derived from a hydroxyl group of the compound or a carbamoyl moiety derived from an amino group of the compound. Additionally, any physiologically acceptable equivalents of the compounds of formula (I), similar to metabolically labile esters or carbamates, which are capable of producing the parent compounds of formula (I) in vivo, are within the scope of this invention.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Furthermore, the basic nitrogen-containing groups may be quaternized with agents like lower alkyl halides, such as methyl, ethyl, propyl and butyl chlorides, bromides and iodides; dialkyl sulfates, such as dimethyl, diethyl, dibutyl and diamyl sulfates, long chain halides, such as decyl, lauryl, myristyl and stearyl chlorides, bromides and iodides; aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system, etc.), increase oral availability, increase solubility to allow administration by injection, alter metabolism and alter rate of excretion.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, bioavailability modifiers and combinations of these.

Pharmaceutical formulations may be prepared as liquid suspensions or solutions using a sterile liquid, such as oil, water, alcohol, and combinations thereof. Pharmaceutically suitable surfactants, suspending agents or emulsifying agents, may be added for oral or parenteral administration. Suspensions may include oils, such as peanut oil, sesame oil, cottonseed oil, corn oil and olive oil. Suspension preparation may also contain esters of fatty acids, such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol. Ethers, such as poly(ethyleneglycol), petroleum hydrocarbons, such as mineral oil and petrolatum, and water may also be used in suspension formulations.

Pharmaceutically acceptable carriers that may be used in these compositions include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being. Such pharmaceutical compositions of the invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously. The formulations of the invention may be designed as short-acting, fast-releasing, or long-acting. Still further, compounds can be administered in a local rather than systemic means, such as administration (e.g., injection) as a sustained release formulation.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The pharmaceutical compositions of this invention may be in any orally acceptable dosage form, including capsules, tablets, aqueous suspensions or solutions. In the case of tablets for oral use, carriers that are commonly used include lactose and corn starch. Lubricating agents, such as magnesium stearate, are also typically added. For a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be in a topical form, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include mineral oil, sorbitan monostearate, polysorbate 60, cetyl esters, wax, cetyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative, such as benzylalkonium chloride. Alternatively, for ophthalmic uses, the pharmaceutical compositions may be formulated in an ointment, such as petrolatum.

The pharmaceutical compositions of this invention may also be administered by nasal aerosol or inhalation. Such compositions are prepared according to techniques known in the art of pharmaceutical formulation and may be prepared as solutions in saline, employing benzyl alcohol or other suitable preservatives, absorption promoters to enhance bioavailability, fluorocarbons and/or other conventional solubilizing or dispersing agents.

Any of the above dosage forms containing effective amounts are within the bounds of routine experimentation and within the scope of the invention. A therapeutically effective dose may vary depending upon the route of administration and dosage form. The preferred compound or compounds of the invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

Besides those representative dosage forms described above, pharmaceutically acceptable excipients and carriers and dosage forms are generally known to those skilled in the art and are included in the invention. It should be understood that a specific dosage and treatment regimen for any particular patient will depend upon a variety of factors, including the activity of the specific compound employed, the age, body weight, general health, sex and diet of the patient, and the time of administration, rate of excretion, drug combination, judgment of the treating physician and severity of the particular disease being treated. The amount of active ingredient(s) will also depend upon the particular compound and other therapeutic agent, if present, in the composition.

Methods of Use

The invention provides methods of inhibiting or decreasing Factor Xa activity as well as treating or ameliorating a Factor Xa associated state, symptom, disorder or disease in a patient in need thereof (e.g., human or non-human). "Treating" within the context of the invention means an alleviation of symptoms associated with a disorder or disease, or halt of further progression or worsening of those symptoms, or prevention or prophylaxis of the disease or disorder.

The term "mammal" includes organisms which express Factor Xa. Examples of mammals include mice, rats, cows, sheep, pigs, goats, horses, bears, monkeys, dogs, cats and, preferably, humans. Transgenic organisms which express Factor Xa are also included in this definition.

The inventive methods comprise administering an effective amount of a compound or composition described herein to a mammal or non-human animal. As used herein, "effective amount" of a compound or composition of the invention includes those amounts that antagonize or inhibit Factor Xa. An amount which antagonizes or inhibits Factor Xa is detectable, for example, by any assay capable of determining Factor Xa activity, including the one described below as an illustrative testing method. Effective amounts may also include those amounts which alleviate symptoms of a Factor Xa associated disorder treatable by inhibiting Factor Xa. Accordingly, "antagonists of Factor Xa" include compounds which interact with the Factor Xa and modulate, e.g., inhibit or decrease, the ability of a second compound, e.g., another Factor Xa ligand, to interact with the Factor Xa. The Factor Xa binding compounds are preferably antagonists of Factor Xa. The language "Factor Xa binding compound" (e.g., exhibits binding affinity to the receptor) includes those compounds which interact with Factor Xa resulting in modulation of the activity of Factor Xa. Factor Xa binding compounds may be identified using an in vitro (e.g., cell and non-cell based) or in vivo method. A description of an in vitro method is provided below.

The amount of compound present in the methods and compositions described herein should be sufficient to cause a detectable decrease in the severity of the disorder, as measured by any of the assays described in the examples. The amount of Factor Xa modulator needed will depend on the effectiveness of the modulator for the given cell type and the length of time required to treat the disorder. In certain embodiments, the compositions of this invention may further comprise another therapeutic agent. When a second agent is used, the second agent may be administered either as a separate dosage form or as part of a single dosage form with the compounds or compositions of this invention. While one or more of the inventive compounds can be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the two or more therapeutic agents concurrently or sequentially. The agents may be administered in any order. Alternatively, the multiple therapeutic agents can be combined into a single composition that can be administered to the patient. For instance, a single pharmaceutical composition could comprise the compound or pharmaceutically acceptable salt or solvate according to the formula I, another therapeutic agent (e.g., methotrexate) or a pharmaceutically acceptable salt or solvate thereof, and a pharmaceutically acceptable excipient or carrier.

The invention comprises a compound having the formula I, a method for making an inventive compound, a method for making a pharmaceutical composition from at least one inventive compound and at least one pharmaceutically acceptable carrier or excipient, and a method of using one or more inventive compounds to treat a variety of disorders, symptoms and diseases (e.g., inflammatory, autoimmune, neurological, neurodegenerative, oncology and cardiovascular), such as RA, osteoarthritis, irritable bowel disease IBD, asthma, chronic obstructive pulmonary disease COPD and MS. The inventive compounds and their pharmaceutically acceptable salts and/or neutral compositions may be formulated together with a pharmaceutically acceptable excipient or carrier and the resulting composition may be administered in vivo to mammals, such as men, women and animals, to treat a variety of disorders, symptoms and diseases. Furthermore, the inventive compounds can be used to prepare a medicament that is useful for treating a variety of disorders, symptoms and diseases.

Kits

Still another aspect of this invention is to provide a kit comprising separate containers in a single package, wherein the inventive pharmaceutical compounds, compositions and/or salts thereof are used in combination with pharmaceutically acceptable carriers to treat states, disorders, symptoms and diseases where Factor Xa plays a role.

EXAMPLES

Example 1

5-Chloro-thiophene-2-carboxylic acid [3-(4-bromo-phenyl)-4,5-dihydro-isoxazol-5-ylmethyl]-amide (7)

SCHEME 1

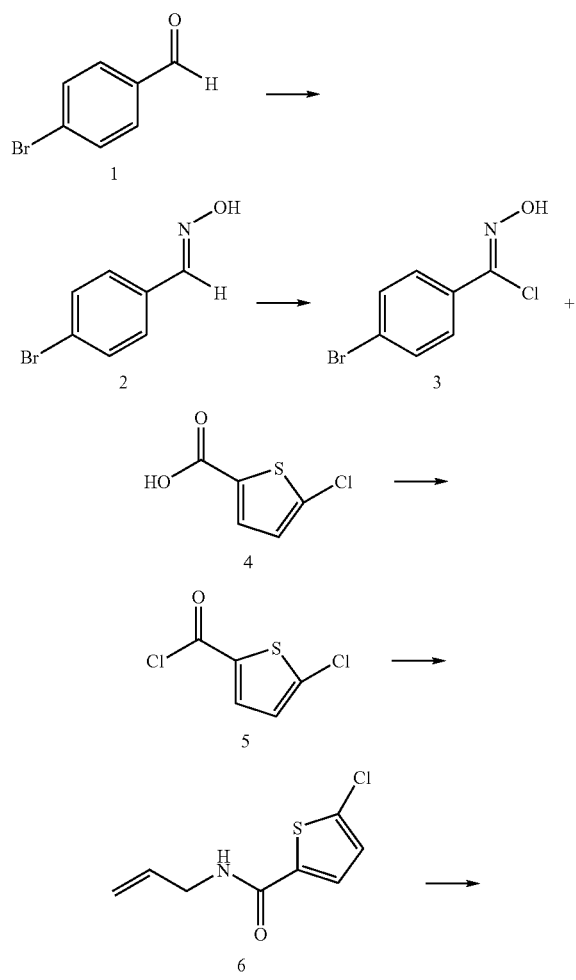

-continued

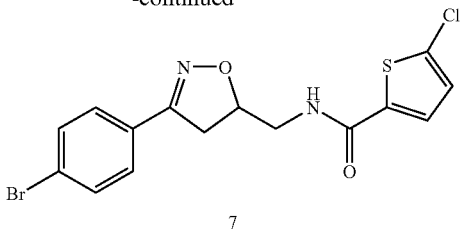

Step 1:

Aldehyde 1 was dissolved in 200 mL ethanol, then treated with pyridine (24 mL, 297 mmol) and hydroxylamine hydrochloride (19.58 g, 284 mmol) affording a clear colorless solution which was stirred overnight. The following day the reaction was determined to be complete by HPLC and TLC and was diluted with water (1 L) and filtered affording 2 as a white solid (69 g, quantitative) which contained a small amount of ethanol. $^1$H NMR (DMSO-$d_6$, 400 MHz): δ 11.38 (s, 1H), δ 8.09 (s, 1H), δ 7.79 (d, 2H), δ 7.50 (d, 2H).

Step 2:

The undried product from the previous step (270 mmol, theoretical) was dissolved in DMF (140 mL) and treated with N-chlorosuccinimide (38 g, 284 mmol) affording a yellow suspension which was stirred at room temperature overnight. The following day the reaction was diluted with water (1 L), filtered, then aspirated to dryness affording desired product 3 as a slightly yellow solid (75.6 g, quantitative) which contained a small amount of DMF. $^1$H NMR (DMSO-$d_6$, 400 MHz): δ 7.71 (d, 2H), δ 7.68 (d, 2H).

Step 3:

Carboxylic acid 4 (40 g, 246 mmol) was suspended in dichloromethane (200 mL) then treated with oxalyl chloride (32 mL, 368 mmol) and 15 drops of DMF. The reaction generated a steady flow of gas and was stirred at room temperature overnight. The following day all solids had dissolved and the reaction was pale brown. A small amount was removed, diluted with methanol and a small amount of triethyl amine, concentrated and examined by NMR which showed only the methyl ester. It was concentrated to a brown oil, the flask was then stoppered and sealed with Teflon tape. No yield calculated. Methyl ester: $^1$H NMR (DMSO-$d_6$, 400 MHz): δ 7.58 (d, 1H), δ 6.90 (d, 1H), δ 3.82 (s, 3H).

Step 4:

Allyl amine (56.8 mL, 91 mmol) was dissolved in 100 mL dichloromethane, cooled to 0° C., then treated with triethylamine (21 mL, 155 mmol) followed by slow addition of acid chloride 5 (15 g, 83 mmol) in a small amount of dichloromethane. After the addition was determined to be complete by TLC it was then partitioned with aqueous NaHCO$_3$ separated, and the organic layer extracted once again with dichloromethane. The combined organic layers were dried over Na$_2$SO$_4$, concentrated then purified by filtration through a short plug of silica gel affording the desired product (6) as a light beige crystalline solid (24 g, quant.). $^1$H NMR (DMSO-$d_6$, 400 MHz): δ 8.79 (m, 1H), 7.64 (d, 1H), 7.15 (d, 1H), 5.81 (m, 1H), 5.11 (d, 1H), 5.05 (d, 1H), 3.80 (m, 2H).

Step 5:

Alkene 6 (4.00 g, 20 mmol) and triethylamine (3.62 mL, 26 mmol) were heated to 90° C. until all solids dissolved. The mixture was then treated with 3 (5.14 g, 22 mmol) slowly over 5 min. After all 3 was added the reaction was checked by TLC and more 3 was added if any starting alkene was present. Upon complete consumption of 6 the reaction mixture was cooled to room temperature, concentrated in vacuo, then suspended in a small amount of methanol (ca. 5 mL) and triturated with water affording a white solid. The solid was filtered and dried affording the desired isoxazolidinone (7) as a white solid (6.02 g, 75%). $^1$H NMR (DMSO-$d_6$, 400 MHz): δ 8.88 (m, 1H), δ 7.89 (d, 2H), δ 7.80 (d, 2H), δ 7.61 (s, 1H), δ 7.14 (s, 1H), δ 4.90 (m, 1H), δ 3.52 (m, 1H), δ 3.40 (t, 1H), δ 3.21 (dd, 1H).

Example 2

5-Chloro-thiophene-2-carboxylic acid [3-(4-bromo-phenyl)-isoxazol-5-ylmethyl]-amide

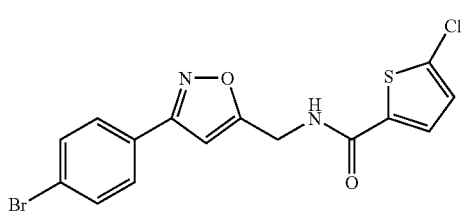

The titled compound was made by the procedure similar to that described in Example 1 using propargyl amine in place of allyl amine. $^1$H NMR (DMSO-$d_6$, 400 MHz): δ 9.50(m, 1H), δ 7.79 (d, 2H), 7.62 (m, 3H), δ 7.18 (d, 1H), δ 6.94 (s, 1H), δ 4.78 (d, 2H).

Example 3

5-Chloro-thiophene-2-carboxylic acid [3-(3-bromo-phenyl)-4,5-dihydro-isoxazol-5-ylmethyl]-amide

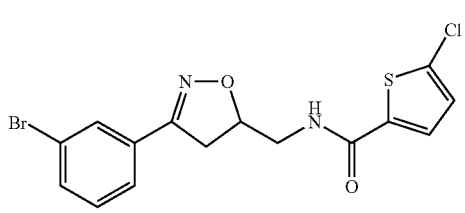

The titled compound was made by the procedure similar to that described in Example 1. $^1$H NMR (DMSO-$d_6$, 400 MHz): δ 8.87 (t, 1H), δ 7.78 (s, 1H), δ 7.63 (m, 3H), δ 7.37 (t, 1H), δ 7.15 (s, 1H), 4.81δ (m, 1H), 3.47 (dd, 1H), δ 3.39 (t, 1H), δ 3.19 (dd, 1H).

Example 4

5-Chloro-thiophene-2-carboxylic acid [3-(3-bromo-phenyl)-isoxazol-5-ylmethyl]-amide

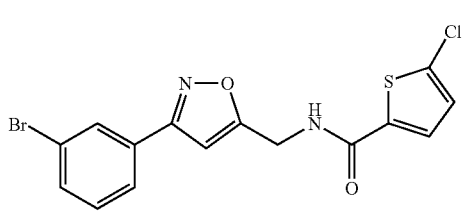

The titled compound was made by the procedure similar to that described in Example 2. $^1$H NMR (DMSO-$d_6$, 400 MHz): δ 9.30 (t, 1H), δ 8.02 (s, 1H), δ 7.87 (d, 1H), δ 7.62 (m, 3H), δ 7.42 (t, 1H), δ 7.18 (m, 2H), 7.02 (s, 1H), δ 4.59 (d, 2H).

Example 5

5-Chloro-thiophene-2-carboxylic acid [3-(4-phenoxy-phenyl)-4,5-dihydro-isoxazol-5-ylmethyl]-amide

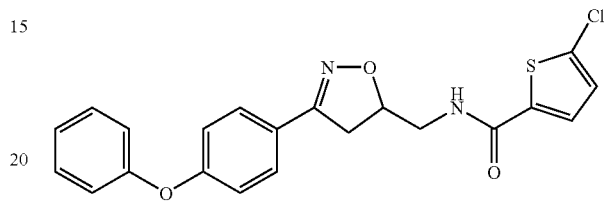

The titled compound was made by the procedure similar to that described in Example 1. MS found for $C_{21}H_{17}ClN_2O_3S$ as $(M+H)^+$ 413.5.

Example 6

5-Chloro-thiophene-2-carboxylic acid [3-(4-phenoxy-phenyl)-isoxazol-5-ylmethyl]-amide

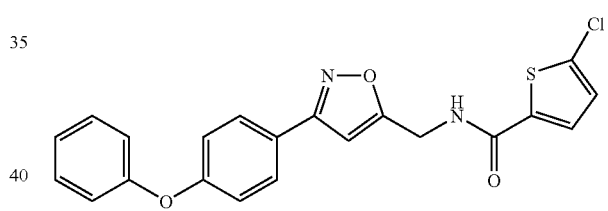

The titled compound was made by the procedure similar to that described in Example 2. MS found for $C_{21}H_{15}ClN_2O_3S$ as $(M+H)^+$ 411.4, 413.4.

Example 7

5-Chloro-thiophene-2-carboxylic acid [3-(4-cyano-phenyl)-4,5-dihydro-isoxazol-5-ylmethyl]-amide

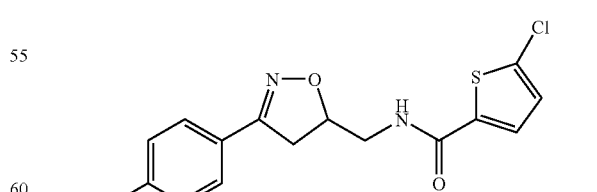

The titled compound was made by the procedure similar to that described in Example 1. $^1$H NMR (DMSO-$d_6$, 400 MHz): δ 8.89 (t, 1H), δ 7.88 (d, 2H), δ 7.78 (d, 2H), δ 7.61 (d, 1H), δ 7.12 (d, 1H), δ 7.90 (m, 1H), δ 3.51 (dd, 1H), 3.41 (t, 1H), 3.20 (dd, 1H).

Example 8

5-Chloro-thiophene-2-carboxylic acid {3-[4-(N,N-dimethyl-carbamimidoyl)-phenyl]-4,5-dihydro-isoxazol-5-ylmethyl}-amide

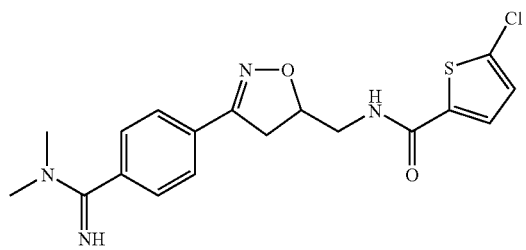

The nitrile from example 7 (1.00 g, 2.9 mmol) and triethylamine (1.62 mL, 11.6 mmol) were combined with 30 mL of 1,4-dioxane and placed under an atmosphere of $H_2S$ overnight. The next day the crude mixture was evaporated in vacuo then diluted with 30 mL of acetone and methyl iodide (1.44 mL, 23.2 mmol), then refluxed until all of the starting thioamide was converted to the imidate (two hours). The reaction mixture was then cooled and concentrated by rotary evaporation affording a thick orange foam. The orange foam was dissolved in 30 mL of THF and a 7.5 mL aliquot was removed and treated with 7.5 mL of a THF solution containing dimethyl amine (0.5 M) and acetic acid (7.5 M). The resulting light yellow mixture was stirred at rt overnight giving clean conversion to the amidine. The reaction mixture was concentrated and purified by prep-HPLC affording the titled compound as a white powder containing TFA. MS found for $C_{18}H_{19}ClN_4O_2S$ as $(M+H)^+$ 391.0, 393.0.

Example 9

5-Chloro-thiophene-2-carboxylic acid {3-[4-(1-methyl-4,5-dihydro-1H-imidazol-2-yl)-phenyl]-4,5-dihydro-isoxazol-5-ylmethyl}-amide

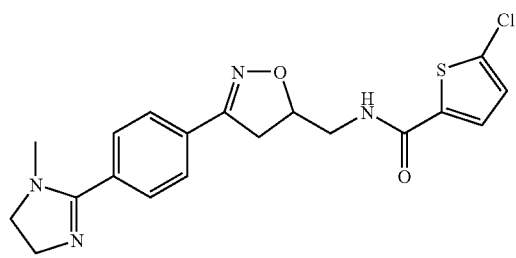

The titled compound was made by the procedure similar to that described in Example 8. MS found for $C_{19}H_{19}ClN_4O_2S$ as $(M+H)^+$ 403.1, 405.1.

Example 10

5-Chloro-thiophene-2-carboxylic acid {3-[4-(imino-pyrrolidin-1-yl-methyl)-phenyl]-4,5-dihydro-isoxazol-5-ylmethyl}-amide

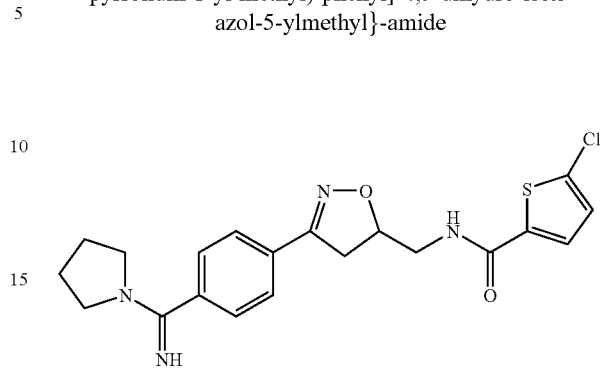

The titled compound was made by the procedure similar to that described in Example 8. MS found for $C_{20}H_{21}ClN_4O_2S$ as $(M+H)^+$ 417.1, 419.1.

Example 11

5-Chloro-thiophene-2-carboxylic acid {3-[4-(imino-piperidin-1-yl-methyl)-phenyl]-4,5-dihydro-isoxazol-5-ylmethyl}-amide

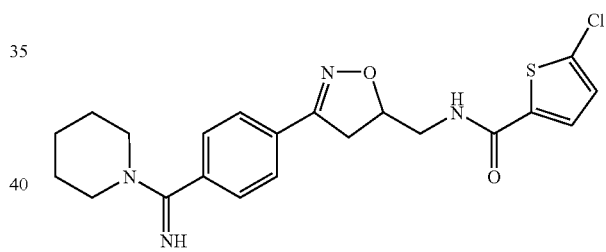

The titled compound was made by the procedure similar to that described in Example 8. MS found for $C_{21}H_{23}ClN_4O_2S$ as $(M+H)^+$ 431.1, 433.1.

Example 12

1-{[4-(5-{[(5-Chloro-thiophene-2-carbonyl)-amino]-methyl}-4,5-dihydro-isoxazol-3-yl)-phenyl]-imino-methyl}-piperidine-4-carboxylic acid ethyl ester

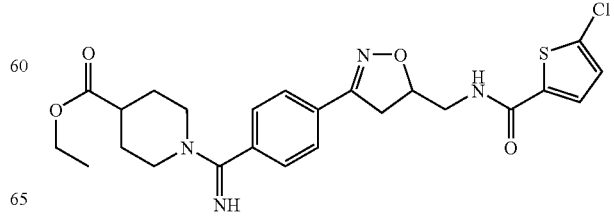

The titled compound was made by the procedure similar to that described in Example 8. MS found for $C_{24}H_{27}ClN_4O_4S$ as $(M+H)^+$ 503.1, 505.1.

Example 13

5-Chloro-thiophene-2-carboxylic acid {3-[4-(N-methyl-N-prop-2-ynyl-carbamimidoyl)-phenyl]-4,5-dihydro-isoxazol-5-ylmethyl}-amide

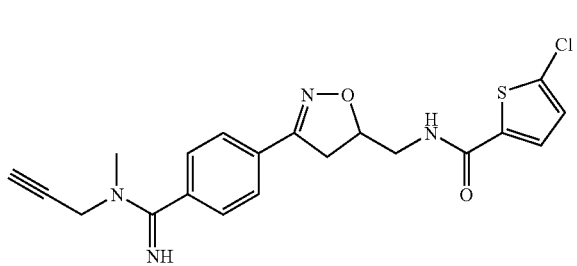

The titled compound was made by the procedure similar to that described in Example 8. MS found for $C_{20}H_{19}ClN_4O_2S$ as $(M+H)^+$ 415.1, 417.1.

Example 14

5-Chloro-thiophene-2-carboxylic acid (3-{4-[N-(2-methoxy-ethyl)-N-methyl-carbamimidoyl]-phenyl}-4,5-dihydro-isoxazol-5-ylmethyl)-amide

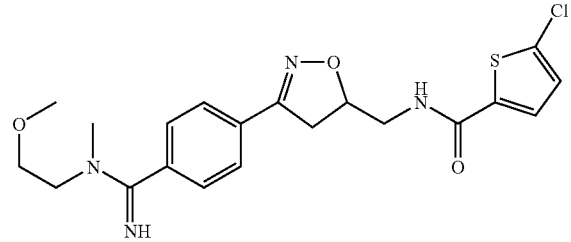

The titled compound was made by the procedure similar to that described in Example 8. MS found for $C_{20}H_{23}ClN_4O_3S$ as $(M+H)^+$ 435.1, 437.1.

Example 15

5-Chloro-thiophene-2-carboxylic acid {3-[4-(N-furan-2-ylmethyl-N-methyl-carbamimidoyl)-phenyl]-4,5-dihydro-isoxazol-5-ylmethyl}-amide

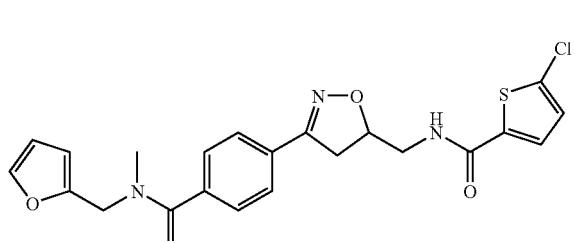

The titled compound was made by the procedure similar to that described in Example 8. MS found for $C_{22}H_{21}ClN_4O_3S$ as $(M+H)^+$ 457.1, 459.1.

Example 16

5-Chloro-thiophene-2-carboxylic acid (3-{4-[N-(2-dimethylamino-ethyl)-N-methyl-carbamimidoyl]-phenyl}-4,5-dihydro-isoxazol-5-ylmethyl)-amide

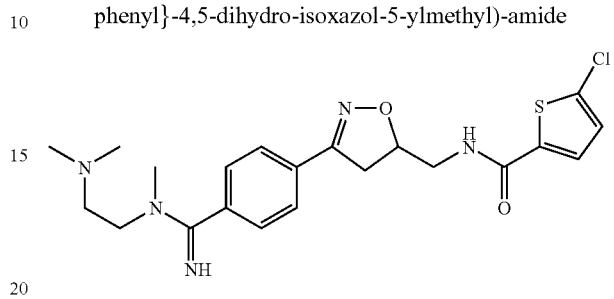

The titled compound was made by the procedure similar to that described in Example 8. MS found for $C_{21}H_{26}ClN_5O_2S$ as $(M+H)^+$ 448.1, 450.1.

Example 17

5-Chloro-thiophene-2-carboxylic acid {3-[4-(N-methyl-N-propyl-carbamimidoyl)-phenyl]-4,5-dihydro-isoxazol-5-ylmethyl}-amide

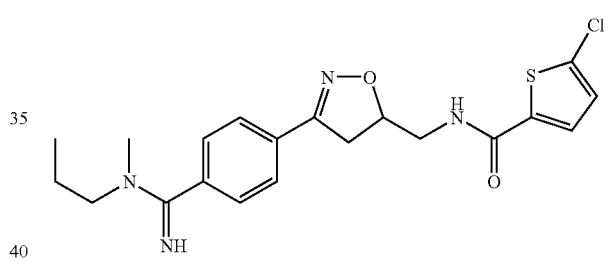

The titled compound was made by the procedure similar to that described in Example 8. MS found for $C_{20}H_{23}ClN_4O_2S$ as $(M+H)^+$ 419.1, 421.1.

Example 18

5-Chloro-thiophene-2-carboxylic acid {3-[4-(N-ethyl-N-methyl-carbamimidoyl)-phenyl]-4,5-dihydro-isoxazol-5-ylmethyl}-amide

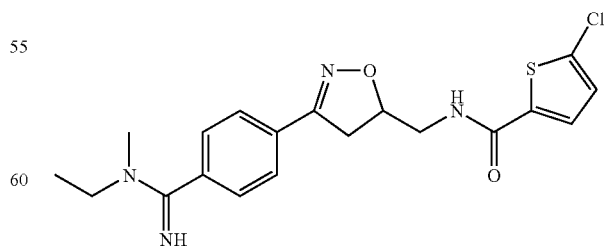

The titled compound was made by the procedure similar to that described in Example 8. MS found for $C_{19}H_{21}ClN_4O_2S$ as $(M+H)^+$ 405.1, 407.0

Example 19

5-Chloro-thiophene-2-carboxylic acid {3-[4-(azetidin-1-yl-imino-methyl)-phenyl]-4,5-dihydro-isoxazol-5-ylmethyl}-amide

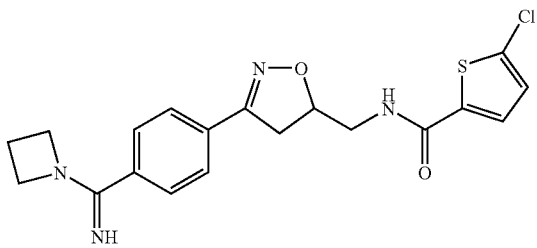

The titled compound was made by the procedure similar to that described in Example 8. MS found for $C_{19}H_{19}ClN_4O_2S$ as $(M+H)^+$ 403.1, 405.1.

Example 20

5-Chloro-thiophene-2-carboxylic acid [3-(4-cyanophenyl)-isoxazol-5-ylmethyl]-amide

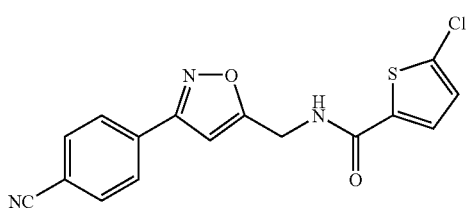

The titled compound was made by the procedure similar to that described in Example 2. $^1$H NMR (DMSO-$d_6$, 400 MHz): δ 9.32 (t, 1H), δ 8.03 (d, 2H), δ 7.91 (d, 2H), δ 7.68 (s, 1H), δ 7.13 (s, 1H), δ 7.05 (s, 1H), δ 4.60 (d, 2H).

Example 21

5-Chloro-thiophene-2-carboxylic acid {3-[4-(N,N-dimethyl-carbamimidoyl)-phenyl]-isoxazol-5-ylmethyl}-amide

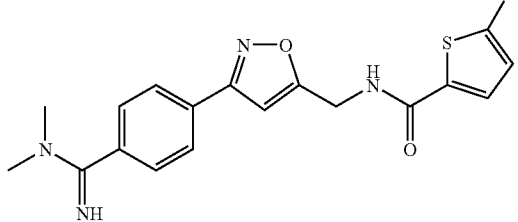

The titled compound was made by the procedure similar to that described in Example 8, using the nitrile from Example 20. MS found for $C_{18}H_{17}ClN_4O_2S$ as $(M+H)^+$ 389.1, 391.1.

Example 22

5-Chloro-thiophene-2-carboxylic acid {3-[4-(1-methyl-4,5-dihydro-1H-imidazol-2-yl)-phenyl]-isoxazol-5-ylmethyl}-amide

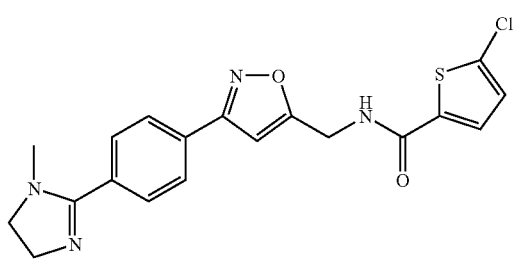

The titled compound was made by the procedure similar to that described in Example 8, using the nitrile from Example 20. MS found for $C_{19}H_{17}ClN_4O_2S$ as $(M+H)^+$ 401.1, 403.1.

Example 23

5-Chloro-thiophene-2-carboxylic acid {3-[4-(iminopyrrolidin-1-yl-methyl)-phenyl]-isoxazol-5-ylmethyl}-amide

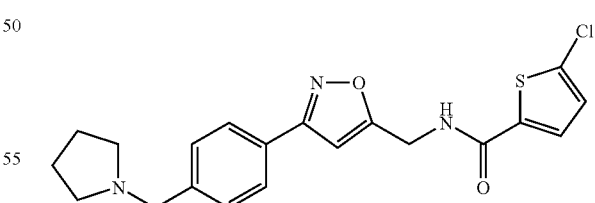

The titled compound was made by the procedure similar to that described in Example 8, using the nitrile from Example 20. MS found for $C_{20}H_{19}ClN_4O_2S$ as $(M+H)^+$ 415.1, 417.1.

Example 24

5-Chloro-thiophene-2-carboxylic acid {3-[4-(imino-piperidin-1-yl-methyl)-phenyl]-isoxazol-5-ylmethyl}-amide

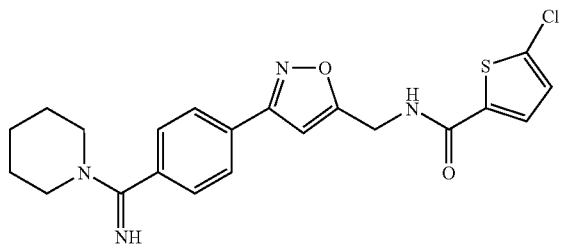

The titled compound was made by the procedure similar to that described in Example 8, using the nitrile from Example 20. MS found for $C_{21}H_{21}ClN_4O_2S$ as $(M+H)^+$ 429.1, 431.1.

Example 25

1-{[4-(5-{[(5-Chloro-thiophene-2-carbonyl)-amino]-methyl}-isoxazol-3-yl)-phenyl]-imino-methyl}-piperidine-4-carboxylic acid ethyl ester

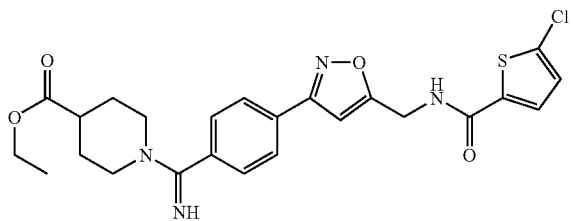

The titled compound was made by the procedure similar to that described in Example 8, using the nitrile from Example 20. MS found for $C_{24}H_{25}ClN_4O_4S$ as $(M+H)^+$ 501.0, 503.1.

Example 26

5-Chloro-thiophene-2-carboxylic acid {3-[4-(azetidin-1-yl-imino-methyl)-phenyl]-isoxazol-5-ylmethyl}-amide

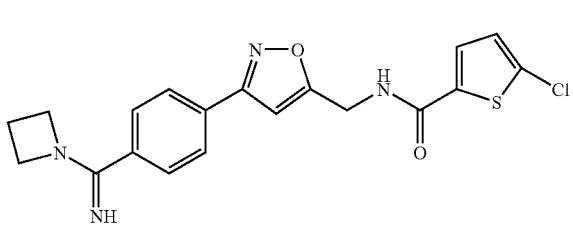

The titled compound was made by the procedure similar to that described in Example 8, using the nitrile from Example 20. MS found for $C_{19}H_{17}ClN_4O_2S$ as $(M+H)^+$ 401.1, 403.1.

Example 27

5-Chloro-thiophene-2-carboxylic acid {3-[4-(azetidin-1-yl-azetidin-1-ylidene-methyl)-phenyl]-isoxazol-5-ylmethyl}-amide

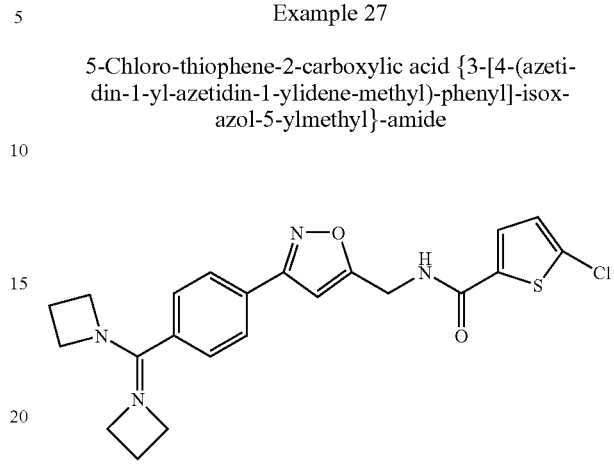

The titled compound was made by the procedure similar to that described in Example 8, using the nitrile from Example 20. MS found for $C_{22}H_{22}ClN_4O_2S$ as $(M)^+$ 441.1, 443.1.

Example 28

5-Chloro-thiophene-2-carboxylic acid {3-[4-(N-ethyl-N-methyl-carbamimidoyl)-phenyl]-isoxazol-5-ylmethyl}-amide

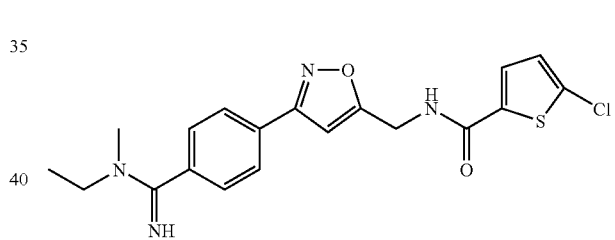

The titled compound was made by the procedure similar to that described in Example 8, using the nitrile from Example 20. MS found for $C_{19}H_{19}ClN_4O_2S$ as $(M+H)^+$ 403.1, 405.1.

Example 29

5-Chloro-thiophene-2-carboxylic acid {3-[4-(N-methyl-N-propyl-carbamimidoyl)-phenyl]-isoxazol-5-ylmethyl}-amide

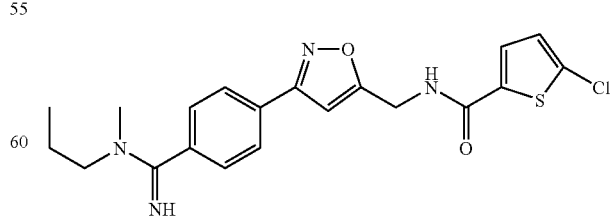

The titled compound was made by the procedure similar to that described in Example 8, using the nitrile from Example 20. MS found for $C_{20}H_{21}ClN_4O_2S$ as $(M+H)^+$ 417.1, 419.1.

Example 30

5-Chloro-thiophene-2-carboxylic acid (3-{4-[N-(2-dimethylamino-ethyl)-N-methyl-carbamimidoyl]-phenyl}-isoxazol-5-ylmethyl)-amide

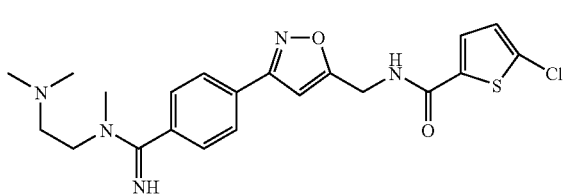

The titled compound was made by the procedure similar to that described in Example 8, using the nitrile from Example 20. MS found for $C_{21}H_{24}ClN_5O_2S$ as $(M+H)^+$ 446.1, 448.1.

Example 31

5-Chloro-thiophene-2-carboxylic acid {3-[4-(N-furan-2-ylmethyl-N-methyl-carbamimidoyl)-phenyl]-isoxazol-5-ylmethyl}-amide

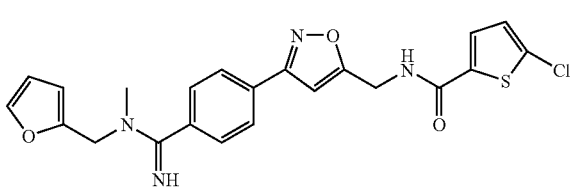

The titled compound was made by the procedure similar to that described in Example 8, using the nitrile from Example 20. MS found for $C_{22}H_{19}ClN_4O_3S$ as $(M+H)^+$ 455.1, 457.1.

Example 32

5-Chloro-thiophene-2-carboxylic acid (3-{4-[N-(2-methoxy-ethyl)-N-methyl-carbamimidoyl]-phenyl}-isoxazol-5-ylmethyl)-amide

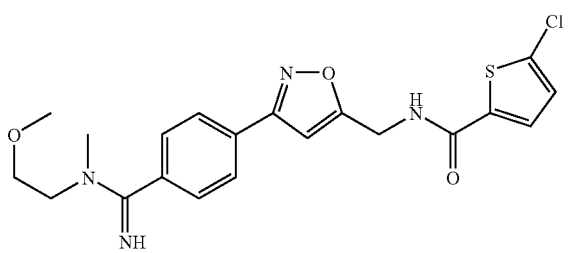

The titled compound was made by the procedure similar to that described in Example 8, using the nitrile from Example 20. MS found for $C_{20}H_{21}ClN_4O_3S$ as $(M+H)^+$ 433.1, 435.1.

Example 33

5-Chloro-thiophene-2-carboxylic acid {3-[4-(N-methyl-N-prop-2-ynyl-carbamimidoyl)-phenyl]-isoxazol-5-ylmethyl}-amide

The titled compound was made by the procedure similar to that described in Example 8, using the nitrile from Example 20. MS found for $C_{20}H_{17}ClN_4O_2S$ as $(M+H)^+$ 413.1, 415.1.

Example 34

5-Chloro-thiophene-2-carboxylic acid {3-[4-(N-methylcarbamimidoyl)-phenyl]-isoxazol-5-ylmethyl}-amide

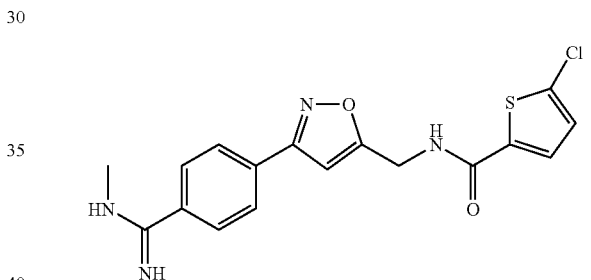

The titled compound was made by the procedure similar to that described in Example 8, using the nitrile from Example 20. MS found for $C_{17}H_{15}ClN_4O_2S$ as $(M+H)+$ 375.1, 377.1.

Example 35

5-Chloro-thiophene-2-carboxylic acid {3-[4-(N,N-dimethyl-carbamimidoyl)-phenyl]-isoxazol-5-ylmethyl}-methyl-amide

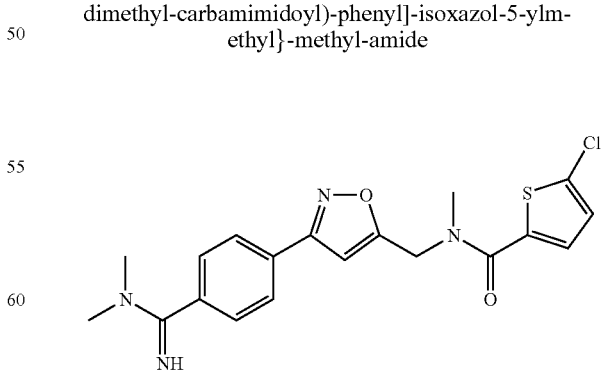

The titled compound was made by the procedure similar to that described in Example 8. MS found for $C_{19}H_{19}ClN_4O_2S$ as $(M+H)+$ 403.1, 405.1.

Example 36

5-Chloro-thiophene-2-carboxylic acid methyl-{3-[4-(1-methyl-4,5-dihydro-1H-imidazol-2-yl)-phenyl]-isoxazol-5-ylmethyl}-amide

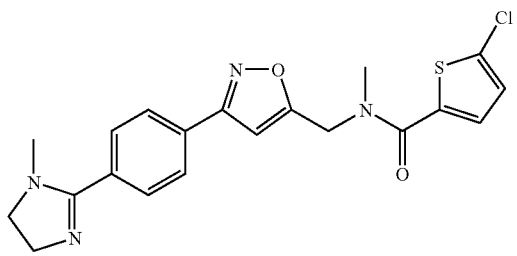

The titled compound was made by the procedure similar to that described in Example 8. MS found for $C_{20}H_{19}ClN_4O_2S$ as (M+H)+ 415.1, 417.1.

Example 37

5-Chloro-thiophene-2-carboxylic acid {3-[4-(imino-pyrrolidin-1-yl-methyl)-phenyl]-isoxazol-5-ylmethyl}-methyl-amide

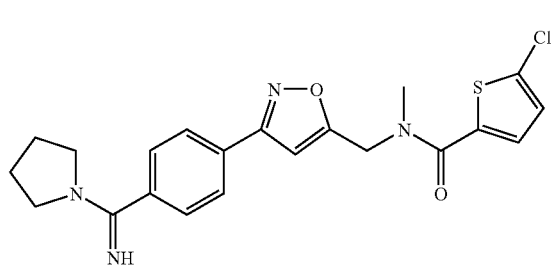

The titled compound was made by the procedure similar to that described in Example 8. MS found for $C_{21}H_{21}ClN_4O_2S$ as (M+H)+ 429.1, 431.1.

Example 38

5-Chloro-thiophene-2-carboxylic acid {3-[4-(imino-piperidin-1-yl-methyl)-phenyl]-isoxazol-5-ylmethyl}-methyl-amide

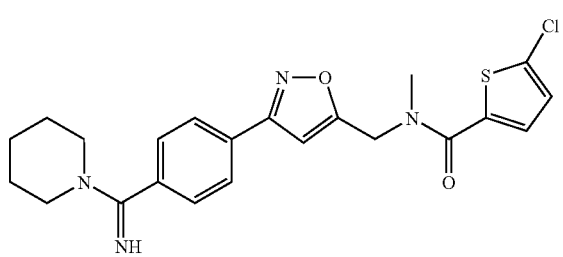

The titled compound was made by the procedure similar to that described in Example 8. MS found for $C_{22}H_{23}ClN_4O_2S$ as (M+H)+ 443.1, 445.1.

Example 39

1-{[4-(5-{[(5-Chloro-thiophene-2-carbonyl)-methyl-amino]-methyl}-isoxazol-3-yl)-phenyl]-imino-methyl}-piperidine-4-carboxylic acid ethyl ester

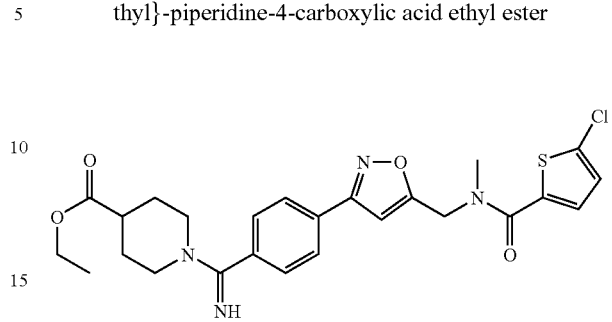

The titled compound was made by the procedure similar to that described in Example 8. MS found for $C_{25}H_{27}ClN_4O_4S$ as (M+H)+ 515.1, 517.1.

Example 40

5-Chloro-thiophene-2-carboxylic acid {3-[4-(azetidin-1-yl-imino-methyl)-phenyl]-isoxazol-5-ylmethyl}-methyl-amide

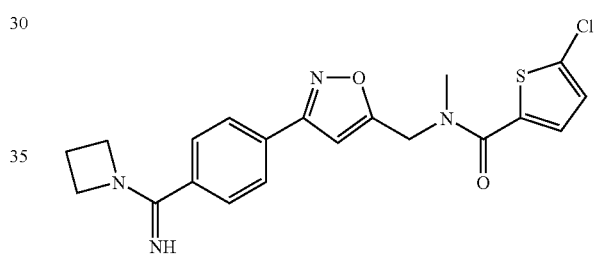

The titled compound was made by the procedure similar to that described in Example 8. MS found for $C_{20}H_{19}ClN_4O_2S$ as (M+H)+ 415.1, 417.0.

Example 41

5-Chloro-thiophene-2-carboxylic acid {3-[4-(azetidin-1-yl-azetidin-1-ylidene-methyl)-phenyl]-isoxazol-5-ylmethyl}-methyl-amide

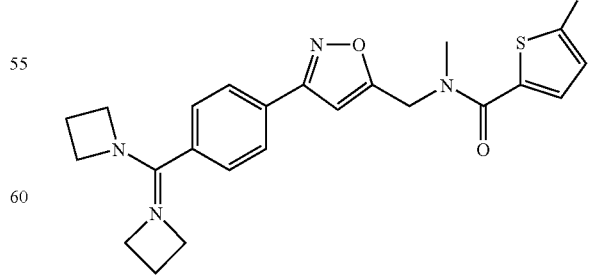

The titled compound was made by the procedure similar to that described in Example 8. MS found for $C_{23}H_{24}ClN_4O_2S$ as (M)+ 455.1, 457.1.

Example 42

5-Chloro-thiophene-2-carboxylic acid {3-[4-(N-ethyl-N-methyl-carbamimidoyl)-phenyl]-isoxazol-5-ylmethyl}-methyl-amide

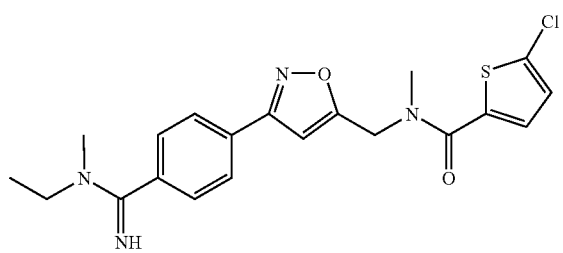

The titled compound was made by the procedure similar to that described in Example 8. MS found for $C_{20}H_{21}ClN_4O_2S$ as $(M+H)^+$ 417.1, 419.1.

Example 43

5-Chloro-thiophene-2-carboxylic acid methyl-{3-[4-(N-methyl-N-propyl-carbamimidoyl)-phenyl]-isoxazol-5-ylmethyl}-amide

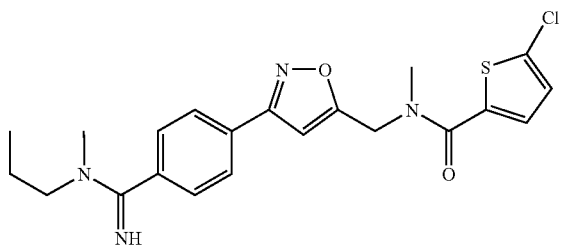

The titled compound was made by the procedure similar to that described in Example 8. MS found for $C_{21}H_{23}ClN_4O_2S$ as $(M+H)^+$ 431.1, 433.1.

Example 44

5-Chloro-thiophene-2-carboxylic acid (3-{4-[N-(2-dimethylamino-ethyl)-N-methyl-carbamimidoyl]-phenyl}-isoxazol-5-ylmethyl)-methyl-amide

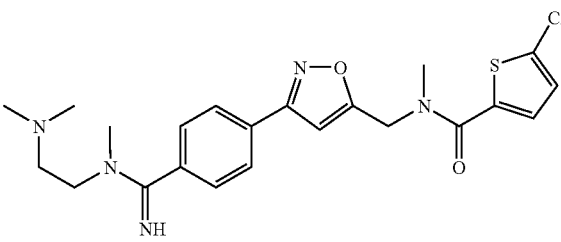

The titled compound was made by the procedure similar to that described in Example 8. MS found for $C_{22}H_{26}ClN_5O_2S$ as $(M+H)^+$ 460.1, 462.1.

Example 45

1-{[4-(5-{[(5-Chloro-thiophene-2-carbonyl)-methyl-amino]-methyl}-isoxazol-3-yl)-phenyl]-imino-methyl}-piperidine-4-carboxylic acid amide

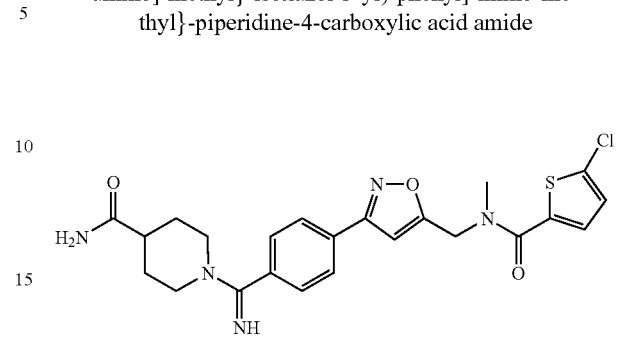

The titled compound was made by the procedure similar to that described in Example 8. MS found for $C_{23}H_{24}ClN_5O_3S$ as $(M+H)^+$ 486.1, 488.1.

Example 46

5-Chloro-thiophene-2-carboxylic acid (3-{4-[N-(2-methoxy-ethyl)-N-methyl-carbamimidoyl]-phenyl}-isoxazol-5-ylmethyl)-methyl-amide

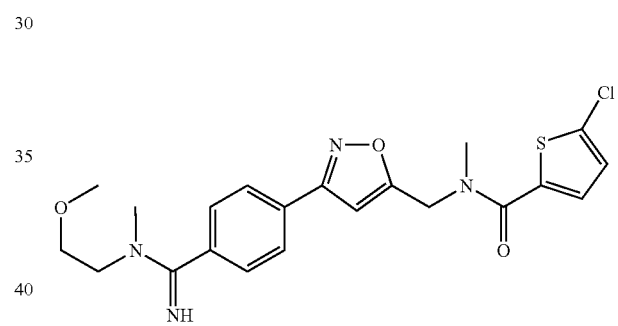

The titled compound was made by the procedure similar to that described in Example 8. MS found for $C_{21}H_{23}ClN_4O_3S$ as $(M+H)^+$ 447.1, 449.1.

Example 47

5-Chloro-thiophene-2-carboxylic acid methyl-{3-[4-(N-methyl-N-prop-2-ynyl-carbamimidoyl)-phenyl]-isoxazol-5-ylmethyl}-amide

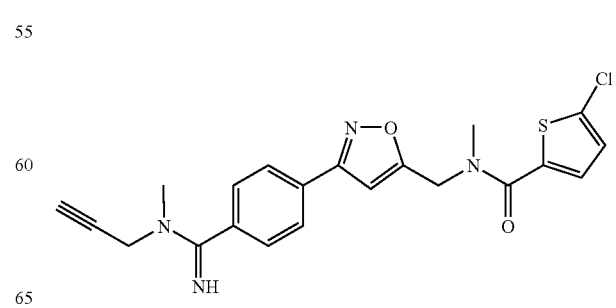

The titled compound was made by the procedure similar to that described in Example 8. MS found for $C_{21}H_{19}ClN_4O_2S$ as $(M+H)^+$ 427.0, 429.1.

Example 48

5-Chloro-thiophene-2-carboxylic acid methyl-{3-[4-(N-methylcarbamimidoyl)-phenyl]-isoxazol-5-ylm-ethyl}-amide

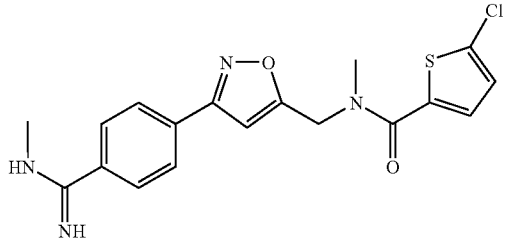

The titled compound was made by the procedure similar to that described in Example 8. MS found for $C_{18}H_{17}ClN_4O_2S$ as $(M+H)^+$ 389.1, 391.1.

SCHEME 2

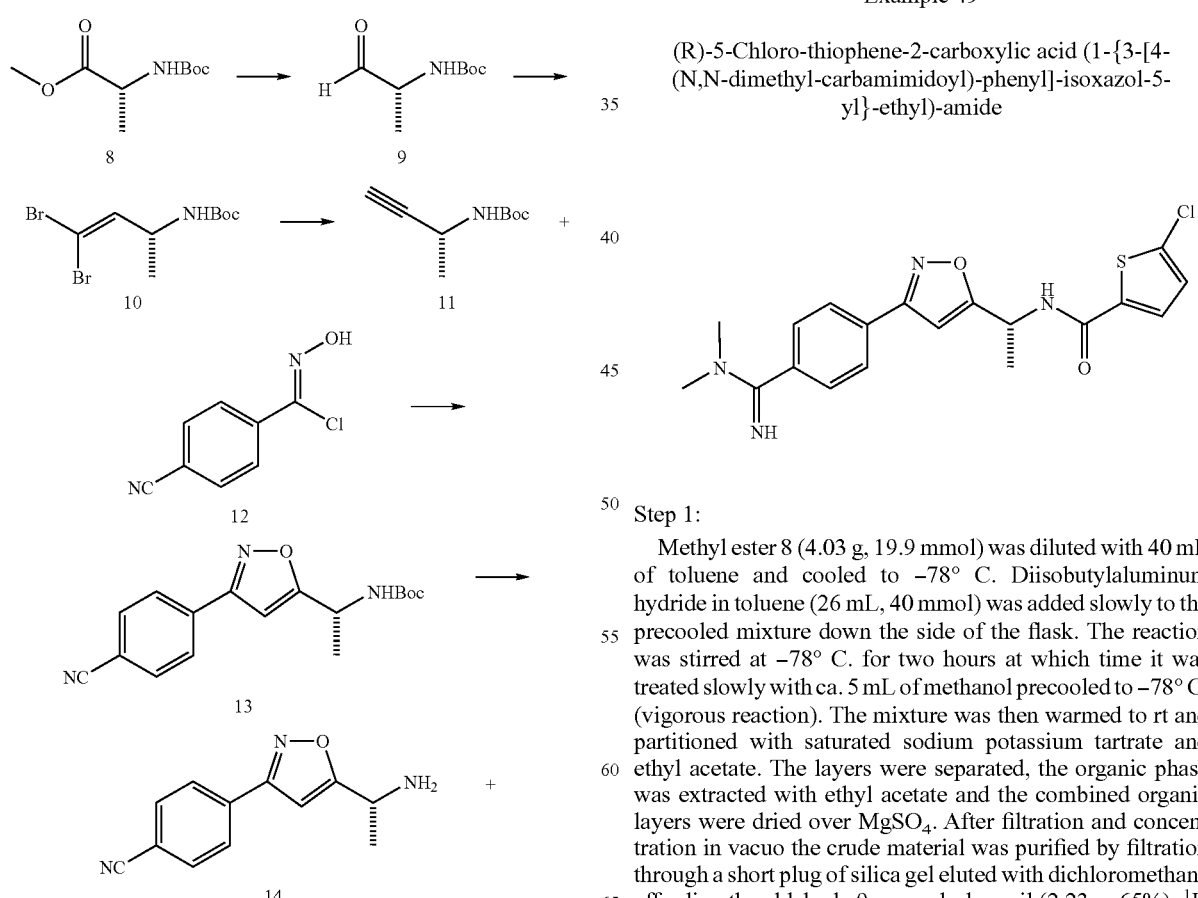

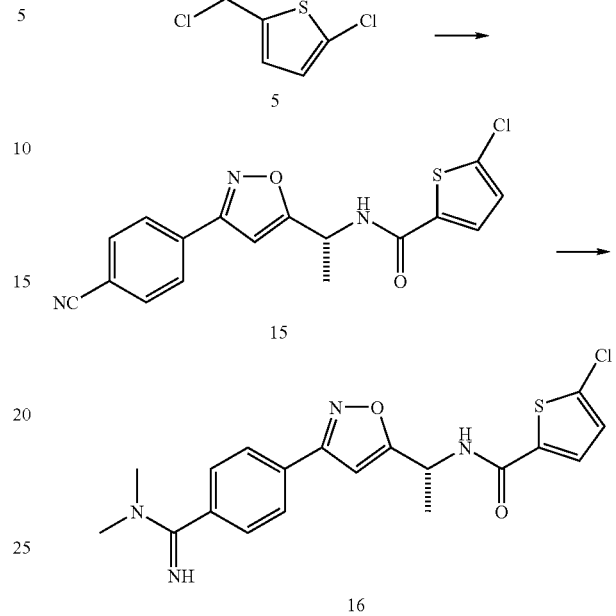

Example 49

(R)-5-Chloro-thiophene-2-carboxylic acid (1-{3-[4-(N,N-dimethyl-carbamimidoyl)-phenyl]-isoxazol-5-yl}-ethyl)-amide Step 1:

Methyl ester 8 (4.03 g, 19.9 mmol) was diluted with 40 mL of toluene and cooled to −78° C. Diisobutylaluminum hydride in toluene (26 mL, 40 mmol) was added slowly to the precooled mixture down the side of the flask. The reaction was stirred at −78° C. for two hours at which time it was treated slowly with ca. 5 mL of methanol precooled to −78° C. (vigorous reaction). The mixture was then warmed to rt and partitioned with saturated sodium potassium tartrate and ethyl acetate. The layers were separated, the organic phase was extracted with ethyl acetate and the combined organic layers were dried over $MgSO_4$. After filtration and concentration in vacuo the crude material was purified by filtration through a short plug of silica gel eluted with dichloromethane affording the aldehyde 9 as a colorless oil (2.23 g, 65%). $^1$H NMR (DMSO-$d_6$, 400 MHz): δ 9.38 (s, 1H), δ 7.30 (d, 1H), δ 3.79 (m, 1H), δ 1.31 (s, 9H), 1.06 (d, 3H).

Step 2:

Triphenylphosphine (6.0 g, 23.1 mmol) was dissolved in 30 mL of dichloromethane and cooled to 0° C. To this was added CBr$_4$ (3.84 g, 11.6 mmol), slowly, resulting in a clear orange solution. After stirring 10 min aldehyde 9 (1.o g, 5.78 mmol) was added slowly resulting in a dark red, cloudy solution. This was then checked by TLC which showed complete consumption of the starting material and a less polar spot. The reaction was concentrated in vacuo then filtered through a short pad of silica gel (eluted with dichloromethane) affording the desired olefin 10 as an off-white crystalline solid (1.25 g, 66%). %). $^1$H NMR (DMSO-d$_6$, 400 MHz): δ 7.36 (d, 1H), δ 5.18 (s, 1H), δ 4.23 (m, 1H), δ 1.35 (s, 9H), δ 1.28 (d, 3H).

Step 3:

Dibromoolefin 10 (1.25 g, 3.8 mmol) was dissolved with THF (10 mL), cooled to 0° C., then treated with freshly prepared lithium diisopropyl amide (1.7 M, 20 mL) during which time the reaction changed from colorless to dark yellow-orange. The ice bath was removed and the reaction stirred for 10 min. The reaction was then partitioned with 1 M HCl and ethyl acetate, the layers separated and the aqueous phase extracted again with ethyl acetate. The combined organic layers were dried over MgSO$_4$, filtered, concentrated and purified by silica gel chromatography (dichloromethane) affording the desired alkyne (11) as a white solid (0.3652 g, 57%). $^1$H NMR (CDCl$_3$, 400 MHz): δ 4.71 (br s, 1H), δ 4.42 (br s, 1H), δ 2.20 (s, 1H), δ 1.38 (s, 9H), δ 1.32 (d, 3H).

Step 4:

Performed in the same manner as in step 5, Example 1. NMR (DMSO-d$_6$, 400 MHz): δ 8.01 (d, 2H), δ 7.95 (d, 2H), δ 7.54 (d, 1H), δ 6.91 (s, 1H), δ 4.81(m, 1H), δ 1.36 (m, 12H).

Step 5:

Boc protected amine 12 was diluted with 4 M HCl/dioxane (10 mL) and stirred for 2 hrs at which time it was determined to be complete by TLC. The reaction was concentrated affording the desired amine as a white solid which was used immediately for the next step. NMR (DMSO-d$_6$, 400 MHz): δ 8.72 (s, 3H), δ 8.06 (d, 2H), δ 8.02 (d, 2H), δ 7.29 (s, 1H), δ 4.73 (m, 1H), δ 1.59 (d, 3H).

Step 6:

Performed in the same manner as in step 5, Example 1. NMR (DMSO-d$_6$, 400 MHz): δ 9.11 (d, 1H), δ 8.03 (d, 2H), δ 7.95 (d, 2H), δ 7.70 (d, 2H), δ 7.18 (d, 1H), δ 7.51 (s, 1H), δ 5.29 (m, 1H), δ 1.50 (d, 3H).

Step 7:

Performed in the same manner as in Example 8. MS found for C$_{19}$H$_{19}$ClN$_4$O$_2$S as (M+H)$^+$ 403.1, 405.1.

Example 50

(R)-5-Chloro-thiophene-2-carboxylic acid (1-{3-[4-(1-methyl-4,5-dihydro-1H-imidazol-2-yl)-phenyl]-isoxazol-5-yl}-ethyl)-amide

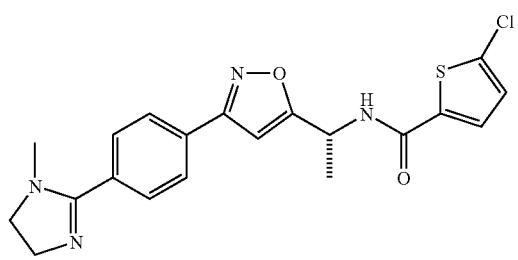

The titled compound was made by the procedure similar to that described in Example 49. MS found for C$_{20}$H$_{19}$ClN$_4$O$_2$S as (M+H)$^+$ 415.1, 417.1.

Example 51

(R)-5-Chloro-thiophene-2-carboxylic acid (1-{3-[4-(imino-pyrrolidin-1-yl-methyl)-phenyl]-isoxazol-5-yl}-ethyl)-amide

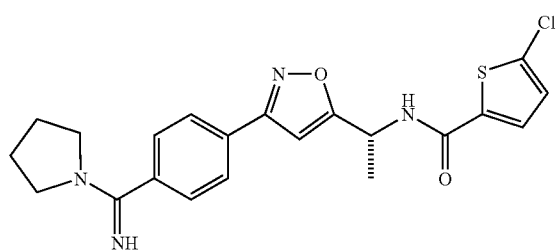

The titled compound was made by the procedure similar to that described in Example 49. MS found for C$_{21}$H$_{21}$ClN$_4$O$_2$S as (M+H)$^+$ 429.1, 430.0.

Example 52

(R)-5-Chloro-thiophene-2-carboxylic acid (1-{3-[4-(imino-piperidin-1-yl-methyl)-phenyl]-isoxazol-5-yl}-ethyl)-amide

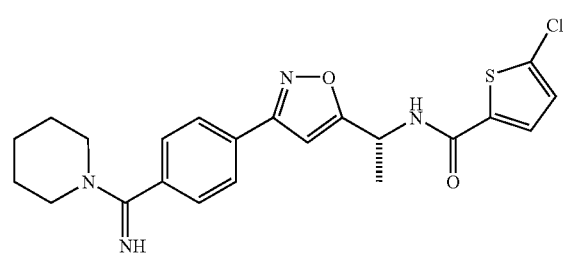

The titled compound was made by the procedure similar to that described in Example 49. MS found C$_{22}$H$_{23}$ClN$_4$O$_2$S as (M+H)$^+$ 443.1, 445.1.

Example 53

(R)-5-Chloro-thiophene-2-carboxylic acid (1-{3-[4-(N,N-dimethyl-carbamimidoyl)-phenyl]-isoxazol-5-yl}-ethyl)-amide

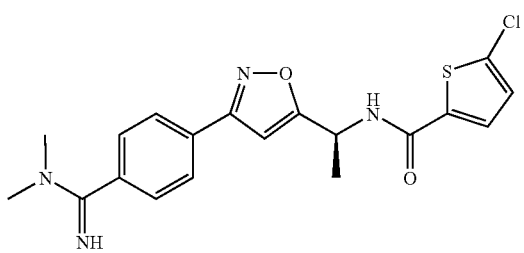

The titled compound was made by the procedure similar to that described in Example 49. MS found for $C_{19}H_{19}ClN_4O_2S$ as $(M+H)^+$ 403.0, 405.0

Example 54

(S)-5-Chloro-thiophene-2-carboxylic acid (1-{3-[4-(1-methyl-4,5-dihydro-1H-imidazol-2-yl)-phenyl]-isoxazol-5-yl}-ethyl)-amide

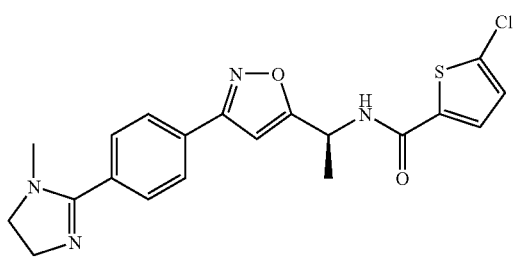

The titled compound was made by the procedure similar to that described in Example 49. MS found for $C_{20}H_{19}ClN_4O_2S$ as $(M+H)^+$ 415.0, 417.0.

Example 55

(S)-5-Chloro-thiophene-2-carboxylic acid (1-{3-[4-(imino-pyrrolidin-1-yl-methyl)-phenyl]-isoxazol-5-yl}-ethyl)-amide

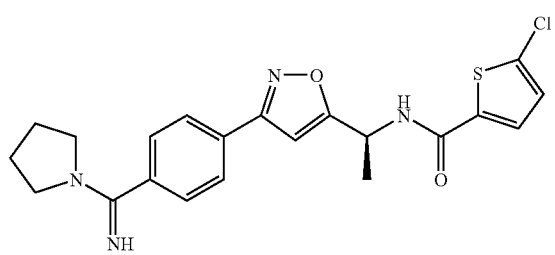

The titled compound was made by the procedure similar to that described in Example 49. MS found for $C_{21}H_{21}ClN_4O_2S$ as $(M+H)^+$ 429.0, 430.0.

Example 56

(S)-5-Chloro-thiophene-2-carboxylic acid (1-{3-[4-(imino-piperidin-1-yl-methyl)-phenyl]-isoxazol-5-yl}-ethyl)-amide

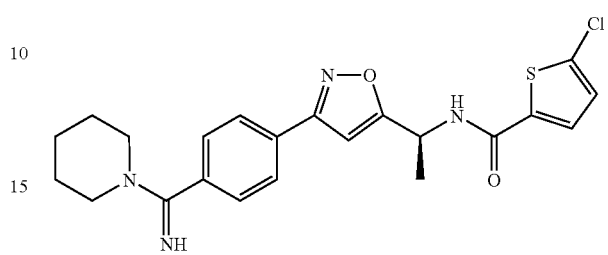

The titled compound was made by the procedure similar to that described in Example 49. MS found $C_{22}H_{23}ClN_4O_2S$ as $(M+H)^+$ 443.0, 445.0.

Example 57

5-Chloro-thiophene-2-carboxylic acid {3-[4-(N,N-dimethyl-carbamimidoyl)-phenyl]-5-methyl-4,5-dihydro-isoxazol-5-ylmethyl}-amide

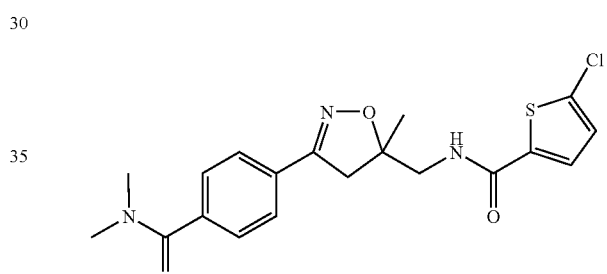

The titled compound was made by the procedure similar to that described in Example 8. MS found for $C_{19}H_{21}ClN_4O_2S$ as $(M+H)^+$ 405.1, 407.1

Example 58

5-Chloro-thiophene-2-carboxylic acid {5-methyl-3-[4-(1-methyl-4,5-dihydro-1H-imidazol-2-yl)-phenyl]-4,5-dihydro-isoxazol-5-ylmethyl}-amide

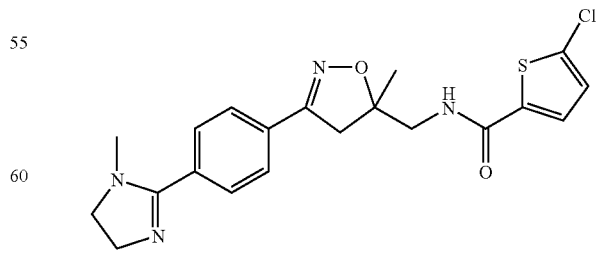

The titled compound was made by the procedure similar to that described in Example 8. MS found for $C_{20}H_{21}ClN_4O_2S$ as (M+H)+ 417.1, 419.1

Example 59

5-Chloro-thiophene-2-carboxylic acid {3-[4-(imino-pyrrolidin-1-yl-methyl)-phenyl]-5-methyl-4,5-dihydro-isoxazol-5-ylmethyl}-amide

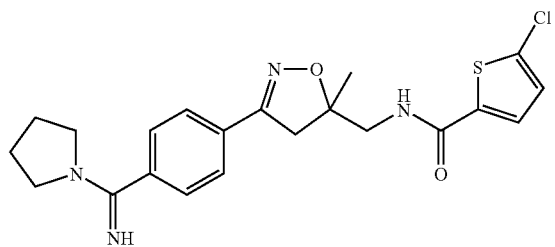

The titled compound was made by the procedure similar to that described in Example 8. MS found for $C_{21}H_{23}ClN_4O_2S$ as (M+H)+ 431.1, 433.1

Example 60

5-Chloro-thiophene-2-carboxylic acid {3-[4-(imino-piperidin-1-yl-methyl)-phenyl]-5-methyl-4,5-dihydro-isoxazol-5-ylmethyl}-amide

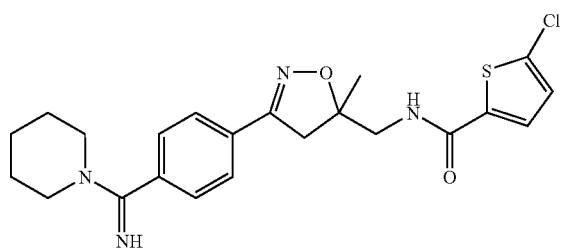

The titled compound was made by the procedure similar to that described in Example 8. MS found for $C_{22}H_{25}ClN_4O_2S$ as (M+H)+ 445.1, 447.1

Example 61

1-{[4-(5-{[(5-Chloro-thiophene-2-carbonyl)-amino]-methyl}-5-methyl-4,5-dihydro-isoxazol-3-yl)-phenyl]-imino-methyl}-piperidine-4-carboxylic acid ethyl ester

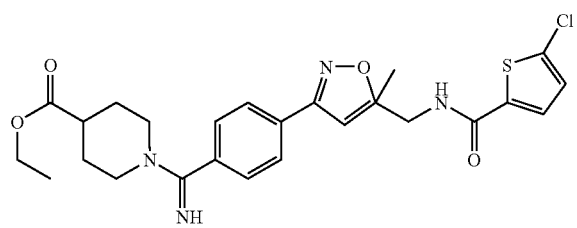

The titled compound was made by the procedure similar to that described in Example 8. MS found for $C_{25}H_{29}ClN_4O_4S$ as (M+H)+ 517.1, 519.1

Example 62

5-Chloro-thiophene-2-carboxylic acid {3-[4-(azetidin-1-yl-imino-methyl)-phenyl]-5-methyl-4,5-dihydro-isoxazol-5-ylmethyl}-amide

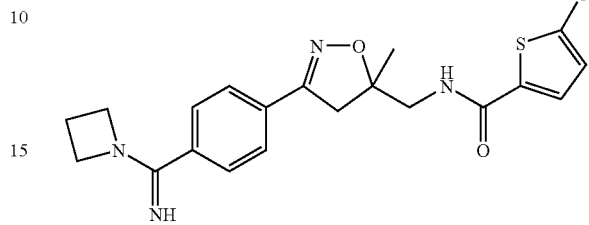

The titled compound was made by the procedure similar to that described in Example 8. MS found for $C_{20}H_{21}ClN_4O_2S$ as (M+H)+ 418.0, 420.0

Example 63

5-Chloro-thiophene-2-carboxylic acid {3-[4-(azetidin-1-yl-azetidin-1-ylidene-methyl)-phenyl]-5-methyl-4,5-dihydro-isoxazol-5-ylmethyl}-amide

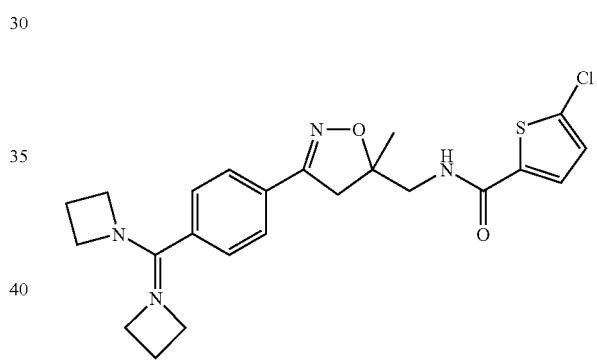

The titled compound was made by the procedure similar to that described in Example 8. MS found for $C_{23}H_{26}ClN_4O_2S$ as (M+H)+ 457.1, 459.1

Example 64

5-Chloro-thiophene-2-carboxylic acid {3-[4-(N-ethyl-N-methyl-carbamimidoyl)-phenyl]-5-methyl-4,5-dihydro-isoxazol-5-ylmethyl}-amide

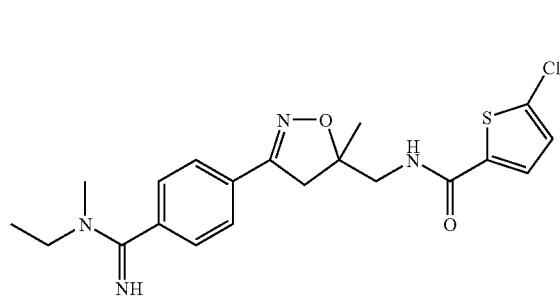

The titled compound was made by the procedure similar to that described in Example 8. MS found for $C_{20}H_{23}ClN_4O_2S$ as (M+H)+419.1, 421.1

Example 65

5-Chloro-thiophene-2-carboxylic acid (3-{4-[N-(2-dimethylamino-ethyl)-N-methyl-carbamimidoyl]-phenyl}-5-methyl-4,5-dihydro-isoxazol-5-ylmethyl)-amide

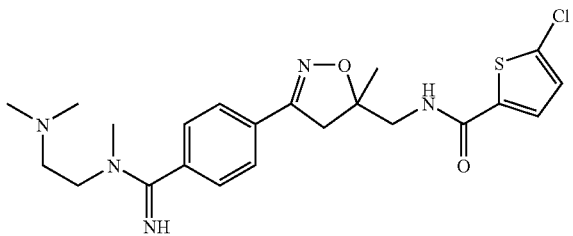

The titled compound was made by the procedure similar to that described in Example 8. MS found for $C_{22}H_{28}ClN_5O_2S$ as (M+H)$^+$ 462.1, 464.1

Example 66

5-Chloro-thiophene-2-carboxylic acid (3-{4-[N-(2-methoxy-ethyl)-N-methyl-carbamimidoyl]-phenyl}-5-methyl-4,5-dihydro-isoxazol-5-ylmethyl)-amide

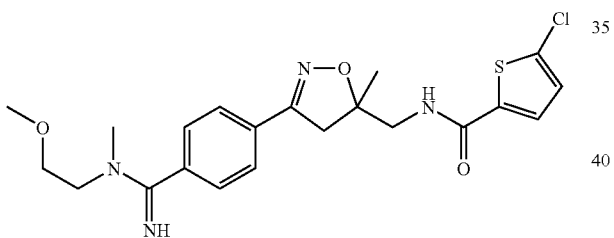

The titled compound was made by the procedure similar to that described in Example 8. MS found for $C_{21}H_{25}ClN_4O_3S$ as (M+H)+ 449.1, 451.1

Example 67

5-Chloro-thiophene-2-carboxylic acid {3-[4-(N-furan-2-ylmethyl-N-methyl-carbamimidoyl)-phenyl]-5-methyl-4,5-dihydro-isoxazol-5-ylmethyl}-amide

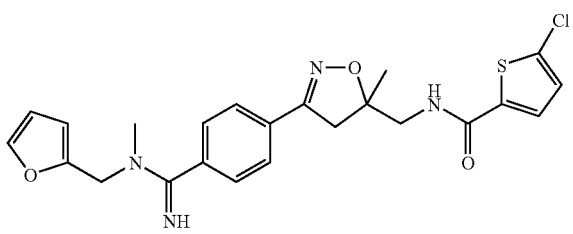

The titled compound was made by the procedure similar to that described in Example 8. MS found for $C_{21}H_{25}ClN_4O_3S$ as (M+H)+ 444.1, 446.1

Example 68

1-{[4-(5-{[(5-Chloro-thiophene-2-carbonyl)-amino]-methyl}-5-methyl-4,5-dihydro-isoxazol-3-yl)-phenyl]-imino-methyl}-piperidine-4-carboxylic acid amide

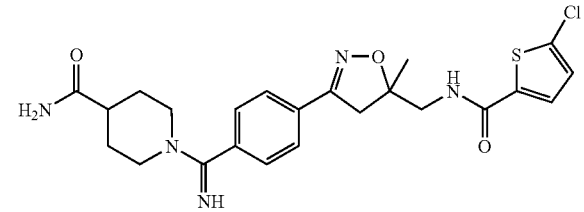

The titled compound was made by the procedure similar to that described in Example 8. MS found for $C_{23}H_{26}ClN_5O_3S$ as (M+H)+ 488.1, 490.1

Example 69

5-Chloro-thiophene-2-carboxylic acid {5-methyl-3-[4-(N-methylcarbamimidoyl)-phenyl]-4,5-dihydro-isoxazol-5-ylmethyl}-amide

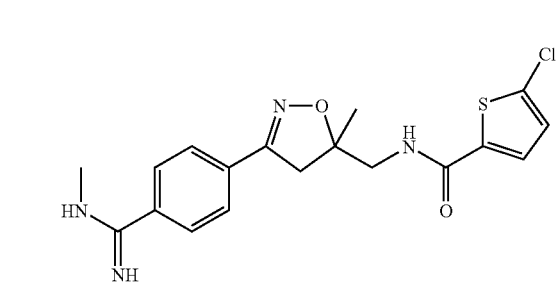

The titled compound was made by the procedure similar to that described in Example 8. MS found for $C_{18}H_{19}ClN_4O_2S$ as (M+H)+ 391.1, 393.1

SCHEME 3

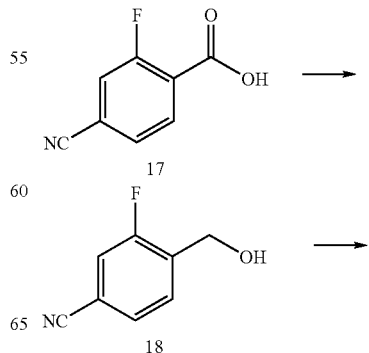

-continued

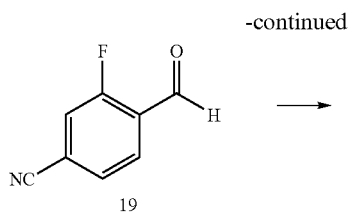

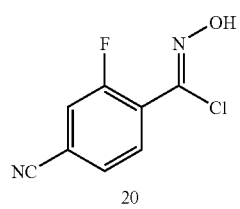

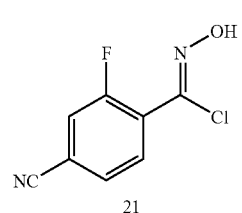

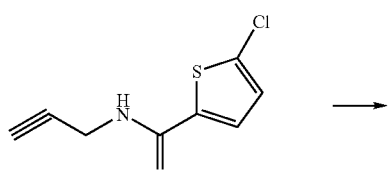

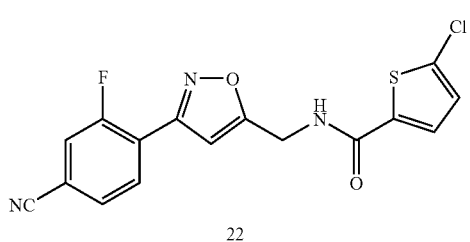

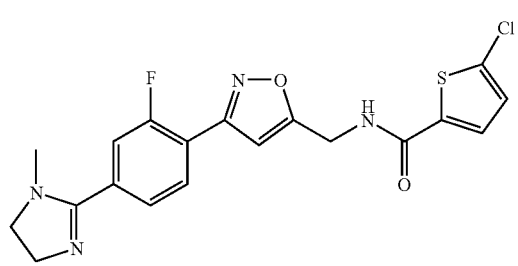

Example 70

5-Chloro-thiophene-2-carboxylic acid {3-[2-fluoro-4-(1-methyl-4,5-dihydro-1H-imidazol-2-yl)-phenyl]-isoxazol-5-ylmethyl}-amide

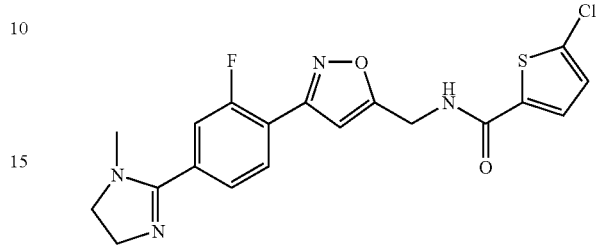

Step 1:

Carboxylic acid 17 (20.18g, 138 mmol) was diluted with 150 mL of THF and cooled to 0° C. To this stirring solution was added BH$_3$—S(CH$_3$)$_2$ complex (26 mL, 276 mmol) slowly which resulted in a vigorous reaction and significant gas evolution. The bath was removed and the reaction stirred at rt for 2 hrs at which time TLC and HPLC showed consumption of the starting material. The reaction was quenched by slow addition of water (vigorous exotherm), then the crude mixture was concentrated, diluted with ethyl acetate and filtered. The filtrate was concentrated to dryness affording the desired alcohol (18) as a white solid (17 g, 93%). NMR (DMSO-d$_6$, 400 MHz): δ 7.76 (d, 1H), δ 7.67 (m, 3H), δ 5.50 (t, 1H), δ 4.55 (d, 2H).

Step 2:

Benzyl alcohol 18 (17 g, 129 mmol) was dissolved in 300 mL of dichloromethane then treated with 33 g of celite followed by PCC (33 g, 155 mmol) resulting in a dark brown suspension which was stirred vigorously. After stirring 3 hrs the reaction was complete by TLC and was filtered through a short pad (2 in.×5 in.) of silica gel and eluted slowly with dichloromethane. The filtrate was concentrated affording the desired aldehyde (19) as a white solid (15.62 g, 93%). NMR (DMSO-d$_6$, 400 MHz): δ 10.38 (s, 1H), δ 7.95 (t, 1H), δ 7.59 (d, 1H), δ 7.48 (d, 1H).

Step 3:

Performed in the same manner as in step 1, Example 1. NMR (DMSO-d$_6$, 400 MHz): δ 12.03 (s, 1H), δ 8.20 (s, 1H), δ 7.90 (m, 2H), δ 7.64 (d, 1H).

Step 4:

Performed in the same manner as in step 2, Example 1. NMR (DMSO-d$_6$, 400 MHz): δ 8.00 (d, 1H), 7.82 (m, 3H).

Step 5:

Performed in the same manner as in step 5, Example 1. NMR (DMSO-d$_6$, 400 MHz): δ 8.85 (distorter t, 1H), δ 7.93 (d, 1H), δ 7.85 (t, 1H), δ 7.70 (d, 1H), δ 7.60 (s, 1H), δ 7.11 (s, 1H), 4.89 (m, 1H), δ 3.20-3.55 (m, 4H).

Step 6:

Performed in the same manner as in Example 8. MS found C$_{19}$H$_{16}$ClFN$_4$O$_2$S as (M+H)$^+$ 419.1, 421.1.

Example 71

5-Chloro-thiophene-2-carboxylic acid {3-[2-fluoro-4-(imino-pyrrolidin-1-yl-methyl)-phenyl]-isoxazol-5-ylmethyl}-amide

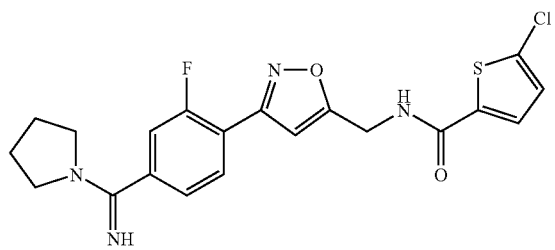

The titled compound was made by the procedure similar to that described in Example 70. MS found for $C_{20}H_{18}ClFN_4O_2S$ as (M+H)+ 433.0, 435.0

Example 72

5-Chloro-thiophene-2-carboxylic acid {3-[2-fluoro-4-(imino-piperidin-1-yl-methyl)-phenyl]-isoxazol-5-ylmethyl}-amide

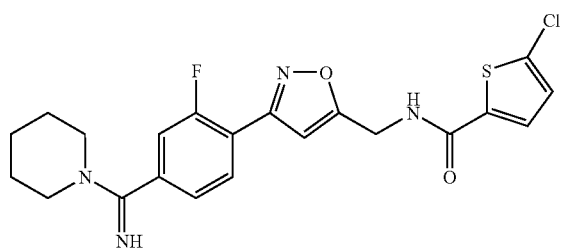

The titled compound was made by the procedure similar to that described in Example 70. MS found for $C_{21}H_{20}ClFN_4O_2S$ as (M+H)+ 447.0, 449.0

Example 73

5-Chloro-thiophene-2-carboxylic acid {3-[4-(N,N-dimethyl-carbamimidoyl)-2-fluoro-phenyl]-dihydro-isoxazol-5-ylmethyl}-amide

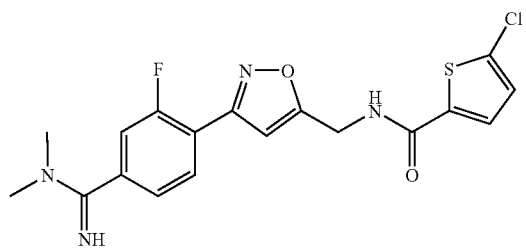

The titled compound was made by the procedure similar to that described in Example 70. MS found for $C_{18}H_{16}ClFN_4O_2S$ as (M+H)+ 407.0, 409.0

Example 74

5-Chloro-thiophene-2-carboxylic acid {3-[2-dimethylamino-4-(N,N-dimethyl-carbamimidoyl)-phenyl]-4,5-dihydro-isoxazol-5-ylmethyl}-amide

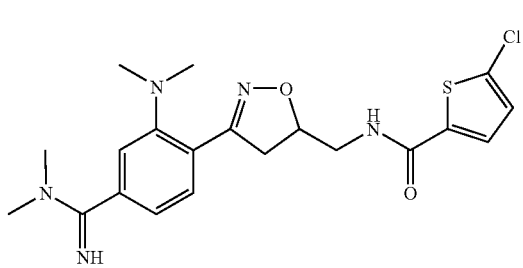

A solution of nitrile (Example 70, step 5) (0.090 g, 0.248 mmol) and dimethylamine (0.28 ml, 2.0M solution in tetrahydrofuran) in dimethylsulfoxide (5 mL) was treated with diisopropylethylamine (0.08 ml, 0.58 mmol) in a flask equipped with a reflux condenser. The mixture was heated to reflux overnight. The following day the reaction was checked by TLC which showed complete consumption of the starting material and a new polar spot. The crude reaction mixture was loaded onto a silica gel plug and eluted with dichloromethane affording the substituted dimethylamino compound as the major product. The product was treated with the procedure from Example 8 to obtain the titled compound. MS found for $C_{20}H_{24}ClN_5O_2S$ as (M+H)+ 434.1, 436.0

Example 75

5-Chloro-thiophene-2-carboxylic acid {3-[2-dimethylamino-4-(1-methyl-4,5-dihydro-1H-imidazol-2-yl)-phenyl]-4,5-dihydro-isoxazol-5-ylmethyl}-amide

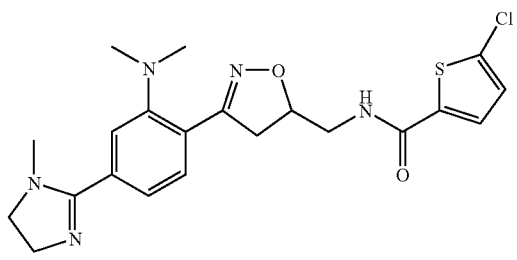

The titled compound was made by the procedure similar to that described in Example 74. MS found for $C_{21}H_{24}ClN_5O_2S$ as (M+H)+ 446.1, 448.1

Example 76

5-Chloro-thiophene-2-carboxylic acid {3-[2-dimethylamino-4-(imino-pyrrolidin-1-yl-methyl)-phenyl]-4,5-dihydro-isoxazol-5-ylmethyl}-amide

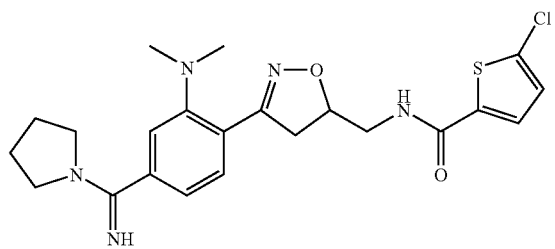

The titled compound was made by the procedure similar to that described in Example 74. MS found for $C_{22}H_{26}ClN_5O_2S$ as (M+H)+ 460.1, 462.1

Example 77

5-Chloro-thiophene-2-carboxylic acid {3-[2-dimethylamino-4-(imino-piperidin-1-yl-methyl)-phenyl]-4,5-dihydro-isoxazol-5-ylmethyl}-amide

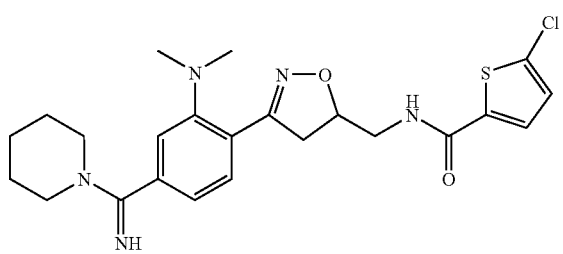

The titled compound was made by the procedure similar to that described in Example 74. MS found for $C_{23}H_{28}ClN_5O_2S$ as (M+H)+ 474.1, 476.1

Example 78

5-Chloro-thiophene-2-carboxylic acid {3-[4-(N,N-dimethyl-carbamimidoyl)-2-pyrrolidin-1-yl-phenyl]-4,5-dihydro-isoxazol-5-ylmethyl}-amide

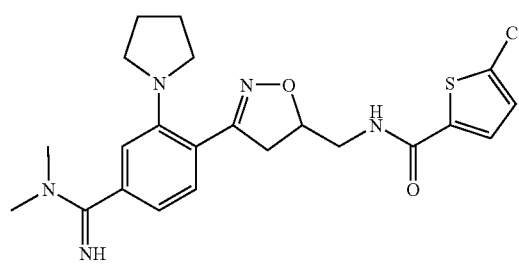

The titled compound was made by the procedure similar to that described in Example 74. MS found for $C_{22}H_{26}ClN_5O_2S$ as (M+H)+ 460.1, 462.1

Example 79

5-Chloro-thiophene-2-carboxylic acid {3-[4-(1-methyl-4,5-dihydro-1H-imidazol-2-yl)-2-pyrrolidin-1-yl-phenyl]-4,5-dihydro-isoxazol-5-ylmethyl}-amide

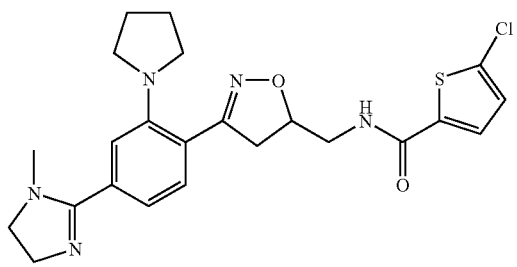

The titled compound was made by the procedure similar to that described in Example 74. MS found for $C_{23}H_{26}ClN_5O_2S$ as (M+H)+ 472.1, 474.1

Example 80

5-Chloro-thiophene-2-carboxylic acid {3-[4-(iminopyrrolidin-1-yl-methyl)-2-pyrrolidin-1-yl-phenyl]-4,5-dihydro-isoxazol-5-ylmethyl}-amide

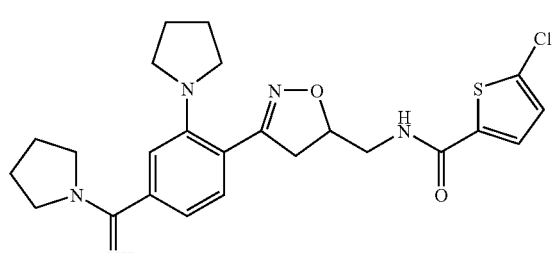

The titled compound was made by the procedure similar to that described in Example 74. MS found for $C_{24}H_{28}ClN_5O_2S$ as (M+H)+ 486.1, 488.1

Example 81

5-Chloro-thiophene-2-carboxylic acid {3-[4-(iminopiperidin-1-yl-methyl)-2-pyrrolidin-1-yl-phenyl]-4,5-dihydro-isoxazol-5-ylmethyl}-amide

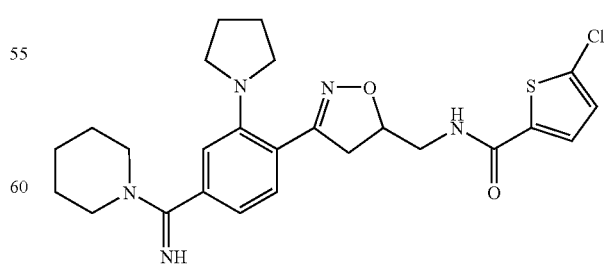

The titled compound was made by the procedure similar to that described in Example 74. MS found for $C_{25}H_{30}ClN_5O_2S$ as (M+H)+ 500.1, 502.1

Example 82

5-Chloro-thiophene-2-carboxylic acid {3-[4-(N,N-dimethyl-carbamimidoyl)-2-morpholin-4-yl-phenyl]-4,5-dihydro-isoxazol-5-ylmethyl}-amide

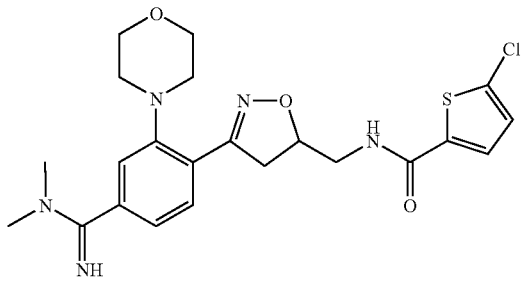

The titled compound was made by the procedure similar to that described in Example 74. MS found for $C_{22}H_{26}ClN_5O_3S$ as (M+H)+ 474.1, 476.1

Example 83

5-Chloro-thiophene-2-carboxylic acid {3-[4-(1-methyl-4,5-dihydro-1H-imidazol-2-yl)-2-morpholin-4-yl-phenyl]-4,5-dihydro-isoxazol-5-ylmethyl}-amide

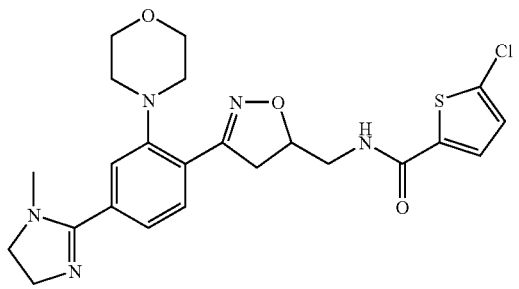

The titled compound was made by the procedure similar to that described in Example 74. MS found for $C_{23}H_{26}ClN_5O_3S$ as (M+H)+ 486.1, 488.1

Example 84

5-Chloro-thiophene-2-carboxylic acid {3-[4-(imino-pyrrolidin-1-yl-methyl)-2-morpholin-4-yl-phenyl]-4,5-dihydro-isoxazol-5-ylmethyl}-amide

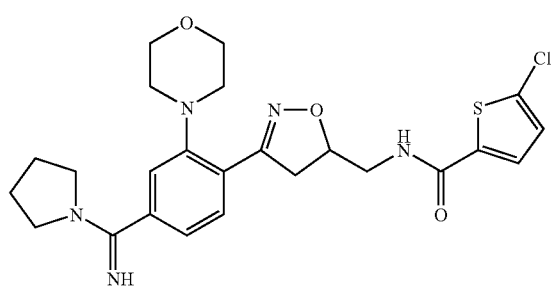

The titled compound was made by the procedure similar to that described in Example 74. MS found for $C_{24}H_{28}ClN_5O_3S$ as (M+H)+ 500.1, 502.1

Example 85

5-Chloro-thiophene-2-carboxylic acid {3-[4-(imino-piperidin-1-yl-methyl)-2-morpholin-4-yl-phenyl]-4,5-dihydro-isoxazol-5-ylmethyl}-amide

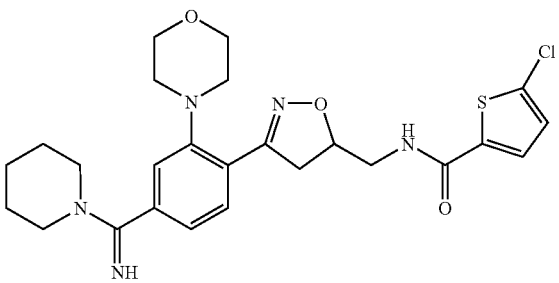

The titled compound was made by the procedure similar to that described in Example 74. MS found for $C_{25}H_{30}ClN_5O_3S$ as (M+H)+ 514.1, 516.1

Example 86

5-Chloro-thiophene-2-carboxylic acid (3-{4-(N,N-dimethyl-carbamimidoyl)-2-[(2-methoxy-ethyl)-methyl-amino]-phenyl}-4,5-dihydro-isoxazol-5-ylmethyl)-amide

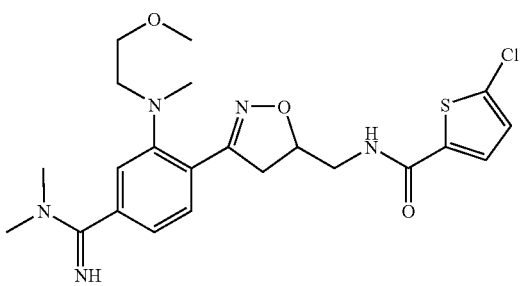

The titled compound was made by the procedure similar to that described in Example 74. MS found for $C_{22}H_{28}ClN_5O_3S$ as (M+H)+ 478.1, 480.1

Example 87

5-Chloro-thiophene-2-carboxylic acid {3-[2-[(2-methoxy-ethyl)-methyl-amino]-4-(1-methyl-4,5-dihydro-1H-imidazol-2-yl)-phenyl]-4,5-dihydro-isoxazol-5-ylmethyl}-amide

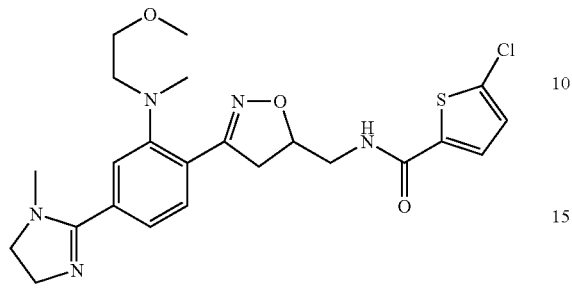

The titled compound was made by the procedure similar to that described in Example 74. MS found for $C_{23}H_{28}ClN_5O_3S$ as (M+H)+ 490.1, 492.1.

Example 88

5-Chloro-thiophene-2-carboxylic acid (3-{4-(imino-pyrrolidin-1-yl-methyl)-2-[(2-methoxy-ethyl)-methyl-amino]-phenyl}-4,5-dihydro-isoxazol-5-ylmethyl)-amide

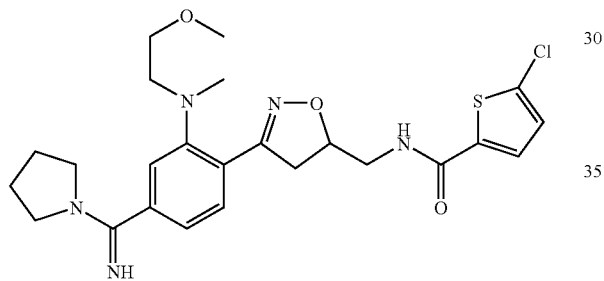

The titled compound was made by the procedure similar to that described in Example 74. MS found for $C_{24}H_{30}ClN_5O_3S$ as (M+H)+ 504.1, 506.1

Example 89

5-Chloro-thiophene-2-carboxylic acid (3-{4-(imino-piperidin-1-yl-methyl)-2-[(2-methoxy-ethyl)-methyl-amino]-phenyl}-4,5-dihydro-isoxazol-5-ylmethyl)-amide

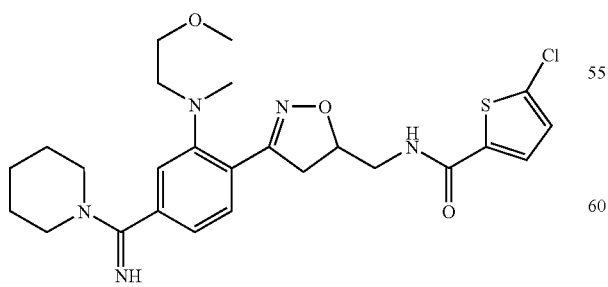

The titled compound was made by the procedure similar to that described in Example 74. MS found for $C_{25}H_{32}ClN_5O_3S$ as (M+H)+ 518.1, 520.2

Example 90

5-Chloro-thiophene-2-carboxylic acid {3-[2-azepan-1-yl-4-(N,N-dimethyl-carbamimidoyl)-phenyl]-4,5-dihydro-isoxazol-5-ylmethyl}-amide

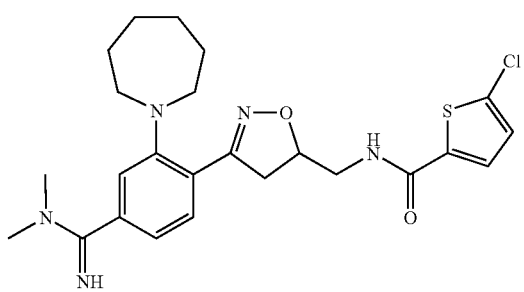

The titled compound was made by the procedure similar to that described in Example 74. MS found for $C_{24}H_{30}ClN_5O_2S$ as (M+H)+ 489.2, 491.2

Example 91

5-Chloro-thiophene-2-carboxylic acid {3-[2-azepan-1-yl-4-(1-methyl-4,5-dihydro-1H-imidazol-2-yl)-phenyl]-4,5-dihydro-isoxazol-5-ylmethyl}-amide

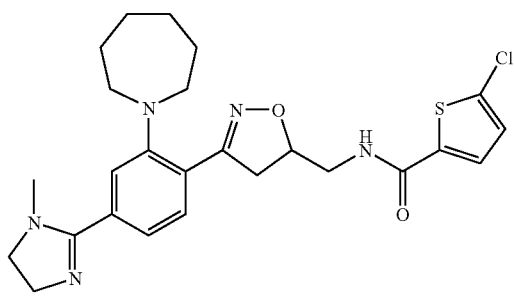

The titled compound was made by the procedure similar to that described in Example 74. MS found for $C_{25}H_{30}ClN_5O_2S$ as (M+H)+ 501.1, 503.1

Example 92

5-Chloro-thiophene-2-carboxylic acid {3-[2-azepan-1-yl-4-(imino-pyrrolidin-1-yl-methyl)-phenyl]-4,5-dihydro-isoxazol-5-ylmethyl}-amide

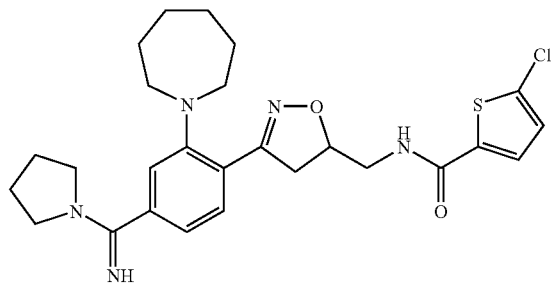

The titled compound was made by the procedure similar to that described in Example 74. MS found for $C_{26}H_{32}ClN_5O_2S$ as (M+H)+ 515.1, 517.1

Example 93

5-Chloro-thiophene-2-carboxylic acid {3-[2-azepan-1-yl-4-(imino-piperidin-1-yl-methyl)-phenyl]-4,5-dihydro-isoxazol-5-ylmethyl}-amide

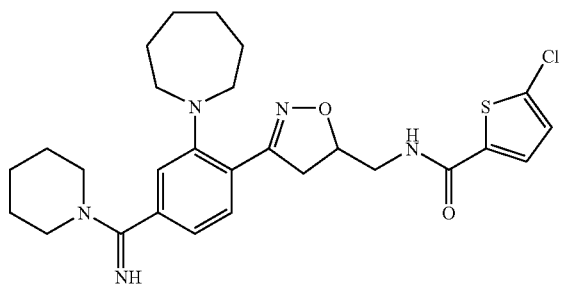

The titled compound was made by the procedure similar to that described in Example 74. MS found for $C_{27}H_{34}ClN_5O_2S$ as (M+H)+ 529.2, 531.2

Example 94

5-Chloro-thiophene-2-carboxylic acid {3-[2-dimethylamino-4-(N,N-dimethyl-carbamimidoyl)-phenyl]-isoxazol-5-ylmethyl}-amide

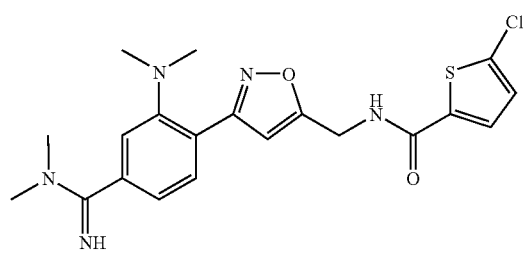

The titled compound was made by the procedure similar to that described in Example 74. MS found for $C_{20}H_{22}ClN_5O_2S$ as (M+H)+ 432.1, 434.1

Example 95

5-Chloro-thiophene-2-carboxylic acid {3-[2-dimethylamino-4-(1-methyl-4,5-dihydro-1H-imidazol-2-yl)-phenyl]-isoxazol-5-ylmethyl}-amide

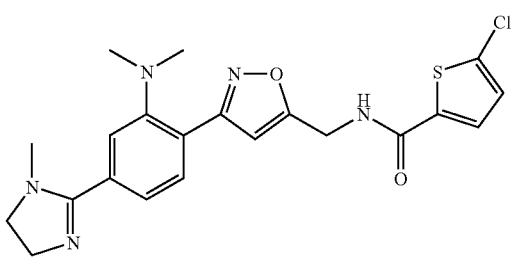

The titled compound was made by the procedure similar to that described in Example 74. MS found for $C_{21}H_{22}ClN_5O_2S$ as (M+H)+ 444.1, 446.1

Example 96

5-Chloro-thiophene-2-carboxylic acid {3-[2-dimethylamino-4-(imino-pyrrolidin-1-yl-methyl)-phenyl]-isoxazol-5-ylmethyl}-amide

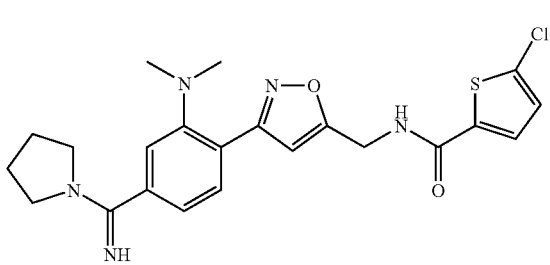

The titled compound was made by the procedure similar to that described in Example 74. MS found for $C_{22}H_{24}ClN_5O_2S$ as (M+H)+ 458.1, 460.1

Example 97

5-Chloro-thiophene-2-carboxylic acid {3-[2-dimethylamino-4-(imino-piperidin-1-yl-methyl)-phenyl]-isoxazol-5-ylmethyl}-amide

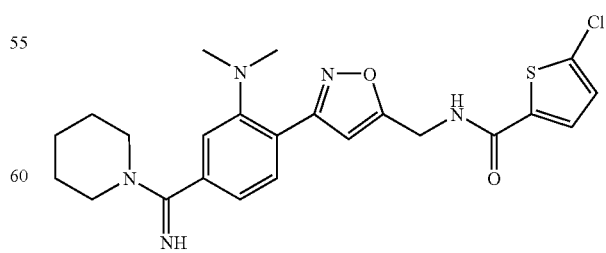

The titled compound was made by the procedure similar to that described in Example 74. MS found for $C_{23}H_{26}ClN_5O_2S$ as (M+H)+ 472.1, 474.1

Example 98

5-Chloro-thiophene-2-carboxylic acid {3-[4-(N,N-dimethyl-carbamimidoyl)-2-morpholin-4-yl-phenyl]-isoxazol-5-ylmethyl}-amide

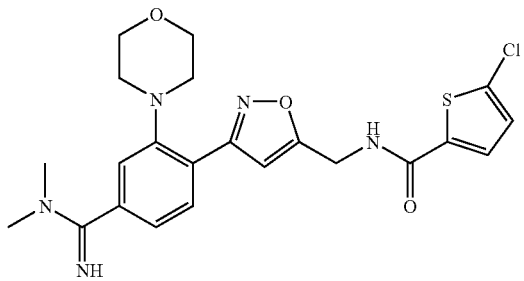

The titled compound was made by the procedure similar to that described in Example 74. MS found for $C_{22}H_{24}ClN_5O_3S$ as $(M+H)^+$ 474.1, 476.1

Example 99

5-Chloro-thiophene-2-carboxylic acid {3-[4-(1-methyl-4,5-dihydro-1H-imidazol-2-yl)-2-morpholin-4-yl-phenyl]-isoxazol-5-ylmethyl}-amide

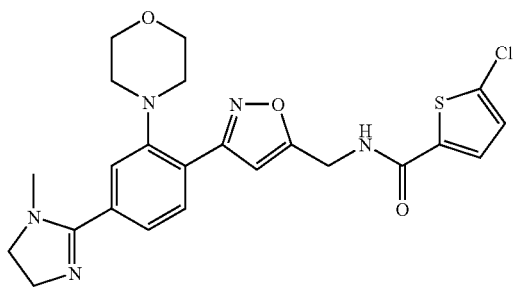

The titled compound was made by the procedure similar to that described in Example 74. MS found for $C_{23}H_{24}ClN_5O_3S$ as (M+H)+ 486.1, 488.1

Example 100

5-Chloro-thiophene-2-carboxylic acid {3-[4-(imino-pyrrolidin-1-yl-methyl)-2-morpholin-4-yl-phenyl]-isoxazol-5-ylmethyl}-amide

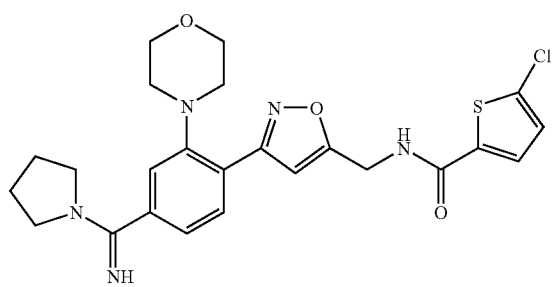

The titled compound was made by the procedure similar to that described in Example 74. MS found for $C_{24}H_{26}ClN_5O_3S$ as (M+H)+ 500.1, 502.1

Example 101

5-Chloro-thiophene-2-carboxylic acid {3-[4-(imino-piperidin-1-yl-methyl)-2-morpholin-4-yl-phenyl]-isoxazol-5-ylmethyl}-amide

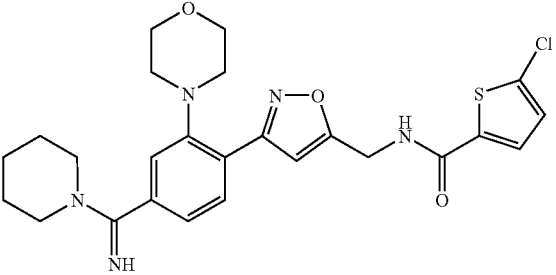

The titled compound was made by the procedure similar to that described in Example 74. MS found for $C_{25}H_{28}ClN_5O_3S$ as (M+H)+ 514.1, 516.1

Example 102

5-Chloro-thiophene-2-carboxylic acid {3-[4-(N,N-dimethyl-carbamimidoyl)-2-methoxy-phenyl]-4,5-dihydro-isoxazol-5-ylmethyl}-amide

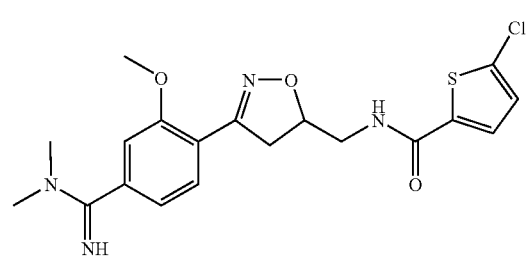

A solution of the nitrile compound (Example 70, step 5) (0.264 g, 0.727 mmol) in dimethylsulfoxide was treated with sodium methoxide (0.086 g, 1.60 mmol). The mixture was stirred at room temperature for 2 hours and was checked by TLC which showed complete consumption of the starting material and a new polar spot. The crude reaction mixture was loaded onto a silica gel plug and eluted with dichloromethane affording the substituted methoxy compound as the major product. The product was treated with the procedure similar to that described in Example 8 to obtain the titled compound. MS found for C19H21ClN4O3S as (M+H)+ 421.0, 423.0.

Example 103

5-Chloro-thiophene-2-carboxylic acid {3-[2-methoxy-4-(1-methyl-4,5-dihydro-1H-imidazol-2-yl)-phenyl]-4,5-dihydro-isoxazol-5-ylmethyl}-amide

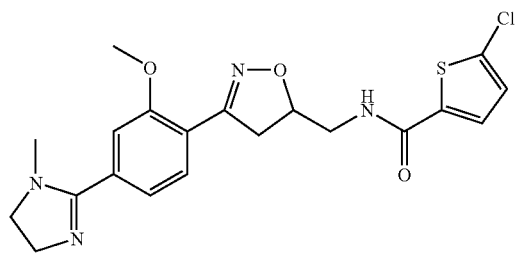

The titled compound was made by the procedure similar to that described in Example 102. MS found for $C_{20}H_{21}ClN_4O_3S$ as (M+H)+ 433.0, 435.0

Example 104

5-Chloro-thiophene-2-carboxylic acid {3-[4-(imino-pyrrolidin-1-yl-methyl)-2-methoxy-phenyl]-4,5-dihydro-isoxazol-5-ylmethyl}-amide

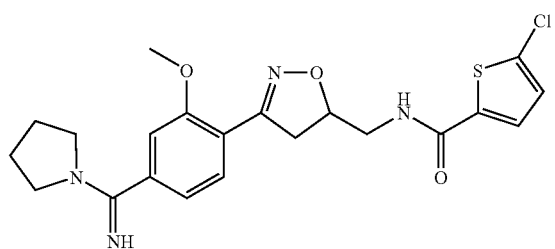

The titled compound was made by the procedure similar to that described in Example 102. MS found for $C_{21}H_{23}ClN_4O_3S$ as (M+H)+ 447.1, 449.1

Example 105

5-Chloro-thiophene-2-carboxylic acid {3-[4-(imino-piperidin-1-yl-methyl)-2-methoxy-phenyl]-4,5-dihydro-isoxazol-5-ylmethyl}-amide

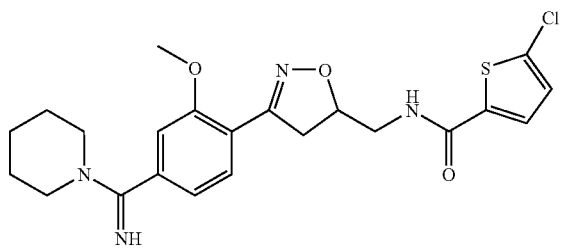

The titled compound was made by the procedure similar to that described in Example 102. MS found for $C_{22}H_{25}ClN_4O_3S$ as (M+H)+ 461.1, 463.1

Example 106

5-Chloro-thiophene-2-carboxylic acid {3-[4-(N,N-dimethyl-carbamimidoyl)-2-ethoxy-phenyl]-4,5-dihydro-isoxazol-5-ylmethyl}-amide

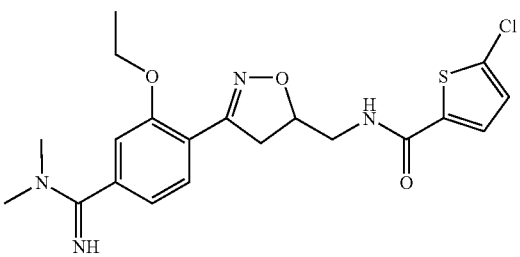

The titled compound was made by the procedure similar to that described in Example 102. MS found for $C_{20}H_{23}ClN_4O_3S$ as (M+H)+ 435.1, 437.1

Example 107

5-Chloro-thiophene-2-carboxylic acid {3-[2-ethoxy-4-(1-methyl-4,5-dihydro-1H-imidazol-2-yl)-phenyl]-4,5-dihydro-isoxazol-5-ylmethyl}-amide

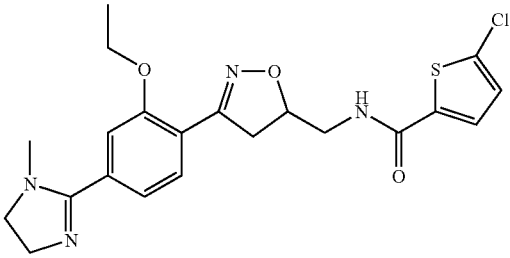

The titled compound was made by the procedure similar to that described in Example 102. MS found for $C_{21}H_{23}ClN_4O_3S$ as (M+H)+ 447.1, 449.1

Example 108

5-Chloro-thiophene-2-carboxylic acid {3-[2-ethoxy-4-(imino-pyrrolidin-1-yl-methyl)-phenyl]-4,5-dihydro-isoxazol-5-ylmethyl}-amide

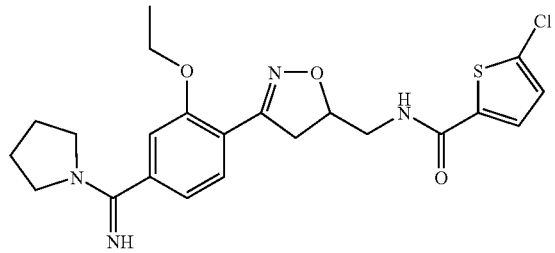

The titled compound was made by the procedure similar to that described in Example 102. MS found for $C_{22}H_{25}ClN_4O_3S$ as (M+H)+ 461.1, 463.1

Example 109

5-Chloro-thiophene-2-carboxylic acid {3-[4-(N,N-dimethyl-carbamimidoyl)-2-isopropoxy-phenyl]-4,5-dihydro-isoxazol-5-ylmethyl}-amide

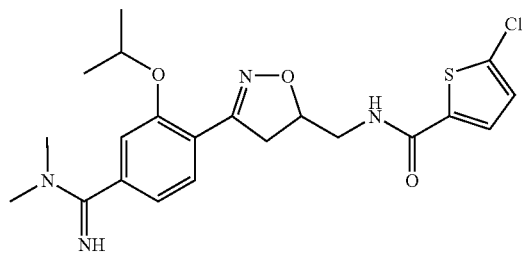

The titled compound was made by the procedure similar to that described in Example 102. MS found for $C_{21}H_{25}ClN_4O_3S$ as (M+H)+ 449.1, 451.1

Example 110

5-Chloro-thiophene-2-carboxylic acid {3-[2-isopropoxy-4-(1-methyl-4,5-dihydro-1H-imidazol-2-yl)-phenyl]-4,5-dihydro-isoxazol-5-ylmethyl}-amide

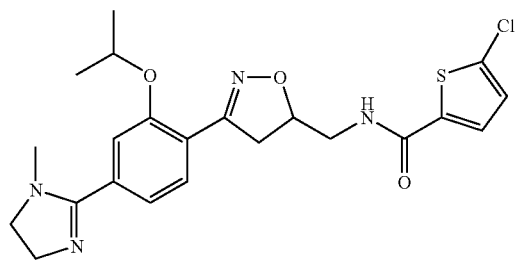

The titled compound was made by the procedure similar to that described in Example 102. MS found for $C_{22}H_{25}ClN_4O_3S$ as (M+H)+ 461.1, 463.1

Example 111

5-Chloro-thiophene-2-carboxylic acid {3-[4-(imino-pyrrolidin-1-yl-methyl)-2-isopropoxy-phenyl]-4,5-dihydro-isoxazol-5-ylmethyl}-amide

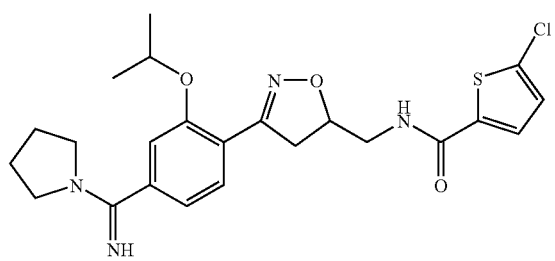

The titled compound was made by the procedure similar to that described in Example 102. MS found for $C_{23}H_{27}ClN_4O_3S$ as (M+H)+ 475.1, 477.1

Example 112

5-Chloro-thiophene-2-carboxylic acid {3-[2-cyclopentyloxy-4-(N,N-dimethyl-carbamimidoyl)-phenyl]-4,5-dihydro-isoxazol-5-ylmethyl}-amide

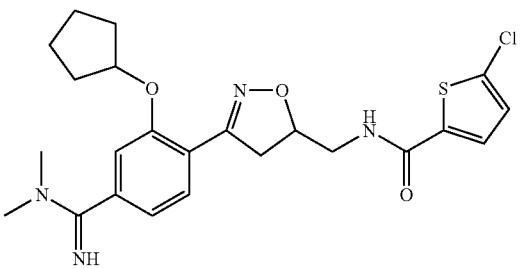

The titled compound was made by the procedure similar to that described in Example 102. MS found for $C_{23}H_{27}ClN_4O_3S$ as (M+H)+ 475.5, 477.5

Example 113

5-Chloro-thiophene-2-carboxylic acid {3-[2-cyclopentyloxy-4-(1-methyl-4,5-dihydro-1H-imidazol-2-yl)-phenyl]-4,5-dihydro-isoxazol-5-ylmethyl}-amide

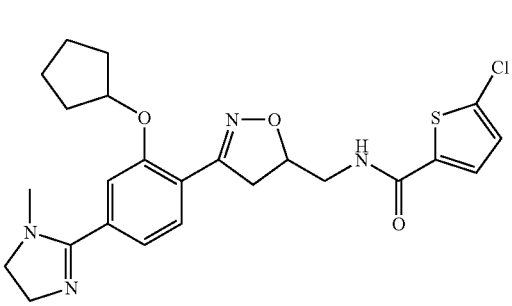

The titled compound was made by the procedure similar to that described in Example 102. MS found for $C_{24}H_{27}ClN_4O_3S$ as (M+H)+ 487.5, 489.5

Example 114

5-Chloro-thiophene-2-carboxylic acid {3-[2-cyclopentyloxy-4-(imino-pyrrolidin-1-yl-methyl)-phenyl]-4,5-dihydro-isoxazol-5-ylmethyl}-amide

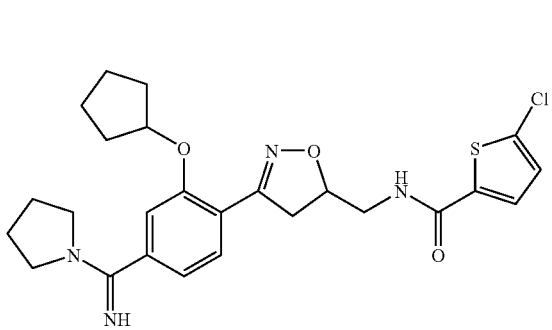

that described in Example 102. MS found for C$_{25}$H$_{29}$ClN$_4$O$_3$S as (M+H)+ 501.6, 503.6

Example 115

5-Chloro-thiophene-2-carboxylic acid {3-[2-cyclo-hexyloxy-4-(N,N-dimethyl-carbamimidoyl)-phenyl]-4,5-dihydro-isoxazol-5-ylmethyl}-amide

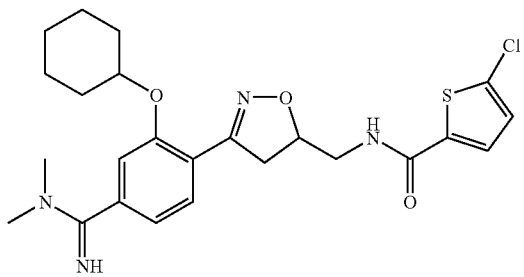

The titled compound was made by the procedure similar to that described in Example 102. MS found for C$_{24}$H$_{29}$ClN$_4$O$_3$S as (M+H)+ 489.6, 491.6

Example 116

5-Chloro-thiophene-2-carboxylic acid {3-[2-cyclo-hexyloxy-4-(1-methyl-4,5-dihydro-1H-imidazol-2-yl)-phenyl]-4,5-dihydro-isoxazol-5-ylmethyl}-amide

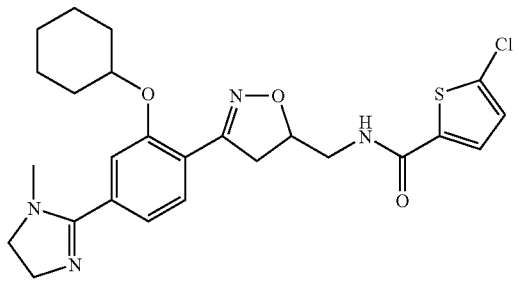

The titled compound was made by the procedure similar to that described in Example 102. MS found for C$_{25}$H$_{29}$ClN$_4$O$_3$S as (M+H)+ 501.6, 503.6

Example 117

5-Chloro-thiophene-2-carboxylic acid {3-[2-cyclo-hexyloxy-4-(imino-pyrrolidin-1-yl-methyl)-phenyl]-4,5-dihydro-isoxazol-5-ylmethyl}-amide

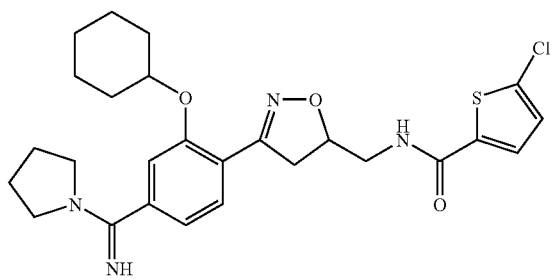

The titled compound was made by the procedure similar to that described in Example 102. MS found for C$_{26}$H$_{31}$ClN$_4$O$_3$S as (M+H)+ 515.6, 517.6

Example 118

5-Chloro-thiophene-2-carboxylic acid {3-[4-(N,N-dimethyl-carbamimidoyl)-2-methoxy-phenyl]-isoxazol-5-ylmethyl}-amide

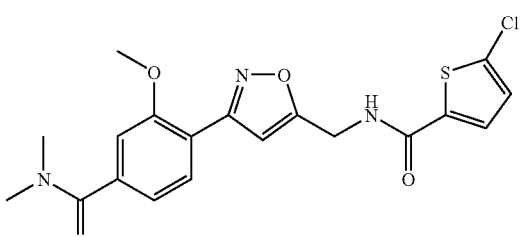

The titled compound was made by the procedure similar to that described in Example 102. MS found for C$_{19}$H$_{19}$ClN$_4$O$_3$S as (M+H)+ 419.0, 421.0

Example 119

5-Chloro-thiophene-2-carboxylic acid {3-[2-methoxy-4-(1-methyl-4,5-dihydro-1H-imidazol-2-yl)-phenyl]-isoxazol-5-ylmethyl}-amide

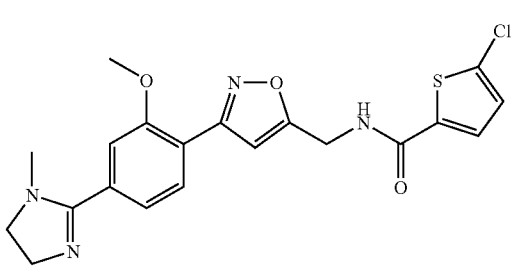

The titled compound was made by the procedure similar to that described in Example 102. MS found for C$_{20}$H$_{19}$ClN$_4$O$_3$S as (M+H)+ 431.0, 433.0

Example 120

5-Chloro-thiophene-2-carboxylic acid {3-[4-(imino-pyrrolidin-1-yl-methyl)-2-methoxy-phenyl]-isoxazol-5-ylmethyl}-amide

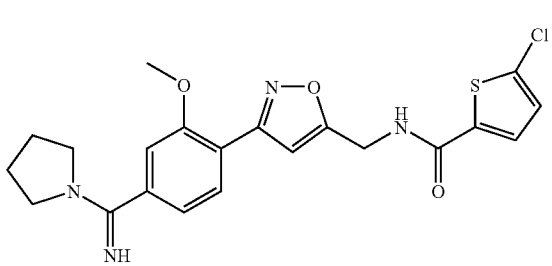

The titled compound was made by the procedure similar to that described in Example 102. MS found for C$_{21}$H$_{21}$ClN$_4$O$_3$S as (M+H)+ 445.0, 447.1

Example 121

5-Chloro-thiophene-2-carboxylic acid {3-[4-(imino-piperidin-1-yl-methyl)-2-methoxy-phenyl]-isoxazol-5-ylmethyl}-amide

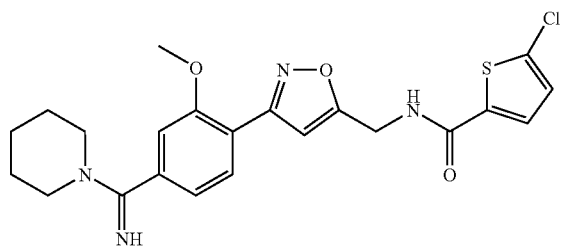

The titled compound was made by the procedure similar to that described in Example 102. MS found for $C_{22}H_{23}ClN_4O_3S$ as (M+H)+ 459.1, 461.1

Example 122

5-Chloro-thiophene-2-carboxylic acid {3-[4-(N,N-dimethyl-carbamimidoyl)-2-ethoxy-phenyl]-isoxazol-5-ylmethyl}-amide

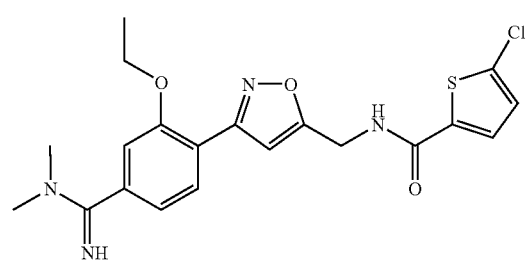

The titled compound was made by the procedure similar to that described in Example 102. MS found for $C_{20}H_{21}ClN_4O_3S$ as (M+H)+ 433.1, 435.1

Example 123

5-Chloro-thiophene-2-carboxylic acid {3-[2-ethoxy-4-(1-methyl-4,5-dihydro-1H-imidazol-2-yl)-phenyl]-isoxazol-5-ylmethyl}-amide

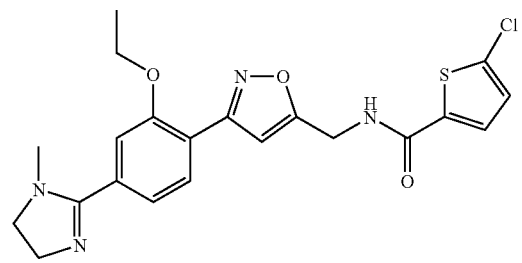

The titled compound was made by the procedure similar to that described in Example 102. MS found for $C_{21}H_{21}ClN_4O_3S$ as (M+H)+ 445.1, 447.1

Example 124

5-Chloro-thiophene-2-carboxylic acid {3-[2-ethoxy-4-(imino-pyrrolidin-1-yl-methyl)-phenyl]-isoxazol-5-ylmethyl}-amide

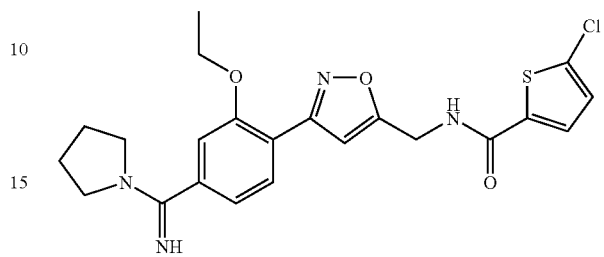

The titled compound was made by the procedure similar to that described in Example 102. MS found for $C_{22}H_{23}ClN_4O_3S$ as (M+H)+ 459.1, 461.1

Example 125

5-Chloro-thiophene-2-carboxylic acid {3-[2-ethoxy-4-(imino-piperidin-1-yl-methyl)-phenyl]-isoxazol-5-ylmethyl}-amide

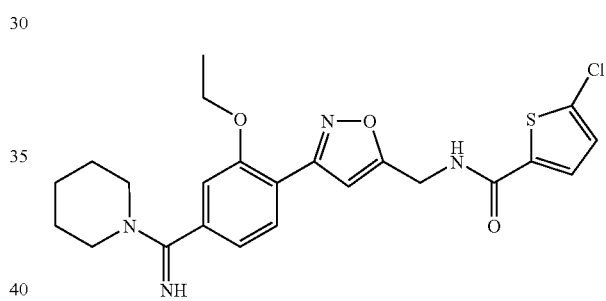

The titled compound was made by the procedure similar to that described in Example 102. MS found for $C_{23}H_{25}ClN_4O_3S$ as (M+H)+ 473.1, 475.1

Example 126

5-Chloro-thiophene-2-carboxylic acid {3-[4-(N,N-dimethyl-carbamimidoyl)-2-isopropoxy-phenyl]-isoxazol-5-ylmethyl}-amide

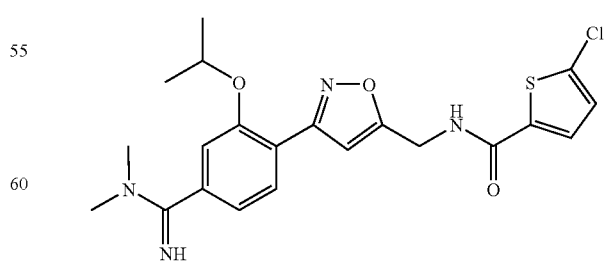

The titled compound was made by the procedure similar to that described in Example 102. MS found for $C_{23}H_{25}ClN_4O_3S$ as (M+H)+ 447.1, 449.1

Example 127

5-Chloro-thiophene-2-carboxylic acid {3-[2-isopropoxy-4-(1-methyl-4,5-dihydro-1H-imidazol-2-yl)-phenyl]-isoxazol-5-ylmethyl}-amide

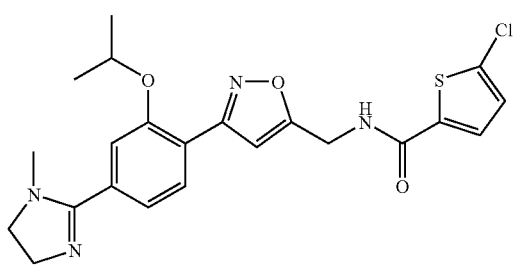

The titled compound was made by the procedure similar to that described in Example 102. MS found for $C_{22}H_{23}ClN_4O_3S$ as (M+H)+ 459.1, 461.1

Example 128

5-Chloro-thiophene-2-carboxylic acid {3-[4-(iminopyrrolidin-1-yl-methyl)-2-isopropoxy-phenyl]-isoxazol-5-ylmethyl}-amide

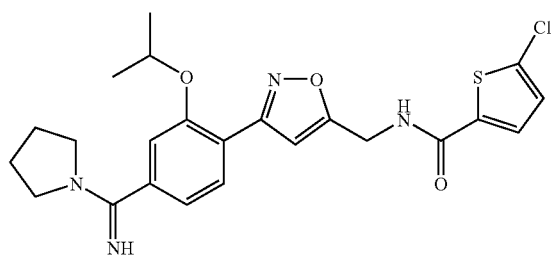

The titled compound was made by the procedure similar to that described in Example 102. MS found for $C_{23}H_{25}ClN_4O_3S$ as (M+H)+ 473.1, 475.1

Example 129

5-Chloro-thiophene-2-carboxylic acid {3-[4-(iminopiperidin-1-yl-methyl)-2-isopropoxy-phenyl]-isoxazol-5-ylmethyl}-amide

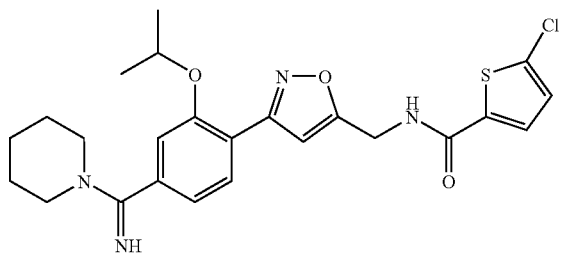

The titled compound was made by the procedure similar to that described in Example 102. MS found for $C_{24}H_{27}ClN_4O_3S$ as (M+H)+ 487.1, 489.1

Example 130

5-Chloro-thiophene-2-carboxylic acid {3-[4-(N,N-dimethyl-carbamimidoyl)-2-phenoxy-phenyl]-isoxazol-5-ylmethyl}-amide

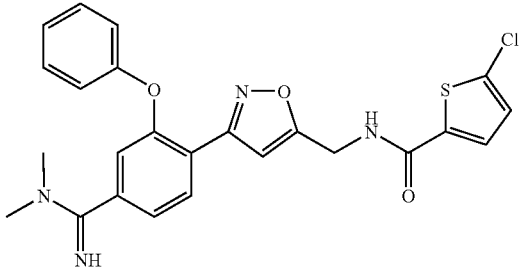

The titled compound was made by the procedure similar to that described in Example 102. MS found for $C_{24}H_{21}ClN_4O_3S$ as (M+H)+ 511.1, 513.1

Example 131

5-Chloro-thiophene-2-carboxylic acid {3-[4-(1-methyl-4,5-dihydro-1H-imidazol-2-yl)-2-phenoxy-phenyl]-isoxazol-5-ylmethyl}-amide

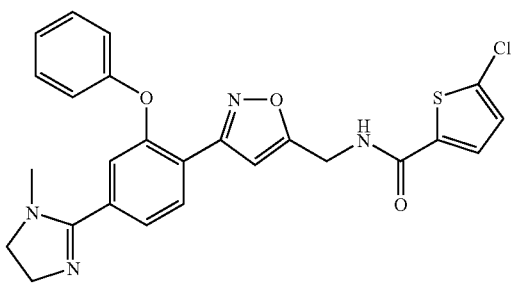

The titled compound was made by the procedure similar to that described in Example 102. MS found for $C_{24}H_{21}ClN_4O_3S$ as (M+H)+ 523.1, 525.1

Example 132

5-Chloro-thiophene-2-carboxylic acid {3-[4-(iminopyrrolidin-1-yl-methyl)-2-phenoxy-phenyl]-isoxazol-5-ylmethyl}-amide

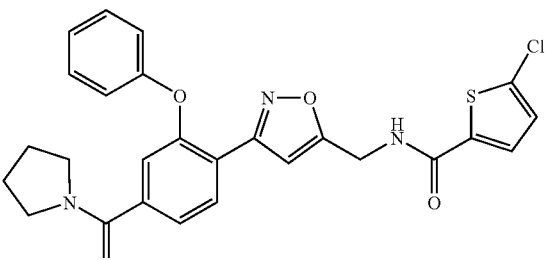

123

The titled compound was made by the procedure similar to that described in Example 102. MS found for $C_{26}H_{23}ClN_4O_3S$ as (M+H)+ 537.1, 539.1

Example 133

5-Chloro-thiophene-2-carboxylic acid {3-[4-(N,N-dimethyl-carbamimidoyl)-2-(4-methoxy-phenoxy)-phenyl]-isoxazol-5-ylmethyl}-amide

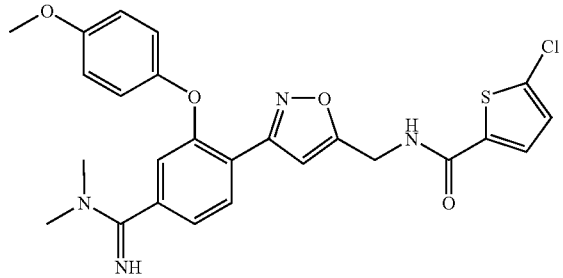

The titled compound was made by the procedure similar to that described in Example 102. MS found for $C_{25}H_{23}ClN_4O_4S$ as (M+H)+ 481.1, 483.1

Example 134

5-Chloro-thiophene-2-carboxylic acid {3-[2-(4-methoxy-phenoxy)-4-(1-methyl-4,5-dihydro-1H-imidazol-2-yl)-phenyl]-isoxazol-5-ylmethyl}-amide

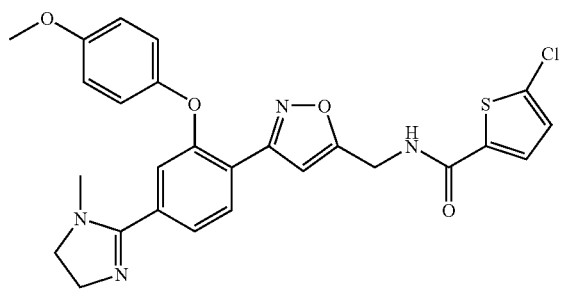

The titled compound was made by the procedure similar to that described in Example 102. MS found for $C_{26}H_{23}ClN_4O_4S$ as (M+H)+ 493.1, 495.1

Example 135

5-Chloro-thiophene-2-carboxylic acid {3-[4-(imino-pyrrolidin-1-yl-methyl)-2-(4-methoxy-phenoxy)-phenyl]-isoxazol-5-ylmethyl}-amide

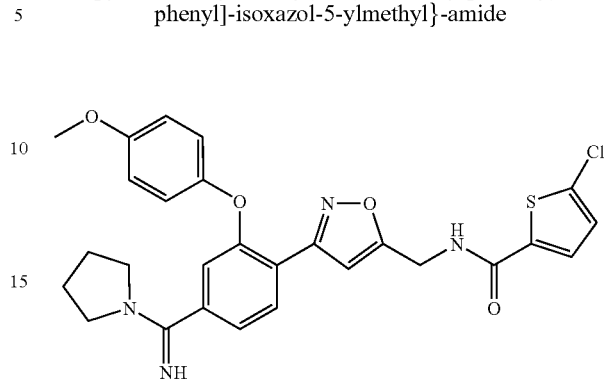

The titled compound was made by the procedure similar to that described in Example 102. MS found for $C_{27}H_{25}ClN_4O_4S$ as (M+H)+ 507.1, 509.1

Example 136

5-Chloro-thiophene-2-carboxylic acid {3-[4-(N,N-dimethyl-carbamimidoyl)-2-methylsulfanyl-phenyl]-4,5-dihydro-isoxazol-5-ylmethyl}-amide

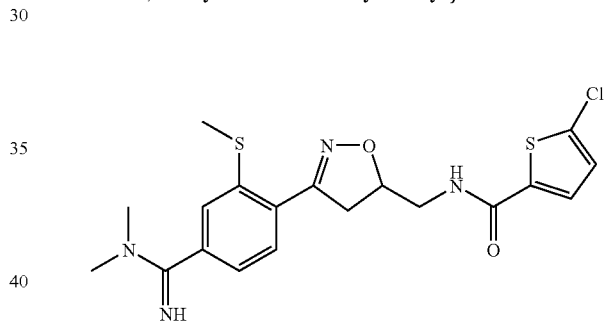

The titled compound was made by the procedure similar to that described in Example 102 using sodium thiomethoxide in place of sodium methoxide. MS found for $C_{19}H_{21}ClN_4O_2S_2$ as (M+H)+ 437.0, 439.0

Example 137

5-Chloro-thiophene-2-carboxylic acid {3-[4-(1-methyl-4,5-dihydro-1H-imidazol-2-yl)-2-methylsulfanyl-phenyl]-4,5-dihydro-isoxazol-5-ylmethyl}-amide

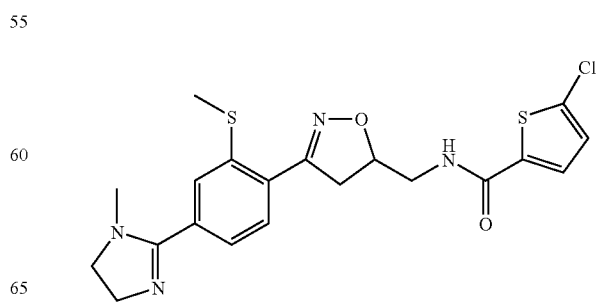

The titled compound was made by the procedure similar to that described in Example 136. MS found for $C_{20}H_{21}ClN_4O_2S_2$ as (M+H)+ 449.0, 451.0

Example 138

5-Chloro-thiophene-2-carboxylic acid {3-[4-(imino-pyrrolidin-1-yl-methyl)-2-methylsulfanyl-phenyl]-4,5-dihydro-isoxazol-5-ylmethyl}-amide

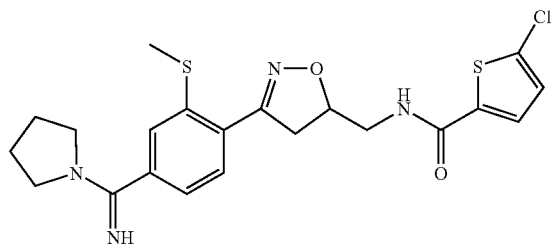

The titled compound was made by the procedure similar to that described in Example 136. MS found for $C_{21}H_{23}ClN_4O_2S_2$ as (M+H)+ 463.0, 465.1

Example 139

5-Chloro-thiophene-2-carboxylic acid {3-[4-(imino-piperidin-1-yl-methyl)-2-methylsulfanyl-phenyl]-4,5-dihydro-isoxazol-5-ylmethyl}-amide

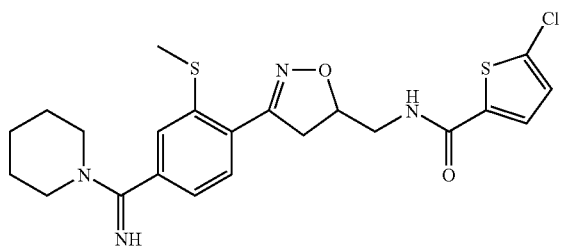

The titled compound was made by the procedure similar to that described in Example 136. MS found for $C_{22}H_{25}ClN_4O_2S_2$ as (M+H)+ 477.0, 479.1

Example 140

5-Chloro-thiophene-2-carboxylic acid {3-[4-(N,N-dimethyl-carbamimidoyl)-2-methylsulfanyl-phenyl]-isoxazol-5-ylmethyl}-amide

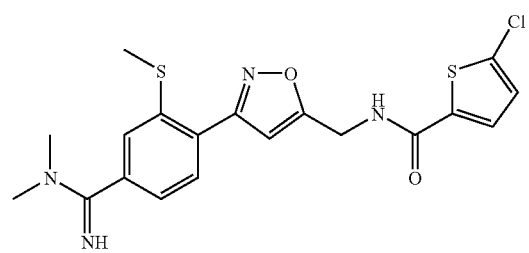

The titled compound was made by the procedure similar to that described in Example 136. MS found for $C_{19}H_{19}ClN_4O_2S_2$ as (M+H)+ 435.0, 437.0

Example 141

5-Chloro-thiophene-2-carboxylic acid {3-[4-(1-methyl-4,5-dihydro-1H-imidazol-2-yl)-2-methylsulfanyl-phenyl]-isoxazol-5-ylmethyl}-amide

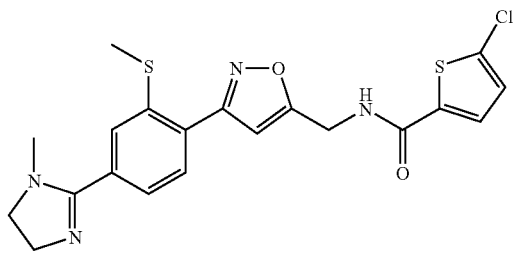

The titled compound was made by the procedure similar to that described in Example 136. MS found for $C_{20}H_{19}ClN_4O_2S_2$ as (M+H)+ 447.0, 449.0

Example 142

5-Chloro-thiophene-2-carboxylic acid {3-[4-(imino-pyrrolidin-1-yl-methyl)-2-methylsulfanyl-phenyl]-isoxazol-5-ylmethyl}-amide

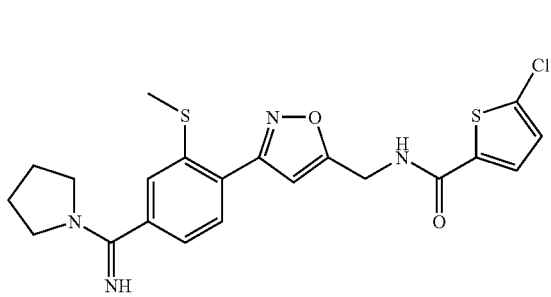

The titled compound was made by the procedure similar to that described in Example 136. MS found for $C_{21}H_{21}ClN_4O_2S_2$ as (M+H)+ 461.0, 463.0

Example 143

5-Chloro-thiophene-2-carboxylic acid {3-[4-(imino-piperidin-1-yl-methyl)-2-methylsulfanyl-phenyl]-isoxazol-5-ylmethyl}-amide

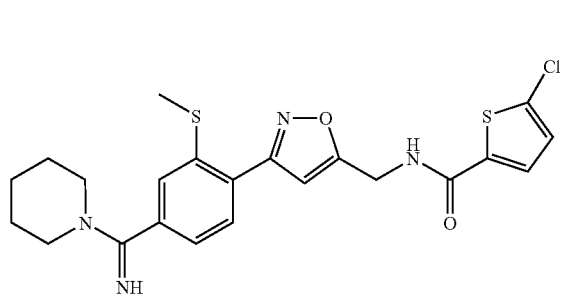

The titled compound was made by the procedure similar to that described in Example 136. MS found for $C_{22}H_{23}ClN_4O_2S_2$ as (M+H)+ 475.1, 477.0

Example 144

5-Chloro-thiophene-2-carboxylic acid (3-phenyl-4,5-dihydro-isoxazol-5-ylmethyl)-amide

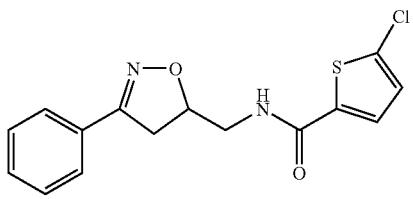

The titled compound was made by the procedure similar to that described in Example 1. MS found for $C_{15}H_{13}ClN_2O_2S$ as (M+H)+ 321.3, 323.3

Example 145

5-Chloro-thiophene-2-carboxylic acid (5-methyl-3-phenyl-4,5-dihydro-isoxazol-5-ylmethyl)-amide

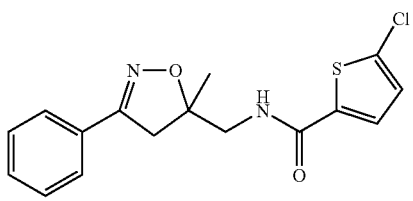

The titled compound was made by the procedure similar to that described in Example 1. MS found for $C_{16}H_{15}ClN_2O_2S$ as (M+H)+ 335.4, 337.3

Example 146

5-Chloro-thiophene-2-carboxylic acid (3-phenyl-isoxazol-5-ylmethyl)-amide

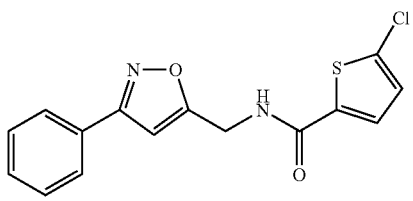

The titled compound was made by the procedure similar to that described in Example 1. MS found for $C_{15}H_{11}ClN_2O_2S$ as (M+H)+ 319.2, 321.1

Example 147

5-Chloro-thiophene-2-carboxylic acid (3-p-tolyl-4,5-dihydro-isoxazol-5-ylmethyl)-amide

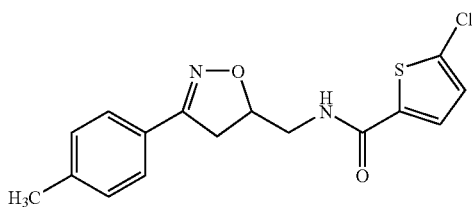

The titled compound was made by the procedure similar to that described in Example 1. MS found for $C_{16}H_{15}ClN_2O_2S$ as (M+H)+ 335.2, 337.2

Example 148

5-Chloro-thiophene-2-carboxylic acid (5-methyl-3-p-tolyl-4,5-dihydro-isoxazol-5-ylmethyl)-amide

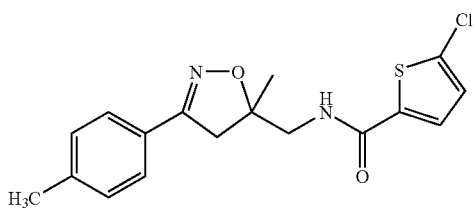

The titled compound was made by the procedure similar to that described in Example 1. MS found for $C_{17}H_{17}ClN_2O_2S$ as (M+H)+ 349.2, 351.2

Example 149

5-Chloro-thiophene-2-carboxylic acid (3-p-tolyl-isoxazol-5-ylmethyl)-amide

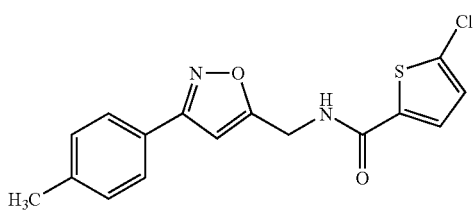

The titled compound was made by the procedure similar to that described in Example 1. MS found for $C_{16}H_{13}ClN_2O_2S$ as (M+H)+ 333.2, 335.1

Example 150

5-Chloro-thiophene-2-carboxylic acid [3-(4-methoxy-phenyl)-4,5-dihydro-isoxazol-5-ylmethyl]-amide

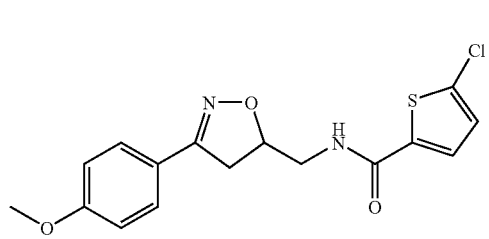

The titled compound was made by the procedure similar to that described in Example 1. MS found for $C_{16}H_{15}ClN_2O_3S$ as (M+H)+ 379.2, 381.2

Example 151

5-Chloro-thiophene-2-carboxylic acid [3-(4-methoxy-phenyl)-5-methyl-4,5-dihydro-isoxazol-5-ylmethyl]-amide

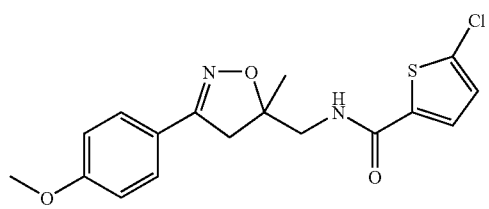

The titled compound was made by the procedure similar to that described in Example 1. MS found for $C_{17}H_{17}ClN_2O_3S$ as (M+H)+ 393.2, 395.1

Example 152

5-Chloro-thiophene-2-carboxylic acid [3-(4-methoxy-phenyl)-isoxazol-5-ylmethyl]-amide

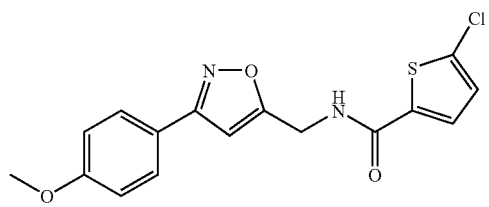

The titled compound was made by the procedure similar to that described in Example 1. MS found for $C_{16}H_{13}ClN_2O_3S$ as (M+H)+ 377.3, 379.3

Example 153

5-Chloro-thiophene-2-carboxylic acid [3-(4-chlorophenyl)-4,5-dihydro-isoxazol-5-ylmethyl]-amide

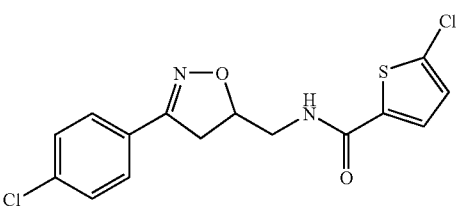

The titled compound was made by the procedure similar to that described in Example 1. MS found for $C_{15}H_{12}Cl_2N_2O_2S$ as (M+H)+ 356.7, 358.7

Example 154

5-Chloro-thiophene-2-carboxylic acid [3-(4-chlorophenyl)-5-methyl-4,5-dihydro-isoxazol-5-ylmethyl]-amide

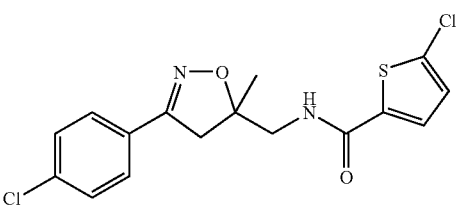

The titled compound was made by the procedure similar to that described in Example 1. MS found for $C_{16}H_{14}Cl_2N_2O_2S$ as (M+H)+ 370.7, 372.8

Example 155

5-Chloro-thiophene-2-carboxylic acid [3-(4-chlorophenyl)-isoxazol-5-ylmethyl]-amide

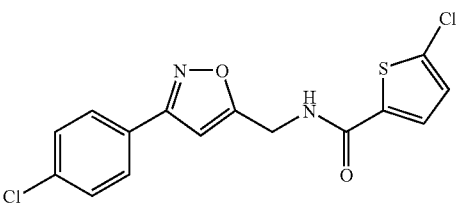

The titled compound was made by the procedure similar to that described in Example 1. MS found for $C_{15}H_{10}Cl_2N_2O_2S$ as (M+H)+ 354.8, 356.7

Example 156

4-(5-{[(5-Chloro-thiophene-2-carbonyl)-amino]-methyl}-4,5-dihydro-isoxazol-3-yl)-benzoic acid methyl ester

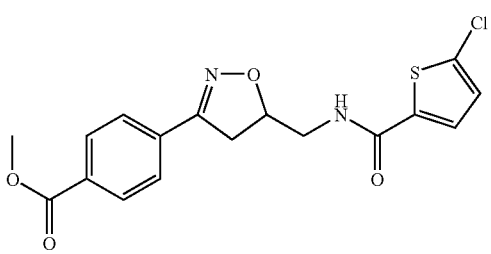

The titled compound was made by the procedure similar to that described in Example 1. MS found for $C_{17}H_{15}ClN_2O_4S$ as (M+H)+ 379.4, 381.4

Example 157

4-(5-{[(5-Chloro-thiophene-2-carbonyl)-amino]-methyl}-isoxazol-3-yl)-benzoic acid methyl ester

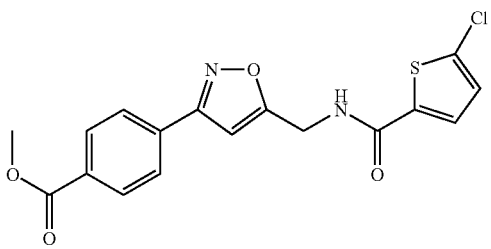

The titled compound was made by the procedure similar to that described in Example 1. MS found for $C_{17}H_{13}ClN_2O_4S$ as (M+H)+ 377.3, 379.3

Example 158

4-(5-{[(5-Chloro-thiophene-2-carbonyl)-amino]-methyl}-4,5-dihydro-isoxazol-3-yl)-benzoic acid

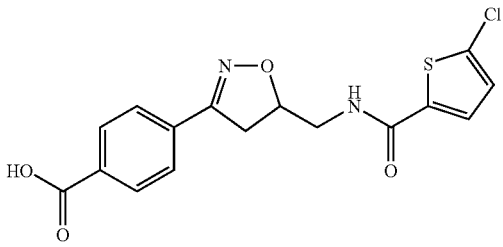

A solution of the compound 156 (0.360 g, 0.952 mmol) in methanol and water was treated with lithium hydroxide (2.86 ml, 1M in methanol). The mixture was stirred at room temperature overnight. The following day the reaction was checked by TLC which showed complete consumption of the starting material and a new, more polar spot. The crude reaction mixture was acidified to pH=3, concentrated in vacuo, then suspended in a small amount of methanol (ca. 5 mL) and triturated with water affording a white solid. The solid was filtered and dried affording the desired product. MS found for $C_{16}H_{13}ClN_2O_4S$ as (M+H)+ 365.3, 367.3

Example 159

4-(5-{[(5-Chloro-thiophene-2-carbonyl)-amino]-methyl}-isoxazol-3-yl)-benzoic acid

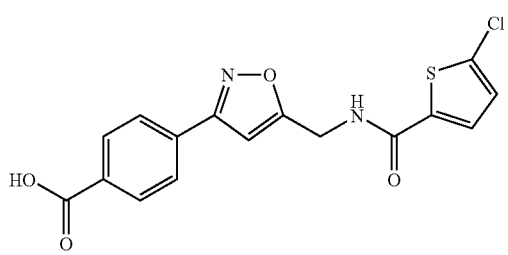

The titled compound was made by the procedure similar to that described in Example 158. MS found for $C_{16}H_{11}ClN_2O_4S$ as (M+H)+ 363.4, 365.4

Example 160

5-Chloro-thiophene-2-carboxylic acid [3-(4-aminophenyl)-4,5-dihydro-isoxazol-5-ylmethyl]-amide

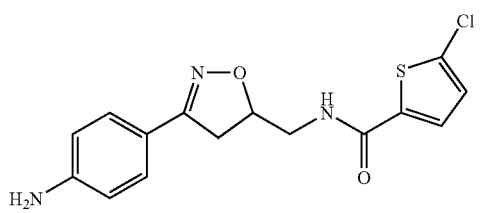

A solution of the nitroisoxazoline (prepared in a similar manner to Example 1 from 4-nitrobenzaldehyde) (0.078 g, 0.214 mmol) in ethanol was treated with tin chloride dihydrate (0.155 g, 0.684 mmol). The mixture was heated to reflux for 2 hour. The reaction was checked by TLC which showed complete consumption of the starting material and a new, less polar spot. The crude reaction mixture was diluted with saturated potassium carbonate, stirred ca. 30 min, then filtered through a pad of Celite. The filtrate was concentrated affording the desired product which was purified by preparative HPLC. MS found for $C_{15}H_{14}ClN_3O_2S$ as (M+H)+ 336.3, 338.3

Example 161

5-Chloro-thiophene-2-carboxylic acid [3-(4-amino-phenyl)-isoxazol-5-ylmethyl]-amide

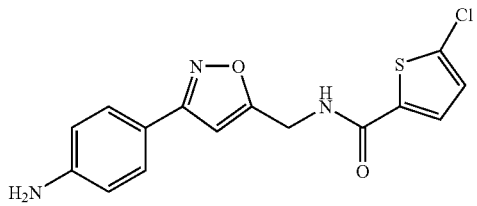

The titled compound was made by the procedure similar to that described in Example 160. MS found for $C_{15}H_{12}ClN_3O_2S$ as (M+H)+ 334.3, 336.3

Example 162

5-Chloro-thiophene-2-carboxylic acid [3-(4-dimethylcarbamoyl-phenyl)-4,5-dihydro-isoxazol-5-ylmethyl]-amide

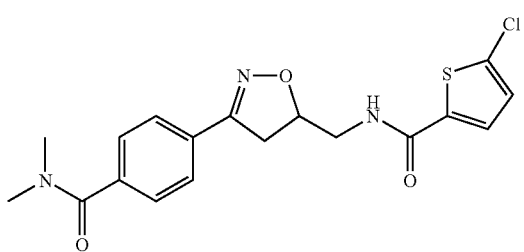

A solution of the acid compound 158 (0.088 g, 0.243 mmol), dimethylamine (0.032 ml, 0.316 mmol) and triethylamine (0.051 ml, 0.365 mmol) in dimethlformide was treated with BOP chloride (0.074 g, 0.292 mmol). The mixture was stirred at room temperature overnight. The following day the reaction was checked by TLC which showed complete consumption of the starting material and a new, less polar spot. The crude reaction mixture was purified by preparative HPLC to give the desired product. MS found for $C_{18}H_{18}ClN_3O_3S$ as (M+H)+ 392.5, 394.5

Example 163

5-Chloro-thiophene-2-carboxylic acid {3-[4-(azetidine-1-carbonyl)-phenyl]-4,5-dihydro-isoxazol-5-ylmethyl}-amide

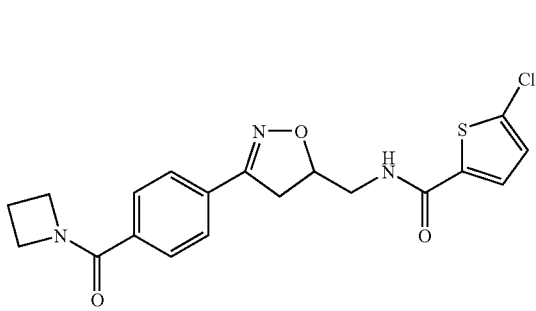

The titled compound was made by the procedure similar to that described in Example 162. MS found for $C_{19}H_{18}ClN_3O_3S$ as (M+H)+ 404.3, 406.3

Example 164

5-Chloro-thiophene-2-carboxylic acid {3-[4-(pyrrolidine-1-carbonyl)-phenyl]-4,5-dihydro-isoxazol-5-ylmethyl}-amide

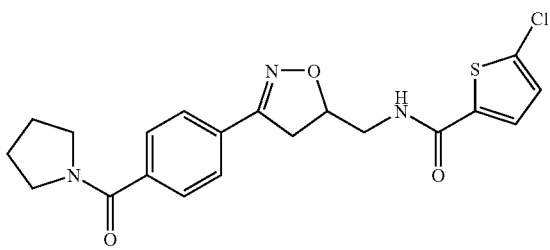

The titled compound was made by the procedure similar to that described in Example 162. MS found for $C_{20}H_{20}ClN_3O_3S$ as (M+H)+ 418.0, 420.0

Example 165

5-Chloro-thiophene-2-carboxylic acid {3-[4-(2-methyl-pyrrolidine-1-carbonyl)-phenyl]-4,5-dihydro-isoxazol-5-ylmethyl}-amide

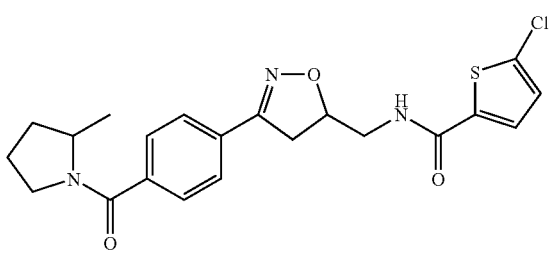

The titled compound was made by the procedure similar to that described in Example 162. MS found for $C_{21}H_{22}ClN_3O_3S$ as (M+H)+ 432.3, 434.3

Example 166

5-Chloro-thiophene-2-carboxylic acid (3-{4-[(2-diethylamino-ethyl)-methyl-carbamoyl]-phenyl}-4,5-dihydro-isoxazol-5-ylmethyl)-amide

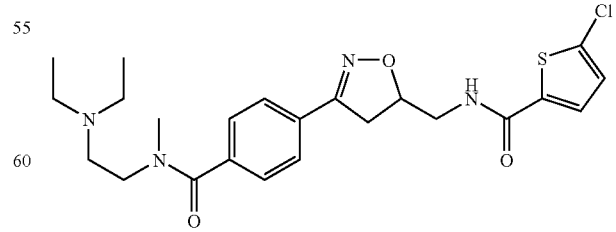

The titled compound was made by the procedure similar to that described in Example 162. MS found for $C_{23}H_{29}ClN_4O_3S$ as (M+H)+ 477.2, 479.1

Example 167

5-Chloro-thiophene-2-carboxylic acid {3-[4-(pyrrolidine-1-carbonyl)-phenyl]-isoxazol-5-ylmethyl}-amide

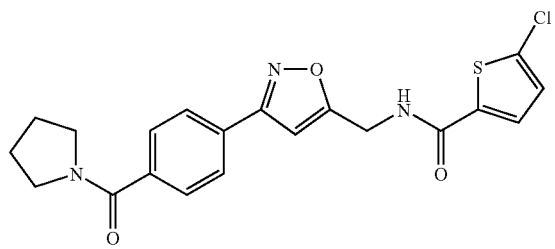

The titled compound was made by the procedure similar to that described in Example 162. MS found for $C_{20}H_{18}ClN_3O_3S$ as (M+H)+ 416.1, 418.0

Example 168

5-Chloro-thiophene-2-carboxylic acid (3-{4-[(2-diethylamino-ethyl)-methyl-carbamoyl]-phenyl}-isoxazol-5-ylmethyl)-amide

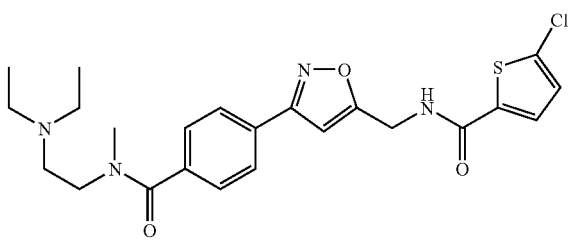

The titled compound was made by the procedure similar to that described in Example 162. MS found for $C_{20}H_{18}ClN_3O_3S$ as (M+H)+ 475.1, 477.1

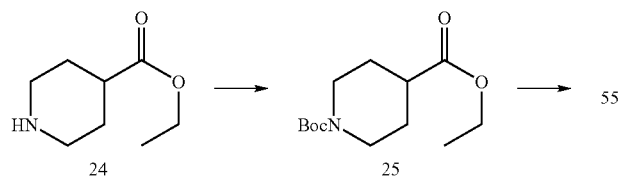

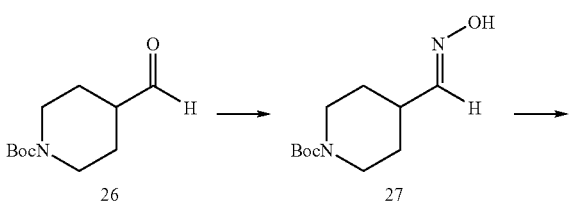

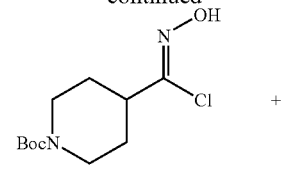

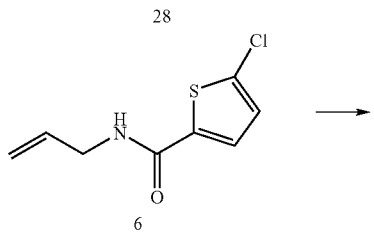

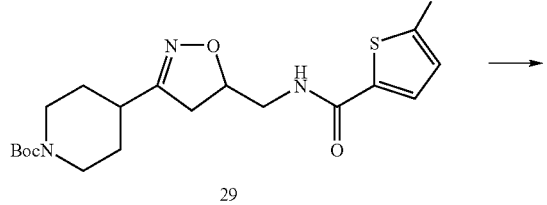

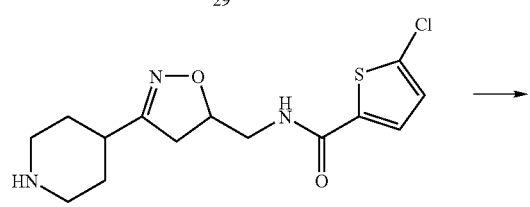

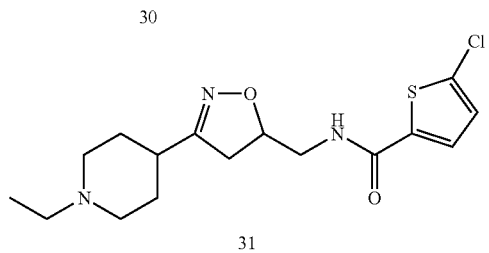

Example 169

5-Chloro-thiophene-2-carboxylic acid [3-(1-ethyl-piperidin-4-yl)-4,5-dihydro-isoxazol-5-ylmethyl]-amide (31)

Step 1:

Ethyl isonepecotate, 24 (9.8 mL, 64 mmol), was diluted with dichloromethane (100 mL) and treated with t-butylpyrocarbonate (16 mL, 70 mmol) which resulted in significant gas evolution. After 20 min the clear solution was checked by TLC (dichloromethane) which showed complete consumption of the starting amine. The reaction mixture was concentrated affording the protected amine (25) as a colorless oil containing a small amount of t-butanol. NMR (DMSO-$d_6$, 400 MHz): δ 4.01 (m, 1H), δ 3.75 (m, 2H), δ 3.28 (m, 1H), δ 2.75 (m, 2H), δ 2.45 (m, 2H), δ 1.69 (m, 2H), δ 1.31 (m, 11H), 1.09 (m, 3H).

Step 2:

Performed in the same manner as in step 1, Example 49. (DMSO-$d_6$, 400 MHz): δ 9.52 (s, 1H), δ 3.72 (m, 2H), 2.81 (m, 2H), δ 1.73 (m, 3H), δ 1.31 (m, 13H).

Step 3:

Performed in the same manner as in step 1, Example 1. (DMSO-$d_6$, 400 MHz): δ 8.88 (d, 0.66H), δ 8.50 (t, 0.33H), δ 8.00 (t, 0.66H), δ 7.20 (d, 0.33H), δ 3.83 (m, 2H), 2.73 (m, 2H), δ 2.26 (m, 1H), δ 1.61 (m, 2H), δ 1.32 (s, 9H), δ 1.10 (m, 2H).

Step 4:

Performed in the same manner as in step 2, Example 1. The material was used immediately for step 5 without purification or characterization.

Step 5:

Performed in the same manner as in step 5, Example 1. (DMSO-$d_6$, 400 MHz): δ 8.78 (m, 1H), δ 7.62 (s, 1H), δ 7.18 (s, 1H), δ 4.58 (m, 1H), 3.82 (m, 2H), δ 3.26 (m, 2H), δ 2.99 (m, 1H), δ 2.72 (m, 2H), δ 2.46 (m, 2H), δ 1.69 (m, 2H), δ 1.36 (m, 11H).

Step 6:

Performed in the same manner as in step 5, Example 49. MS found for $C_{14}H_{18}ClN_3O_2S$ as $(M+H)^+$ 328.1, 330.1.

Step 7:

Amine hydrochloride 30 (40 mg, 0.11 mmol) was diluted with 4 mL dichloroethane then treated with 5 drops of acetaldehyde, triethylamine (18 uL, 0.13 mmol) and Na(OAc)$_3$BH (47 mg, 0.22 mmol). The resulting slightly cloudy mixture was stirred overnight. The next day the reaction was checked by HPLC and determined to be complete. It was then concentrated and purified by preparative HPLC affording the desired tertiary amine salt as a white solid. MS found for $C_{16}H_{22}ClN_3O_2S$ as $(M+H)^+$ 356.4, 358.4.

Example 170

5-Chloro-thiophene-2-carboxylic acid [3-(1-benzyl-piperidin-4-yl)-4,5-dihydro-isoxazol-5-ylmethyl]-amide

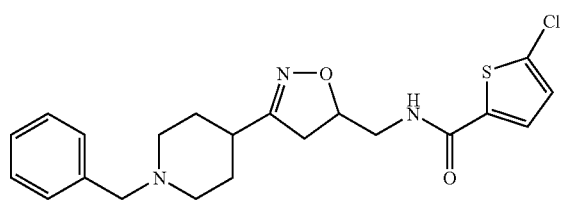

The titled compound was made by the procedure similar to that described in Example 169. MS found for $C_{21}H_{24}ClN_3O_2S$ as $(M+H)^+$ 418.6, 420.6.

Example 171

5-Chloro-thiophene-2-carboxylic acid [3-(1-isopropyl-piperidin-4-yl)-4,5-dihydro-isoxazol-5-ylmethyl]-amide

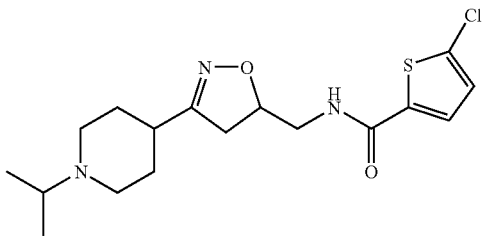

The titled compound was made by the procedure similar to that described in Example 169. MS found for $C_{17}H_{24}ClN_3O_2S$ as $(M+H)^+$ 370.6, 372.5.

Example 172

5-Chloro-thiophene-2-carboxylic acid [3-(1-carbamimidoyl-piperidin-4-yl)-4,5-dihydro-isoxazol-5-ylmethyl]-amide

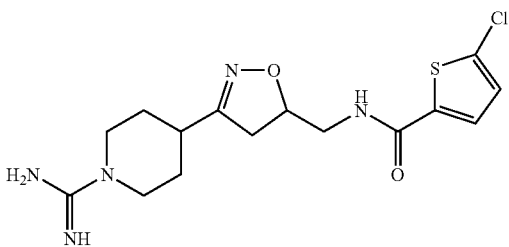

Amine 30 (40 mg, 0.11 mmol) was dissolved in methanol (5 mL) then treated with triethyl amine (46 uL, 0.33 mmol) and 1H-pyrazole-1-carboxamidine (32 mg, 0.22 mmol) overnight. The next day the reaction was concentrated and the crude reaction mixture purified by revererse phase HPLC affording the desired guanidine as a white powder. MS found for $C_{15}H_{20}ClN_5O_2S$ as $(M+H)^+$ 370.6, 372.4.

Example 173

5-Chloro-thiophene-2-carboxylic acid {3-[1-(1-imino-ethyl)-piperidin-4-yl]-4,5-dihydro-isoxazol-5-ylmethyl}-amide

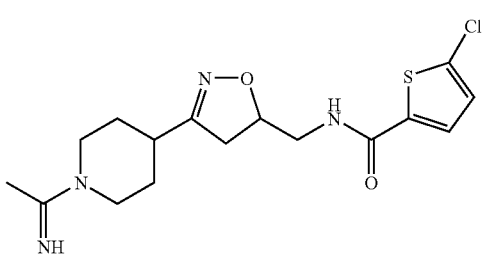

Combined amine 30 (40 mg, 0.11 mmol), triethylamine (46 uL, 0.33 mmol) ethyl acetimidate-hydrochloride (27 mg, 0.22 mmol) and ethanol (5 mL) then stirred the resulting cloudy white solution overnight. The following day the reaction was found to be done by HPLC and was concentrated and purified by preparative HPLC affording the desired amidine as a TFA salt. MS found for $C_{16}H_{21}ClN_4O_2S$ as $(M+H)^+$ 369.5, 371.5.

Example 174

5-Chloro-thiophene-2-carboxylic acid {3-[1-(imino-phenyl-methyl)-piperidin-4-yl]-4,5-dihydro-isoxazol-5-ylmethyl}-amide

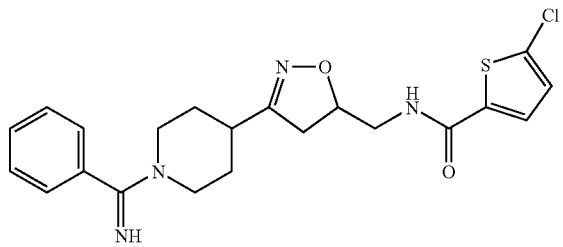

The titled compound was made by the procedure similar to that described in Example 173. MS found for $C_{21}H_{23}ClN_4O_2S$ as $(M+H)^+$ 431.5, 433.5.

Example 175

5-Chloro-thiophene-2-carboxylic acid {3-[1-(imino-pyridin-2-yl-methyl)-piperidin-4-yl]-4,5-dihydro-isoxazol-5-ylmethyl}-amide

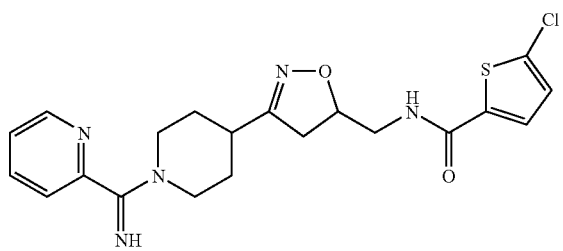

The titled compound was made by the procedure similar to that described in Example 173. MS found for $C_{20}H_{22}ClN_5O_2S$ as $(M+H)^+$ 432.5, 434.5.

Example 176

5-Chloro-thiophene-2-carboxylic acid (3-piperidin-4-yl-isoxazol-5-ylmethyl)-amide

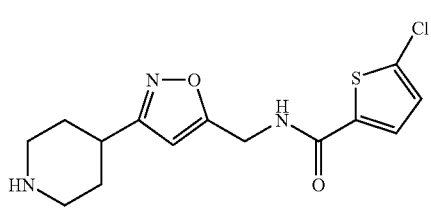

The titled compound was made by the procedure similar to that described in Example 169, step 6. MS found for $C_{14}H_{16}ClN_3O_2S$ as $(M+H)^+$ 326.0, 328.0.

Example 177

5-Chloro-thiophene-2-carboxylic acid [3-(1-ethyl-piperidin-4-yl)-isoxazol-5-ylmethyl]-amide

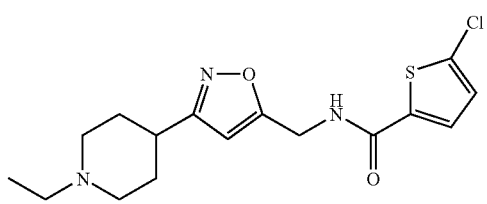

The titled compound was made by the procedure similar to that described in Example 169. MS found for $C_{16}H_{20}ClN_3O_2S$ as $(M+H)^+$ 354.1, 356.1.

Example 178

5-Chloro-thiophene-2-carboxylic acid [3-(1-benzyl-piperidin-4-yl)-isoxazol-5-ylmethyl]-amide

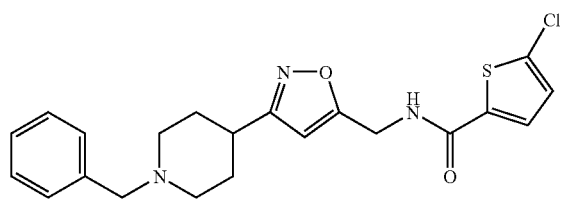

The titled compound was made by the procedure similar to that described in Example 169. MS found for $C_{21}H_{22}ClN_3O_2S$ as $(M+H)^+$ 416.1, 418.1.

Example 179

5-Chloro-thiophene-2-carboxylic acid [3-(1-carbamimidoyl-piperidin-4-yl)-isoxazol-5-ylmethyl]-amide

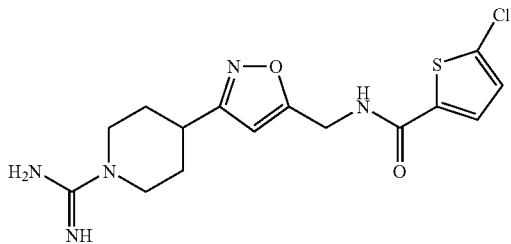

The titled compound was made by the procedure similar to that described in Example 172. MS found for $C_{15}H_{18}ClN_5O_2S$ as $(M+H)^+$ 368.0, 370.1.

Example 180

5-Chloro-thiophene-2-carboxylic acid {3-[1-(1-imino-ethyl)-piperidin-4-yl]-isoxazol-5-ylmethyl}-amide

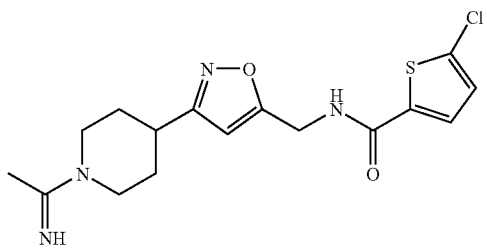

The titled compound was made by the procedure similar to that described in Example 173. MS found for $C_{16}H_{19}ClN_4O_2S$ as $(M+H)^+$ 367.1, 369.1.

Example 181

5-Chloro-thiophene-2-carboxylic acid {3-[1-(imino-phenyl-methyl)-piperidin-4-yl]-isoxazol-5-ylmethyl}-amide

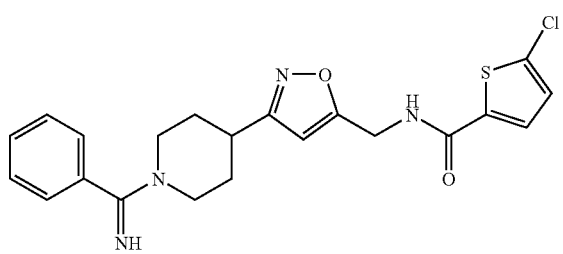

The titled compound was made by the procedure similar to that described in Example 173. MS found for $C_{21}H_{21}ClN_4O_2S$ as $(M+H)^+$ 429.1, 431.1

Example 182

5-Chloro-thiophene-2-carboxylic acid [3-(1-carbamimidoyl-piperidin-4-yl)-4,5-dihydro-isoxazol-5-ylmethyl]-amide

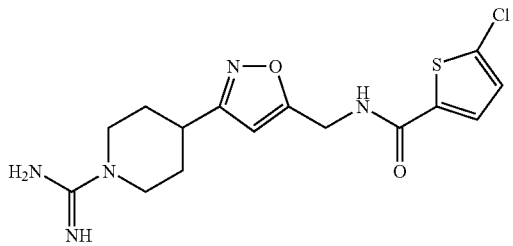

The titled compound was made by the procedure similar to that described in Example 173. MS found for $C_{15}H_{18}ClN_5O_2S$ as $(M+H)^+$ 368.1, 370.1.

Example 183

5-Chloro-thiophene-2-carboxylic acid [3-(2'-formyl-biphenyl-4-yl)-4,5-dihydro-isoxazol-5-ylmethyl]-amide

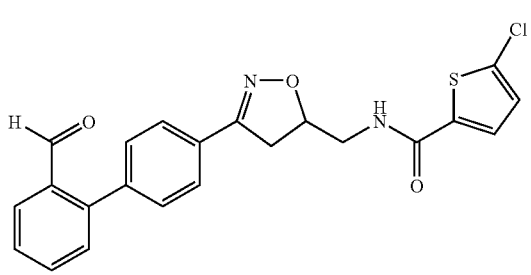

Aryl bromide (Example 1, 200 mg, 0.50 mmol), 2-formylphenylboronic acid (90 mg, 0.60 mmol) and $K_2CO_3$ (106 mg, 1.0 mmol) were diluted with diglyme (5 mL) and water (1 mL). The mixture was degassed for 3-5 min, then treated with $Pd(PPh_3)_4$ (58 mg, 0.05 mmol) and heated to 120° C. until all starting bromide was consumed as determined by HPLC. The resulting mixture was diluted with water, filtered and the remaining solids purified by silica gel chromatography (0-10% Ethyl acetate/dichloromethane) affording the desired biphenyl aldehyde as a white solid. MS found for $C_{22}H_{17}ClN_2O_3S$ as (M+H)+ 425.4, 427.4.

Example 184

5-Chloro-thiophene-2-carboxylic acid [3-(2'-chloro-biphenyl-4-yl)-4,5-dihydro-isoxazol-5-ylmethyl]-amide

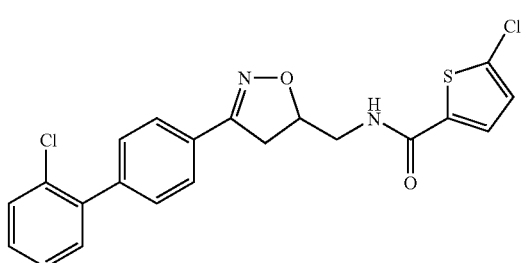

The titled compound was made by the procedure similar to that described in Example 183. MS found for $C_{21}H_{16}Cl_2N_2O_2S$ as (M+H)+ 431.3, 433.0

Example 185

5-Chloro-thiophene-2-carboxylic acid [3-(2'-methyl-sulfanyl-biphenyl-4-yl)-4,5-dihydro-isoxazol-5-ylm-ethyl]-amide

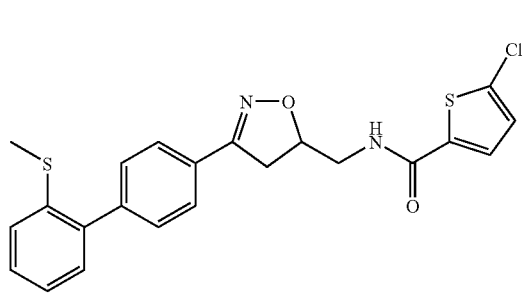

The titled compound was made by the procedure similar to that described in Example 183. MS found for $C_{22}H_{19}ClN_2O_2S_2$ as (M+H)+ 429.0, 431.0

Example 186

5-Chloro-thiophene-2-carboxylic acid [3-(2'-amino-biphenyl-4-yl)-4,5-dihydro-isoxazol-5-ylmethyl]-amide

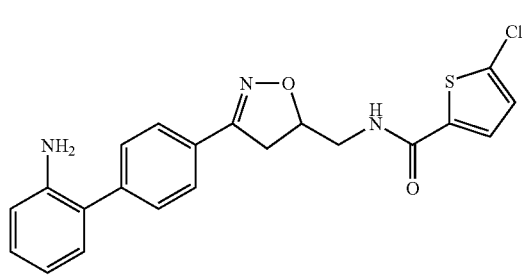

The titled compound was made by the procedure similar to that described in Example 183. MS found for $C_{21}H_{18}ClN_3O_2S$ as (M+H)+ 412.3, 414.3

Example 187

5-Chloro-thiophene-2-carboxylic acid [3-(2'-trifluo-romethyl-biphenyl-4-yl)-4,5-dihydro-isoxazol-5-ylmethyl]-amide

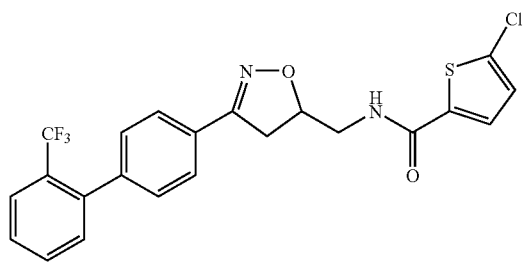

The titled compound was made by the procedure similar to that described in Example 183. MS found for $C_{22}H_{16}ClF_3N_2O_2S$ as (M+H)+ 465.5, 467.5

Example 188

5-Chloro-thiophene-2-carboxylic acid [3-(2'-meth-oxy-biphenyl-4-yl)-4,5-dihydro-isoxazol-5-ylm-ethyl]-amide

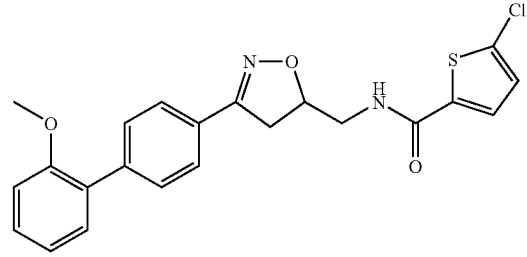

The titled compound was made by the procedure similar to that described in Example 183. MS found for $C_{22}H_{19}ClN_2O_3S$ as (M+H)+ 505.4, 507.4

Example 189

5-Chloro-thiophene-2-carboxylic acid [3-(2'-meth-oxymethyl-biphenyl-4-yl)-isoxazol-5-ylmethyl]-amide

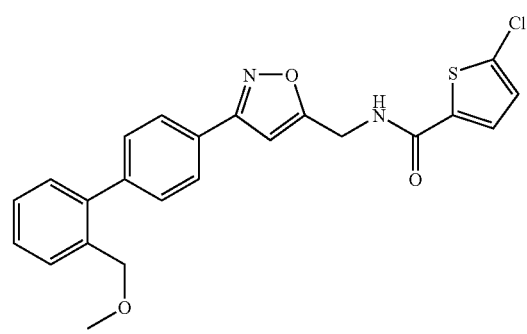

The titled compound was made by the procedure similar to that described in Example 183. MS found for $C_{23}H_{19}ClN_2O_3S$ as (M+H)+ 519.4, 521.4

Example 190

5-Chloro-thiophene-2-carboxylic acid [3-(4-pyridin-3-yl-phenyl)-4,5-dihydro-isoxazol-5-ylmethyl]-amide

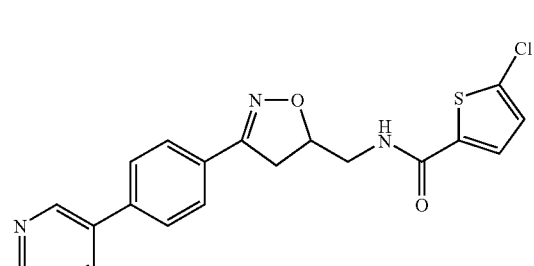

The titled compound was made by the procedure similar to that described in Example 183. MS found for $C_{20}H_{16}ClN_3O_2S$ as (M+H)+ 398.4, 400.4.

Example 191

5-Chloro-thiophene-2-carboxylic acid [3-(4-pyridin-4-yl-phenyl)-4,5-dihydro-isoxazol-5-ylmethyl]-amide

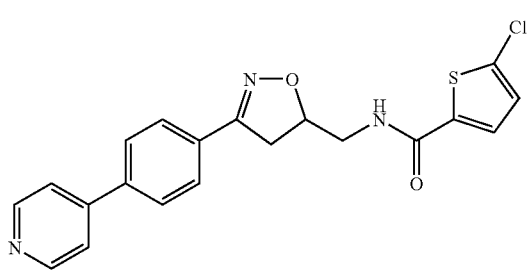

The titled compound was made by the procedure similar to that described in Example 183. MS found for $C_{20}H_{16}ClN_3O_2S$ as (M+H)+ as 398.4, 400.4.

Example 192

5-Chloro-thiophene-2-carboxylic acid [3-(4-pyridin-3-yl-phenyl)-isoxazol-5-ylmethyl]-amide

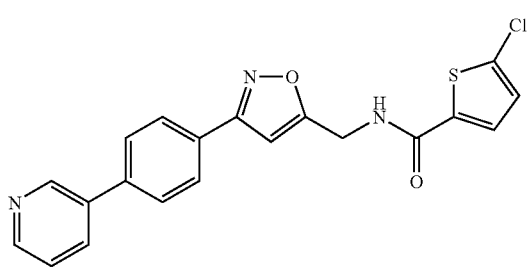

The titled compound was made by the procedure similar to that described in Example 183. MS found for $C_{20}H_{14}ClN_3O_2S$ as (M+H)+ 396.4, 398.4.

Example 193

5-Chloro-thiophene-2-carboxylic acid [3-(4-pyridin-4-yl-phenyl)-isoxazol-5-ylmethyl]-amide

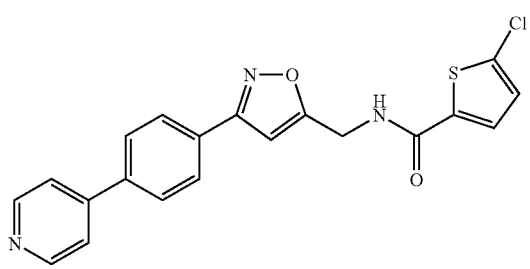

The titled compound was made by the procedure similar to that described in Example 183. MS found for $C_{20}H_{14}ClN_3O_2S$ as (M+H)+ 396.4, 398.4.

Example 194

5-Chloro-thiophene-2-carboxylic acid [3-(2'-dimethylaminomethyl-biphenyl-4-yl)-4,5-dihydro-isoxazol-5-ylmethyl]-amide

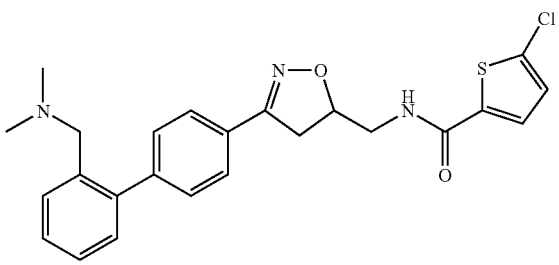

The titled compound was made by the procedure similar to that described in Example 169, step 7 using the material from Example 183 as starting material. MS found for $C_{24}H_{24}ClN_3O_2S$ as (M+H)+ 454.0, 456.0.

Example 195

5-Chloro-thiophene-2-carboxylic acid [3-(2'-pyrrolidin-1-ylmethyl-biphenyl-4-yl)-4,5-dihydro-isoxazol-5-ylmethyl]-amide

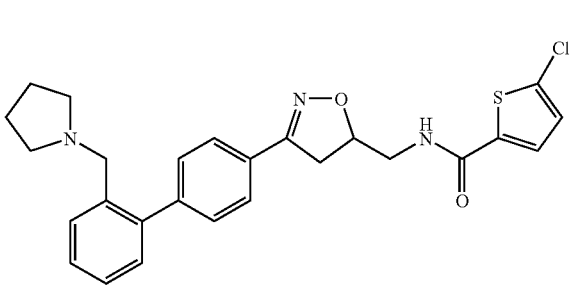

The titled compound was made by the procedure similar to that described in Example 194. MS found for $C_{26}H_{26}ClN_3O_2S$ as (M+H)+ 481.2, 482.2.

Example 196

5-Chloro-thiophene-2-carboxylic acid [3-(2'-piperidin-1-ylmethyl-biphenyl-4-yl)-4,5-dihydro-isoxazol-5-ylmethyl]-amide

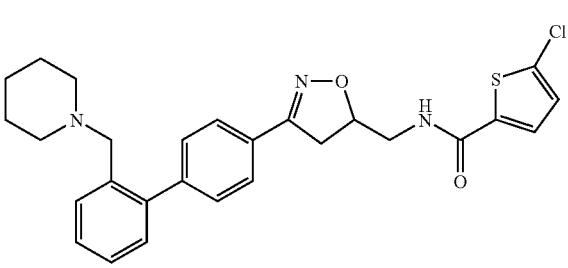

147

The titled compound was made by the procedure similar to that described in Example 194. MS found for $C_{27}H_{28}ClN_3O_2S$ as (M+H)+ 494.3, 496.3

Example 197

5-Chloro-thiophene-2-carboxylic acid [3-(2'-morpholin-4-ylmethyl-biphenyl-4-yl)-4,5-dihydro-isoxazol-5-ylmethyl]-amide

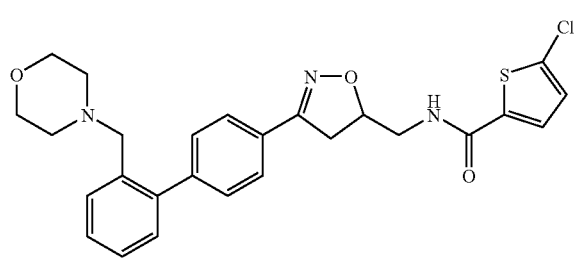

The titled compound was made by the procedure similar to that described in Example 194. MS found for $C_{26}H_{26}ClN_3O_3S$ as (M+H)+ 496.3, 498.3

Example 198

5-Chloro-thiophene-2-carboxylic acid [3-(2'-{[(2-methoxy-ethyl)-methyl-amino]-methyl}-biphenyl-4-yl)-4,5-dihydro-isoxazol-5-ylmethyl]-amide

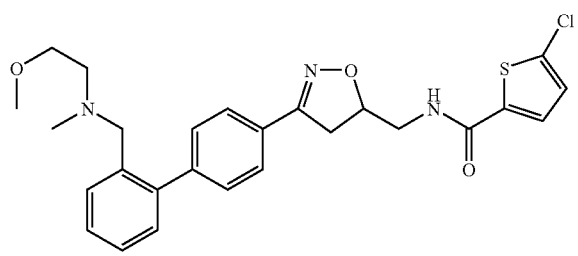

The titled compound was made by the procedure similar to that described in Example 194. MS found for $C_{26}H_{28}ClN_3O_3S$ as (M+H)+ 498.3, 500.3

Example 199

5-Chloro-thiophene-2-carboxylic acid {3-[2'-(4-methyl-piperazin-1-ylmethyl)-biphenyl-4-yl]-4,5-dihydro-isoxazol-5-ylmethyl}-amide

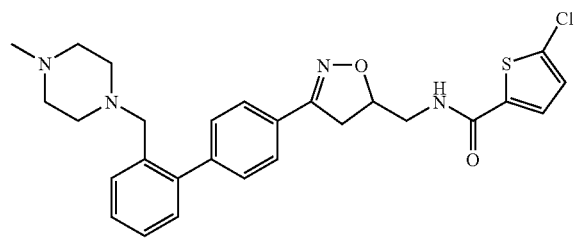

The titled compound was made by the procedure similar to that described in Example 194. MS found for $C_{27}H_{29}ClN_4O_2S$ as (M+H)+ 509.7, 511.7

148

Example 200

5-Chloro-thiophene-2-carboxylic acid [3-(2'-{[(2-dimethylamino-ethyl)-methyl-amino]-methyl}-biphenyl-4-yl)-4,5-dihydro-isoxazol-5-ylmethyl]-amide

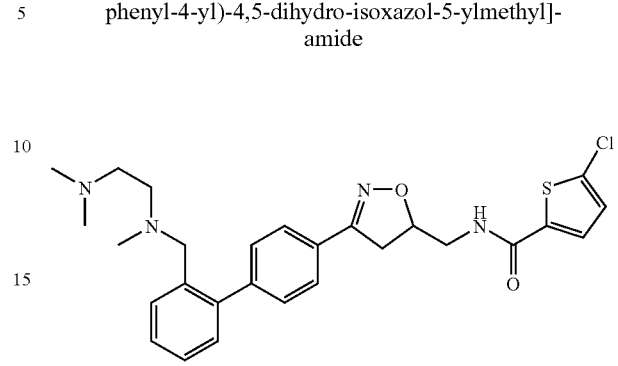

The titled compound was made by the procedure similar to that described in Example 194. MS found for $C_{27}H_{31}ClN_4O_2S$ as (M+H)+ 511.3, 513.3

Example 201

5-Chloro-thiophene-2-carboxylic acid [3-(2'-azepan-1-ylmethyl-biphenyl-4-yl)-4,5-dihydro-isoxazol-5-ylmethyl]-amide

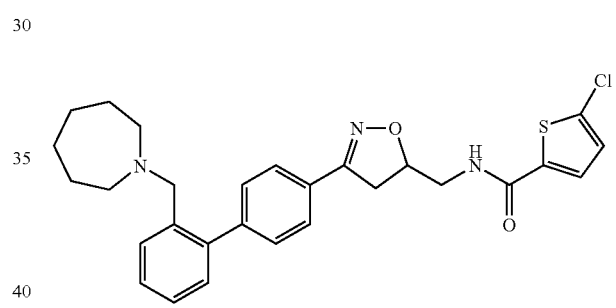

The titled compound was made by the procedure similar to that described in Example 194. MS found for $C_{28}H_{30}ClN_3O_2S$ as (M+H)+ 508.3, 510.4

Example 202

5-Chloro-thiophene-2-carboxylic acid [3-(2'-dimethylaminomethyl-5'-methoxy-biphenyl-4-yl)-4,5-dihydro-isoxazol-5-ylmethyl]-amide

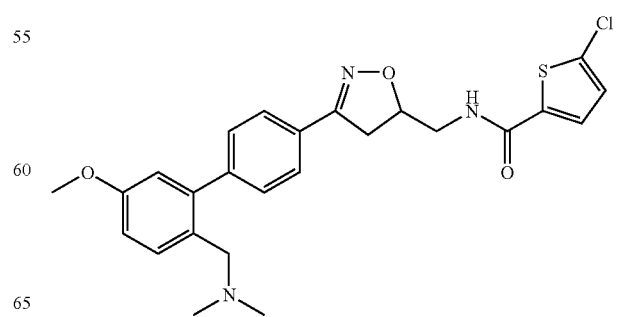

The titled compound was made by the procedure similar to that described in Example 194. MS found for $C_{25}H_{26}ClN_3O_3S$ as $(M+H)^+$ 484.1, 486.1

Example 203

5-Chloro-thiophene-2-carboxylic acid [3-(5'-methoxy-2'-pyrrolidin-1-ylmethyl-biphenyl-4-yl)-4,5-dihydro-isoxazol-5-ylmethyl]-amide

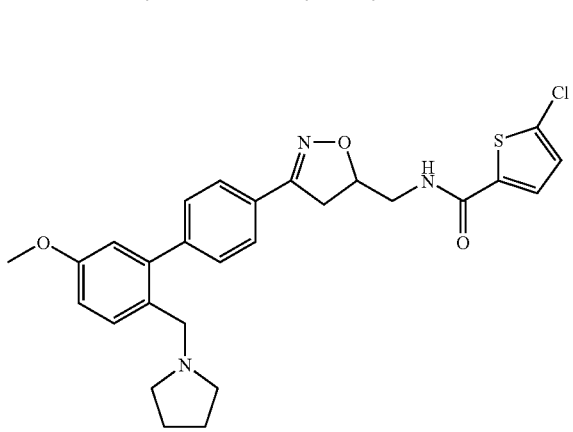

The titled compound was made by the procedure similar to that described in Example 194. MS found for $C_{27}H_{28}ClN_3O_3S$ as $(M+H)^+$ 510.1, 512.1

Example 204

5-Chloro-thiophene-2-carboxylic acid [3-(5'-chloro-2'-dimethylaminomethyl-biphenyl-4-yl)-4,5-dihydro-isoxazol-5-ylmethyl]-amide

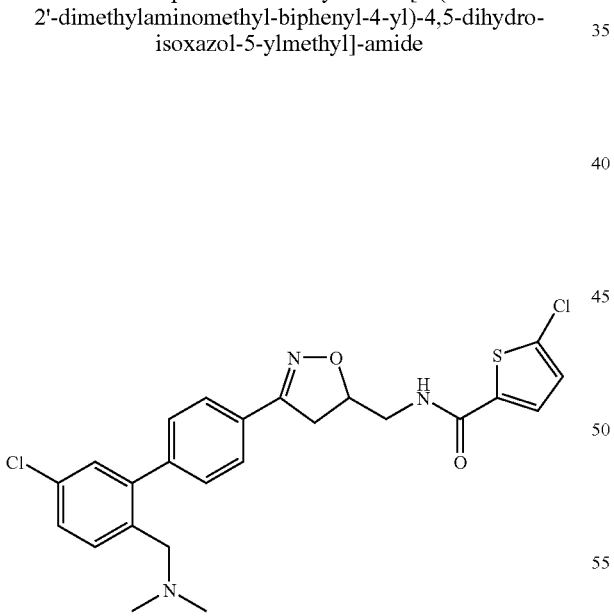

The titled compound was made by the procedure similar to that described in Example 194. MS found for $C_{24}H_{23}Cl_2N_3O_2S$ as $(M+H)+$ 488.3, 490.3

Example 205

5-Chloro-thiophene-2-carboxylic acid [3-(5'-chloro-2'-pyrrolidin-1-ylmethyl-biphenyl-4-yl)-4,5-dihydro-isoxazol-5-ylmethyl]-amide

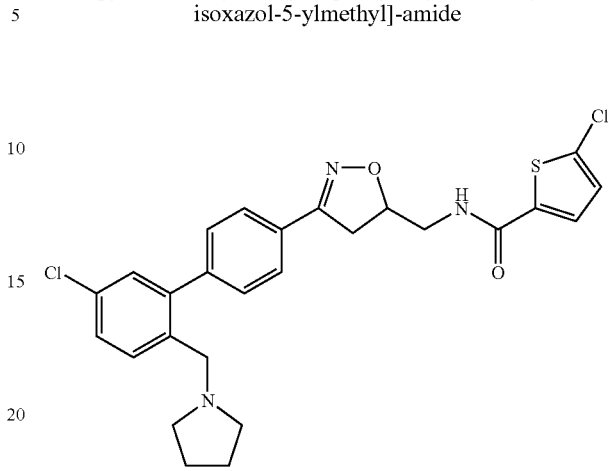

The titled compound was made by the procedure similar to that described in Example 194. MS found for $C_{26}H_{25}Cl_2N_3O_2S$ as $(M+H)+$ 514.3, 516.3

Example 206

5-Chloro-thiophene-2-carboxylic acid [3-(5'-chloro-2'-{[(2-methoxy-ethyl)-methyl-amino]-methyl}-biphenyl-4-yl)-4,5-dihydro-isoxazol-5-ylmethyl]-amide

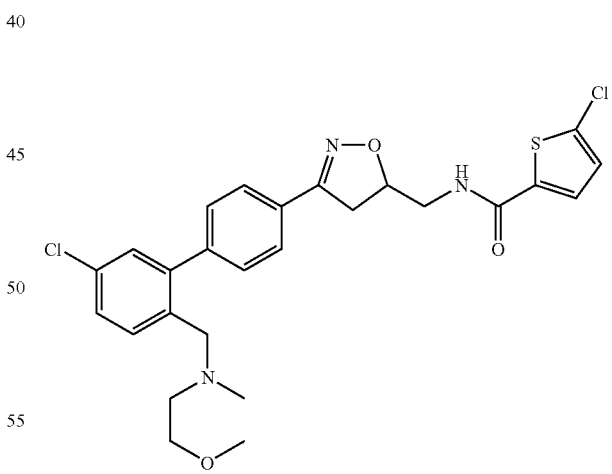

The titled compound was made by the procedure similar to that described in Example 194. MS found for $C_{26}H_{27}Cl_2N_3O_3S$ as $(M+H)+$ 532.4, 534.4

Example 207

5-Chloro-thiophene-2-carboxylic acid [3-(2'-hydroxymethyl-4'-methoxy-biphenyl-4-yl)-4,5-dihydro-isoxazol-5-ylmethyl]-amide

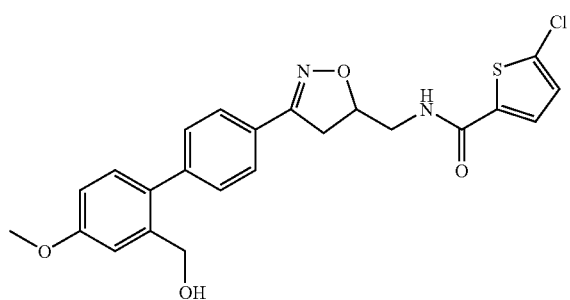

The titled compound was made by the procedure similar to that described in Example 183. MS found for $C_{23}H_{21}ClN_2O_4S$ as (M+H)+ 457.5, 459.5

Example 208

5-Chloro-thiophene-2-carboxylic acid [3-(2'-formyl-biphenyl-4-yl)-isoxazol-5-ylmethyl]-amide

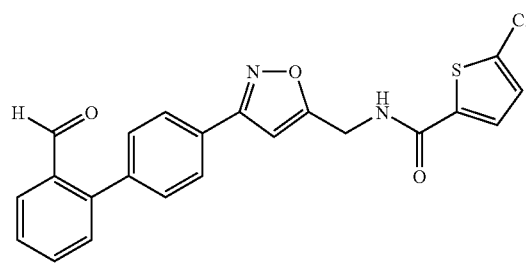

The titled compound was made by the procedure similar to that described in Example 183. MS found for $C_{22}H_{15}ClN_2O_3S$ as (M+H)+ 423.4, 425.4

Example 209

5-Chloro-thiophene-2-carboxylic acid [3-(2'-dimethylaminomethyl-biphenyl-4-yl)-isoxazol-5-ylmethyl]-amide

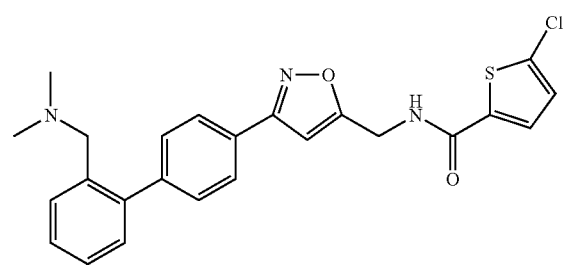

The titled compound was made by the procedure similar to that described in Example 169 using material from Example 208. MS found for $C_{24}H_{22}ClN_3O_2S$ as (M+H)+ 452.1, 454.1

Example 210

5-Chloro-thiophene-2-carboxylic acid [3-(2'-pyrrolidin-1-ylmethyl-biphenyl-4-yl)-isoxazol-5-ylmethyl]-amide

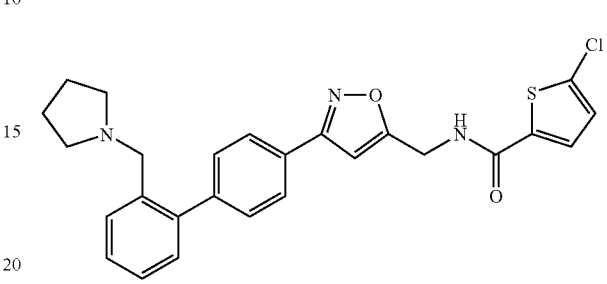

The titled compound was made by the procedure similar to that described in Example 209. MS found for $C_{26}H_{24}ClN_3O_2S$ as (M+H)+ 478.1, 480.1

Example 211

5-Chloro-thiophene-2-carboxylic acid [3-(3'-dimethylaminomethyl-biphenyl-4-yl)-isoxazol-5-ylmethyl]-amide

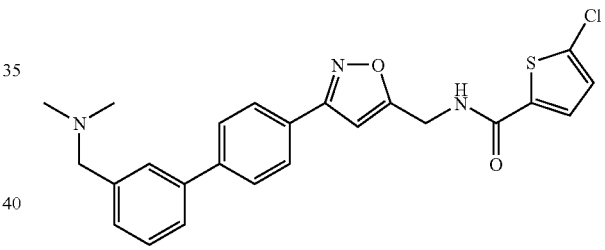

The titled compound was made by the procedure similar to that described in Example 209. MS found for $C_{24}H_{22}ClN_3O_2S$ as (M+H)+ 452.5, 454.5.

Example 212

5-Chloro-thiophene-2-carboxylic acid [3-(3'-pyrrolidin-1-ylmethyl-biphenyl-4-yl)-isoxazol-5-ylmethyl]-amide

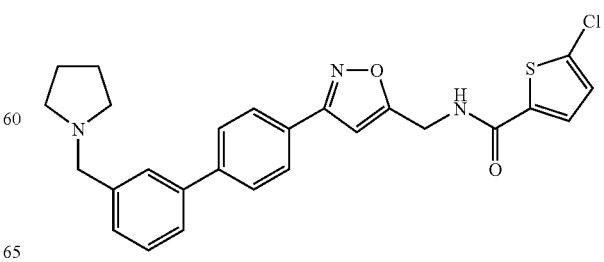

The titled compound was made by the procedure similar to that described in Example 209. MS found for $C_{26}H_{24}ClN_3O_2S$ as (M+H)$^+$ 478.5, 480.5

Example 213

5-Chloro-thiophene-2-carboxylic acid [3-(4'-dimethylaminomethyl-biphenyl-4-yl)-isoxazol-5-ylmethyl]-amide

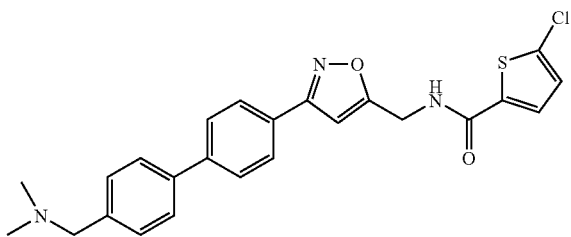

The titled compound was made by the procedure similar to that described in Example 209. MS found for $C_{24}H_{22}ClN_3O_2S$ as (M+H)$^+$ 452.5, 454.5.

Example 214

5-Chloro-thiophene-2-carboxylic acid [3-(4'-pyrrolidin-1-ylmethyl-biphenyl-4-yl)-isoxazol-5-ylmethyl]-amide

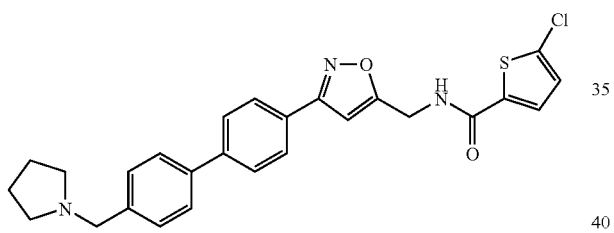

The titled compound was made by the procedure similar to that described in Example 209. MS found for $C_{26}H_{24}ClN_3O_2S$ as (M+H)$^+$ 478.5, 480.5

Example 215

5-Chloro-thiophene-2-carboxylic acid [3-(2'-dimethylaminomethyl-5'-methoxy-biphenyl-4-yl)-isoxazol-5-ylmethyl]-amide

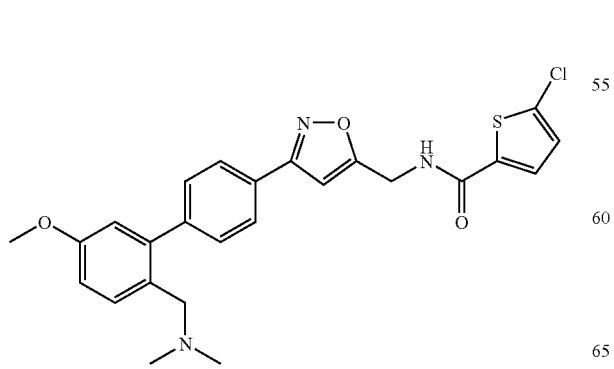

The titled compound was made by the procedure similar to that described in Example 209. MS found for $C_{25}H_{24}ClN_3O_3S$ as (M+H)$^+$ 482.1, 484.1.

Example 216

5-Chloro-thiophene-2-carboxylic acid [3-(5'-methoxy-2'-pyrrolidin-1-ylmethyl-biphenyl-4-yl)-isoxazol-5-ylmethyl]-amide

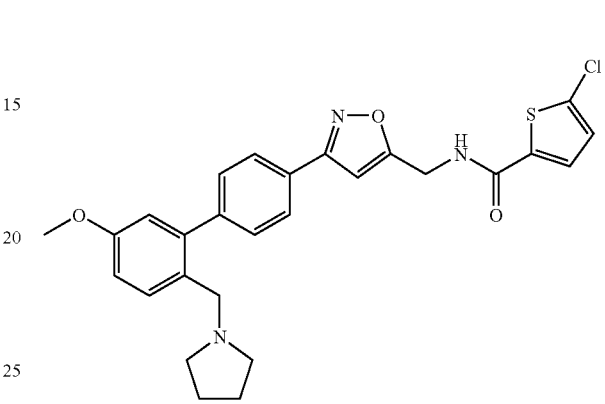

The titled compound was made by the procedure similar to that described in Example 209. MS found for $C_{27}H_{26}ClN_3O_3S$ as (M+H)$^+$ 508.1, 510.1

Example 217

5-Chloro-thiophene-2-carboxylic acid [3-(2'-dimethylaminomethyl-4'-methoxy-biphenyl-4-yl)-isoxazol-5-ylmethyl]-amide The titled compound was made by the procedure similar to that described in Example 209. MS found for $C_{25}H_{24}ClN_3O_3S$ as (M+H)+

Example 218

5-Chloro-thiophene-2-carboxylic acid [3-(4'-methoxy-2'-pyrrolidin-1-ylmethyl-biphenyl-4-yl)-isoxazol-5-ylmethyl]-amide

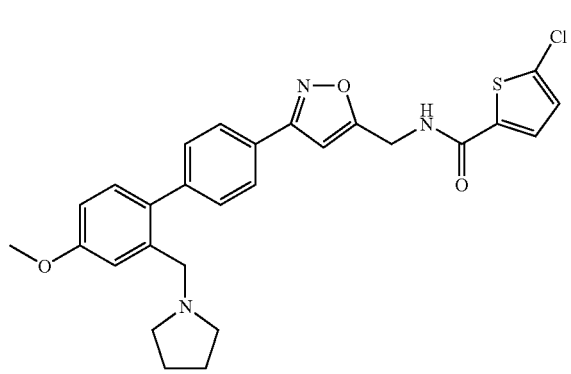

The titled compound was made by the procedure similar to that described in Example 209. MS found for $C_{27}H_{26}ClN_3O_3S$ as (M+H)+

Example 219

5-Chloro-thiophene-2-carboxylic acid [3-(4-pyridin-2-yl-phenyl)-4,5-dihydro-isoxazol-5-ylmethyl]-amide

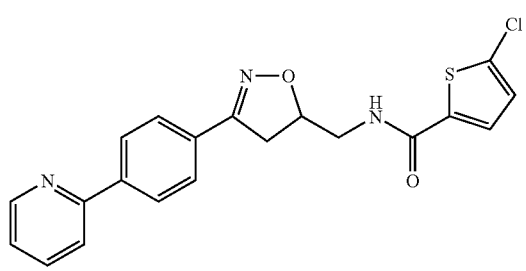

Combined the bromide from Example 1 (50 mg, 0.13 mmol) with 2-pyridyltributyl stannane (55 mg, 0.15 mmol) and 5 mL of toluene. The mixture was degassed for three minutes then treated with tetrakistriphenylphosphine palladium (14 mg, 0.013 mmol) and stirred at reflux overnight. The following day the reaction was checked by TLC which showed consumption of the starting bromide and a more polar spot. The reaction was partitioned with aqueous sodium fluoride and ethyl acetate, separated and dried over magnesium sulfate. After filtration and concentration the crude residue was purified by preparative HPLC affording the desired product as a white solid. MS found for $C_{20}H_{16}ClN_3O_2S$ as $(M+H)^+$ 398.1, 400.1

Example 220

5-Chloro-thiophene-2-carboxylic acid [3-(4-pyridin-2-yl-phenyl)-isoxazol-5-ylmethyl]-amide

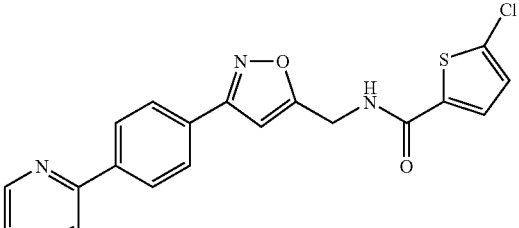

The titled compound was made by the procedure similar to that described in Example 219. MS found for $C_{20}H_{14}ClN_3O_2S$ as $(M+H)^+$ 396.1, 398.1.

Example 221

5-Chloro-thiophene-2-carboxylic acid [3-(4-benzylamino-phenyl)-4,5-dihydro-isoxazol-5-ylmethyl]-amide

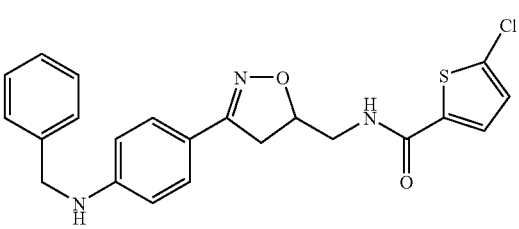

The titled compound was made by the procedure similar to that described in Example 169, step 7. MS found for $C_{22}H_{20}ClN_3O_2S$ as (M+H)+ 426.1, 428.1

Example 222

5-Chloro-thiophene-2-carboxylic acid [3-(4-phenylamino-phenyl)-4,5-dihydro-isoxazol-5-ylmethyl]-amide

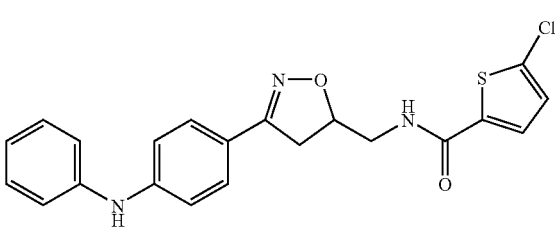

Aryl Bromide (Example 1, 100 mg, 0.25 mmol), aniline (27 uL, 0.30 mmol), $Cs_2CO_3$ (163 mg, 0.50 mmol) and Xantphos (43 mg, 0.075 mmol) were diluted with 4 mL of degassed THF. The resulting suspension was degassed for an additional 3 min then $Pd_2$ (dba)$_3$ (23 mg, 0.25 mmol) was added giving a dark violet suspension which became dark yellow-orange within a few minutes. The mixture was then refluxed overnight, changing to cloudy orange as the aryl bromide was consumed. The next day the mixture was partitioned with water and ethyl acetate, separated, and the organic layer extracted twice with ethyl acetate. The combined organic layers were dried over $MgSO_4$, filtered, concentrated and purified by preparative HPLC affording the desired product as a white powder. MS found for $C_{21}H_{18}ClN_3O_2S$ as $(M+H)^+$ 412.0, 414.0.

Example 223

5-Chloro-thiophene-2-carboxylic acid {3-[4-(4-fluoro-phenylamino)-phenyl]-4,5-dihydro-isoxazol-5-ylmethyl}-amide

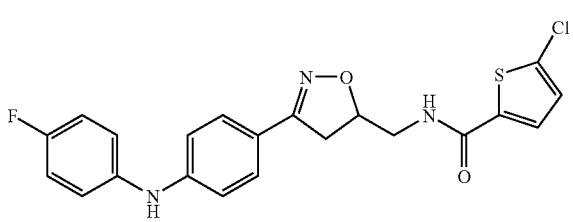

The titled compound was made by the procedure similar to that described in Example 222. MS found for $C_{21}H_{17}ClFN_3O_2S$ as (M+H)+ 430.1, 433.1.

Example 224

5-Chloro-thiophene-2-carboxylic acid {3-[4-(pyridin-2-ylamino)-phenyl]-4,5-dihydro-isoxazol-5-ylmethyl}-amide

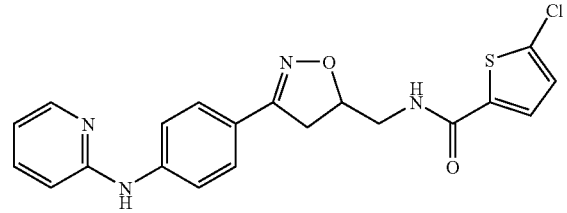

The titled compound was made by the procedure similar to that described in Example 222. MS found for $C_{20}H_{17}ClN_4O_2S$ as $(M+H)^+$ 413.0, 415.0.

Example 225

5-Chloro-thiophene-2-carboxylic acid {3-[4-(pyridin-3-ylamino)-phenyl]-4,5-dihydro-isoxazol-5-ylmethyl}-amide

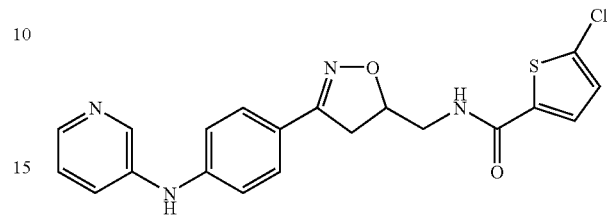

The titled compound was made by the procedure similar to that described in Example 222. found for $C_{20}H_{17}ClN_4O_2S$ as $(M+H)^+$ 413.0, 415.0.

Example 226

5-Chloro-thiophene-2-carboxylic acid {3-[4-(pyridin-4-ylamino)-phenyl]-4,5-dihydro-isoxazol-5-ylmethyl}-amide

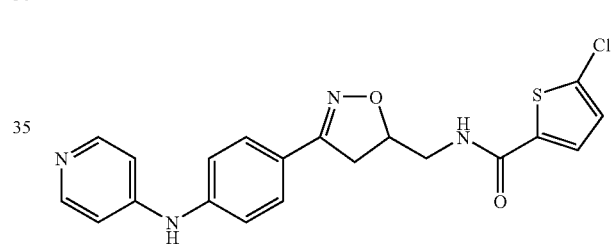

The titled compound was made by the procedure similar to that described in Example 222. found for $C_{20}H_{17}ClN_4O_2S$ as $(M+H)^+$ 413.0, 415.0.

Example 227

5-Chloro-thiophene-2-carboxylic acid {3-[4-(methyl-pyridin-4-yl-amino)-phenyl]-4,5-dihydro-isoxazol-5-ylmethyl}-amide

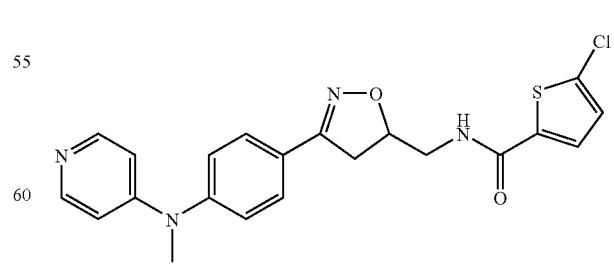

The titled compound was made by the procedure similar to that described in Example 222. MS found for $C_{21}H_{19}ClN_4O_2S$ as (M+H)+ 427.4, 429.4.

Example 228

5-Chloro-thiophene-2-carboxylic acid {3-[4-(2-methyl-pyridin-4-ylamino)-phenyl]-4,5-dihydro-isoxazol-5-ylmethyl}-amide

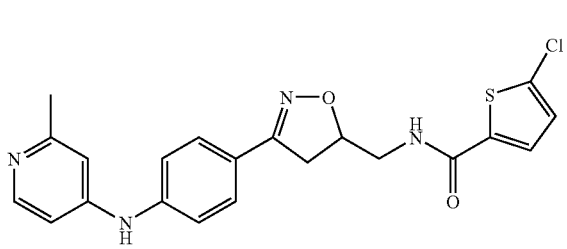

The titled compound was made by the procedure similar to that described in Example 222. MS found for $C_{21}H_{19}ClN_4O_2S$ as (M+H)+ 427.1, 429.1.

Example 229

5-Chloro-thiophene-2-carboxylic acid {3-[4-(2-chloro-pyridin-4-ylamino)-phenyl]-4,5-dihydro-isoxazol-5-ylmethyl}-amide

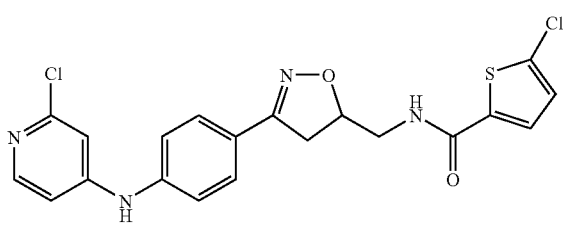

The titled compound was made by the procedure similar to that described in Example 222. MS found for $C_{20}H_{16}Cl_2N_4O_2S$ as (M+H)+ 447.2, 449.2.

Example 230

5-Chloro-thiophene-2-carboxylic acid {3-[4-(pyrimidin-4-ylamino)-phenyl]-4,5-dihydro-isoxazol-5-ylmethyl}-amide

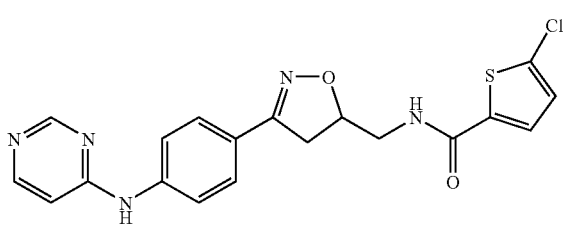

The titled compound was made by the procedure similar to that described in Example 222. MS found for $C_{19}H_{16}ClN_5O_2S$ as (M+H)+ 414.1, 416.1, (M+Na)+ 436.0, 438.0

Example 231

5-Chloro-thiophene-2-carboxylic acid (3-{4-[(2-amino-pyrimidin-4-yl)-methyl-amino]-phenyl}-4,5-dihydro-isoxazol-5-ylmethyl)-amide

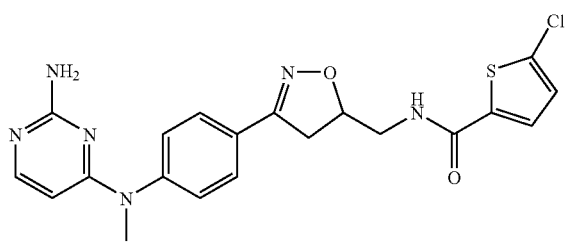

The titled compound was made by the procedure similar to that described in Example 222. MS found for $C_{20}H_{19}ClN_6O_2S$ as (M+H)+ 433.3, 435.3.

Example 232

5-Chloro-thiophene-2-carboxylic acid {3-[4-(2-ethyl-2H-pyrazol-3-ylamino)-phenyl]-4,5-dihydro-isoxazol-5-ylmethyl}-amide

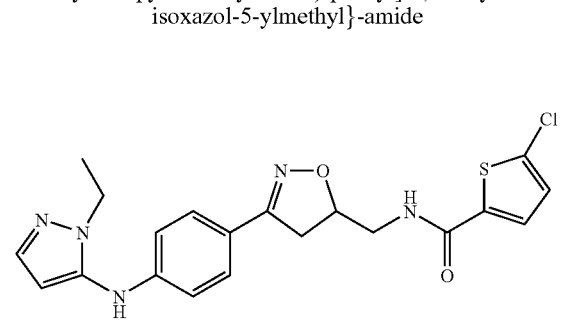

The titled compound was made by the procedure similar to that described in Example 222. MS found for $C_{20}H_{20}ClN_5O_2S$ as (M+H)+ 430.2, 432.3.

Example 233

5-Chloro-thiophene-2-carboxylic acid {3-[4-(1-methyl-1H-pyrazol-3-ylamino)-phenyl]-4,5-dihydro-isoxazol-5-ylmethyl}-amide

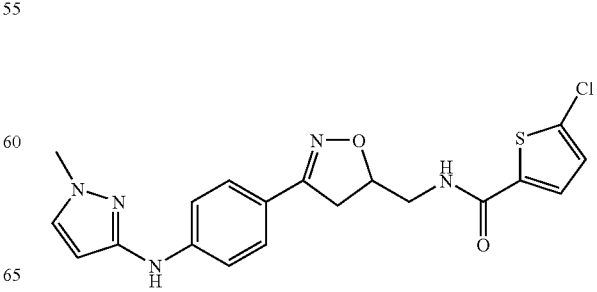

The titled compound was made by the procedure similar to that described in Example 222. MS found for $C_{19}H_{18}ClN_5O_2S$ as (M+H)+ 416.5, 418.5.

Example 234

5-Chloro-thiophene-2-carboxylic acid [3-(4-morpholin-4-yl-phenyl)-4,5-dihydro-isoxazol-5-ylmethyl]-amide

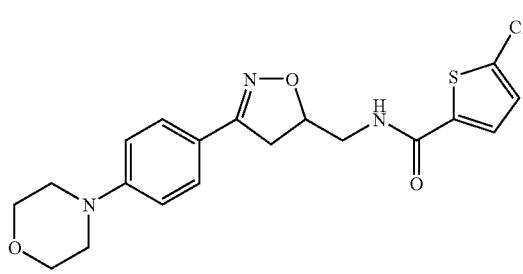

The titled compound was made by the procedure similar to that described in Example 222. MS found for $C_{19}H_{20}ClN_3O_3S$ as (M+H)$^+$ 406.3, 408.3; (M+Na)$^+$ 428.2, 430.2.

Example 235

5-Chloro-thiophene-2-carboxylic acid {3-[4-(4-methyl-piperazin-1-yl)-phenyl]-4,5-dihydro-isoxazol-5-ylmethyl}-amide

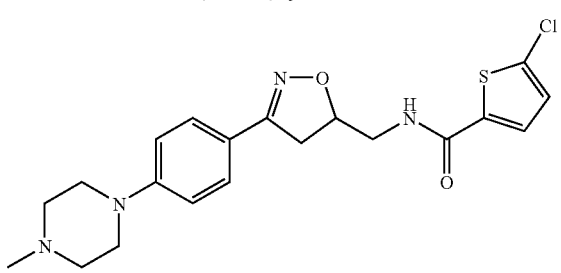

The titled compound was made by the procedure similar to that described in Example 222. MS found for $C_{20}H_{23}ClN_4O_2S$ as (M+H)$^+$ 419.3, 421.3.

Example 236

5-Chloro-thiophene-2-carboxylic acid {3-[4-(2-methoxymethyl-pyrrolidin-1-yl)-phenyl]-4,5-dihydro-isoxazol-5-ylmethyl}-amide

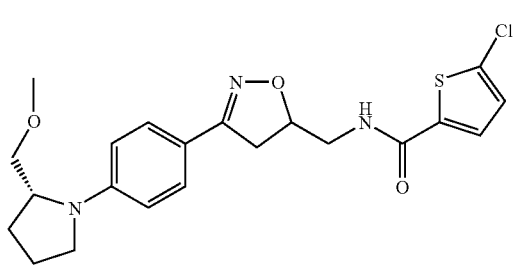

The titled compound was made by the procedure similar to that described in Example 222. MS found for $C_{21}H_{24}ClN_3O_3S$ as (M+H)$^+$ 434.0, 436.0.

Example 237

5-Chloro-thiophene-2-carboxylic acid {3-[4-(1-methyl-piperidin-4-ylamino)-phenyl]-4,5-dihydro-isoxazol-5-ylmethyl}-amide

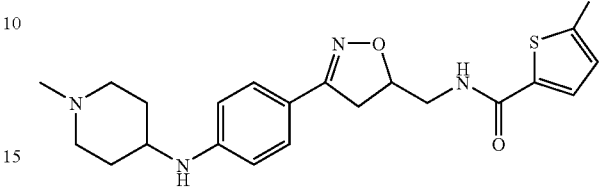

The titled compound was made by the procedure similar to that described in Example 222. MS found for $C_{21}H_{25}ClN_4O_2S$ as (M+H)$^+$ 433.3, 435.3.

Example 238

5-Chloro-thiophene-2-carboxylic acid (3-{4-[(2-dimethylamino-ethyl)-methyl-amino]-phenyl}-4,5-dihydro-isoxazol-5-ylmethyl)-amide

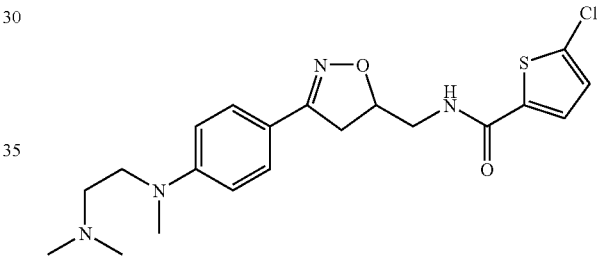

The titled compound was made by the procedure similar to that described in Example 222. MS found for $C_{20}H_{25}ClN_4O_2S$ as (M+H)+ 421.3, 423.3.

Example 239

5-Chloro-thiophene-2-carboxylic acid (3-{4-[(3-dimethylamino-propyl)-methyl-amino]-phenyl}-4,5-dihydro-isoxazol-5-ylmethyl)-amide

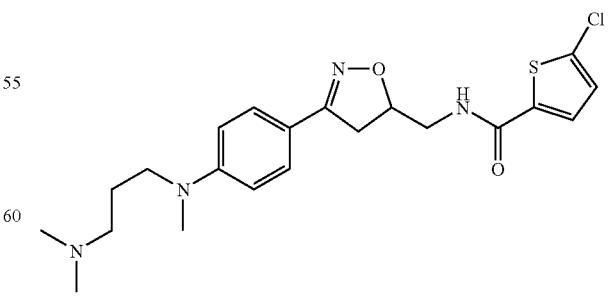

The titled compound was made by the procedure similar to that described in Example 222. MS found for $C_{21}H_{27}ClN_4O_2S$ as (M+H)$^+$ 421.0, 423.0.

Example 240

5-Chloro-thiophene-2-carboxylic acid {3-[4-(2-oxo-pyrrolidin-1-yl)-phenyl]-4,5-dihydro-isoxazol-5-ylmethyl}-amide

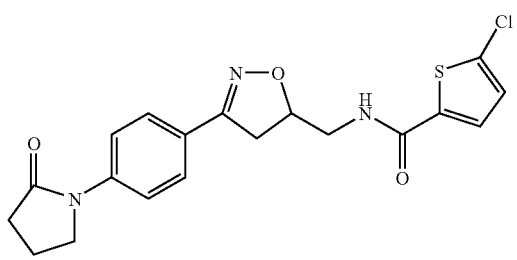

The titled compound was made by the procedure similar to that described in Example 222. MS found for $C_{19}H_{18}ClN_3O_3S$ as $(M+H)^+$ 404.2, 406.2.

Example 241

5-Chloro-thiophene-2-carboxylic acid {3-[4-(2-oxo-piperidin-1-yl)-phenyl]-4,5-dihydro-isoxazol-5-ylmethyl}-amide

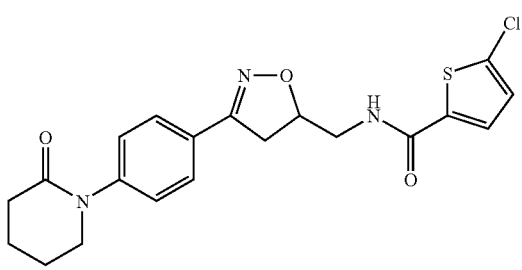

The titled compound was made by the procedure similar to that described in Example 222. MS found for $C_{20}H_{20}ClN_3O_3S$ as $(M+H)^+$ 418.2, 420.2

Example 242

4-[4-(5-{[(5-Chloro-thiophene-2-carbonyl)-amino]-methyl}-4,5-dihydro-isoxazol-3-yl)-phenyl]-3-oxo-piperazine-1-carboxylic acid benzyl ester

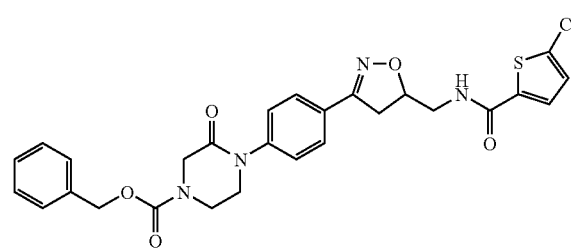

The titled compound was made by the procedure similar to that described in Example 222. MS found for $C_{27}H_{25}ClN_4O_5S$ as $(M+H)^+$ 553.3, 555.3

Example 243

5-Chloro-thiophene-2-carboxylic acid {3-[4-(3-oxo-morpholin-4-yl)-phenyl]-4,5-dihydro-isoxazol-5-ylmethyl}-amide

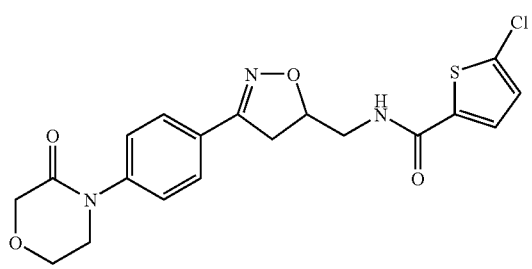

The titled compound was made by the procedure similar to that described in Example 222. MS found for $C_{19}H_{18}ClN_3O_4S$ as $(M-H)^+$ 418.1, 420.1.

Example 244

5-Chloro-thiophene-2-carboxylic acid {3-[4-(3-oxo-thiomorpholin-4-yl)-phenyl]-4,5-dihydro-isoxazol-5-ylmethyl}-amide

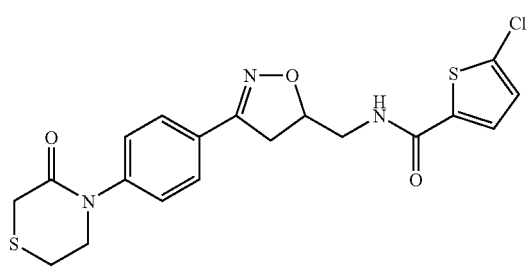

The titled compound was made by the procedure similar to that described in Example 222. MS found for $C_{19}H_{18}ClN_3O_3S_2$ as $(M+H)^+$ 436.2, 438.2.

Example 245

5-Chloro-thiophene-2-carboxylic acid {3-[4-(3-methyl-2-oxo-imidazolidin-1-yl)-phenyl]-4,5-dihydro-isoxazol-5-ylmethyl}-amide

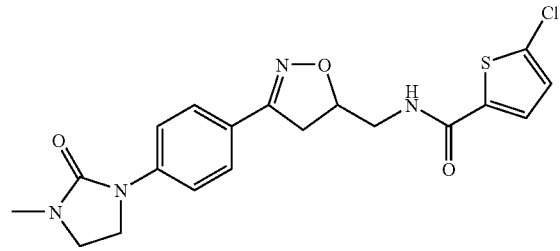

The titled compound was made by the procedure similar to that described in Example 222. MS found for $C_{19}H_{19}ClN_4O_3S$ as $(M+H)^+$ 419.2, 421.2.

Example 246

5-Chloro-thiophene-2-carboxylic acid {3-[4-(5-oxo-[1,4]oxazepan-4-yl)-phenyl]-4,5-dihydro-isoxazol-5-ylmethyl}-amide

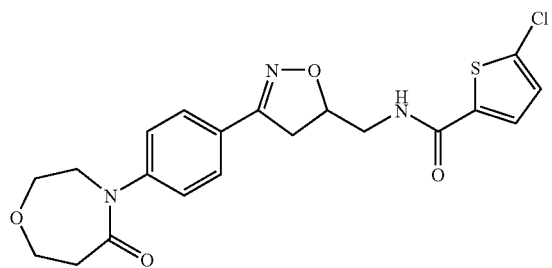

The titled compound was made by the procedure similar to that described in Example 222. MS found for $C_{20}H_{20}ClN_3O_4S$ as $(M+H)^+$ 434.5, 436.5.

Example 247

5-Chloro-thiophene-2-carboxylic acid {3-[2-fluoro-4-(pyridin-4-ylamino)-phenyl]-4,5-dihydro-isoxazol-5-ylmethyl}-amide

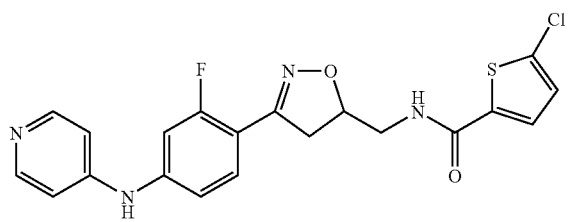

The titled compound was made by the procedure similar to that described in Example 222. MS found for $C_{20}H_{16}ClFN_4O_2S$ as $(M+H)^+$ 431.1, 433.1.

Example 248

5-Chloro-thiophene-2-carboxylic acid {3-[2-fluoro-4-(4-methyl-[1,4]diazepan-1-yl)-phenyl]-4,5-dihydro-isoxazol-5-ylmethyl}-amide

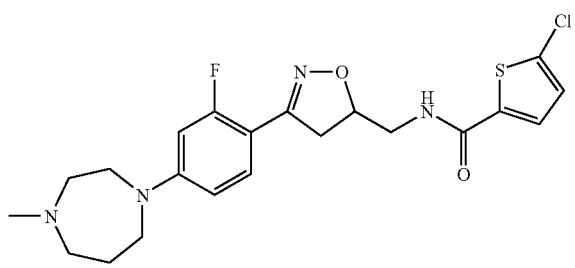

The titled compound was made by the procedure similar to that described in Example 222. MS found for $C_{21}H_{24}ClFN_4O_2S$ as $(M+H)^+$ 451.2, 453.3

Example 249

5-Chloro-thiophene-2-carboxylic acid {3-[2-fluoro-4-(5-oxo-[1,4]oxazepan-4-yl)-phenyl]-4,5-dihydro-isoxazol-5-ylmethyl}-amide

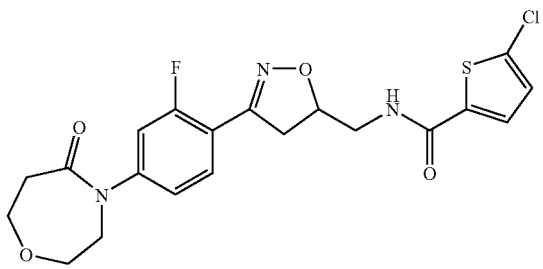

The titled compound was made by the procedure similar to that described in Example 222. MS found for $C_{20}H_{19}ClFN_3O_4S$ as $(M+H)^+$ 452.0, 454.0

Example 250

5-Chloro-thiophene-2-carboxylic acid [3-(4-phenylamino-phenyl)-isoxazol-5-ylmethyl]-amide

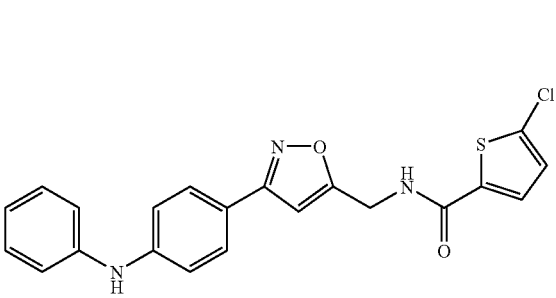

The titled compound was made by the procedure similar to that described in Example 222. MS found for $C_{21}H_{16}ClN_3O_2S$ as (M+H)+ 410.4, 412.3.

Example 251

5-Chloro-thiophene-2-carboxylic acid {3-[4-(4-methoxy-phenylamino)-phenyl]-isoxazol-5-ylmethyl}-amide

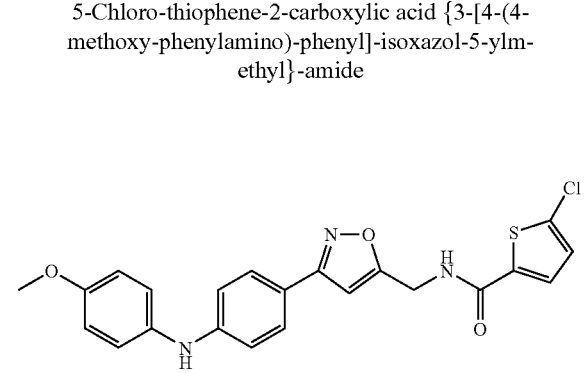

The titled compound was made by the procedure similar to that described in Example 222. MS found for $C_{22}H_{18}ClN_3O_3S$ as (M+H)+ 440.0, 442.0.

Example 252

5-Chloro-thiophene-2-carboxylic acid {3-[4-(pyridin-2-ylamino)-phenyl]-isoxazol-5-ylmethyl}-amide

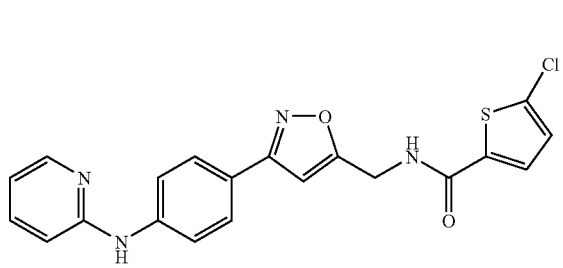

The titled compound was made by the procedure similar to that described in Example 222. MS found for $C_{20}H_{15}ClN_4O_2S$ as (M+H)+ 411.0, 413.0.

Example 253

5-Chloro-thiophene-2-carboxylic acid {3-[4-(pyridin-3-ylamino)-phenyl]-isoxazol-5-ylmethyl}-amide

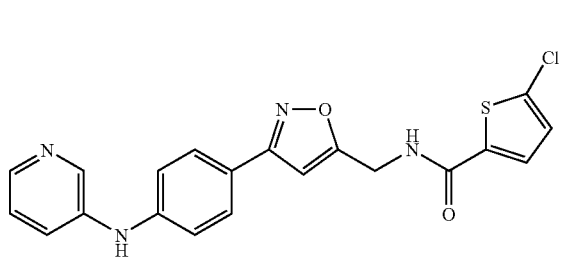

The titled compound was made by the procedure similar to that described in Example 222. MS found for $C_{20}H_{15}ClN_4O_2S$ as (M+H)+ 411.0, 413.1.

Example 254

5-Chloro-thiophene-2-carboxylic acid {3-[4-(pyridin-4-ylamino)-phenyl]-isoxazol-5-ylmethyl}-amide

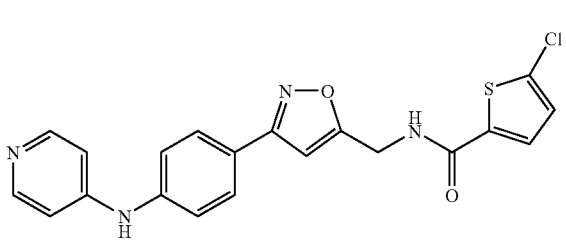

The titled compound was made by the procedure similar to that described in Example 222. MS found for $C_{20}H_{15}ClN_4O_2S$ as (M+H)+ 411.0, 413.0.

Example 255

5-Chloro-thiophene-2-carboxylic acid {3-[4-(methyl-pyridin-4-yl-amino)-phenyl]-isoxazol-5-ylmethyl}-amide

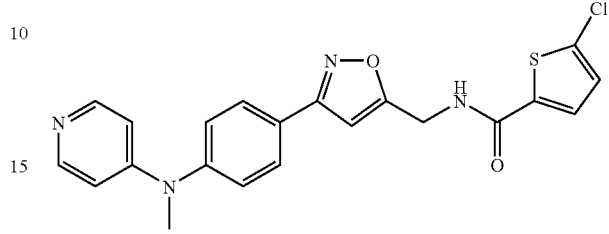

The titled compound was made by the procedure similar to that described in Example 222. MS found for $C_{21}H_{17}ClN_4O_2S$ as (M+H)+ 425.0, 427.0.

Example 256

5-Chloro-thiophene-2-carboxylic acid [3-(4-pyrrolidin-1-yl-phenyl)-isoxazol-5-ylmethyl]-amide

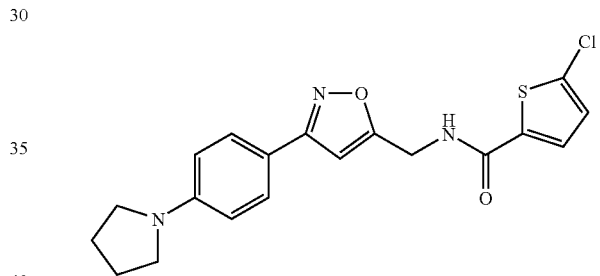

The titled compound was made by the procedure similar to that described in Example 222. MS found for $C_{29}H_{18}ClN_3O_2S$ as (M+H)+ 388.4, 390.4

Example 257

5-Chloro-thiophene-2-carboxylic acid [3-(4-morpholin-4-yl-phenyl)-isoxazol-5-ylmethyl]-amide

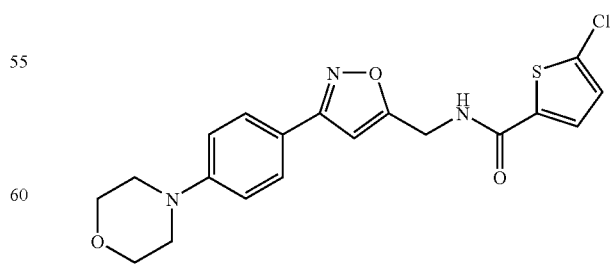

The titled compound was made by the procedure similar to that described in Example 222. MS found for $C_{19}H_{18}ClN_3O_3S$ as (M+H)+ 404.3, 406.3.

Example 258

5-Chloro-thiophene-2-carboxylic acid [3-(4-benzylamino-phenyl)-isoxazol-5-ylmethyl]-amide

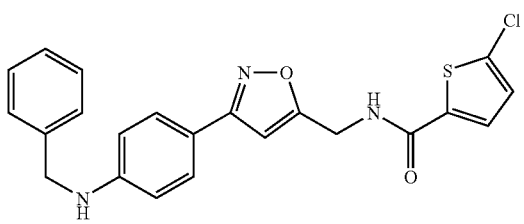

The titled compound was made by the procedure similar to that described in Example 169, step 7. MS found for $C_{22}H_{18}ClN_3O_2S$ as (M+H)+ 424.0, 426.0

Example 259

5-Chloro-thiophene-2-carboxylic acid {3-[4-(1-methyl-piperidin-4-ylamino)-phenyl]-isoxazol-5-ylmethyl}-amide

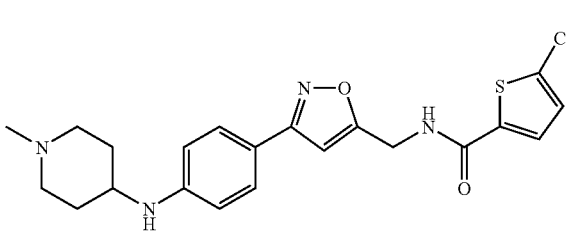

The titled compound was made by the procedure similar to that described in Example 169, step 7. MS found for $C_{21}H_{23}ClN_4O_2S$ as (M+H)$^+$ 431.4, 433.4.

Example 260

2-[4-(5-{[(5-Chloro-thiophene-2-carbonyl)-amino]-methyl}-4,5-dihydro-isoxazol-3-yl)-phenylamino]-benzoic acid methyl ester

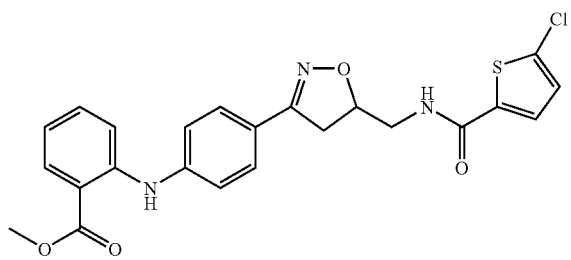

The titled compound was made by the procedure similar to that described in Example 222. MS found for $C_{23}H_{20}ClN_3O_4S$ as (M+H)$^+$ 470.0, 472.0.

Example 261

3-[4-(5-{[(5-Chloro-thiophene-2-carbonyl)-amino]-methyl}-4,5-dihydro-isoxazol-3-yl)-phenylamino]-benzoic acid methyl ester

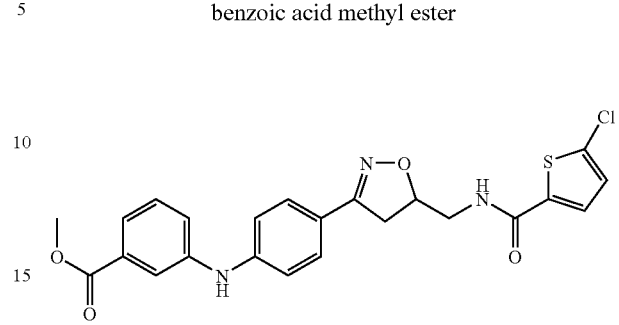

The titled compound was made by the procedure similar to that described in Example 222. MS found for $C_{23}H_{20}ClN_3O_4S$ as (M+H)$^+$ 470.0, 472.0.

Example 262

4-[4-(5-{[(5-Chloro-thiophene-2-carbonyl)-amino]-methyl}-4,5-dihydro-isoxazol-3-yl)-phenylamino]-benzoic acid methyl ester

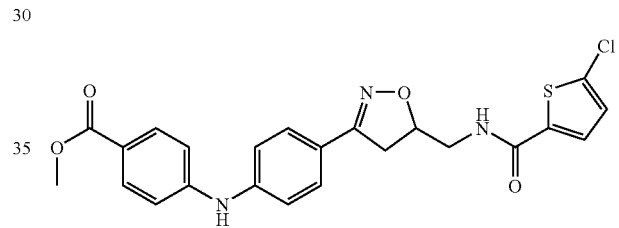

The titled compound was made by the procedure similar to that described in Example 222. MS found for $C_{23}H_{20}ClN_3O_4S$ as (M+H)$^+$ 470.0, 472.0.

Example 263

5-Chloro-thiophene-2-carboxylic acid [3-(2'-pyrrolidin-1-ylmethyl-biphenyl-3-yl)-4,5-dihydro-isoxazol-5-ylmethyl]-amide

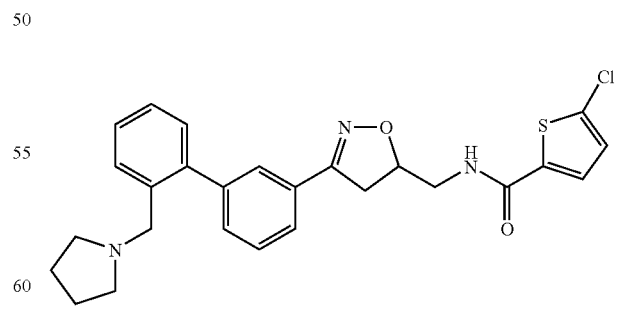

The titled compound was made using the starting bromide from Example 3 by the procedure similar to that described in Example 183, followed by the procedure of Example 169, step 7. MS found for $C_{26}H_{26}ClN_3O_2S$ as (M+H)$^+$ 480.5, 482.5.

Example 264

5-Chloro-thiophene-2-carboxylic acid [3-(3'-dimethylaminomethyl-biphenyl-3-yl)-4,5-dihydro-isoxazol-5-ylmethyl]-amide

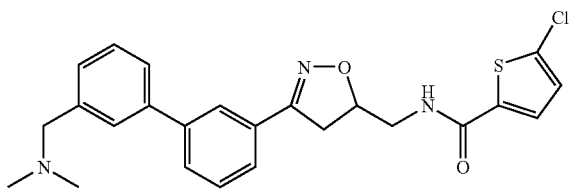

The titled compound was made using the starting bromide from Example 3 by the procedure similar to that described in Example 183, followed by the procedure of Example 169, step 7. MS found for $C_{24}H_{24}ClN_3O_2S$ as $(M+H)^+$ 454.1, 456.1.

Example 265

5-Chloro-thiophene-2-carboxylic acid [3-(3'-pyrrolidin-1-ylmethyl-biphenyl-3-yl)-4,5-dihydro-isoxazol-5-ylmethyl]-amide

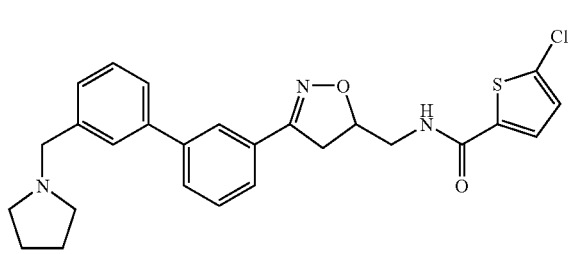

The titled compound was made using the starting bromide from Example 3 by the procedure similar to that described in Example 183, followed by the procedure of Example 169, step 7. MS found for $C_{26}H_{26}ClN_3O_2S$ as $(M+H)^+$ 480.1, 482.1.

Example 266

5-Chloro-thiophene-2-carboxylic acid [3-(4'-dimethylaminomethyl-biphenyl-3-yl)-4,5-dihydro-isoxazol-5-ylmethyl]-amide

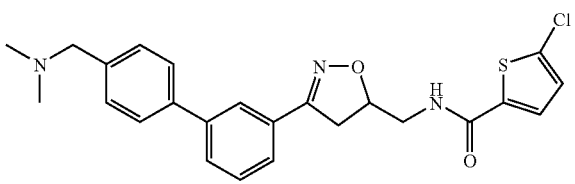

The titled compound was made using the starting bromide from Example 3 by the procedure similar to that described in Example 183, followed by the procedure of Example 169, step 7. MS found for $C_{24}H_{24}ClN_3O_2S$ as $(M+H)^+$ 454.1, 456.1.

Example 267

5-Chloro-thiophene-2-carboxylic acid [3-(4'-pyrrolidin-1-ylmethyl-biphenyl-3-yl)-4,5-dihydro-isoxazol-5-ylmethyl]-amide

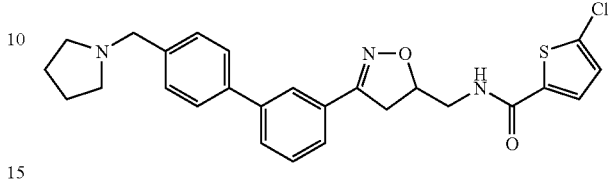

The titled compound was made using the starting bromide from Example 3 by the procedure similar to that described in Example 183, followed by the procedure of Example 169, step 7. MS found for $C_{26}H_{26}ClN_3O_2S$ as $(M+H)^+$ 480.1, 482.1.

Example 268

5-Chloro-thiophene-2-carboxylic acid [3-(2'-dimethylaminomethyl-biphenyl-3-yl)-isoxazol-5-ylmethyl]-amide

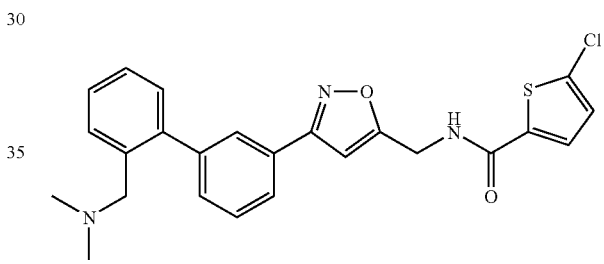

The titled compound was made using the starting bromide from Example 4 by the procedure similar to that described in Example 183, followed by the procedure of Example 169, step 7. MS found for $C_{24}H_{22}ClN_3O_2S$ as $(M+H)^+$ 452.5, 454.5.

Example 269

5-Chloro-thiophene-2-carboxylic acid [3-(2'-pyrrolidin-1-ylmethyl-biphenyl-3-yl)-isoxazol-5-ylmethyl]-amide

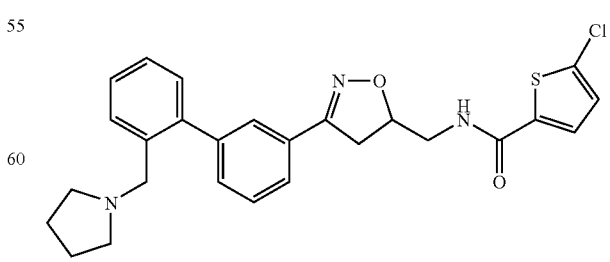

The titled compound was made using the starting bromide from Example 4 by the procedure similar to that described in Example 183, followed by the procedure of Example 169, step 7. MS found for $C_{26}H_{24}ClN_3O_2S$ as $(M+H)^+$ 478.5, 480.5.

Example 270

5-Chloro-thiophene-2-carboxylic acid [3-(3'-dimethylaminomethyl-biphenyl-3-yl)-isoxazol-5-ylmethyl]-amide

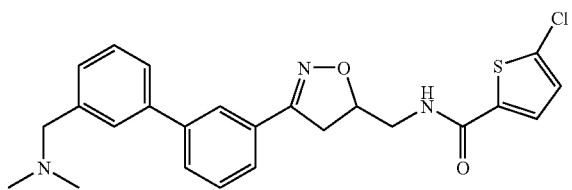

The titled compound was made using the starting bromide from Example 4 by the procedure similar to that described in Example 183, followed by the procedure of Example 169, step 7. MS found for $C_{24}H_{22}ClN_3O_2S$ as (M+H)+ 452.1, 454.1.

Example 271

5-Chloro-thiophene-2-carboxylic acid [3-(3'-pyrrolidin-1-ylmethyl-biphenyl-3-yl)-isoxazol-5-ylmethyl]-amide

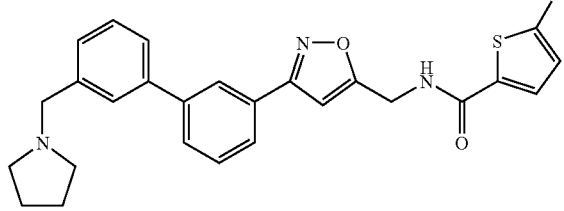

The titled compound was made using the starting bromide from Example 4 by the procedure similar to that described in Example 183, followed by the procedure of Example 169, step 7. MS found for $C_{26}H_{24}ClN_3O_2S$ as $(M+H)^+$ 478.1, 480.1.

Example 272

5-Chloro-thiophene-2-carboxylic acid [3-(4'-dimethylaminomethyl-biphenyl-3-yl)-isoxazol-5-ylmethyl]-amide

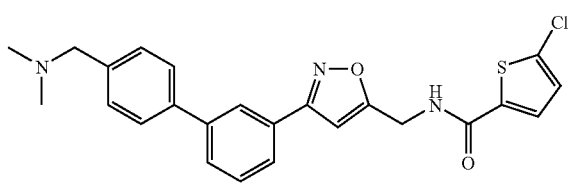

The titled compound was made using the starting bromide from Example 4 by the procedure similar to that described in Example 183, followed by the procedure of Example 169, step 7. MS found for $C_{24}H_{22}ClN_3O_2S$ as (M+H)+ 452.1, 454.1.

Example 273

5-Chloro-thiophene-2-carboxylic acid [3-(4'-pyrrolidin-1-ylmethyl-biphenyl-3-yl)-isoxazol-5-ylmethyl]-amide

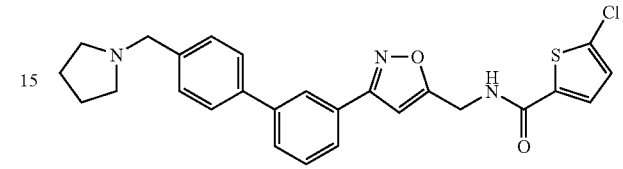

The titled compound was made using the starting bromide from Example 4 by the procedure similar to that described in Example 183, followed by the procedure of Example 169, step 7. MS found for $C_{26}H_{24}ClN_3O_2S$ as $(M+H)^+$ 478.1, 480.1.

Example 274

5-Chloro-thiophene-2-carboxylic acid [3-(3-pyridin-3-yl-phenyl)-4,5-dihydro-isoxazol-5-ylmethyl]-amide

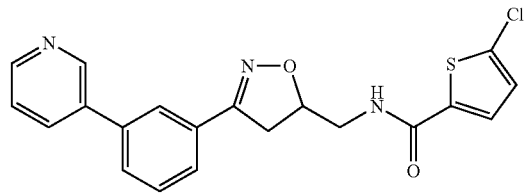

The titled compound was made by the procedure similar to that described in Example 183. $^1$H NMR (DMSO-d$_6$, 400 MHz): δ 9.02 (s, 1H), δ 8.89 (t, 1H), 8.68 (d, 1H), δ 8.38 (d, 1H), 7.92 (s, 1H), 7.82 (d, 1H), δ 7.71 (m, 2H), δ 7.63 (d, 1H), δ 7.58 (t, 1H), δ 7.12 (d, 1H), δ 4.88 (m, 1H), δ 3.53 (dd, 1H), δ 3.41 (m, 2H), δ 3.258 (dd, 1H).

Example 275

5-Chloro-thiophene-2-carboxylic acid [3-(3-pyridin-4-yl-phenyl)-4,5-dihydro-isoxazol-5-ylmethyl]-amide

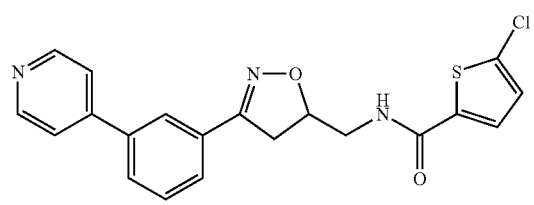

The titled compound was made by the procedure similar to that described in Example 183. $^1$H NMR (DMSO-d$_6$, 400 MHz): δ 8.89 (t, 1H), δ 8.79 (d, 2H), δ 8.04 (m, 3H), δ 7.94 (d, 1H), δ 7.82 (d, 1H), δ 7.62 (m, 2H), δ 7.13 (d, 1H), δ 4.90 (m, 1H), δ 3.59 (dd, 1H), δ 3.41 (m, 2H), δ 3.28 (dd, 1H).

Example 276

5-Chloro-thiophene-2-carboxylic acid [3-(3-pyridin-3-yl-phenyl)-isoxazol-5-ylmethyl]-amide

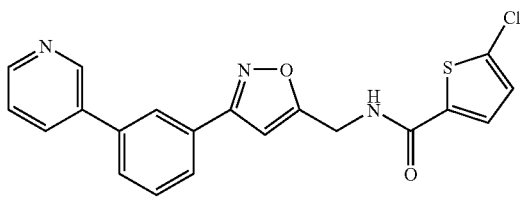

The titled compound was made by the procedure similar to that described in Example 183. $^1$H NMR (DMSO-d$_6$, 400 MHz): δ 9.31 (t, 1H), δ 9.07 (s, 1H), δ 8.65 (s, 1H), δ 8.38 (d, 1H), δ 8.19 (s, 1H), δ 7.91 (d, 1H), δ 7.87 (d, 1H), δ 7.63 (m, 3H), δ 7.19 (d, 1H), δ 7.09 (s, 1H), 4.60 (d, 2H).

Example 277

5-Chloro-thiophene-2-carboxylic acid [3-(3-pyridin-4-yl-phenyl)-isoxazol-5-ylmethyl]-amide

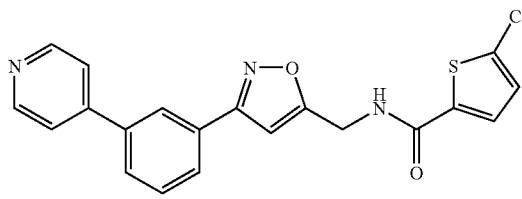

The titled compound was made by the procedure similar to that described in Example 183. $^1$H NMR (DMSO-d$_6$, 400 MHz): δ 9.35 (t, 1H), δ 8.77 (d, 1H), δ 8.30 (s, 1H), δ 8.08 (d, 1H), a 8.02 (d, 1H), δ 7.98 (d, 1H), δ 7.68 (m, 2H), δ 7.19 (d, 1H), δ 7.10 (s, 1H), δ 4.61 (d, 2H).

Example 278

5-Chloro-N-((3-(4-(2-oxopyridin-1 (2H)-yl)phenyl)-4,5-dihydroisoxazol-5-yl)methyl)thiophene-2-carboxamide

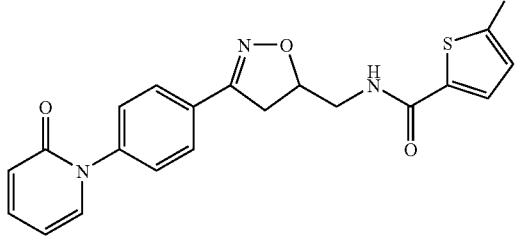

Aryl bromide (Example 1, 100 mg, 0.25 mmol) and 2-hydroxypyridine (95 mg, 1.0 mmol) were dissolved in 1.5 mL dry dioxane and 0.5 mL dry DMSO in a sealed tube. To it were added N,N'-dimethylethylenediamine (27 μL, 0.25 mmol), CuI (95 mg, 0.125 mmol) and K$_3$PO$_4$ (106 mg, 0.5 mmol) in order. The mixture was stirred and heated in 120° C. bath till all the bromide starting material had been consumed (3 hrs, monitored by analytical HPLC). The mixture was filtered and directly subjected to reverse phase preparative HPLC to isolate the title compound as a white powder after lyophilization. MS found for C$_{20}$H$_{26}$ClN$_3$O$_3$S as (M+H)+ 414.1, 416.1

Example 279

5-Chloro-N-((3-(4-(3-fluoro-2-oxopyridin-1 (2H)-yl)phenyl)-4,5-dihydroisoxazol-5-yl)methyl)thiophene-2-carboxamide

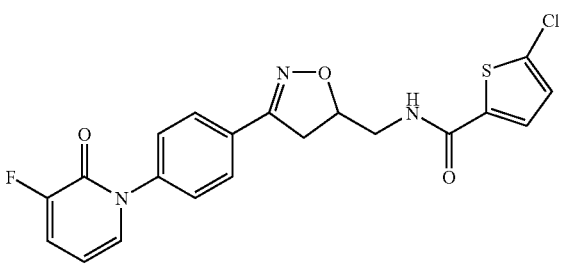

The title compound was prepared by the same procedure described in Example 278 using 3-fluoro-2-hydroxypyridine in place of 2-hydroxypyridine. MS found for C$_{20}$H$_{15}$ClFN$_3$O$_3$S as (M+H)+ 432.1, 434.1

Example 280

5-Chloro-N-((3-(4-(5-fluoro-2-oxopyridin-1 (2H)-yl)phenyl)-4,5-dihydroisoxazol-5 -yl)methyl)thiophene-2-carboxamide

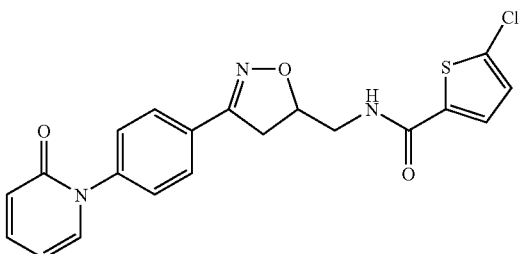

The title compound was prepared by the same procedure described in Example 278 using 5-fluoro-2-hydroxypyridine in place of 2-hydroxypyridine. MS found for C$_{20}$H$_{15}$ClFN$_3$O$_3$S as (M+H)+ 432.1, 434.1

Example 281

5-Chloro-N-((3-(4-(3-methyl-2-oxopyridin-1 (2H)-yl)phenyl)-4,5-dihydroisoxazol-5-yl)methyl)thiophene-2-carboxamide

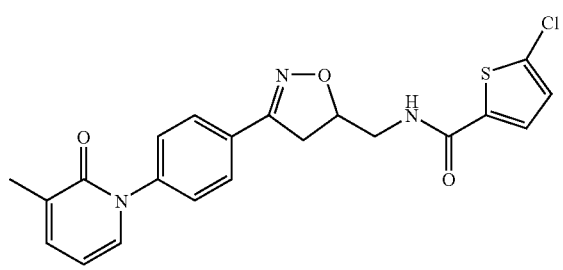

The title compound was prepared by the same procedure described in Example 278 using 3-methyl-2-hydroxypyridine in place of 2-hydroxypyridine. MS found for $C_{21}H_{18}ClN_3O_3S$ as (M+H)+ 428.1, 430.1

Example 282

5-Chloro-N-((3-(4-(3-methoxy-2-oxopyridin-1 (2H)-yl)phenyl)-4,5-dihydroisoxazol-5-yl)methyl)thiophene-2-carboxamide

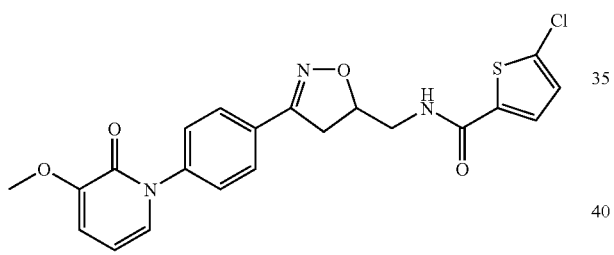

The title compound was prepared by the same procedure described in Example 278 using 3-methoxy-2-hydroxypyridine in place of 2-hydroxypyridine. MS found for $C_{21}H_{18}ClN_3O_4S$ as (M+H)+ 444.1, 446.1

Example 283

5-Chloro-N-((3-(4-(3-chloro-2-oxopyridin-1 (2H)-yl)phenyl)-4,5-dihydroisoxazol-5-yl)methyl)thiophene-2-carboxamide

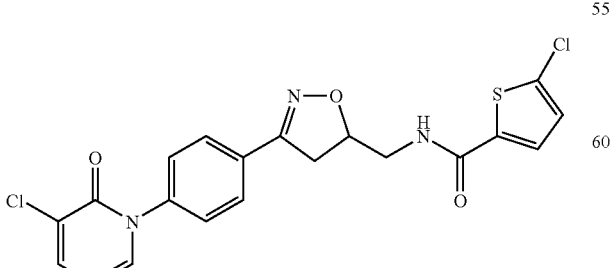

The title compound was prepared by the same procedure described in Example 278 using 3-chloro-2-hydroxypyridine in place of 2-hydroxypyridine. MS found for $C_{20}H_{15}Cl_2N_3O_3S$ as (M+H)+ 448.0, 450.0

Example 284

5-Chloro-N-((3-(4-(4-methyl-2-oxopyridin-1 (2H)-yl)phenyl)-4,5-dihydroisoxazol-5-yl)methyl)thiophene-2-carboxamide

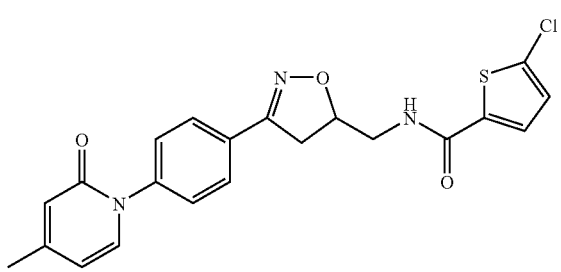

The title compound was prepared by the same procedure described in Example 278 using 4-methyl-2-hydroxypyridine in place of 2-hydroxypyridine. MS found for $C_{21}H_{18}ClN_3O_3S$ as (M+H)+ 428.1, 430.1

Example 285

5-Chloro-N-((3-(4-(5-methyl-2-oxopyridin-1 (2H)-yl)phenyl)-4,5-dihydroisoxazol-5-yl)methyl)thiophene-2-carboxamide

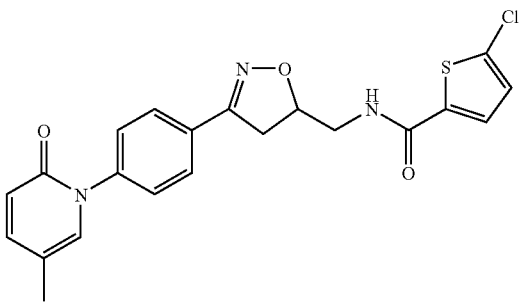

The title compound was prepared by the same procedure described in Example 278 using 5-methyl-2-hydroxypyridine in place of 2-hydroxypyridine. MS found for $C_{21}H_{18}ClN_3O_3S$ as (M+H)+ 428.1, 430.1

Example 286

5-Chloro-N-((3-(4-(5-methoxy-2-oxopyridin-1 (2H)-yl)phenyl)-4,5-dihydroisoxazol-5-yl)methyl)thiophene-2-carboxamide

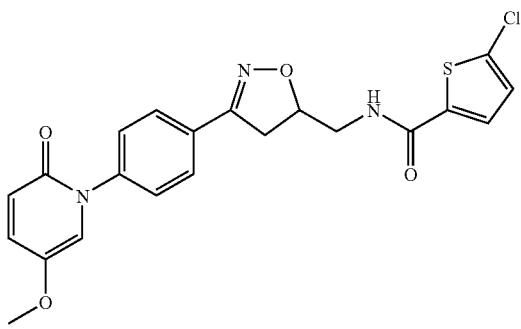

The title compound was prepared by the same procedure described in Example 278 using 5-methoxy-2-hydroxypyridine in place of 2-hydroxypyridine. MS found for $C_{21}H_{18}ClN_3O_4S$ as (M+H)+ 444.1, 446.1

Example 287

5-Chloro-N-((3-(4-(5-chloro-2-oxopyridin-1 (2H)-yl)phenyl)-4,5-dihydroisoxazol-5-yl)methyl)thiophene-2-carboxamide

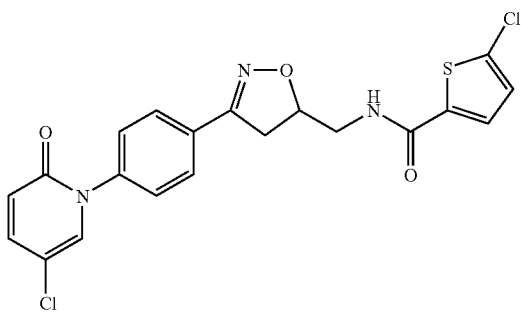

The title compound was prepared by the same procedure described in Example 278 using 5-chloro-2-hydroxypyridine in place of 2-hydroxypyridine. MS found for $C_{20}H_{15}Cl_2N_3O_3S$ as (M+H)+ 448.0, 450.0

Example 288

5-Chloro-N-((3-(4-iodophenyl)isoxazol-5-yl)methyl)thiophene-2-carboxamide

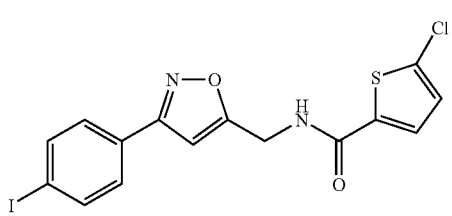

The title compound was prepared by the same procedure described in Example 2 using 4-iodobenzaldehyde in place of 4-bromobenzaldehyde. MS found for $C_{15}H_{10}ClIN_2O_2S$ as (M+H)+ 445.0, 447.0

Example 289

5-Chloro-N-((3-(4-(2-oxopyridin-1 (2H)-yl)phenyl)isoxazol-5-yl)methyl)thiophene-2-carboxamide

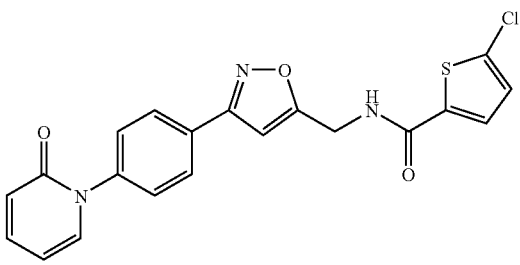

Aryl iodide (Example 288, 43 mg, 0.1 mmol) and 2-hydroxypyridine (38 mg, 0.4 mmol) were dissolved in 1.2 mL dry dioxane and 0.5 mL dry DMSO in a sealed tube. To it were added N,N'-dimethylethylenediamine (11 μL, 0.1 mmol), CuI (10 mg, 0.05 mmol) and $K_3PO_4$ (42 mg, 0.2 mmol) in order. The mixture was stirred and heated in 120° C. bath for 6 hrs. The mixture was filtered and directly subjected to reverse phase preparative HPLC to isolate the title compound as a white powder after lyophilization. MS found for $C_{20}H_{14}ClN_3O_3S$ as (M+H)+ 412.0, 414.0

Example 290

5-Chloro-N-((1-(4-(2-oxopyridin-1 (2H)-yl)phenyl)-1H-1,2,3-triazol-4-yl)methyl)thiophene-2-carboxamide (36)

SCHEME 5

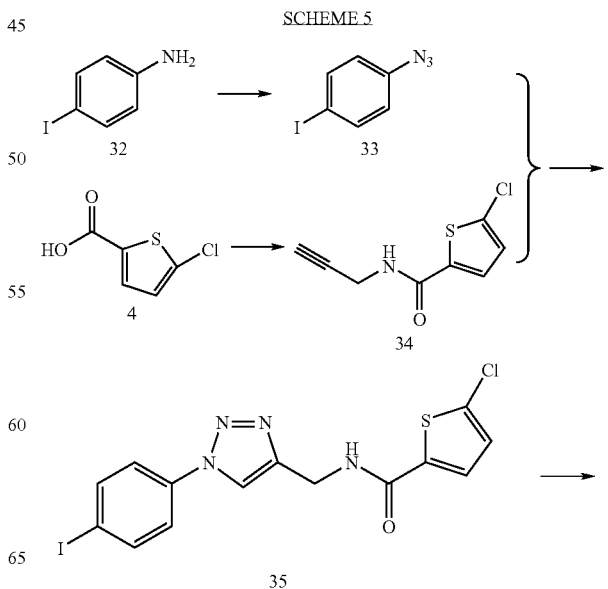

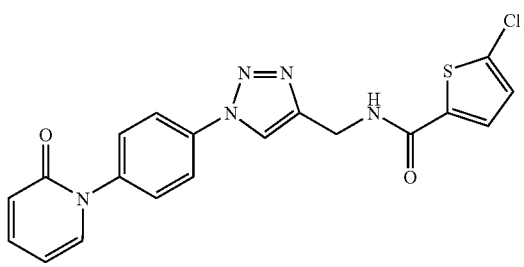

36

Step 1:

4-Iodoaniline (32, 6.00 g, 27.4 mmol) was dissolved in 25 mL TFA and stirred in ice bath. Solid NaNO$_2$ (2.07 g, 30.1 mmol) was added in small portions. The resulting mixture was stirred for 30 min in the ice bath. Sodium azide (1.87 g, 28.8 mmol) was dissolved in 10 mL water and chilled in ice bath. This cold solution was then added to the TFA solution in three portions. The mixture was stirred in ice bath for 1 hr and concentrated in vacuo to remove TFA. The residue was taken into 600 mL DCM and washed with water three times. The organic phase was dried using MgSO$_4$ and concentrated in vacuo to afford 1-azido-4-iodobenzene 33 as a brownish waxy solid in >99% yield. In the mean time, 5-chlorothiophene-2-carboxylic acid (4, 9.13 g, 56 mmol) was dissolved in 200 mL dry DCM along with 0.5 mL dry DMF. To the vigorously stirred solution was carefully added oxalyl chlororide (14.7 mL, 169 mmol) dropwise. The resulting solution was stirred for 3 hrs at RT and concentrated in vacuo. The residue was pumped to dryness and then dissolved in 300 mL dry DCM. To this solution was added propargylamine (5.8 mL, 84 mmol) dropwise. The mixture was stirred at RT for overnight and a lot of solid precipitated out. To this mixture was added 600 mL hexane. The mixture was vigorously stirred for a few hours and filtered for the solid (product 34). The solid (9.47 g, 85%) was washed with hexane and was pure enough for direct use without further purification. MS found for C$_8$H$_6$ClNOS as (M+H)+ 200.0, 202.0.

Step 2:

Aryl azide 33 (27 mmol) and alkyne 34 (5.37 g, 27 mmol) were dissolved in 40 mL dry DMF. To it was added 200 mL toluene. The mixture was refluxed in 135° C. bath for 1 day. The mixture was concentrated in vacuo and subjected to flash column chromatography to isolate 1,4-disubstituted triazole 35 (major product: Rf=0.30 in 1:1hexane/EtOAc) and its 1,5-disubstituted triazole isomer (minor product: Rf=0.17 in 1:1hexane/EtOAc). MS found for 35C$_{14}$H$_{10}$ClIN$_4$OS as (M+H)+ 444.9, 446.9.

Step 3:

Aryl iodide 35 (100 mg, 0.22 mmol) and 2-hydroxypyridine (42 mg, 0.44 mmol) were dissolved in 5 mL dry DMSO in a sealed tube. To it were added 8-hydroxyquinoline (10 mg, 0.007 mmol), CuI (13 mg, 0.07 mmol) and Cs$_2$CO$_3$ (145 mg, 0.44 mmol). The mixture was stirred in 120° C. bath for overnight. Then it was filtered and the filtrate was directly subjected to reverse phase preparative HPLC to isolate the title compound 36 as a white powder in 60-75% yield after lyophilization. MS found for C$_{19}$H$_{14}$ClN$_5$O$_2$S as (M+H)+ 412.1, 414.1.

Example 291

5-Chloro-N-((1-(4-(3-fluoro-2-oxopyridin-1 (2H)-yl) phenyl)-1H-1,2,3-triazol-4-yl)methyl)thiophene-2-carboxamide

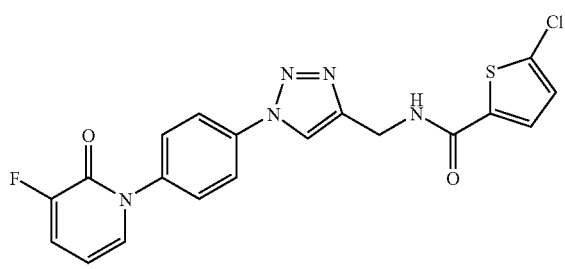

Aryl iodide 35 (Example 290, 50 mg, 0.11 mmol) and 3-fluoro-2-hydroxypyridine (38 mg, 0.33 mmol) were dissolved in 1.0 mL dry dioxane and 0.3 mL dry DMSO in a sealed tube. To it were added N,N'-dimethylethylenediamine (8 µL, 0.066 mmol), CuI (11 mg, 0.055 mmol) and K$_3$PO$_4$ (48 mg, 0.22 mmol) in order. The mixture was stirred and heated in 120° C. bath for overnight. The mixture was filtered and directly subjected to reverse phase preparative HPLC to isolate the title compound as a white powder after lyophilization. MS found for C$_{19}$H$_{13}$ClFN$_5$O$_2$S as (M+H)+ 430.0, 432.0.

Example 292

5-Chloro-N-((1-(4-(3-chloro-2-oxopyridin-1 (2H)-yl)phenyl)-1H-1,2,3-triazol-4-yl)methyl)thiophene-2-carboxamide

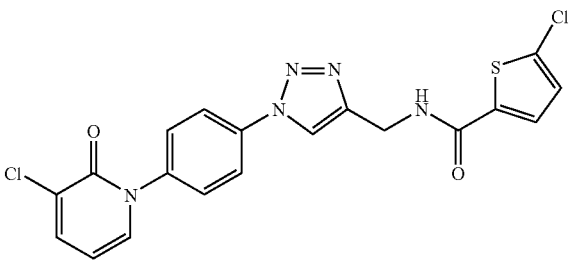

The title compound was prepared by the same procedure described in Example 290 using 3-chloro-2-hydroxypyridine in place of 3-fluoro-2-hydroxypyridine. MS found for C$_{19}$H$_{13}$Cl$_2$N$_5$O$_2$S as (M+H)+ 446.0, 448.0

Example 293

5-Chloro-N-((1-(4-(3-methyl-2-oxopyridin-1 (2H)-yl)phenyl)-1H-1,2,3-triazol-4-yl)methyl)thiophene-2-carboxamide

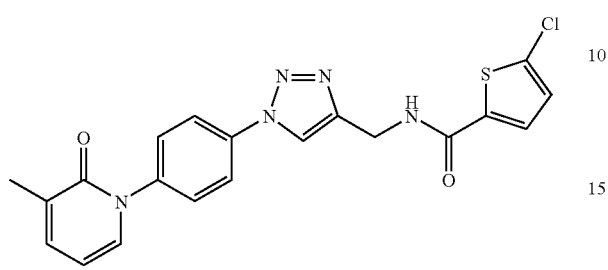

The title compound was prepared by the same procedure described in Example 290 using 3-methyl-2-hydroxypyridine in place of 3-fluoro-2-hydroxypyridine. MS found for $C_{20}H_{16}ClN_5O_2S$ as (M+H)+ 426.1, 428.1

Example 294

5-Chloro-N-((1-(4-(3-methoxy-2-oxopyridin-1 (2H)-yl)phenyl)-1H-1,2,3-triazol-4-yl)methyl)thiophene-2-carboxamide

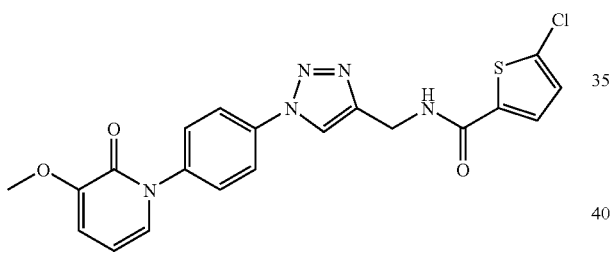

The title compound was prepared by the same procedure described in Example 290 using 3-methoxy-2-hydroxypyridine in place of 3-fluoro-2-hydroxypyridine. MS found for $C_{20}H_{16}ClN_5O_3S$ as (M+H)+ 442.1, 444.1

Example 295

5-Chloro-N-((1-(4-(4-methyl-2-oxopyridin-1 (2H)-yl)phenyl)-1H-1,2,3-triazol-4-yl)methyl)thiophene-2-carboxamide

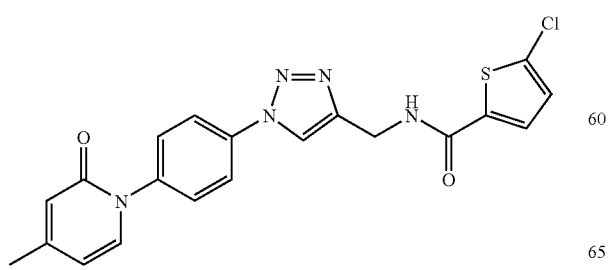

The title compound was prepared by the same procedure described in Example 290 using 4-methyl-2-hydroxypyridine in place of 3-fluoro-2-hydroxypyridine. MS found for $C_{20}H_{16}ClN_5O_2S$ as (M+H)+ 426.1, 428.1

Example 296

5-Chloro-N-((1-(4-(5-methyl-2-oxopyridin-1 (2H)-yl)phenyl)-1H-1,2,3-triazol-4-yl)methyl)thiophene-2-carboxamide

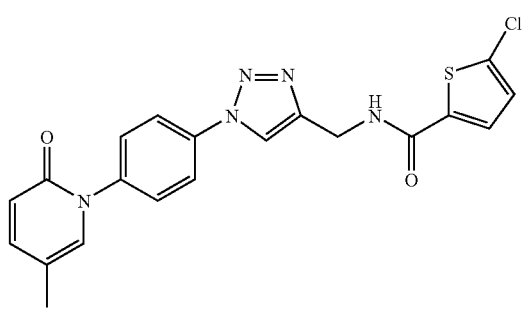

The title compound was prepared by the same procedure described in Example 290 using 5-methyl-2-hydroxypyridine in place of 3-fluoro-2-hydroxypyridine. MS found for $C_{20}H_{16}ClN_5O_2S$ as (M+H)+ 426.1, 428.1

Example 297

5-Chloro-N-((1-(4-(5-methoxy-2-oxopyridin-1 (2H)-yl)phenyl)-1H-1,2,3-triazol-4-yl)methyl)thiophene-2-carboxamide

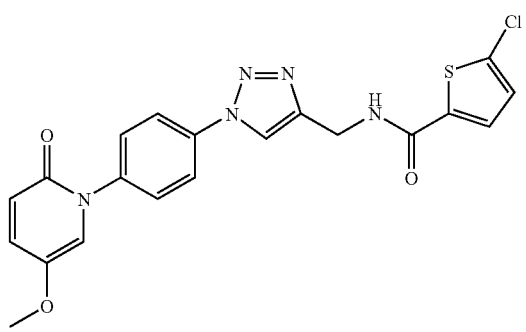

The title compound was prepared by the same procedure described in Example 290 using 5-methoxy-2-hydroxypyridine in place of 3-fluoro-2-hydroxypyridine. MS found for $C_{20}H_{16}ClN_5O_3S$ as (M+H)+ 442.1, 444.1

Example 298

5-Chloro-N-((1-(4-(5-fluoro-2-oxopyridin-1(2H)-yl)phenyl)-1H-1,2,3-triazol-4-yl)methyl)thiophene-2-carboxamide

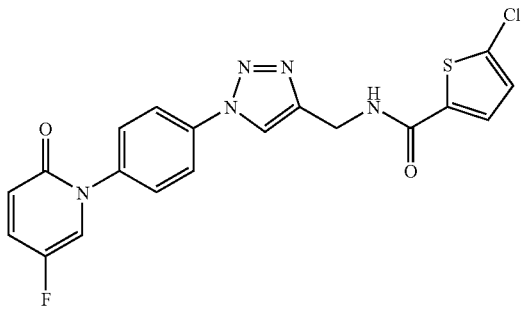

The title compound was prepared by the same procedure described in Example 290 using 5-fluoro-2-hydroxypyridine in place of 3-fluoro-2-hydroxypyridine. MS found for $C_{19}H_{13}ClFN_5O_2S$ as (M+H)+ 430.0, 432.0

Example 299

5-Chloro-N-((1-(4-(5-chloro-2-oxopyridin-1(2H)-yl)phenyl)-1H-1,2,3-triazol-4-yl)methyl)thiophene-2-carboxamide

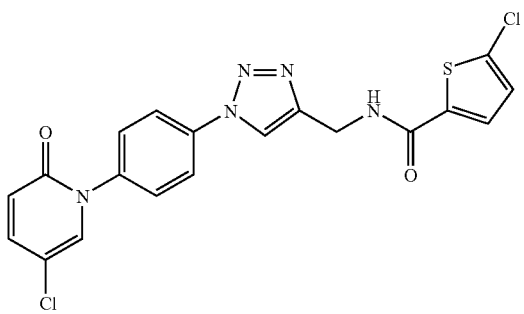

The title compound was prepared by the same procedure described in Example 290 using 5-chloro-2-hydroxypyridine in place of 3-fluoro-2-hydroxypyridine. MS found for $C_{19}H_{13}Cl_2N_5O_2S$ as (M+H)+ 446.0, 448.0

Example 300

5-Chloro-N-((1-(4-(2-oxopiperidin-1-yl)phenyl)-1H-1,2,3-triazol-4-yl)methyl)thiophene-2-carboxamide

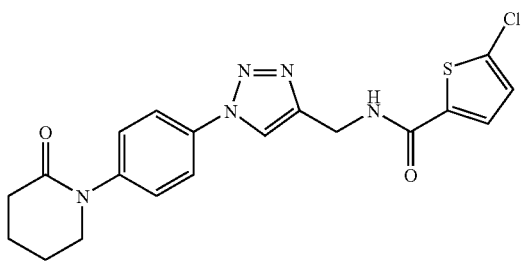

The title compound was prepared by the same procedure described in Example 290 using δ-valerolactam (2-piperidone) in place of 3-fluoro-2-hydroxypyridine. MS found for $C_{19}H_{18}ClN_5O_2S$ as (M+H)+ 416.1, 418.1

Example 301

5-Chloro-N-((1-(4-(3-oxomorpholino)phenyl)-1H-1,2,3-triazol-4-yl)methyl)thiophene-2-carboxamide

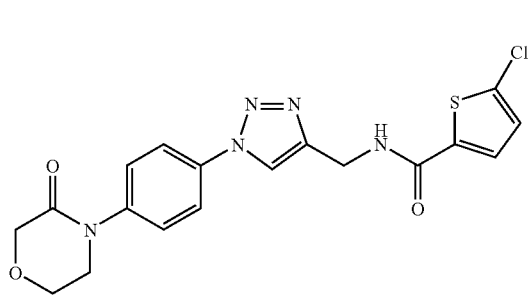

The title compound was prepared by the same procedure described in Example 290 using 3-morpholinone in place of 3-fluoro-2-hydroxypyridine. MS found for $C_{18}H_{16}ClN_5O_3S$ as (M+H)+ 418.1, 420.1

Example 302

5-Chloro-N-((1-(4-(3-oxothiomorpholino)phenyl)-1H-1,2,3-triazol-4-yl)methyl)thiophene-2-carboxamide

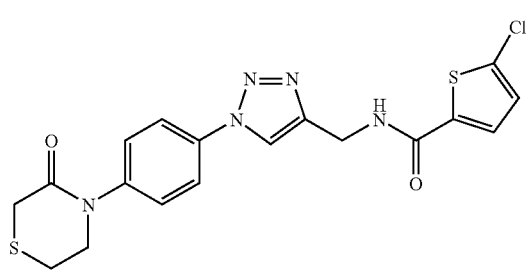

The title compound was prepared by the same procedure described in Example 290 using 3-thiomorpholinone in place of 3-fluoro-2-hydroxypyridine. MS found for $C_{18}H_{16}ClN_5O_2S_2$ as (M+H)+ 434.0, 436.0

Example 303

5-Chloro-N-((1-(4-(5-oxo-1,4-oxazepan-4-yl)phenyl)-1H-1,2,3-triazol-4-yl)methyl)thiophene-2-carboxamide

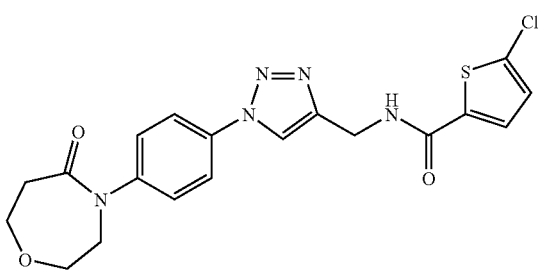

The title compound was prepared by the same procedure described in Example 290 using 1,4-oxazepan-5-one in place of 3-fluoro-2-hydroxypyridine. MS found for $C_{19}H_{18}ClN_5O_3S$ as (M+H)+ 432.1, 434.1

Example 304

5-Chloro-N-((1-(2-fluoro-4-iodophenyl)-1H-1,2,3-triazol-4-yl)methyl)thiophene-2-carboxamide

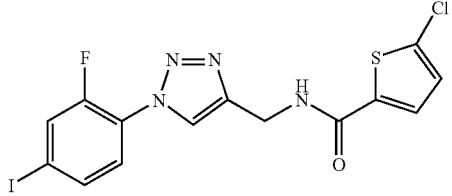

The title compound was prepared by the same procedure for compound 35 described in Example 290 in Scheme 5, using 4-iodo-2-fluoroaniline in place of 4-iodoaniline. MS found for $C_{14}H_9ClFIN_4OS$ as (M+H)+ 462.0, 464.0

Example 305

5-Chloro-N-((1-(2-fluoro-4-(2-oxopyridin-1 (2H)-yl)phenyl)-1H-1,2,3-triazol-4-yl)methyl)thiophene-2-carboxamide

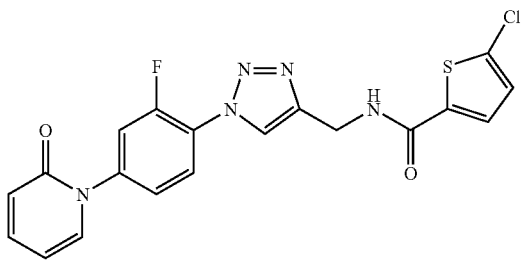

Example 306

5-Chloro-N-((1-(2-fluoro-4-(3-oxomorpholino)phenyl)-1H-1,2,3-triazol-4-yl)methyl)thiophene-2-carboxamide

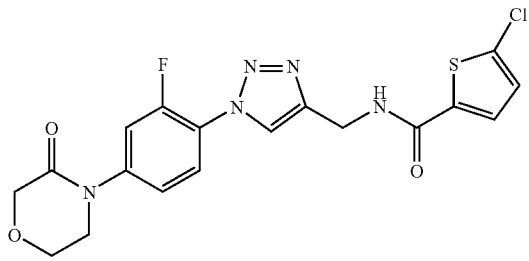

The title compound was prepared by the same procedure described in Example 305 using 3-morpholinone in place of 2-hydroxypyridine. MS found for $C_{18}H_{15}ClFN_5O_3S$ as (M+H)+ 436.1, 438.1

Example 307

5-Chloro-N-((1-(2-hyroxy-4-(2-oxopyridin-1 (2H)-yl)phenyl)-1H-1,2,3-triazol-4-yl)methyl)thiophene-2-carboxamide

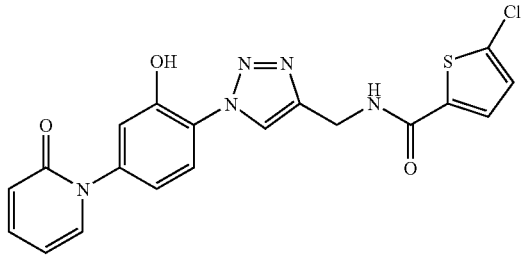

Example 304 (50 mg, 0.11 mmol) and 2-hydroxypyridine (42 mg, 0.44 mmol) were dissolved in 1.2 mL dry dioxane and 0.5 mL dry DMSO in a sealed tube. To it were added N,N'-dimethylethylenediamine (12 μL, 0.11 mmol), CuI (11 mg, 0.055 mmol) and $K_3PO_4$ (47 mg, 0.22 mmol). The mixture was stirred in 120° C. bath for 2.5 hr. The mixture was filtered and the filtrate was directly subjected to reverse phase preparative HPLC to isolate the title compound in 50-65% yield. MS found for $C_{19}H_{13}ClFN_5O_2S$ as (M+H)+ 430.0, 432.0

Example 305 (58 mg, 0.13 mmol) was dissolved in 2 mL DMSO and 1 mL water in a sealed tube. To it was added $Cs_2CO_3$ (88 mg, 0.26 mmol). The mixture was stirred in 120° C. bath for overnight. It was cooled to RT and directly subjected to reverse phase HPLC to isolate the title compound as a white powder after lyophilization. MS found for $C_{19}H_{14}ClN_5O_3S$ as (M+H)+ 428.1.0, 430.1

Example 308

5-Chloro-N-((1-(2-(4-methylpiperazin-1-yl)-4-(2-oxopyridin-1 (2H)-yl)phenyl)-1H-1,2,3-triazol-4-yl)methyl)thiophene-2-carboxamide

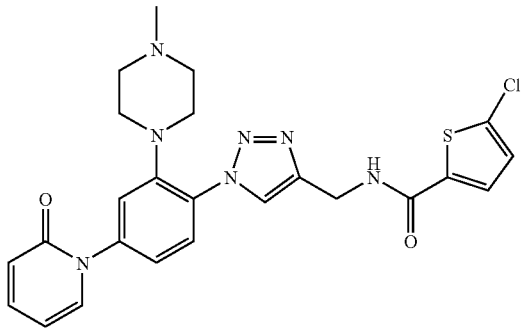

Example 305 (58 mg, 0.13 mmol) was dissolved in 2 mL anhydrous DMSO water in a sealed tube. To it were added N-methylpiperazine (44 μL, 0.40 mmol) and Cs$_2$CO$_3$ (88 mg, 0.26 mmol). The mixture was stirred in 120° C. bath for overnight. It was cooled to RT and directly subjected to reverse phase HPLC to isolate the title compound as a white powder after lyophilization. MS found for C$_{24}$H$_{24}$ClN$_7$O$_2$S (M+H)+ 510.1, 512.1

Example 309

5-Chloro-N-((1-(5-(2-oxopyridin-1 (2H)-yl)pyridin-2-yl)-1H-1,2,3-triazol-4-yl)methyl)thiophene-2-carboxamide (40)

SCHEME 6

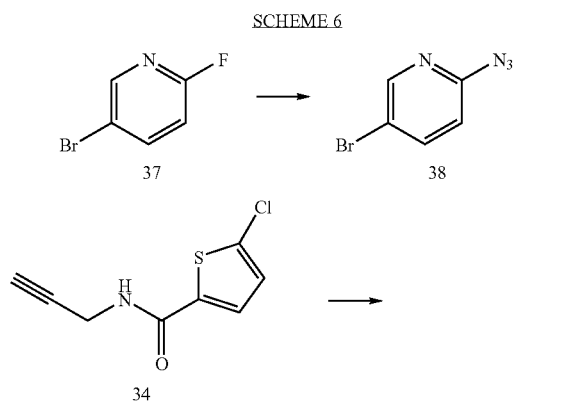

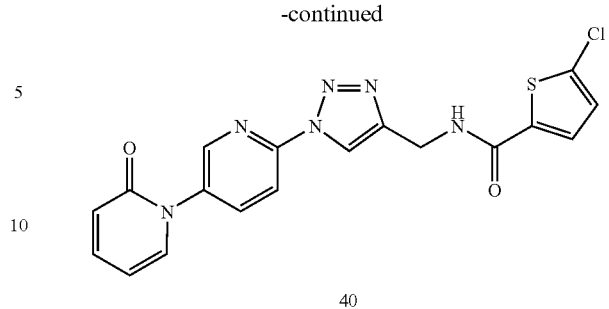

40

Step 1:

2-Fluoro-5-bromopyridine (2.18 g, 12.3 mmol) was dissolved in 25 mL anhydrous DMSO. To it was added NaN$_3$ (1.61 g, 24.6 mmol) and the mixture was stirred in 120° C. bath for overnight. It was diluted with 300 mL ETOAc and washed with brine three times. The organic phase was dried and concentrated in vacuo to afford compound 38 (1.00 g, 41%) in high purity. MS found for C$_5$H$_3$BrN$_4$ as (M+H)+ 199.0, 201.0.

Step 2:

Azidopyridine 38 (65 mg, 0.33 mmol) and alkyne 34 (see Example 290 and Scheme 5; 66 mg, 0.33 mmol) were dissolved in 4 mL dry MeOH in a sealed tube. To it were added DIPEA (0.29 μL, 1.64 mmol) and CuI (312 mg, 1.64 mmol). The mixture was stirred in 100° C. bath for 3 hr and cooled to RT. It was diluted with 200 mL acetone, stirred well, and filtered to remove the insoluble copper salt. The filtrate was concentrated in vacuo and purified by flash column to yield 1,4-disubstituted triazole 39 (52 mg, 40%). MS found for C$_{13}$H$_9$BrClN$_5$OS as (M+H)+ 398.0, 400.0.

Step 3:

Aryl bromide 39 (52 mg, 0.13 mmol) and 2-hydroxypyridine (37 mg, 0.39 mmol) were dissolved in 2 mL anhydrous dioxane and 2 mL anhydrous DMSO in a sealed tube. To it were added N,N'-dimethylethylenediamine (14 μL, 0.13 mmol), CuI (13 mg, 0.07 mmol) and K$_3$PO$_4$ (55 mg, 0.26 mmol). The mixture was stirred in 120° C. bath for overnight. Then it was filtered and the filtrate was directly subjected to reverse phase preparative HPLC to isolate the title compound 40 as a white powder in 50% yield after lyophilization. MS found for C$_{18}$H$_{13}$ClN$_6$O$_2$S as (M+H)+ 413.1, 415.1.

Example 310

5-Chloro-N-((3-(6-(2-oxopyridin-1 (2H)-yl)pyridin-3-yl)isoxazol-5-yl)methyl)thiophene-2-carboxamide (44)

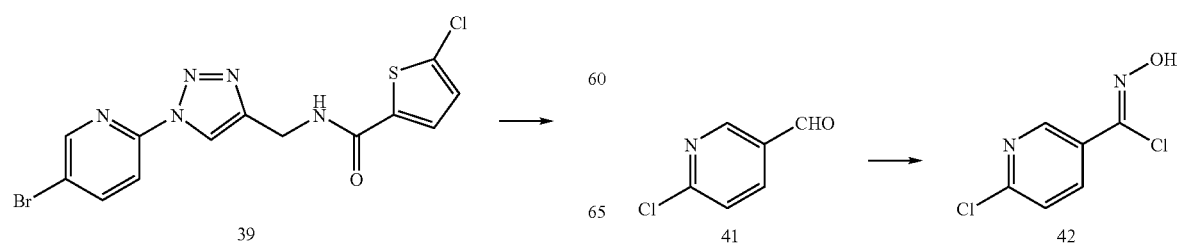

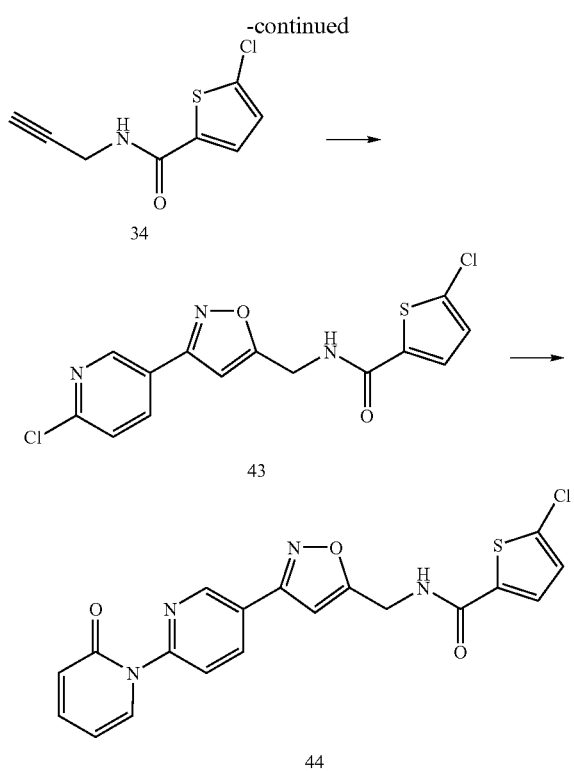

added hydroxylamine hydrochloride (1.48 g, 21.1 mmol). The mixture was stirred at RT for 2 hr and then was concentrated in vacuo. The dry residue was dissolved in 50 mL anhydrous DMF and stirred in ice bath. To it was added NCS (3.25 g, 24.4 mmol). The mixture was stirred for overnight and diluted with 600 mL EtOAc. It was washed with brine four times, dried and concentrated in vacuo to give compound 42 in quantitative yield in high purity as a white solid. MS found for $C_6H_4Cl_2N_2O$ as (M+H)+ 191.0, 193.0.

Step 2:

Compound 42 (3.80 g, 20 mmol) and alkyne 34 (see Example 290 and Scheme 5; 3.98 g, 20 mmol) were dissolved in 200 mL dry toluene. To it was added triethylamine (3.4 mL, 24 mmol). The mixture was refluxed for 3 hr and cooled to RT. White solid (compound 43) precipitated out and was collected by filtration. It was washed by cold toluene and dried in vacuo. MS found for $C_{14}H_9Cl_2N_3O_2S$ as (M+H)+ 354.0, 356.0.

Step 3:

Compound 43 (53 mg, 0.15 mmol) and 2-hydroxypyridine (43 mg, 0.45 mmol) were dissolved in 2 mL anhydrous DMSO in a sealed tube. To it was added $Cs_2CO_3$ (73 mg, 0.22 mmol). The mixture was stirred in 100° C. bath for overnight. Then it was filtered and the filtrate was directly subjected to reverse phase preparative HPLC to isolate the title compound 44 as a white powder in 40% yield after lyophilization. MS found for $C_{19}H_{13}ClN_4O_3S$ as (M+H)+ 413.0, 415.0.

Example 311

5-Chloro-N-((3-(4-(2-oxopyridin-1 (2H)-yl)phenyl)-1,2,4-oxadiazol-5-yl)methyl)thiophene-2-carboxamide (51)

Step 1:

2-Chloropyridine-5-carbaldehyde (3.00 g, 21.2 mmol) was dissolved in 20 mL pyridine and 20 mL ethanol. To it was

SCHEME 8

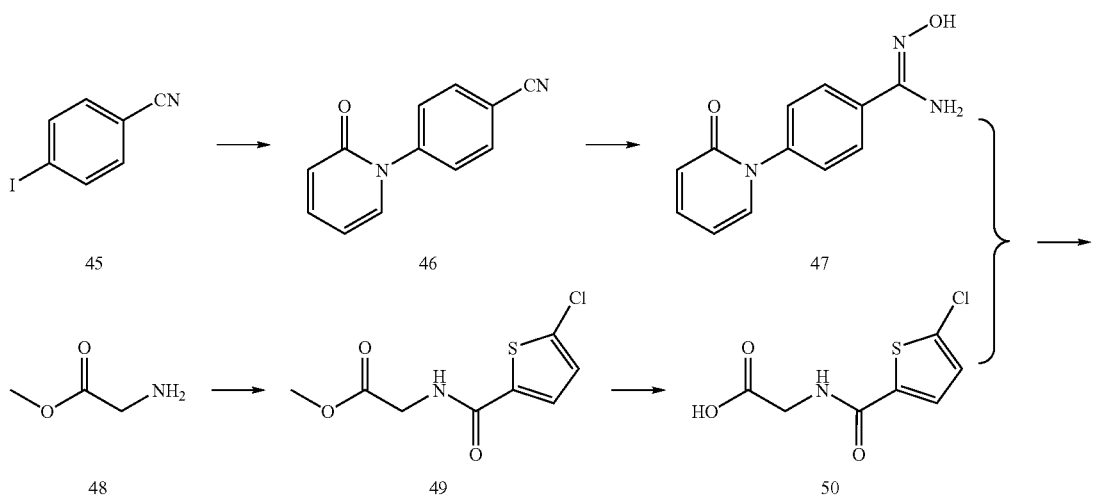

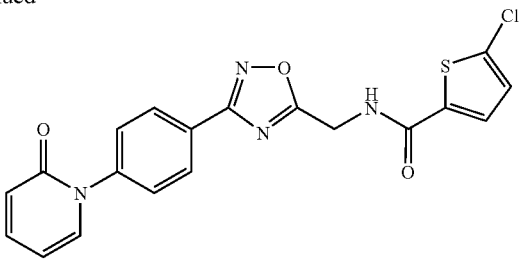

51

Step 1:

4-Iodobenzonitrile (3.00 g, 13 mmol) and 2-hydroxypyridine (2.47 g, 26 mmol) were dissolved in 30 mL anhydrous DMSO in a sealed tube. To it were added 8-hydroxyquinoline (0.57 g, 4 mmol), CuI (0.74 g, 4 mmol) and $Cs_2CO_3$ (8.5 g, 26 mmol). The mixture was stirred in 120° C. bath for overnight. The mixture was partitioned in 500 mL EtOAc and 250 mL water. The organic phase was separated, and the aqueous was extracted with EtOAc three times. All the organic phases were combined, dried, concentrated and purified using flash column to give compound 46 (1.67 g, 66%). MS found for $C_{12}H_8N_2O$ as (M+H)+ 197.1.

Step 2:

Compound 46 (1.67 g, 8.5 mmol) was dissolved in 40 mL DMSO. To it were added DIPEA (7.5 mL, 42.6 mmol) and hydroxylamine hydrochloride (3.0 g, 42.6 mmol). The mixture was stirred for 3 hr and to it was added 250 mL brine. White solid (compound 47) crashed out and was collected. It was washed with brine and cold water, and was dried in vacuo for overnight. MS found for $C_{12}H_{11}N_3O_2$ as (M+H)+ 230.1.

Step 3:

Glycine methyl ester hydrochloride (48, 2.00 g, 16 mmol) and 5-chlorothiophene-2-carboxylic acid (2.60 g, 16 mmol) were dissolved in 50 mL pyridine and stirred in ice bath. To it was added $POCl_3$ (4.5 mL, 48 mmol) dropwise. After 5 minutes, ice chips were added into the mixture, followed by addition of 500 mL water. The mixture was well stirred and filtered. The aqueous filtrate was extracted with EtOAc four times. All the organic phases were combined, dried and concentrated in vacuo to give compound 49 was a light yellow solid (2.27 g, 61%). MS found for $C_8H_8ClNO_3S$ as (M+H)+ 234.0, 236.0.

Step 4:

Methyl ester 49 (2.27 g, 9.7 mmol) was dissolved in 20 mL MeOH, 20 mL dioxane and 20 mL water. To it was added lithium hydroxide monohydrate (1.22 g, 29 mmol). The mixture was stirred for 2 hr at RT and acidified using 2M HCl till pH=7. The neutral mixture was concentrated in vacuo to remove organic solvent. The aqueous residue was extracted with EtOAc four times. The organic phases were combined, dried and concentrated in vacuo to afford acid 50 in quantitative yield. MS found for $C_7H_6ClNO_3S$ as (M+H)+ 220.0, 222.0.

Step 5:

Acid 50 (219 mg, 1.0 mmol) was dissolved in 10 mL dry DMF. To it was added carbonyldiimidazole (180 mg, 1.1 mmol). The mixture was stirred for 1 hr at RT. To it was then added compound 47 (229 mg, 1.0 mmol). The mixture was stirred at RT for 30 min and slowly heated to 120° C. via an oil bath. It was stirred then for 2 hr. After cooling down to RT, to the mixture was added 50 mL brine. The mixture was extracted with EtOAc four times. All the organic phases were combined, dried and concentrated in vacuo. The resulting mixture was purified with reverse phase preparative HPLC to give the title compound 51. MS found for $C_{19}H_{13}ClN_4O_3S$ as (M+H)+ 413.0, 415.0.

Example 312

5-Chloro-N-((1-(4-(1-methyl-4,5-dihydro-1H-imidazol-2-yl)phenyl)-1H-1,2,3-triazol-4-yl)methyl)thiophene-2-carboxamide (55)

SCHEME 9

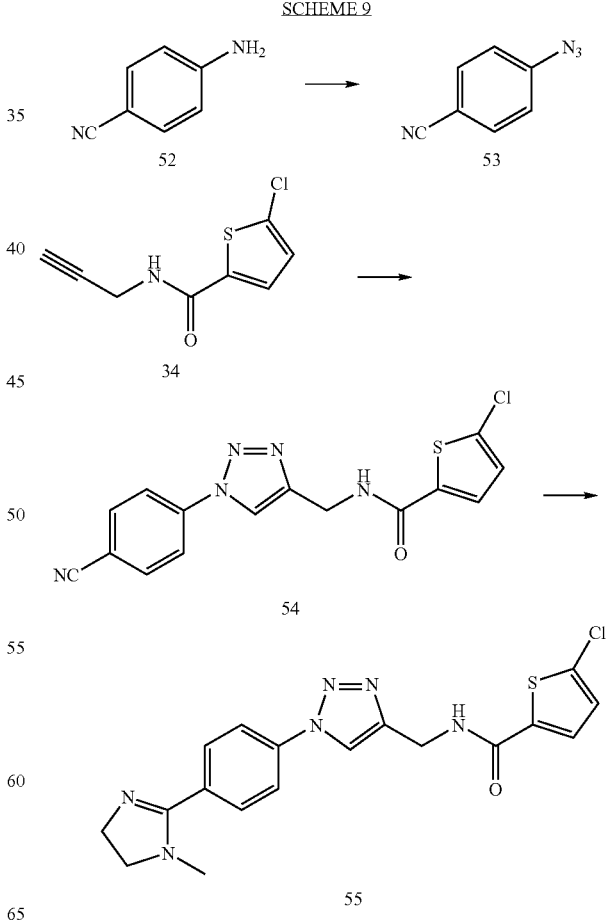

Step 1:

4-Aminobenzonitrile (52, 2.0 g, 17 mmol) was dissolved in 8 mL TFA and stirred in ice bath. To it was added NaNO$_2$ (1.3 g, 18.7 mmol) in small portions. The mixture was stirred for 30 min in ice bath. Then NaN$_3$ (1.1 g, 17 mmol) was dissolved in 6 mL water and chilled in ice. This solution was added into the reaction mixture. After stirring for 1 hr in ice bath, the mixture was concentrated in vacuo to remove TFA, and diluted with water. The aqueous mixture was extracted with DCM three times. The organic phases were combined, dried and concentrated in vacuo to give compound 53 (2.35 g, 96%). MS found for C$_7$H$_4$N$_4$ as (M+H)+ 145.0.

Step 2:

Azidobenzene 53 (1.77 g, 12.3 mmol) and alkyne 34 (see Scheme 5 in Example 290; 2.45 g, 12.3 mmol) were refluxed in 200 mL toluene for overnight. The mixture was then concentrated in vacuo to half of the volume and chilled in ice bath. The solid precipitated out was pure major product 1,4-disubstituted triazole 54, which was collected by filtration and washed with cold toluene. The minor product (the corresponding 1,5-triazole isomer) completely stayed in the filtrate along with some 1,4-disubstituted triazole 54, which might be further recovered by multiple recystalization process using DCM or EtOAc as solvent. 1,4-Disubstituted triazole 54 was dried in vacuo. MS found for C$_{15}$H$_{10}$ClN$_5$OS as (M+H)+ 344.0, 346.0.

Step 3:

1,4-Disubstituted triazole 54 (100 mg, 0.29 mmol) was dissolved in 50 mL anhydrous dioxane and 20 mL triethylamine. To this solution was bubbled in dry H$_2$S gas till saturation. The mixture was stirred for overnight at RT and was concentrated in vacuo. The residue was placed in 50 mL dry acetone. To it was added 1.0 mL iodomathane. The mixture was refluxed for 1.5 hr and concentrated in vacuo. The residue was then dissolved in 20 mL anhydrous methanol. To it were added 0.5 mL acetic acid and 0.2 mL N-methylethylenediamine. The mixture was refluxed for 1 hr, concentrated in vacuo and subjected to reverse phase preparative HPLC to isolate the title compound 55 as a white powder after lyophilization. MS found for C$_{18}$H$_{17}$ClN$_6$OS as (M+H)+ 401.1, 403.1.

Example 313

N-((1-(4-(N,N-Dimethylcarbamimidoyl)phenyl)-1H-1,2,3-triazol-4-yl)methyl)-5-chlorothiophene-2-carboxamide

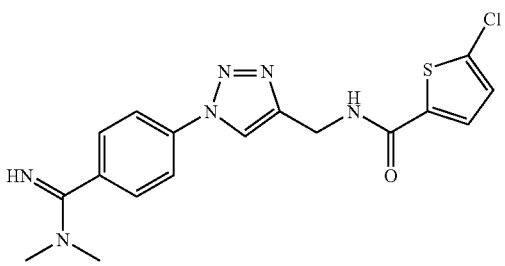

The title compound was prepared by the same procedure described in Scheme 9 in Example 312, using dimethylamine in place of N-methylethylenediamine. MS found for C$_{17}$H$_{17}$ClN$_6$OS as (M+H)+ 389.1, 391.1.

Example 314

N-((1-(4-(N-Ethyl-N-methylcarbamimidoyl)phenyl)-1H-1,2,3-triazol-4-yl)methyl)-5-chlorothiophene-2-carboxamide

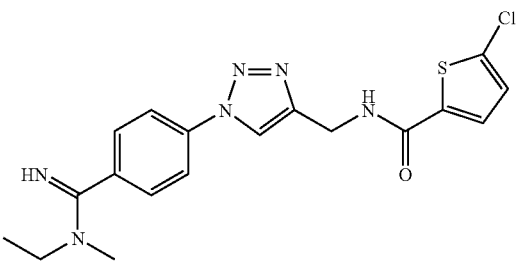

The title compound was prepared by the same procedure described in Scheme 9 in Example 312, using N-ethyl-N-methylamine in place of N-methylethylenediamine. MS found for C$_{18}$H$_{19}$ClN$_6$OS as (M+H)+ 403.1, 405.1.

Example 315

N-((1-(4-(N-Methyl-N-propylcarbamimidoyl)phenyl)-1H-1,2,3-triazol-4-yl)methyl)-5-chlorothiophene-2-carboxamide

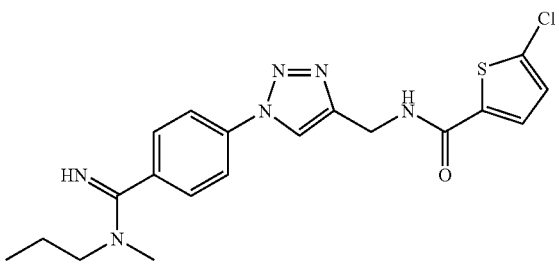

The title compound was prepared by the same procedure described in Scheme 9 in Example 312, using N-methyl-N-propylamine in place of N-methylethylenediamine. MS found for C$_{19}$H$_{21}$ClN$_6$OS as (M+H)+ 417.1, 419.1.

Example 316

N-((1-(4-(N-(2-Methoxyethyl)-N-methylcarbamimidoyl)phenyl)-1H-1,2,3-triazol-4-yl)methyl)-5-chlorothiophene-2-carboxamide

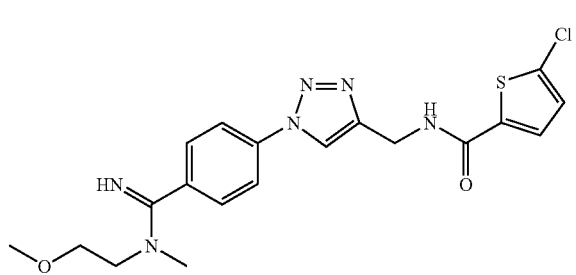

The title compound was prepared by the same procedure described in Scheme 9 in Example 312, using N-(2-methoxyethyl)-N-methylamine in place of N-methylethylenediamine. MS found for $C_{19}H_{21}ClN_6O_2S$ as (M+H)+ 433.1, 435.1.

Example 317

N-((1-(4-(Azetidin-1-yl(imino)methyl)phenyl)-1H-1,2,3-triazol-4-yl)methyl)-5-chlorothiophene-2-carboxamide

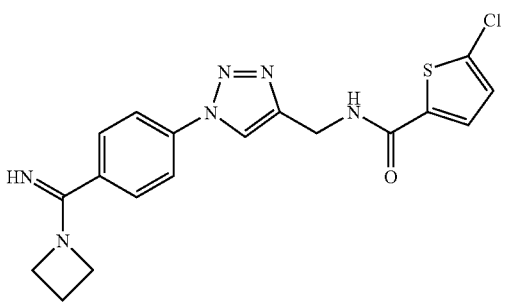

The title compound was prepared by the same procedure described in Scheme 9 in Example 312, using azetidine in place of N-methylethylenediamine. MS found for $C_{18}H_{17}ClN_6OS$ as (M+H)+ 401.1, 403.1.

Example 318

5-Chloro-N-((1-(4-(imino(pyrrolidin-1-yl)methyl)phenyl)-1H-1,2,3-triazol-4-yl)methyl)thiophene-2-carboxamide

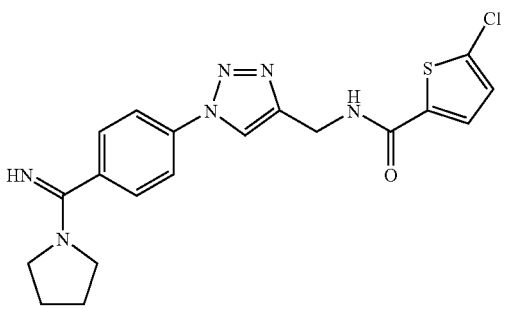

The title compound was prepared by the same procedure described in Scheme 9 in Example 312, using pyrrolidine in place of N-methylethylenediamine. MS found for $C_{19}H_{19}ClN_6OS$ as (M+H)+ 415.1, 417.1.

Example 319

5-Chloro-N-((1-(4-(imino(piperidin-1-yl)methyl)phenyl)-1H-1,2,3-triazol-4-yl)methyl)thiophene-2-carboxamide

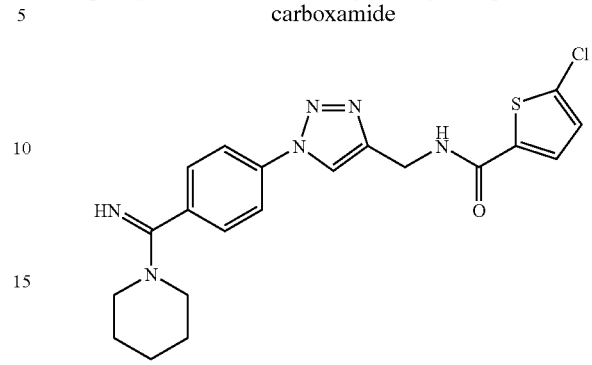

The title compound was prepared by the same procedure described in Scheme 9 in Example 312, using piperidine in place of N-methylethylenediamine. MS found for $C_{20}H_{21}ClN_6OS$ as (M+H)+ 429.1, 431.1.

Example 320

N-((1-(4-(N,N-Dimethylcarbamimidoyl)-2-fluorophenyl)-1H-1,2,3-triazol-4-yl)methyl)-5-chlorothiophene-2-carboxamide (59)

SCHEME 10

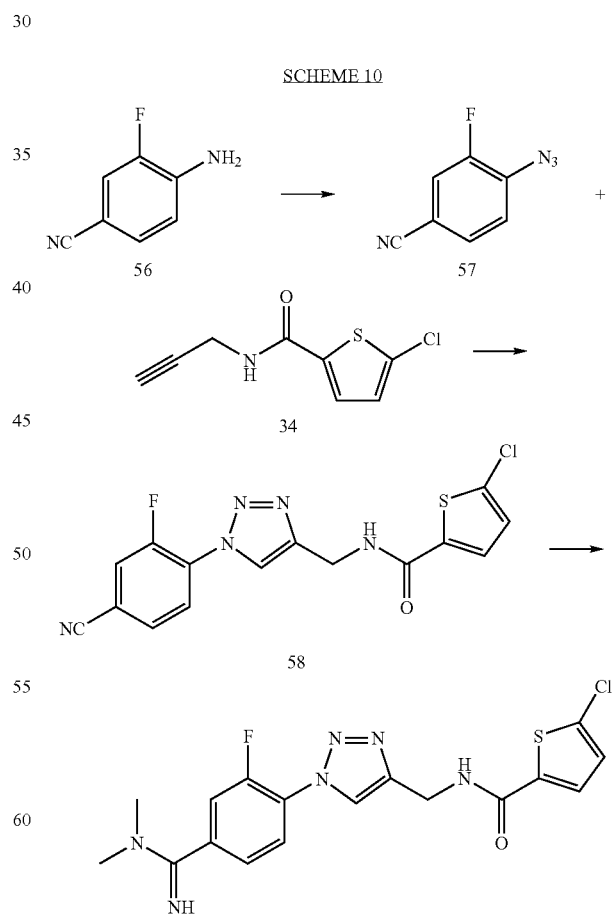

Step 1:

To a solution of 4-amino-3-fluorobenzonitrile (56, 1.0 g, 7.35 mmol) in 5 mL TFA at 0° C. was added $NaNO_2$ (558 mg, 8.09 mmol) in small portions. The reaction mixture was stirred at 0° C. for 0.5 hr. Then a solution of $NaN_3$ (478 mg, 7.35 mmol) in 4 mL water was added. The resulting mixture was stirred at 0° C. for 2 hr. The reaction solution was concentrated in avcuo and then neutralized to pH=7 with the aqueous saturated $NaHCO_3$ solution and extracted with DCM three times. The combined organic phase was washed with water and brine, dried over $Na_2SO_4$ and evaporated in vacuo to give compound 57 (0.94 g, 79%).

Step 2:

A solution of azidobenzene 57 (0.94 g, 5.80 mmol) and alkyne 34 (see Scheme 5 in Example 290; 1.3 g, 6.53 mmol) in 30 mL toluene was refluxed for 3 hr and concentrated in vacuo. The residue was dissolved into chloroform and was washed with water and brine, dried, evaporated and subjected to flash column chromatography to give compound 58. MS found for $C_{15}H_9ClFN_5OS$ as $(M+Na)^+$: 384.0, 386.0.

Step 3:

To a solution of compound 58 (111 mg, 0.31 mmol) in the 1.2 mL triethylamine and 12 mL dioxane was bubbled dry $H_2S$ gas to saturation. The mixture was stirred at RT for overnight and concentrated in vacuo. The residue was placed with 10 mL dry acetone and followed by the addition of 0.4 mL iodomethane. The reaction mixture was refluxed for 2 hr and was then concentrated in vacuo. The residue was dissoolved with 9 mL dry methanol. To it were added 0.2 mL acetic acid and dimethylamine (0.8 mL, 2.0M in THF). The resulting mixture was refluxed for 1 hr, concentrated in vacuo and subjected to reverse phase preparative HPLC to give the title compound 59 as a white powder after lyophilization. MS found for $C_{17}H_{16}ClFN_6OS$ as (M+H)+: 407.1, 409.1.

Example 321

N-((1-(4-(Azetidin-1-yl(imino)methyl)-2-fluorophenyl)-1H-1,2,3-triazol-4-yl)methyl)-5-chlorothiophene-2-carboxamide

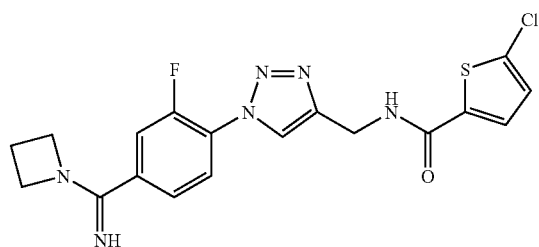

The title compound was prepared by the same procedure described in Scheme 10 in Example 320, using azetidine in place of dimethylamine. MS found for $C_{18}H_{16}ClFN_6OS$ as (M+H)+ 419.1, 421.1.

Example 322

5-Chloro-N-((1-(2-fluoro-4-(imino(pyrrolidin-1-yl)methyl)phenyl)-1H-1,2,3-triazol-4-yl)methyl)thiophene-2-carboxamide

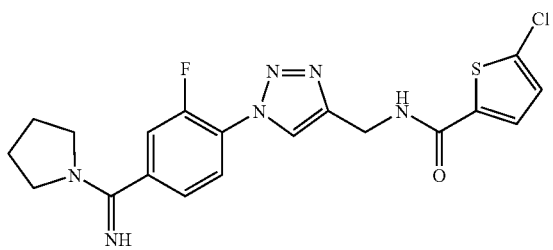

The title compound was prepared by the same procedure described in Scheme 10 in Example 320, using pyrrolidine in place of dimethylamine. MS found for $C_{19}H_{18}ClFN_6OS$ as (M+H)+ 433.1, 435.1.

Example 323

5-Chloro-N-((1-(2-fluoro-4-(imino(piperidin-1-yl)methyl)phenyl)-1H-1,2,3-triazol-4-yl)methyl)thiophene-2-carboxamide

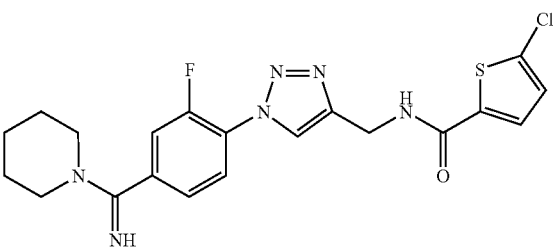

The title compound was prepared by the same procedure described in Scheme 10 in Example 320, using piperidine in place of dimethylamine. MS found for $C_{20}H_{20}ClFN_6OS$ as (M+H)+ 447.1, 449.1.

Example 324

5-Chloro-N-((1-(2-fluoro-4-(1-methyl-4,5-dihydro-1H-imidazol-2-yl)phenyl)-1H-1,2,3-triazol-4-yl)methyl)thiophene-2-carboxamide

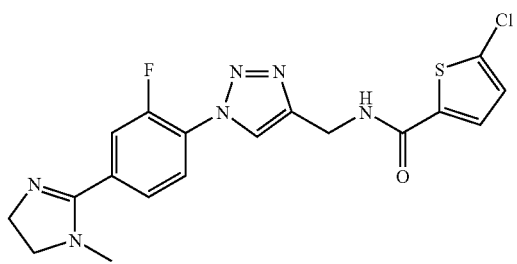

The title compound was prepared by the same procedure described in Scheme 10 in Example 320, using N-methylethylenediamine in place of dimethylamine. MS found for $C_{18}H_{16}ClFN_6OS$ as (M+H)+ 419.1, 421.1.

Example 325

N-((1-(4-(N,N-Dimethylcarbamimidoyl)phenyl)-1H-pyrazol-4-yl)methyl)-5-chlorothiophene-2-carboxamide (66)

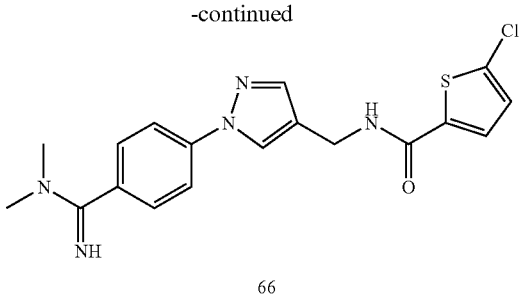

66

SCHEME 11

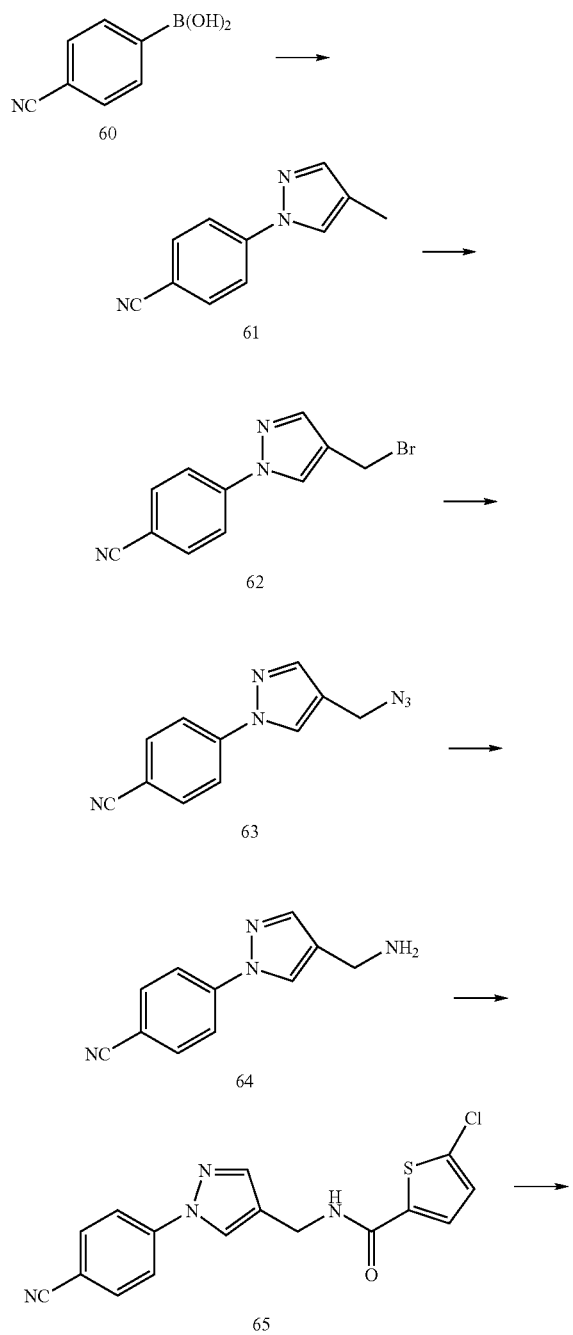

Step 1:

The mixture of 4-cyanobenzeneboronic acid (60, 3.6 g, 24 mmol), 4-methylpyrazole (2.0 mL, 24 mmol), pyridine (5.8 mL, 72 mmol), $Cu(OAc)_2$ (8.7 g, 48 mmol) and activated molecular sieve powder in 100 mL chloroform was refluxed for 24 hr. The reaction was not complete. The mixture was filtered, and the solid cake was washed with plenty amount of methanol. The filtrate was concentrated in vacuo and purified by flash column to give compound 61 (0.93 g, 21%) as a white powder. MS found for $C_{11}H_9N_3$ as (M+H)+ 184.1.

Step 2:

Compound 61 (0.89 g, 4.8 mmol) was dissolved in 100 mL $CCl_4$. To it were added NBS (1.3 g, 7.3 mmol) and benzoyl peroxide (1.18 g, 4.8 mmol). The mixture was refluxed for 1 hr and concentrated in vacuo. The residue was subjected to flash column chromatography to give compound 62 (0.33 g, 26%). MS found for $C_{11}H_8BrN_3$ as (M+H)+ 262.0, 264.0.

Step 3:

Compound 62 (0.33 g, 1.26 mmol) was dissolved in 6 mL dry DMF. To it was added $NaN_3$ (164 mg, 2.52 mmol). The mixture was stirred for 2 hr and taken into 200 mL EtOAc. It was washed with water and brine, dried, concentrated and purified by flash column to give compound 63 (0.27 g, 96%). MS found for $C_{11}H_8N_6$ as (M+H)+ 225.1.

Step 4:

Compound 63 (0.27 g, 1.2 mmol) was dissolved in 10 mL THF and 20 mL MeOH. To it was added tin(II) chloride dihydrate (0.54 g, 2.4 mmol). The mixture was refluxed for 2 hr and was diluted with 500 mL chloroform. It was washed with 0.1 N NaOH and water, dried, concentrated and purified by reverse phase HPLC to give compound 64 (0.13 g, 55%). MS found for $C_{11}H_{10}N_4$ as (M+H)+ 199.1.

Step 5:

Compound 64 (0.13 g, 0.66 mmol) was dissolved in 12 mL dry pyridine. To it was added 5-chlorothiophene-2-carbonyl-chloride (0.24 g, 1.32 mmol). The mixture was stirred for 2 hr at RT, concentrated in vacuo and purified using flash column to give compound 65 (0.22 g, 99%). MS found for $C_{16}H_{11}ClN_4OS$ as (M+H)+ 343.0, 345.0.

Step 6:

Compound 65 (100 mg, 0.30 mmol) was placed in 50 mL anhydrous methanol in ice bath. To it was bubbled dry HCl gas till saturation. The mixture was stirred for overnight at RT and concentrated in vacuo. The dry residue was then dissolved in 50 mL dry methanol. To it was added dimethylamine (1.2 mmol, 0.6 mL of 2.0M dimethylamine/THF solution). The mixture was refluxed for 1 hr, concentrated in vacuo, and purified with reverse phase HPLC to yield the title compound 66 as a white powder after lyophilization. MS found for $C_{18}H_{18}ClN_5OS$ as (M+H)+ 388.1, 390.1.

Example 326

5-Chloro-N-((1-(4-(1-methyl-4,5-dihydro-1H-imidazol-2-yl)phenyl)-1H-pyrazol-4-yl)methyl)thiophene-2-carboxamide

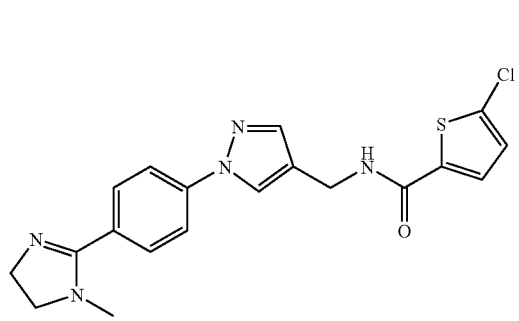

The title compound was prepared by the same procedure described in Scheme 11 in Example 325, using N-methylethylenediamine in place of dimethylamine. MS found for $C_{19}H_{18}ClN_5OS$ as (M+H)+ 400.1, 402.1.

Example 327

N-((1-(4-(Azetidin-1-yl(imino)methyl)phenyl)-1H-pyrazol-4-yl)methyl)-5-chlorothiophene-2-carboxamide

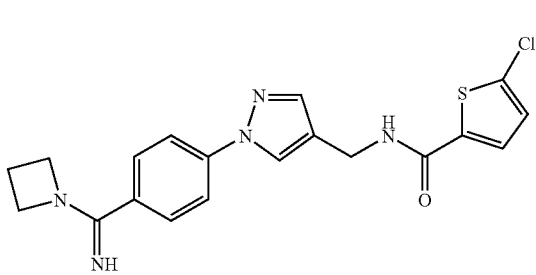

The title compound was prepared by the same procedure described in Scheme 11 in Example 325, using azetidine in place of dimethylamine. MS found for $C_{19}H_{18}ClN_5OS$ as (M+H)+ 400.1, 402.1.

Example 328

5-Chloro-N-((1-(4-(imino(pyrrolidin-1-yl)methyl)phenyl)-1H-pyrazol-4-yl)methyl)thiophene-2-carboxamide

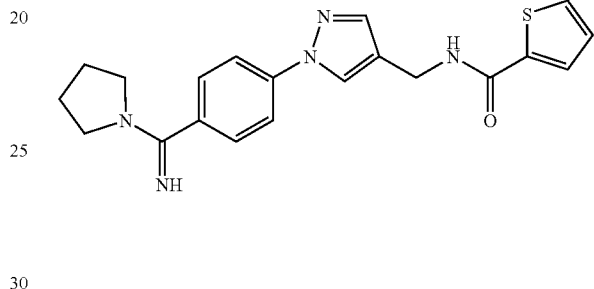

The title compound was prepared by the same procedure described in Scheme 11 in Example 325, using pyrrolidine in place of dimethylamine. MS found for $C_{20}H_{20}ClN_5OS$ as (M+H)+ 414.1, 416.1.

Example 329

5-Chloro-N-((1-(4-(imino(piperidin-1-yl)methyl)phenyl)-1H-pyrazol-4-yl)methyl)thiophene-2-carboxamide The title compound was prepared by the same procedure described in Scheme 11 in Example 325, using piperidine in place of dimethylamine. MS found for $C_{21}H_{22}ClN_5OS$ as (M+H)+ 428.1, 430.1.

Example 330

N-((5-(4-(N,N-Dimethylcarbamimidoyl)phenyl)isoxazol-3-yl)methyl)-5-chlorothiophene-2-carboxamide (74)

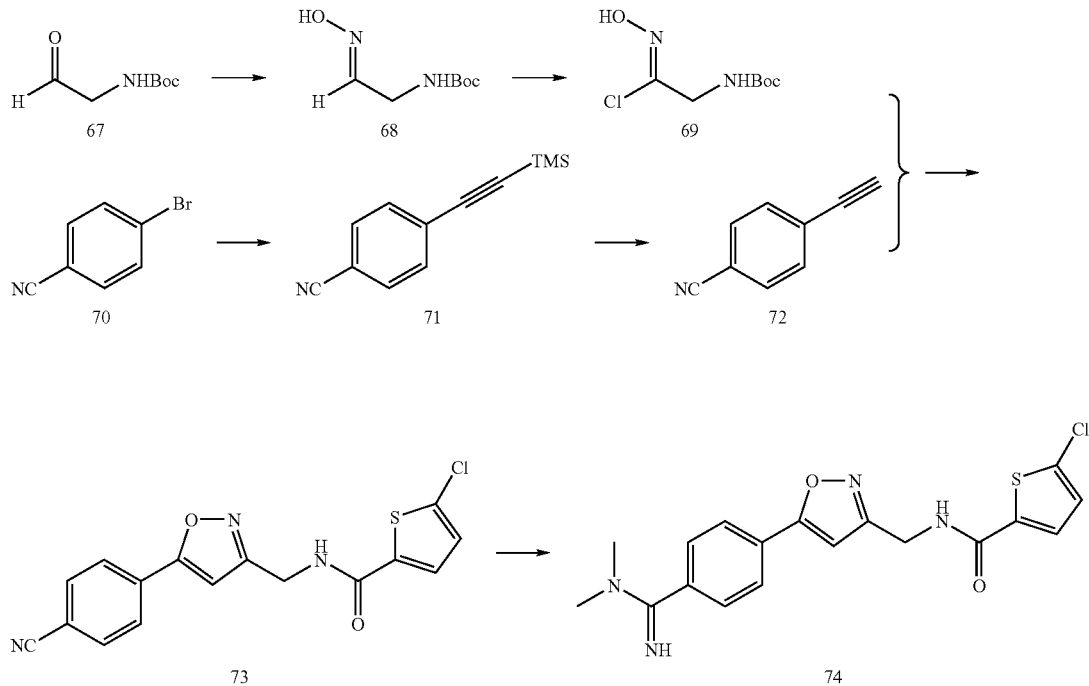

SCHEME 12

Step 1:
Performed in the same manner as in Step 1, Example 1. Compound 68 was used immediately without purification.

Step 2:
Performed in the same manner as in Step 2, Example 1. Crude compound 69 was used for Step 5.

Step 3:
Combined aryl bromide 70 (5.00 g, 27 mmol) with CuI (0.10 g, 0.55 mmol), tri t-butyl phosphine (0.41 mL, 1.6 mmol) and Pd(PhCN)$_2$Cl$_2$ (0.32 g, 0.82 mmol). Degassed 3 min then added TMS acetylene (4.6 mL, 33 mmol) and diisopropylamine (9.5 mL, 68 mmol), the reaction changing colors from pale beige to black as the amine was added. After stirring three hours all starting bromide was consumed as shown by HPLC. The reaction was filtered through a short pad of silica gel (eluted with dichloromethane) and concentrated. The resulting semisolid was triturated with 20 mL of hexane affording the desired product (71) as a brown solid (2.51 g, 47%). $^1$H NMR (DMSO-d$_6$, 400 MHz): δ 7.79 (d, 2H), δ 7.56 (d, 2H), 0.19 (s, 9H).

Step 4:
TMS protected alkyne 71 (1.35 g, 1.01 mmol) was diluted with 10 mL of THF and treated with 1 M tetrabutylammonium fluoride in THF (1.1 mL, 1.1 mmol). After 30 min HPLC showed complete consumption of the starting material and a more polar peak. The reaction was diluted with 90 mL of water and 10 mL of 1 M aqueous HCl. The resulting solid was filtered and washed with water affording 72 as a brown solid (0.6237 g, 49%). $^1$H NMR (DMSO-d$_6$, 400 MHz): δ 7.81 (d, 2H), δ 7.62 (d, 2H), δ 4.53 (s, 1H).

Step 5:

Alkyne 72 (0.36 g, 2.87 mmol) and triethylamine (0.60 mL, 4.31 mmol) were diluted with 10 mL of toluene and heated to 100° C. To this solution was added 69 as the crude reaction mixture from Step 3, slowly. After the addition was complete the reaction was checked by TLC which showed ca. 50% reaction. The reaction mixture was cooled, partitioned with 1 M HCl and ethyl acetate and separated. The aqueous phase was extracted again with ethyl acetate and the combined organic layers were filtered through a short pad of silica gel and concentrated. The resulting brown oil was then purified by silica gel chromatography (10% ethyl acetate/dichloromethane) affording isoxazole 73 as an off white solid (0.37 g, 41%). $^1$H NMR (DMSO-d$_6$, 400 MHz): δ 8.03 (d, 2H), δ 7.94 (d, 2H), δ 7.47 (t, 1H), δ 7.08 (s, 1H), δ 4.18 (d, 2H), δ 1.38 (s, 9H).

Step 6:

Performed in the same manner as in Example 8. MS found for $C_{18}H_{17}ClN_4O_2S$ as $(M+H)^+$ 389.1, 391.1.

Example 331

5-Chloro-N-((5-(4-(1-methyl-4,5-dihydro-1H-imidazol-2-yl)phenyl)isoxazol-3-yl)methyl)thiophene-2-carboxamide

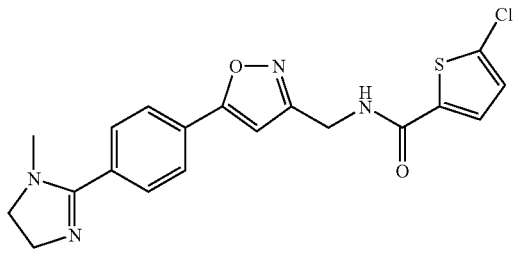

The titled compound was made by the procedure similar to that described in Scheme 12 in Example 330. MS found for $C_{19}H_{17}ClN_4O_2S$ as (M+H)+ 401.0, 403.0.

Example 332

5-Chloro-N-((5-(4-(imino(pyrrolidin-1-yl)methyl)phenyl)isoxazol-3-yl)methyl)thiophene-2-carboxamide

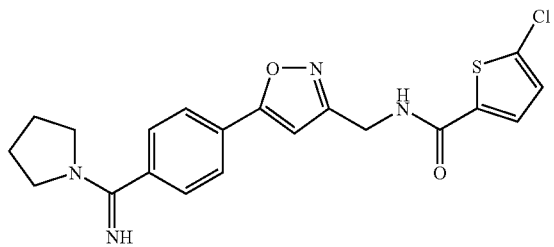

The titled compound was made by the procedure similar to that described in Scheme 12 in Example 330. MS found for $C_{20}H_{19}ClN_4O_2S$ as $(M+H)^+$ 415.0, 417.0.

Example 333

5-Chloro-N-((5-(4-(imino(piperidin-1-yl)methyl)phenyl)isoxazol-3-yl)methyl)thiophene-2-carboxamide

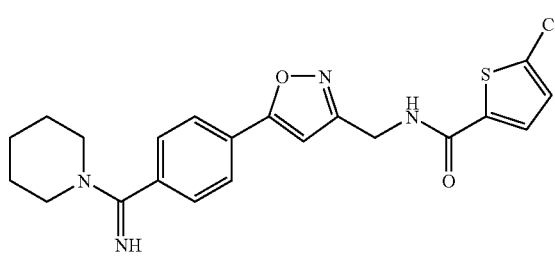

The titled compound was made by the procedure similar to that described in Scheme 12 in Example 330. MS found for $C_{21}H_{21}ClN_4O_2S$ as $(M+H)^+$ 429.0, 431.1.

Example 334

N-((3-(4-(N,N-Dimethylcarbamimidoyl)phenyl)-1,2,4-oxadiazol-5-yl)methyl)-5-chlorothiophene-2-carboxamide (80)

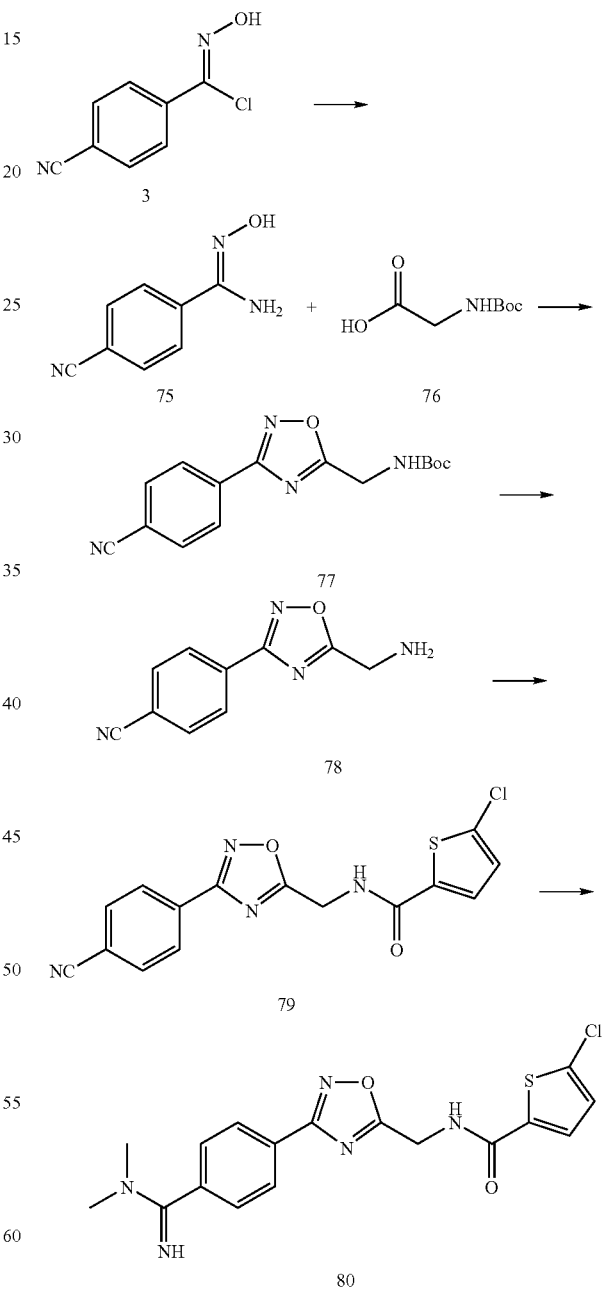

Step 1:

Combined 3 (4.13 g, 23 mmol) and dioxane (40 mL). To this was added gaseous NH₃ as a steady stream for 2 min during which time a white precipitate formed. The reaction was checked after 5 min by HPLC which showed complete consumption of the starting chloride. The reaction mixture was diluted with a small amount of ether and filtered, the filtrate was then concentrated affording desired product 75 as a light yellow powder (3.27 g, 89%). $^1$H NMR (DMSO-$d_6$, 400 MHz): δ 10.00 (s, 1H), δ 7.80 (m, 4H), 5.95 (s, 2H).

Step 2:

Boc protected glycine (76) (0.54 g, 3.11 mmol) was combined with 75 (0.50 g, 3.11 mmol) and 5 mL of DMF followed by carbonyldiimidazole (0.604 g, 3.73 mmol) which resulted in the evolution of gas. The mixture was stirred at RT for 1 hr, then heated to 110° C. After 30 min, another portion of CDI was added to the heated mixture (0.600 g, 3.73 mmol) again resulting in gas evolution. The reaction was checked by HPLC which showed complete consumption of 75 and a new peak. The reaction mixture was dilution with water and filtered, the solid washed with water and a small amount of methanol (which appeared to dissolve the product) affording the desired product (77) as a white solid (0.335 g, 36%). $^1$H NMR (DMSO-$d_6$, 400 MHz): δ 8.10 (d, 1H), δ 7.99 (d, 2H), 7.72 (t, 1H), δ 4.44 (d, 2H), 1.32 (s, 9H).

Step 3:

Performed in the same manner as in Step 5, Example 49. $^1$H NMR (DMSO-$d_6$, 400 MHz): δ 9.03 (broad s, 3H), δ 8.13 (d, 2H), δ 8.02 (d, 2H), δ 4.54 (s, 2H).

Step 4:

Performed in the same manner as in Step 5, Example 325. $^1$H NMR (DMSO-$d_6$, 400 MHz): δ 9.57 (t, 1H), δ 8.11 (d, 2H), δ 7.99 (d, 2H), δ 7.70 (d, 1H), 7.20 (d, 1H), δ 4.78 (d, 2H).

Step 5:

Performed in the same manner as in Step 6, Example 325. MS found for $C_{17}H_{16}ClN_5O_2S$ as (M+H)+ 390.8, 392.5.

Example 335

5-Chloro-N-((3-(4-(1-methyl-4,5-dihydro-1H-imidazol-2-yl)phenyl)-1,2,4-oxadiazol-5-yl)methyl)thiophene-2-carboxamide

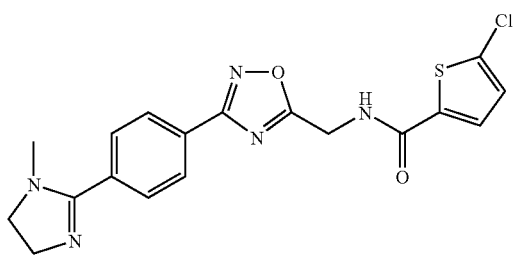

The titled compound was made by the procedure similar to that described in Example 334. MS found for $C_{18}H_{16}ClN_5O_2S$ as (M+H)+ 402.1, 404.1.

Example 336

5-Chloro-N-((3-(4-(imino(pyrrolidin-1-yl)methyl)phenyl)-1,2,4-oxadiazol-5-yl)methyl)thiophene-2-carboxamide

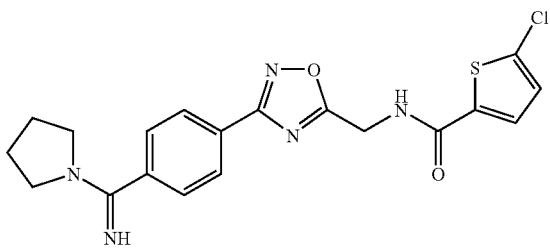

The titled compound was made by the procedure similar to that described in Example 334. MS found for $C_{19}H_{18}ClN_5O_2S$ as (M+H)+ 416.1, 418.1.

Example 337

5-Chloro-N-((3-(4-(imino(piperidin-1-yl)methyl)phenyl)-1,2,4-oxadiazol-5-yl)methyl)thiophene-2-carboxamide

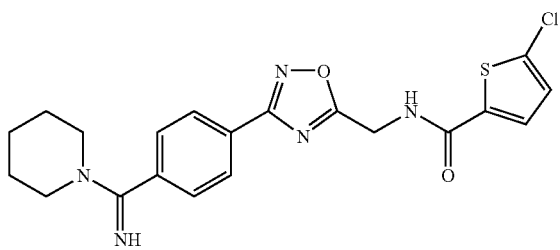

The titled compound was made by the procedure similar to that described in Example 334. MS found for $C_{20}H_{20}ClN_5O_2S$ as (M+H)+ 430.1, 432.1.

Example 338

N-((2-(4-(N,N-Dimethylcarbamimidoyl)phenyl)oxazol-4-yl)methyl)-5-chlorothiophene-2-carboxamide (87).

SCHEME 14

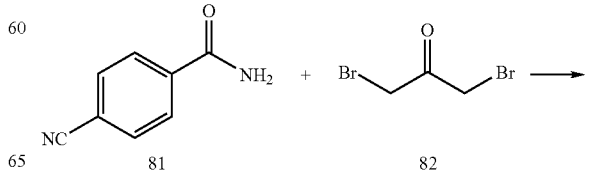

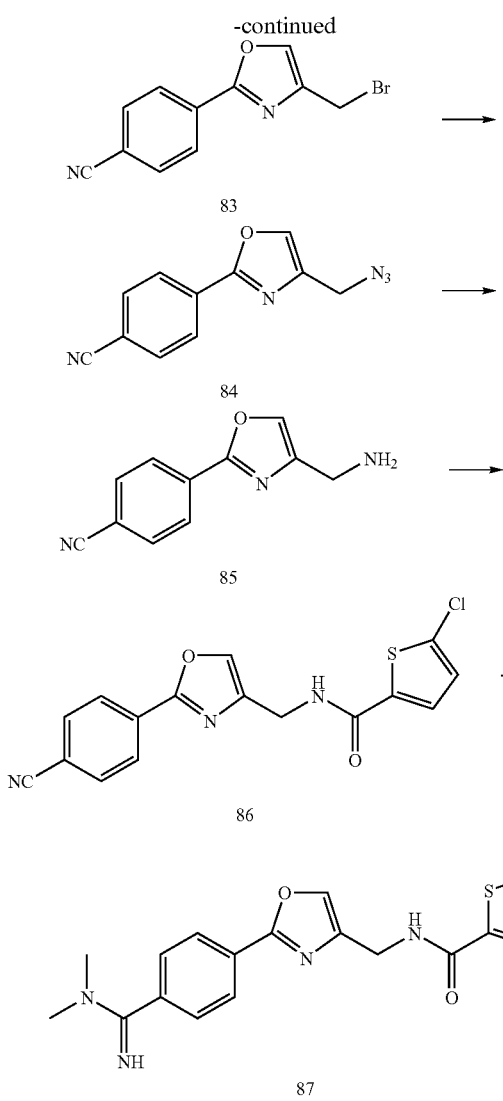

Step 1:

Combined amide 81 (5.00 g, 31 mmol), dibromoacetone 82 (13 g, 62 mmol) and 60 mL of toluene in a flask equipped with a condenser. The mixture was refluxed overnight, then was checked by HPLC the following day which showed complete consumption of the starting material. The reaction was concentrated and purified by silica gel chromatography (dichloromethane as eluent) affording desired product 83 as a beige solid (5.21 g, 60%). $^1$H NMR (DMSO-$d_6$, 400 MHz): δ 8.12 (d, 2H), δ 7.71 (m, 3H), δ 4.40 (s, 2H).

Step 2:

Combined bromide 83 (3.94 g, 15 mmol) and 30 mL DMF. To this was added sodium azide (1.46 g, 23 mmol) and approximately 10 mg of tetrabutylammonium iodide. The reaction was stirred 1 hr, then was checked by mass spectroscopy which showed only the desired azide. The reaction was diluted with 100 mL of water and filtered affording the desired product as a beige solid. $^1$H NMR (DMSO-$d_6$, 400 MHz): δ 8.31 (s, 1H), δ 8.08 (d, 2H), δ 7.93 (d, 2H), δ 4.41 (s, 1H).

Step 3:

Diluted azide 84 (1.19 g, 5.3 mmol) with 20 mL of ethyl acetate. The solution was degassed with argon, treated with ca. 100 mg of 10% Pd/C then purged with hydrogen gas (balloon). After two hours all starting material had been consumed as determined by TLC. The mixture was filtered through a short pad of celite, concentrated to a beige semi-solid and used immediately for the next step.

Step 4:

The titled compound was made by the procedure similar to that described in Step 5, Example 325. MS $^1$H NMR (DMSO-$d_6$, 400 MHz): δ 9.11 (t, 1H), δ 8.14 (s, 1H), δ 8.08 (d, 2H), δ 7.93 (d, 2H), δ 7.64 (d, 1H), δ 7.13 (d, 1H), δ 4.35 (d, 2H).

Step 5:

The titled compound was made by the procedure similar to that described in Step 6, Example 325. MS found for $C_{18}H_{17}ClN_4O_2S$ as (M+H)$^+$ 389.1, 391.1.

Example 339

5-Chloro-N-((2-(4-(1-methyl-4,5-dihydro-1H-imidazol-2-yl)phenyl)oxazol-4-yl)methyl)thiophene-2-carboxamide

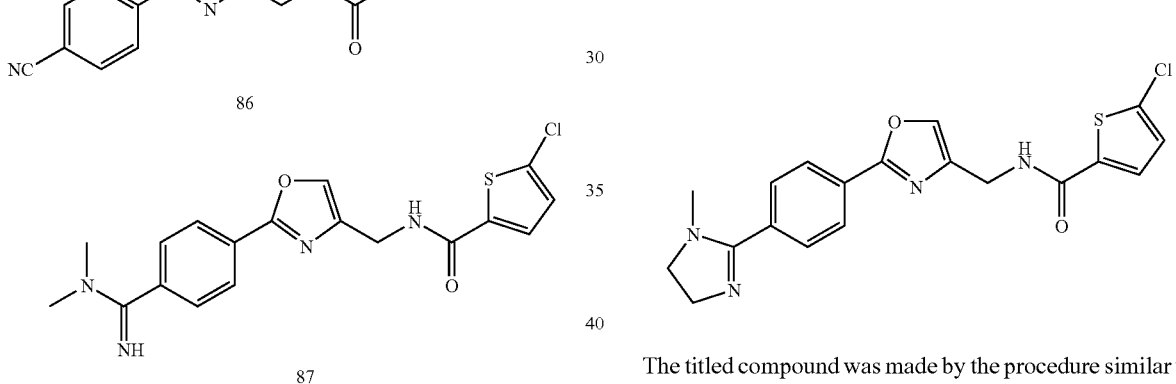

The titled compound was made by the procedure similar to that described in Example 338. MS found for $C_{19}H_{17}ClN_4O_2S$ as (M+H)$^+$ 401.1, 403.1.

Example 340

5-Chloro-N-((2-(4-(imino(pyrrolidin-1-yl)methyl)phenyl)oxazol-4-yl)methyl)thiophene-2-carboxamide

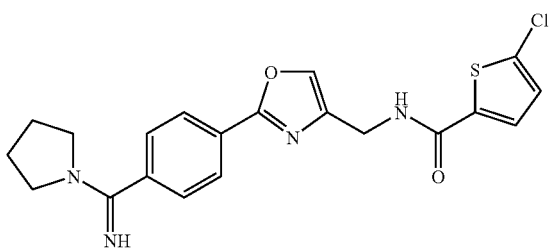

The titled compound was made by the procedure similar to that described in Example 338. MS found for $C_{20}H_{19}ClN_4O_2S$ as (M+H)$^+$ 415.1, 417.1.

Example 341

5-Chloro-N-((2-(4-(imino(piperidin-1-yl)methyl)phenyl)oxazol-4-yl)methyl)thiophene-2-carboxamide

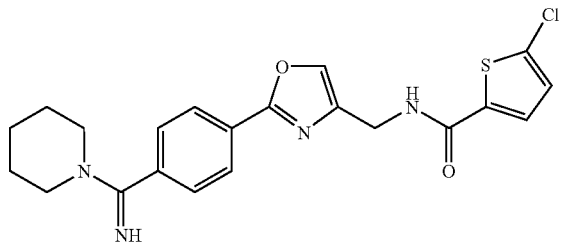

The titled compound was made by the procedure similar to that described in Example 338. MS found for $C_{21}H_{21}ClN_4O_2S$ as $(M+H)^+$ 429.1, 431.1.

Example 342

Ethyl 1-((4-(4-((2-chlorothiophene-5-carboxamido)methyl)oxazol-2-yl)phenyl)(imino)methyl)piperidine-4-carboxylate

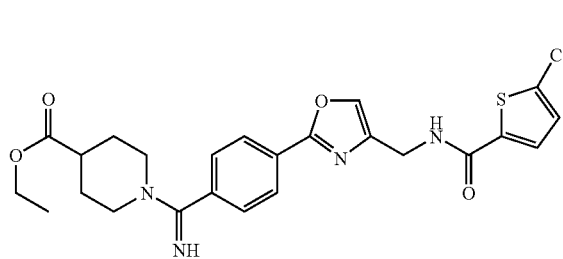

The titled compound was made by the procedure similar to that described in Example 338. MS found for $C_{24}H_{25}ClN_4O_4S$ as $(M+H)^+$ 501.1, 503.1.

Example 343

N-((2-(4-(N-Ethyl-N-methylcarbamimidoyl)phenyl)oxazol-4-yl)methyl)-5-chlorothiophene-2-carboxamide

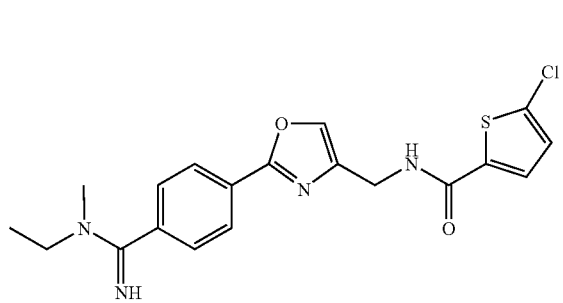

The titled compound was made by the procedure similar to that described in Example 338. MS found for $C_{19}H_{19}ClN_4O_2S$ as $(M+H)^+$ 403.1, 405.1.

Example 344

N-((2-(4-(N-Methyl-N-propylcarbamimidoyl)phenyl)oxazol-4-yl)methyl)-5-chlorothiophene-2-carboxamide

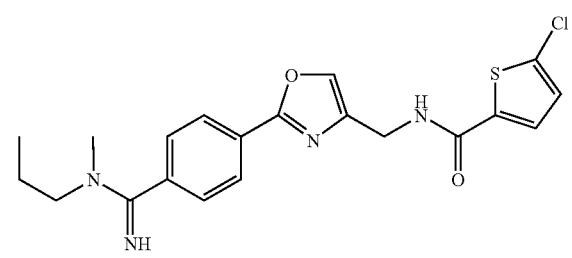

The titled compound was made by the procedure similar to that described in Example 338. MS found for $C_{20}H_{21}ClN_4O_2S$ as $(M+H)^+$ 417.1, 419.1.

Example 345

N-((2-(4-(N-(2-(Dimethylamino)ethyl)-N-methylcarbamimidoyl)phenyl)oxazol-4-yl)methyl)-5-chlorothiophene-2-carboxamide

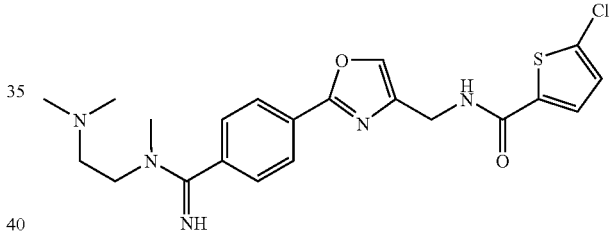

The titled compound was made by the procedure similar to that described in Example 338. MS found for $C_{21}H_{24}ClN_5O_2S$ as $(M+H)^+$ 446.1, 448.1.

Example 346

N-((2-(4-(N-(2-Methoxyethyl)-N-methylcarbamimidoyl)phenyl)oxazol-4-yl)methyl)-5-chlorothiophene-2-carboxamide

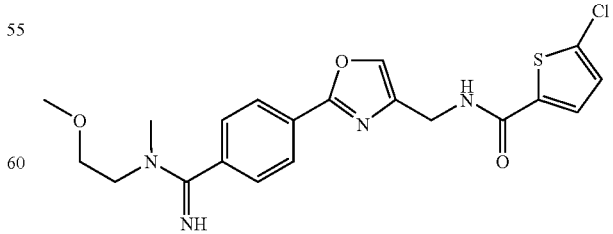

The titled compound was made by the procedure similar to that described in Example 338. MS found for $C_{20}H_{21}ClN_4O_3S$ as $(M+H)^+$ 433.1, 435.1.

Example 347

1-((4-(4-((2-Chlorothiophene-5-carboxamido)methyl)oxazol-2-yl)phenyl)(imino)methyl)piperidine-4-carboxamide

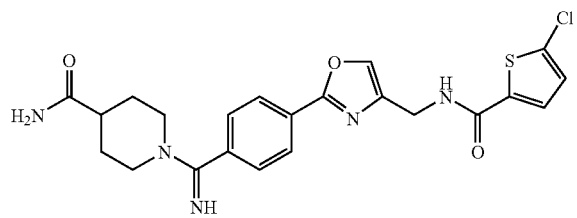

The titled compound was made by the procedure similar to that described in Example 338. MS found for $C_{22}H_{22}ClN_5O_3S$ as (M+H)+ 472.0, 474.0.

Example 348

N-((2-(4-(N-Methylcarbamimidoyl)phenyl)oxazol-4-yl)methyl)-5-chlorothiophene-2-carboxamide

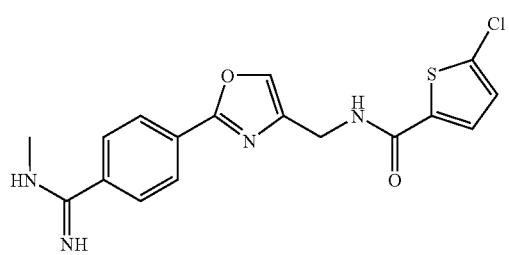

The titled compound was made by the procedure similar to that described in Example 338. MS found for $C_{17}H_{15}ClN_4O_2S$ as (M+H)$^+$ 375.0, 377.0.

Example 349

N-((2-(4-(N-(Furan-2-ylmethyl)-N-methylcarbamimidoyl)phenyl)oxazol-4-yl)methyl)-5-chlorothiophene-2-carboxamide

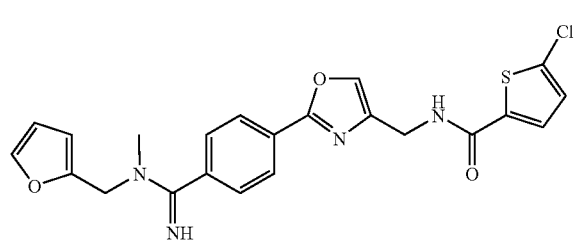

The titled compound was made by the procedure similar to that described in Example 338. MS found for $C_{22}H_{19}ClN_4O_3S$ as (M+H)$^+$ 455.1, 457.1.

Example 350

N-((2-(4-(N,N-Dimethylcarbamimidoyl)phenyl)thiazol-4-yl)methyl)-5-chlorothiophene-2-carboxamide (94)

SCHEME 15

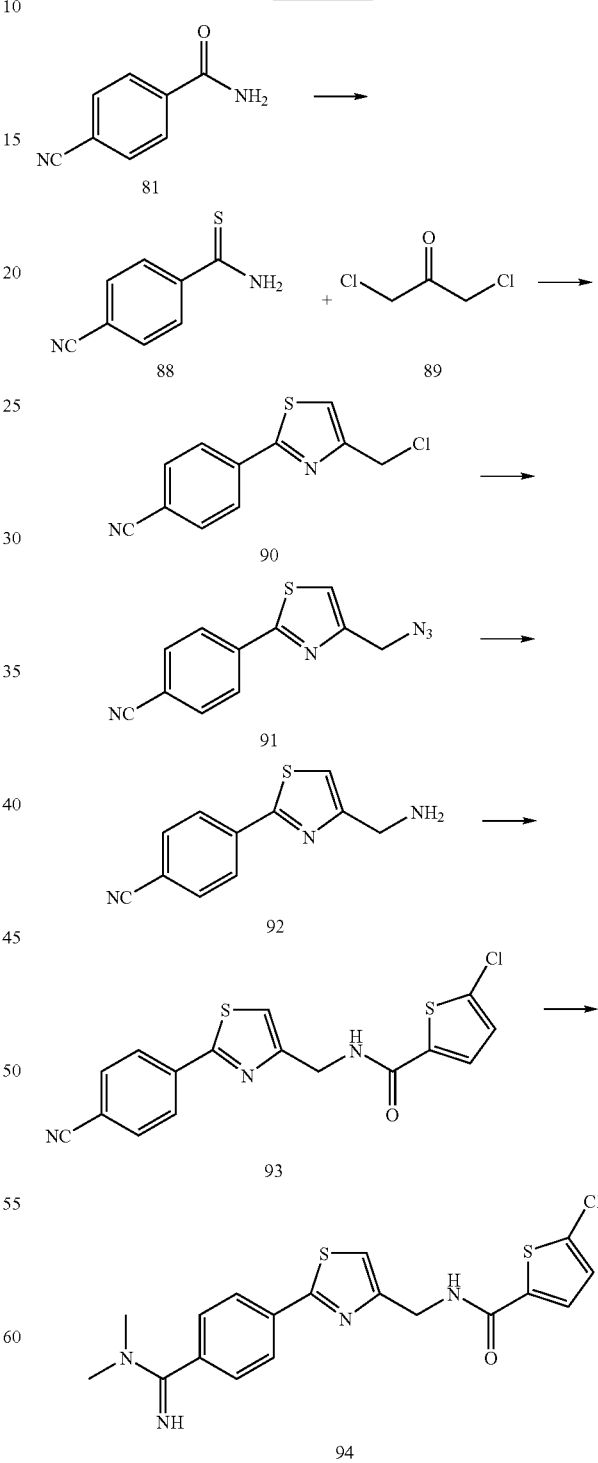

Step 1:

Combined amide 81 (0.64 g, 4.1 mmol), Lawesson's reagent (1.00 g, 2.4 mmol) and 15 mL of toluene in a flask equipped with a condenser. The resulting beige suspension was refluxed for two hrs at which time all starting amide was consumed as determined by HPLC. The reaction was cooled, filtered through silica gel and concentrated, then purified by eluting through a short plug of silica gel (eluted with dichloromethane) affording the desired thioamide (88) as an orange solid (0.260 g, 39%). $^1$H NMR (DMSO-d$_6$, 400 MHz): δ 10.12 (s, 1H), δ 9.71 (s, 1H), δ 7.90 (d, 2H), δ 7.84 (d, 2H).

Step 2:

Thioamide 88 (0.48 g, 30 mmol), dichloroacetone 89 (0.45 g, 36 mmol) and 20 mL of ethanol were combined in a flask equipped with a reflux condenser. The mixture was refluxed for three hours at which time all starting thioamide was consumed as determined by TLC. The mixture was cooled, partitioned with water and ethyl acetate and separated. The aqueous phase was extracted again with ethyl acetate and the combined organic layers were dried over Na$_2$SO$_4$, filtered through a short pad of silica gel and concentrated affording a quantitative amount of thiazole 90 as an off-white solid. $^1$H NMR (DMSO-d$_6$, 400 MHz): δ 8.06 (d, 2H), δ 7.65 (d, 2H), δ 7.39 (s, 1H), δ 4.30 (s, 2H).

Step 3:

Performed in the same manner as in Step 2, Example 338. $C_{11}H_7N_5S$ as $(M+H)^+$ 242.3.

Step 4:

Performed in the same manner as in Step 3, Example 338. $^1$H NMR (DMSO-d$_6$, 400 MHz): δ 8.09 (d, 2H), δ 7.78 (d, 2H), δ 7.44 (s, 1H), 4.88 (s, 2H), δ 3.90 (s, 2H).

Step 5:

Performed in the same manner as in Step 4, Example 338. $^1$H NMR (CDCl$_3$, 400 MHz): δ 8.00 (d, 2H), δ 7.68 (d, 2H), δ 7.27 (m, 2H), δ 6.89 (s, 1H), δ 6.65 (broad s, 1H), δ 4.70 (m, 2H).

Step 6:

Performed in the same manner as in Step 5, Example 338. MS found for $C_{18}H_{17}ClN_4OS_2$ as $(M+H)^+$ 405.0, 407.0.

Example 351

5-Chloro-N-((2-(4-(1-methyl-4,5-dihydro-1H-imidazol-2-yl)phenyl)thiazol-4-yl)methyl)thiophene-2-carboxamide

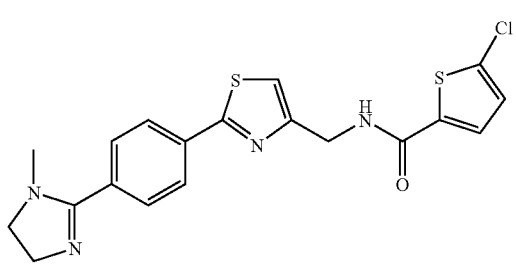

The titled compound was made by the procedure similar to that described in Example 350. MS found for $C_{19}H_{17}ClN_4OS_2$ as $(M+H)^+$ 417.0, 419.0.

Example 352

5-Chloro-N-((2-(4-(imino(pyrrolidin-1-yl)methyl)phenyl)thiazol-4-yl)methyl)thiophene-2-carboxamide

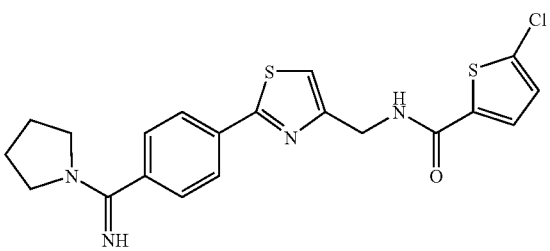

The titled compound was made by the procedure similar to that described in Example 350. MS found for $C_{20}H_{19}ClN_4OS_2$ as $(M+H)^+$ 431.0, 433.0.

Example 353

5-Chloro-N-((2-(4-(imino(piperidin-1-yl)methyl)phenyl)thiazol-4-yl)methyl)thiophene-2-carboxamide

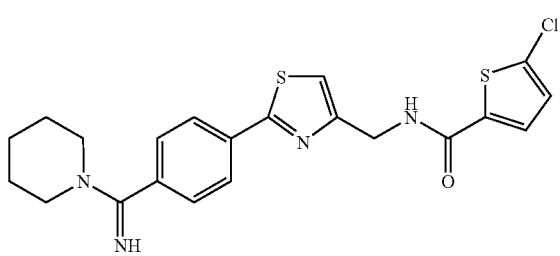

The titled compound was made by the procedure similar to that described in Example 350. MS found for $C_{21}H_{21}ClN_4OS_2$ as $(M+H)^+$ 445.1, 447.0.

Example 354

Ethyl 1-((4-(4-((2-chlorothiophene-5-carboxamido)methyl)thiazol-2-yl)phenyl)(imino)methyl)piperidine-4-carboxylate

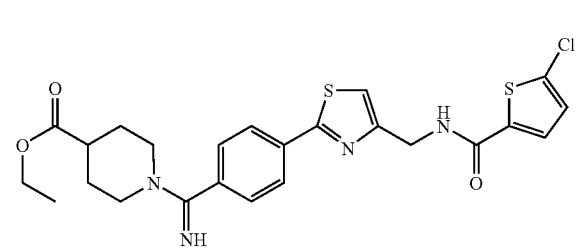

The titled compound was made by the procedure similar to that described in Example 350. MS found for $C_{24}H_{25}ClN_4O_3S_2$ as $(M+H)^+$ 517.1, 519.1.

Example 355

N-((2-(4-(N-(2-(Dimethylamino)ethyl)-N-methylcarbamimidoyl)phenyl)thiazol-4-yl)methyl)-5-chlorothiophene-2-carboxamide

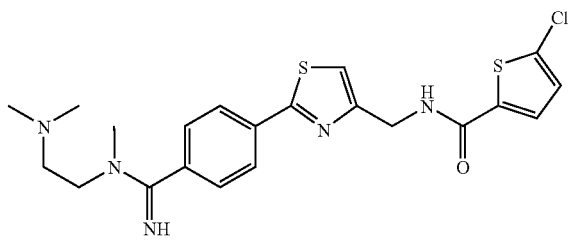

The titled compound was made by the procedure similar to that described in Example 350. MS found for $C_{21}H_{24}ClN_5OS_2$ as $(M+H)^+$ 462.1, 464.1.

Example 356

N-((2-(4-(N-(Furan-2-ylmethyl)-N-methylcarbamimidoyl)phenyl)thiazol-4-yl)methyl)-5-chlorothiophene-2-carboxamide

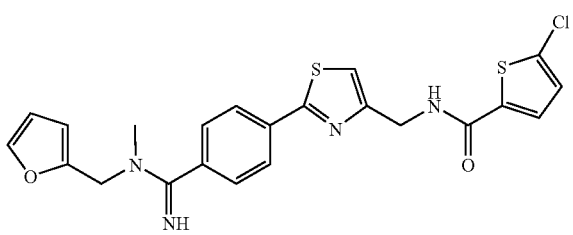

The titled compound was made by the procedure similar to that described in Example 350. MS found for $C_{22}H_{19}ClN_4O_2S_2$ as $(M+H)^+$ 471.0, 473.0.

Example 357

N-((2-(4-(N-Methyl-N-(prop-2-ynyl)carbamimidoyl)phenyl)thiazol-4-yl)methyl)-5-chlorothiophene-2-carboxamide

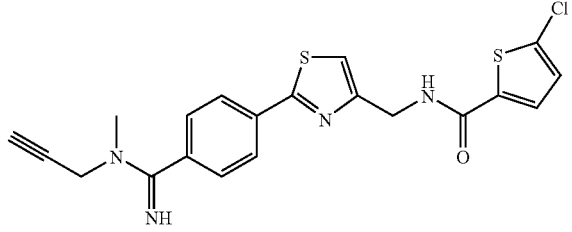

The titled compound was made by the procedure similar to that described in Example 350. MS found for $C_{20}H_{17}ClN_4OS_2$ as $(M+H)^+$ 429.0, 431.0.

Example 358

N-((2-(4-(N-Methylcarbamimidoyl)phenyl)thiazol-4-yl)methyl)-5-chlorothiophene-2-carboxamide

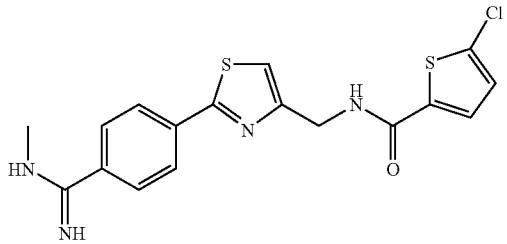

The titled compound was made by the procedure similar to that described in Example 350. MS found for $C_{17}H_{15}ClN_4OS_2$ as $(M+H)^+$ 391.0, 393.0.

Example 359

5-Chloro-N-((4-(4-(imino(pyrrolidin-1-yl)methyl)phenyl)oxazol-2-yl)methyl)thiophene-2-carboxamide (103)

SCHEME 16

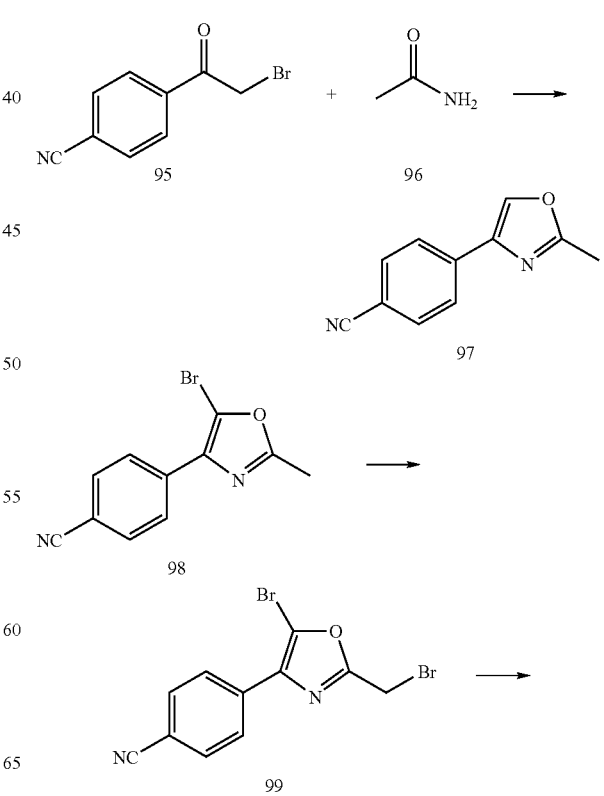

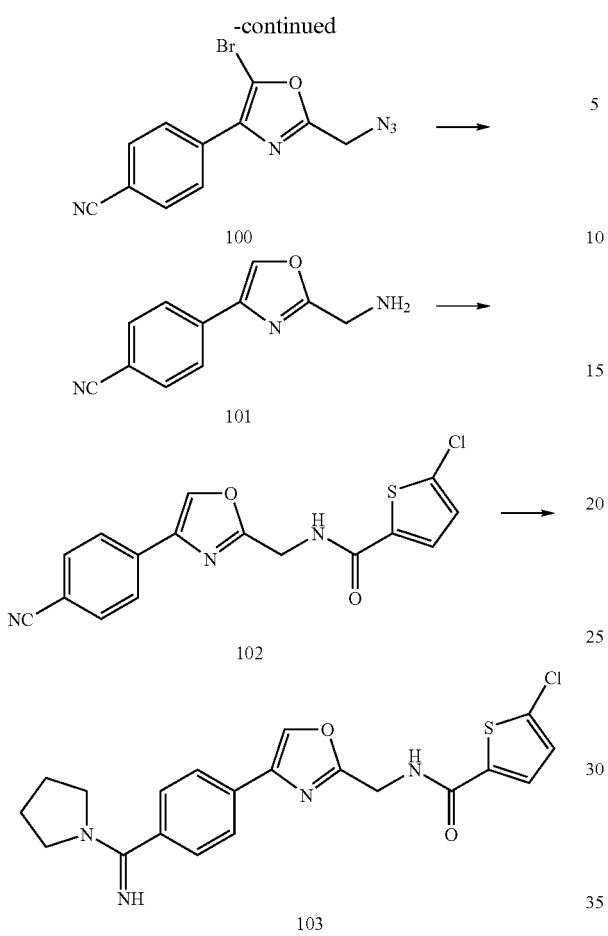

Step 1:
Compound 95 (2.24 g, 10 mmol) and compound 96 (0.59 g, 10 mmol) were refluxed in ethanol for overnight. The mixture was concentrated in vacuo and subjected to flash column chromatography to give compound 97. $^1$H NMR (DMSO-d$_6$, 400 MHz): δ 8.63 (s, 1H), δ 7.89 (d, 2H), δ 7.83 (d, 2H), δ 2.42 (s, 3H).

Step 2:
Combined 97 (0.115 g, 0.62 mmol), N-bromosuccinimide (0.11 g, 0.62 mmol) and carbontetrachloride in a flask equipped with a reflux condenser. To this was added a small amount (ca. 10 mg) of benzoyl peroxide and the mixture heated to reflux overnight. The following day the reaction was checked by TLC which showed complete consumption of the starting material and a new, less polar spot. The crude reaction mixture was loaded onto a silica gel plug and eluted with dichloromethane affording the 5-substituted bromide 98 as the major product as determined by NMR. $^1$H NMR (DMSO-d$_6$, 400 MHz): δ0 7.99 (d, 2H), δ 7.90 (d, 2H), δ 2.44 (s, 3H).

Step 3:
Performed in the same manner as in Step 2 to get compound 99. $^1$H NMR (DMSO-d$_6$, 400 MHz): δ 8.03 (d, 2H), δ 7.93 (d, 2H), δ 4.80 (s, 2H).

Step 4:
Performed in the same manner as in Step 2, Example 338. $^1$H NMR (DMSO-d$_6$, 400 MHz): δ 8.08 (d, 2H), δ 7.71 (d, 2H), δ 4.47 (s, 2H).

Step 5:
Performed in the same manner as in Step 3, Example 338. $^1$H NMR (DMSO-d$_6$, 400 MHz): δ 8.91 (s, 1H), δ 8.50 (broad s, 3H), δ 7.91 (m, 4H), δ 4.32 (s, 2H).

Step 6:
Performed in the same manner as in Step 4, Example 338. $^1$H NMR (CD$_3$OD, 400 MHz): δ 8.71 (s, 1H), δ 8.05 (d, 2H), δ 7.90 (d, 2H), δ 7.77 (d, 1H), δ 7.21 (d, 1H), δ 7.76 (d, 2H).

Step 7:
Performed in the same manner as in Step 5, Example 338. MS found for C$_{20}$H$_{19}$ClN$_4$O$_2$S as (M+H)$^+$ 415.0, 417.0.

Example 360

N-((4-(4-(N,N-Dimethylcarbamimidoyl)phenyl)thiazol-2-yl)methyl)-5-chlorothiophene-2-carboxamide

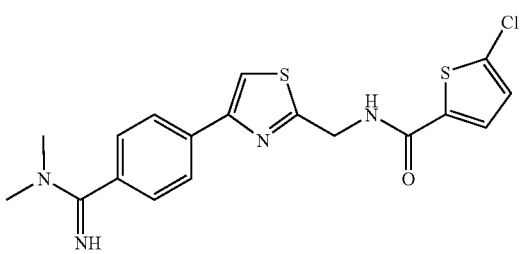

The titled compound was made by the procedure similar to that described in Example 359. MS found for C$_{18}$H$_{17}$ClN$_4$OS$_2$ as (M+H)$^+$ 405.0, 407.0.

Example 361

5-Chloro-N-((4-(4-(1-methyl-4,5-dihydro-1H-imidazol-2-yl)phenyl)thiazol-2-yl)methyl)thiophene-2-carboxamide

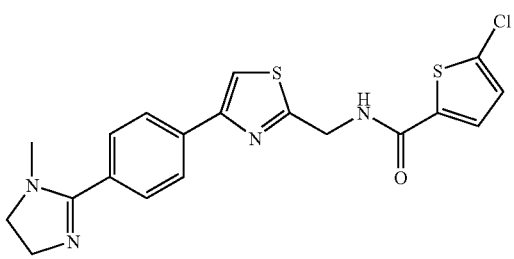

The titled compound was made by the procedure similar to that described in Example 359. MS found for C$_{19}$H$_{17}$ClN$_4$OS$_2$ as (M+H)$^+$ 417.0, 419.0.

Example 362

5-Chloro-N-((4-(4-(imino(pyrrolidin-1-yl)methyl)phenyl)thiazol-2-yl)methyl)thiophene-2-carboxamide

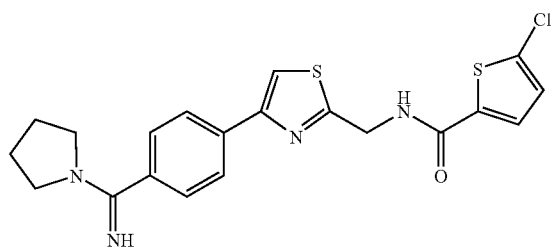

The titled compound was made by the procedure similar to that described in Example 359. MS found for $C_{20}H_{19}ClN_4OS_2$ as $(M+H)^+$ 431.0, 433.0.

Example 363

5-Chloro-N-((4-(4-(imino(piperidin-1-yl)methyl)phenyl)thiazol-2-yl)methyl)thiophene-2-carboxamide

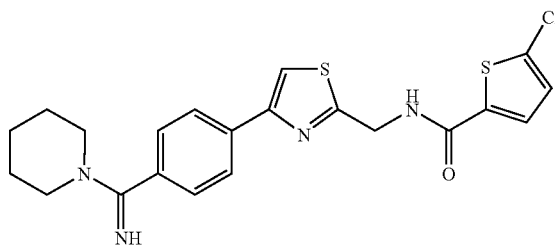

The titled compound was made by the procedure similar to that described in Example 359. MS found for $C_{21}H_{21}ClN_4OS_2$ as (M+H)+ 445.0, 447.0.

Example 364

N-((1-(4-(N,N-Dimethylcarbamimidoyl)phenyl)-1H-imidazol-4-yl)methyl)-5-chlorothiophene-2-carboxamide (110)

SCHEME 17

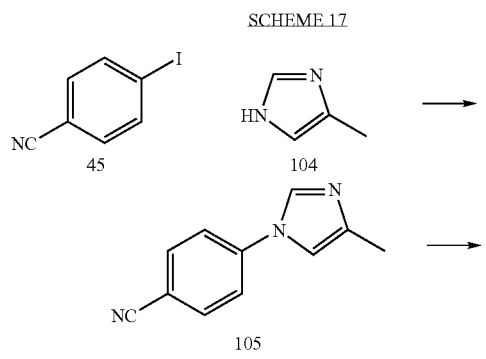

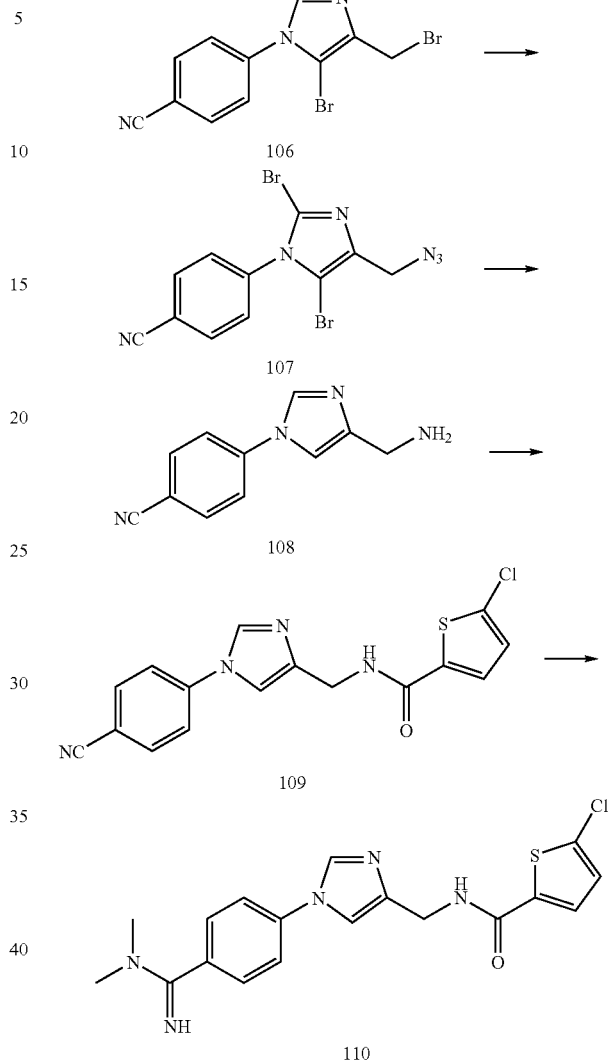

Step 1:

4-Iodobenzonitrile (45, 11.9 g, 52 mmol) and 4-methylimidazole (104, 5.16 g, 62.8 mmol) were dissolved in 100 mL dry dioxane. To it were added trans-1,2-cyclohexanediamine (3.8 mL, 31 mmol), CuI (1.18 mg, 6.2 mmol) and $K_2CO_3$ (14.7 g, 106 mmol). The mixture was refluxed for overnight. It was taken into 1000 mL EtOAc, washed with water and brine, dried, concentrated in vacuo and subjected to flash column chromatography to give compound 105 (8.21 g, 86%). MS found for $C_{11}H_9N_3$ as (M+H)+ 184.1.

Step 2:

Compound 105 (1.88 g, 10.3 mmol) was dissolved in 50 mL $CCl_4$. To it were added NBS (7.05 g, 39.6 mmol) and benzoyl peroxide (480 mg, 1.98 mmol). The mixture was refluxed for 3 hr. It was concentrated in vacuo and subjected to silica flash column chromatography to give compound 106 (60%) as the major product. MS found for $C_{11}H_6Br_3N_3$ as (M+H)+ 417.8, 419.8, 421.8.

Step 3:

Compound 106 (820 mg, 1.95 mmol) was dissolved in 10 mL DMF. To it was added NaN$_3$ (240 mg, 3.7 mmol). The mixture was stirred for 3 hr and concentrated in vacuo. The residue was taken into 300 mL EtOAc and washed with water and brine. The organic phase was dried and concentrated in vacuo to give compound 107 (695 mg, 93%) as a yellow solid.

Step 4:

Compound 107 (390 mg, 1.02 mmol) was dissolved in 20 mL methanol To it were added triethylamine (0.6 mL, 4.1 mmol) and 10% Pd on carbon (337 mg). The mixture was shaken under 10 PSI hydrogen for 30 min. It was then filtered through celite and concentrated in vacuo to give compound 108 as a yellow solid. MS found for $C_{11}H_{10}N_4$ as (M+H)+ 199.1.

Step 5:

The above crude compound 108 was dissolved in 10 mL DMF. To it were added 5-chlorothiophene-2-carboxylic acid (231 mg, 1.42 mmol), EDC (277 mg, 1.44 mmol), 1-hydroxy-7-azabenzotriazole (HOAt, 17 mg, 0.12 mol) and triethylamine (0.8 mL, 5.7 mmol).

The mixture was stirred for overnight at RT and was diluted with brine. The mixture was extracted with DCM three times. The organic phase was combined, dried, concentrated and subjected to flash column to give compound 109 (180 mg, 52% for 2 steps). MS found for $C_{16}H_{11}ClN_4OS$ as (M+H)+ 343.0, 345.0.

Step 6:

Performed in the same manner as in Step 6, Example 325. MS found for $C_{18}H_{18}ClN_5OS$ as (M+H)+ 388.1, 390.1.

Example 365

5-Chloro-N-((1-(4-(1-methyl-4,5-dihydro-1H-imidazol-2-yl)phenyl)-1H-imidazol-4-yl)methyl)thiophene-2-carboxamide

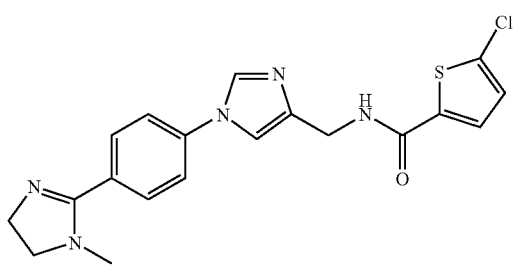

The titled compound was made by the procedure similar to that described in Example 364. MS found for $C_{19}H_{18}ClN_5OS$ as (M+H)+ 400.1, 402.1.

Example 366

N-((1-(4-(Azetidin-1-yl(imino)methyl)phenyl)-1H-imidazol-4-yl)methyl)-5-chlorothiophene-2-carboxamide

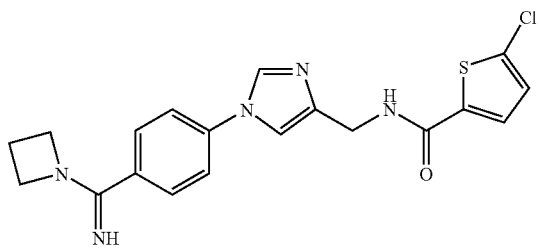

The titled compound was made by the procedure similar to that described in Example 364. MS found for $C_{19}H_{18}ClN_5OS$ as (M+H)+ 400.1, 402.1.

Example 367

5-Chloro-N-((1-(4-(imino(pyrrolidin-1-yl)methyl)phenyl)-1H-imidazol-4-yl)methyl)thiophene-2-carboxamide

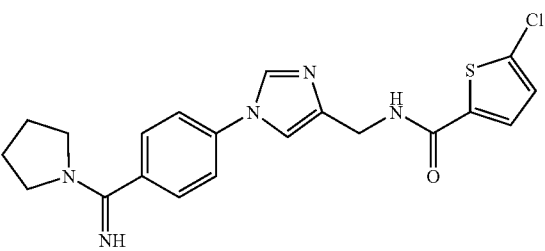

The titled compound was made by the procedure similar to that described in Example 364. MS found for $C_{20}H_{20}ClN_5OS$ as (M+H)+ 414.1, 416.1.

Example 368

5-Chloro-N-((1-(4-(imino(piperidin-1-yl)methyl)phenyl)-1H-imidazol-4-yl)methyl)thiophene-2-carboxamide

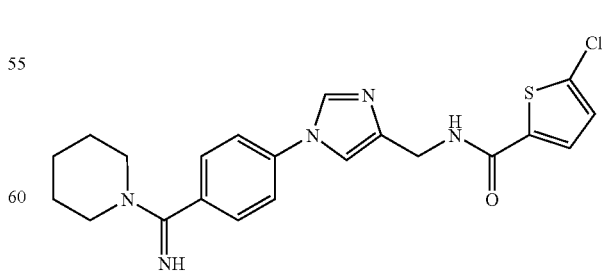

The titled compound was made by the procedure similar to that described in Example 364. MS found for $C_{21}H_{22}ClN_5OS$ as (M+H)+ 428.1, 430.1.

Example 369

N-((5-(4-(N,N-Dimethylcarbamimidoyl)phenyl)pyridin-3-yl)methyl)-5-chlorothiophene-2-carboxamide (115)

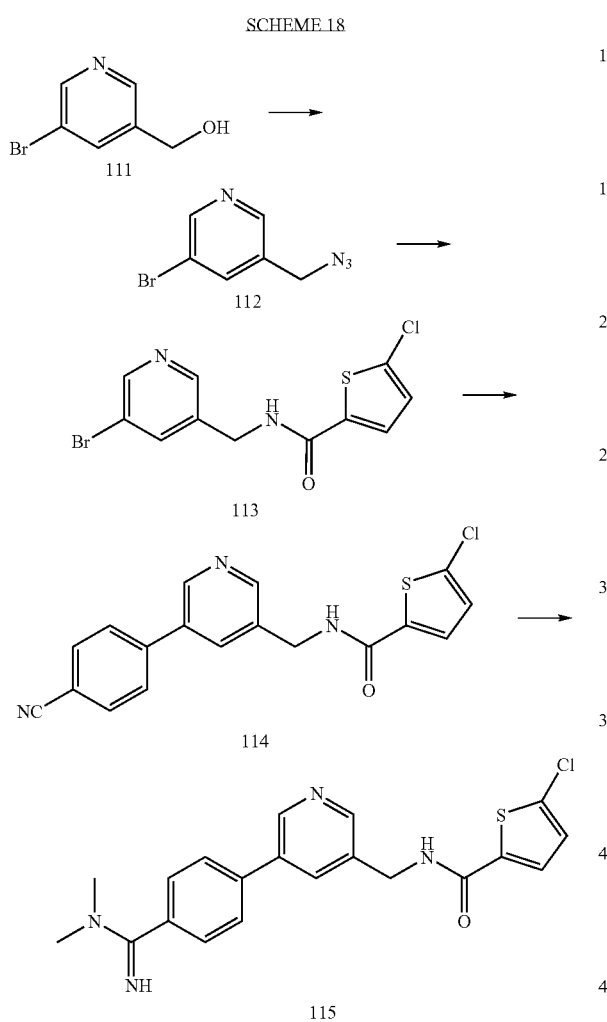

Step 1:

Compound 111 (2.00 g, 10.6 mmol) and triphenylphosphine (3.31 g, 12.6 mmol) were dissolved in 100 mL THF and 50 mL DCM. At 0° C., to it was added DEAD (3.2 mL, 20 mmol) dropwise. After stirring for 2 min, DPPA (4.3 mL, 20 mmol) was added. The mixture was stirred for overnight (from 0° C. to RT). The mixture was diluted with water, and it was extracted with DCM three times. The organic phase was combined, dried, concentrated and purified using flash column to give compound 112 (690 mg, 30%). MS found for $C_6H_5BrN_4$ as (M+H)+ 213.0, 215.0.

Step 2:

Compound 112 (675 mg, 3.17 mmol) was dissolved in 10 mL THF and 1 mL water. To it was added triphenylphosphine (0.96 g, 3.67 mmol). The mixture was stirred for 24 hrs at RT. Then to it were added EDC (617 mg, 3.22 mmol), 5-chlorothiophene-2-carboxylic acid (502 mg, 3.1 mmol) and HOAt (70 mg, 0.51 mmol). The mixture was stirred for overnight at RT. The mixture was diluted with 2N NaOH, and was extracted with DCM three times. The organic phase was combined, dried, concentrated and purified using flash column to give compound 113 (450 mg, 43%). MS found for $C_{11}H_8BrClN_2OS$ as (M+H)+ 331.0, 333.0.

Step 3:

A mixture of compound 113 (450 mg, 1.35 mmol), 4-cyanobenzeneboronic acid (282 mg, 1.92 mmol), Pd(Ph$_3$P)$_4$ (130 mg, 0.11 mmol), K$_2$CO$_3$ (596 mg, 4.31 mmol) in 5 mL Diglyme and 5 mL water was degasses using argon stream for 5 min. The mixture was then stirred in 80° C. bath for overnight. The mixture was poured into water and was extracted with DCM three times. The organic phase was combined, dried, concentrated and purified using flash column to give compound 114 (350 mg, 73%). MS found for $C_{18}H_{12}ClN_3OS$ as (M+H)+ 354.0, 356.0.

Step 4:

Performed in the same manner as in Step 6, Example 325. MS found for $C_{20}H_{19}ClN_4OS$ as (M+H)+ 399.1, 401.1.

Example 370

5-Chloro-N-((5-(4-(1-methyl-4,5-dihydro-1H-imidazol-2-yl)phenyl)pyridin-3-yl)methyl)thiophene-2-carboxamide

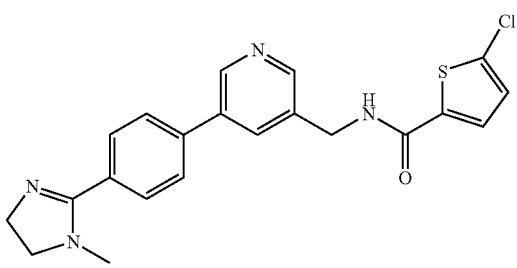

The titled compound was made by the procedure similar to that described in Example 369. MS found for $C_{21}H_{19}ClN_4OS$ as (M+H)+ 411.1, 413.1.

Example 371

N-((5-(4-(Azetidin-1-yl(imino)methyl)phenyl)pyridin-3-yl)methyl)-5-chlorothiophene-2-carboxamide

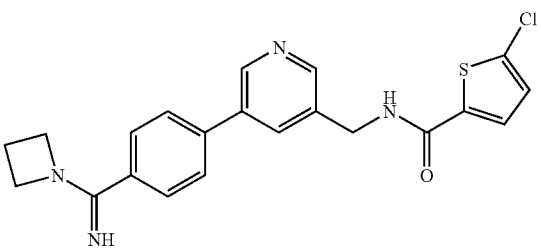

The titled compound was made by the procedure similar to that described in Example 369. MS found for $C_{21}H_{19}ClN_4OS$ as (M+H)+ 411.1, 413.1.

Example 372

5-Chloro-N-((5-(4-(imino(pyrrolidin-1-yl)methyl)phenyl)pyridin-3-yl)methyl)thiophene-2-carboxamide

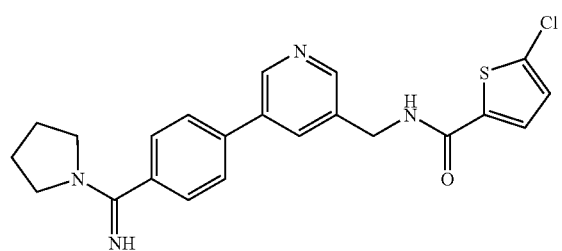

The titled compound was made by the procedure similar to that described in Example 369. MS found for $C_{22}H_{21}ClN_4OS$ as (M+H)+ 425.1, 427.1.

Example 373

5-Chloro-N-((5-(4-(imino(piperidin-1-yl)methyl)phenyl)pyridin-3-yl)methyl)thiophene-2-carboxamide

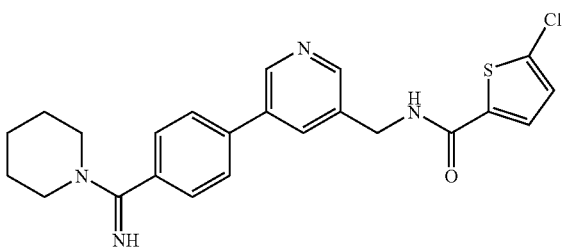

The titled compound was made by the procedure similar to that described in Example 369. MS found for $C_{23}H_{23}ClN_4OS$ as (M+H)+ 439.1, 441.1.

Example 374

N-((5-(4-(N,N-Dimethylcarbamimidoyl)phenyl)-2-fluorophenyl)methyl)-5-chlorothiophene-2-carboxamide (119)

SCHEME 19

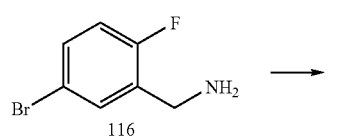

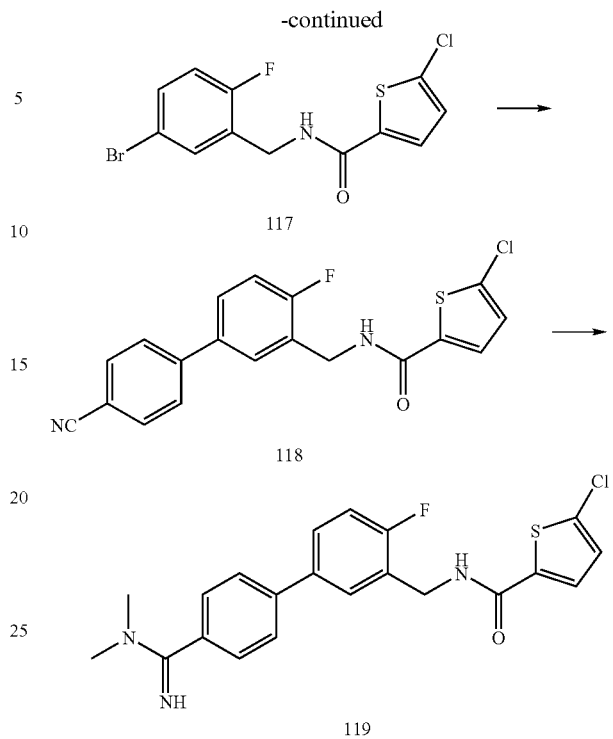

Step 1:
Compound 116 hydrochloide (490 mmol, 2.04 mmol), 5-chlorothiophene-2-carboxylic acid (390 mg, 2.40 mmol) and triethylamine (0.35 mL, 2.51 mmol) were dissolved in 20 mL DCM. To it were added DMAP (25 mg) and EDC (450 mg, 2.35 mmol). The mixture was stirred for overnight. It was diluted with DCM, washed with water, dried, concentrated and purified using flash column to give compound 117 (90%). MS found for $C_{12}H_8BrClFNOS$ as (M+H)+ 348.0, 350.0.

Step 2:
Performed in the same manner as in Step 3, Example 369. MS found for $C_{19}H_{12}ClFN_2OS$ as (M+H)+ 371.0, 373.0

Step 3:
Performed in the same manner as in Step 4, Example 369. MS found for $C_{21}H_{19}ClFN_3OS$ as (M+H)+ 416.1, 418.1.

Example 375

5-Chloro-N-((5-(4-(1-methyl-4,5-dihydro-1H-imidazol-2-yl)phenyl)-2-fluorophenyl)methyl)thiophene-2-carboxamide

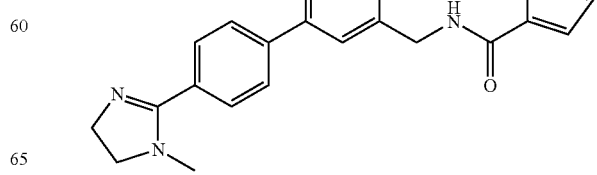

The titled compound was made by the procedure similar to that described in Example 374. MS found for $C_{22}H_{19}ClFN_3OS$ as (M+H)+ 428.1, 430.1.

Example 376

5-Chloro-N-((5-(4-(imino(pyrrolidin-1-yl)methyl)phenyl)-2-fluorophenyl)methyl)thiophene-2-carboxamide

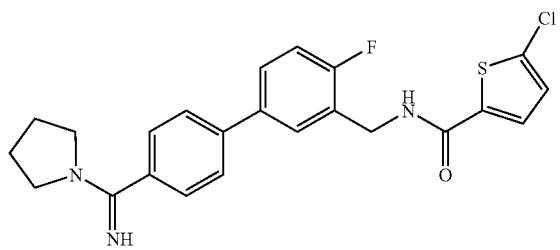

The titled compound was made by the procedure similar to that described in Example 374. MS found for $C_{23}H_{21}ClFN_3OS$ as (M+H)+ 442.1, 444.1.

Example 377

N-((3-(4-(N,N-Dimethylcarbamimidoyl)phenyl)-4-fluorophenyl)methyl)-5-chlorothiophene-2-carboxamide

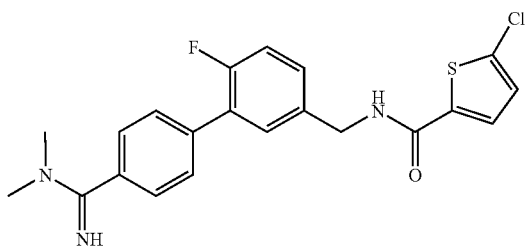

The titled compound was made by the procedure similar to that described in Example 374. MS found for $C_{21}H_{19}ClFN_3OS$ as (M+H)+ 416.1, 418.1.

Example 378

5-Chloro-N-((3-(4-(1-methyl-4,5-dihydro-1H-imidazol-2-yl)phenyl)-4-fluorophenyl)methyl)thiophene-2-carboxamide

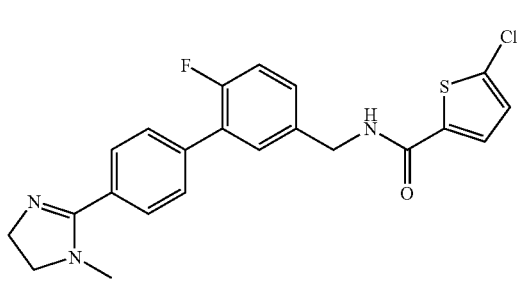

The titled compound was made by the procedure similar to that described in Example 374. MS found for $C_{22}H_{19}ClFN_3OS$ as (M+H)+ 428.1, 430.1.

Example 379

5-Chloro-N-((3-(4-(imino(pyrrolidin-1-yl)methyl)phenyl)-4-fluorophenyl)methyl)thiophene-2-carboxamide

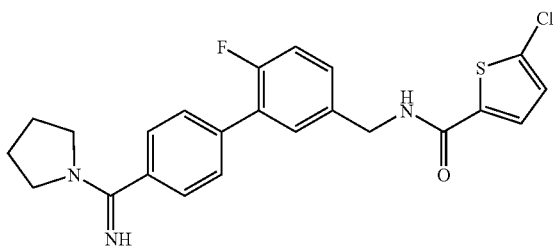

The titled compound was made by the procedure similar to that described in Example 374. MS found for $C_{23}H_{21}ClFN_3OS$ as (M+H)+ 442.1, 444.1.

Example 380

N-((3-(4-(N,N-Dimethylcarbamimidoyl)phenyl)phenyl)methyl)-5-chlorothiophene-2-carboxamide

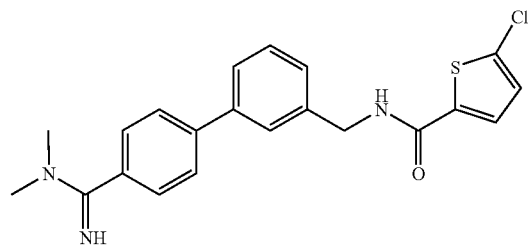

The titled compound was made by the procedure similar to that described in Example 374. MS found for $C_{21}H_{20}ClN_3OS$ as (M+H)+ 398.1, 400.1.

Example 381

5-Chloro-N-((3-(4-(1-methyl-4,5-dihydro-1H-imidazol-2-yl)phenyl)phenyl)methyl)thiophene-2-carboxamide

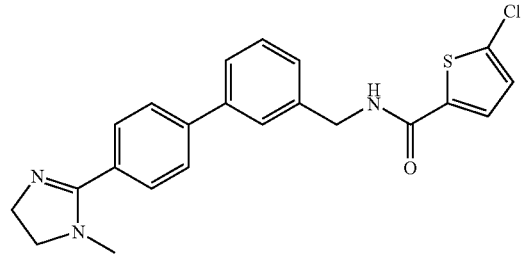

The titled compound was made by the procedure similar to that described in Example 374. MS found for $C_{22}H_{20}ClN_3OS$ as (M+H)+ 410.1, 412.1.

Example 382

5-Chloro-N-((3-(4-(imino(pyrrolidin-1-yl)methyl)phenyl)phenyl)methyl)thiophene-2-carboxamide

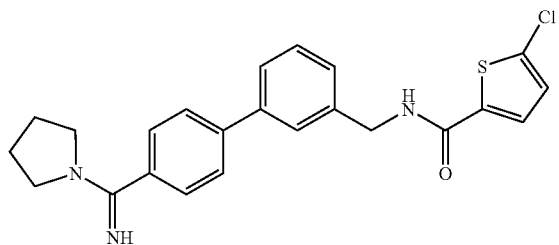

The titled compound was made by the procedure similar to that described in Example 374. MS found for $C_{23}H_{22}ClN_3OS$ as (M+H)+ 424.1, 426.1.

Example 383

5-Chloro-N-((1-(6-(4-methyl-1,4-diazepan-1-yl)pyridin-3-yl)-1H-1,2,3-triazol-4-yl)methyl)thiophene-2-carboxamide (123)

SCHEME 20

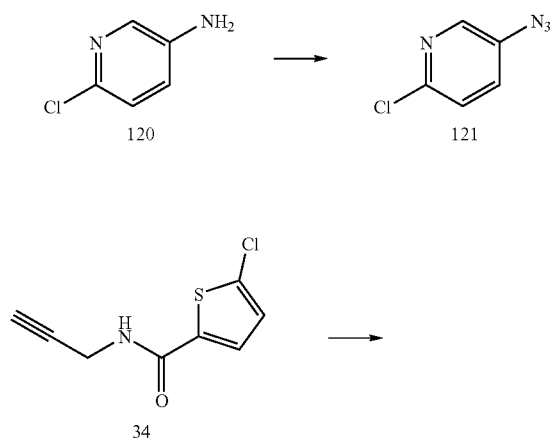

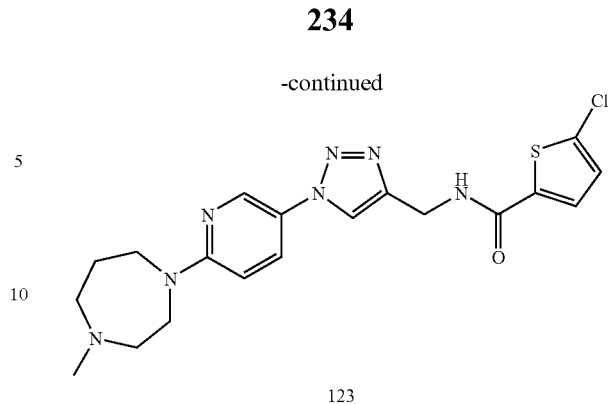

123

Step 1:
5-Amino-2-chloropyridine (120, 4.91 g, 38.3 mmol) was dissolved in 15 mL TFA. In ice bath to it was added $NaNO_2$ (2.91 g, 42.2 mmol) in small portions. The mixture was stirred in the cold bath for 30 min. To it was then added an ice-cold solution of $NaN_3$ (2.50 g, 38.3 mmol, in 10 mL water). The mixture was stirred for 1 hr. The mixture was concentrated in vacuo and diluted with 400 mL chloroform. It was washed with water three times, dried, concentrated and purified by flash column to yield compound 121 (3.46 g, 59%). MS found for $C_5H_3ClN_4$ as (M+H)+ 155.0, 157.0.

Step 2:
Azidopyridine 121 (3.46 g, 22.5 mmol) and alkyne 34 (see Scheme 5 in Example 291; 4.38 g, 22.0 mmol) were refluxed in 10 mL toluene and 15 mL DMF for 7 hr. The reaction was still in complete. The mixture was concentrated and subjected to flash column to isolate major 1,4-disubstituted triazole product 122 (3.19 g, 40%) as a white solid. MS found for $C_{13}H_9Cl_2N5OS$ as (M+H)+ 354.0, 356.0. The minor 1,5-triazole isomer was isolated in 7% yield (0.56 g).

Step 3:
The mixture of compound 122 (50 mg, 0.14 mmol), N-methylhomopiperazine (53 μL, 0.42 mmol) and $Cs_2CO_3$ (91 mg, 0.28 mmol) in 1 mL DMSO in a sealed tube was stirred in 120° C. bath for 2 hr. The mixture was directly subjected to reverse phase preparative HPLC to give the title compound as a white powder after lyophilization. MS found for $C_{19}H_{22}ClN_7OS$ as (M+H)+ 432.1, 434.1.

Example 384

N-((1-(6-(1,4-Diazepan-1-yl)pyridin-3-yl)-1H-1,2,3-triazol-4-yl)methyl)-5-chlorothiophene-2-carboxamide

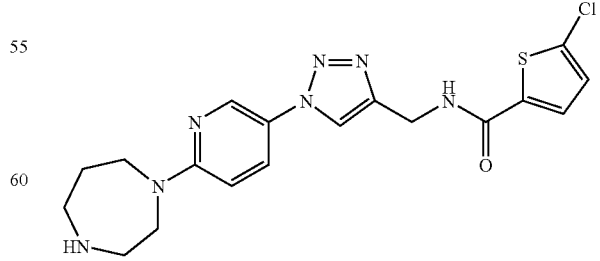

The titled compound was made by the procedure similar to that described in Example 383. MS found for $C_{18}H_{20}ClN_7OS$ as (M+H)+ 418.1, 420.1.

Example 385

N-((1-(6-(1,4-Oxazepan-4-yl)pyridin-3-yl)-1H-1,2,3-triazol-4-yl)methyl)-5-chlorothiophene-2-carboxamide

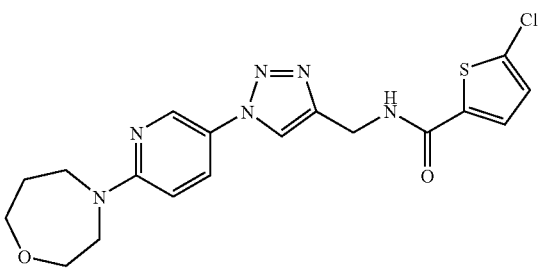

The titled compound was made by the procedure similar to that described in Example 383. MS found for $C_{18}H_{19}ClN_6O_2S$ as (M+H)+ 419.1, 421.1.

Example 386

5-Chloro-N-((1-(6-morpholinopyridin-3-yl)-1H-1,2,3-triazol-4-yl)methyl)thiophene-2-carboxamide

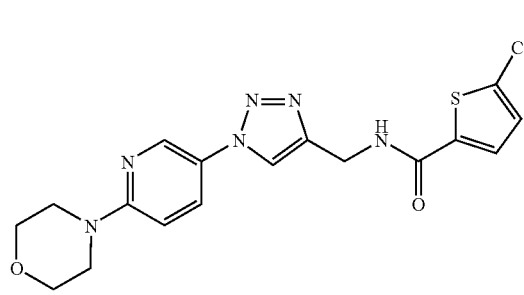

The titled compound was made by the procedure similar to that described in Example 383. MS found for $C_{17}H_{17}ClN_6O_2S$ as (M+H)+ 405.1, 407.1.

Example 387

5-Chloro-N-((1-(6-(3-oxomorpholino)pyridin-3-yl)-1H-1,2,3-triazol-4-yl)methyl)thiophene-2-carboxamide

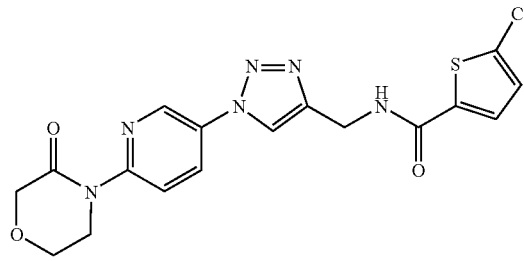

The titled compound was made by the procedure similar to that described in Example 383. MS found for $C_{17}H_{15}ClN_6O_3S$ as (M+H)+ 419.1, 421.1.

Example 388

5-Chloro-N-((1-(6-(2-oxopiperidin-1-yl)pyridin-3-yl)-1H-1,2,3-triazol-4-yl)methyl)thiophene-2-carboxamide

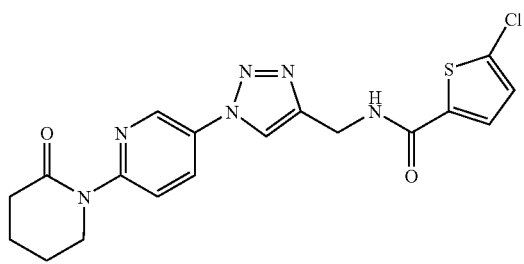

The titled compound was made by the procedure similar to that described in Example 383. MS found for $C_{18}H_{17}ClN_6O_2S$ as (M+H)+ 417.1, 419.1.

Example 389

5-Chloro-N-((1-(6-(2-oxopyridin-1(2H)-yl)pyridin-3-yl)-1H-1,2,3-triazol-4-yl)methyl)thiophene-2-carboxamide

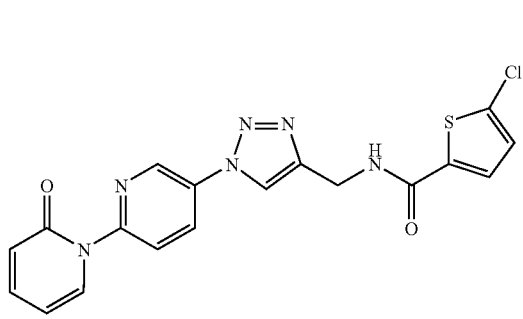

The titled compound was made by the procedure similar to that described in Example 383. MS found for $C_{18}H_{13}ClN_6O_2S$ as (M+H)+ 413.0, 415.0.

Example 390

5-Chloro-N-((1-(6-(piperazin-1-yl)pyridin-3-yl)-1H-1,2,3-triazol-4-yl)methyl)thiophene-2-carboxamide

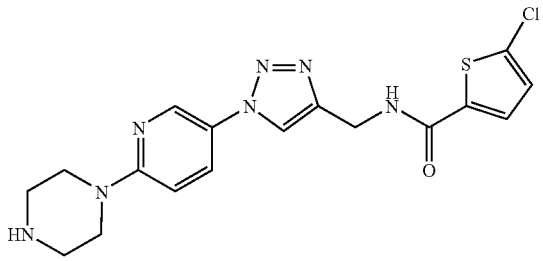

The titled compound was made by the procedure similar to that described in Example 383. MS found for $C_{17}H_{18}ClN_7OS$ as (M+H)+ 404.1, 406.1.

Example 391

5-Chloro-N-((1-(6-(4-methylpiperazin-1-yl)pyridin-3-yl)-1H-1,2,3-triazol-4-yl)methyl)thiophene-2-carboxamide

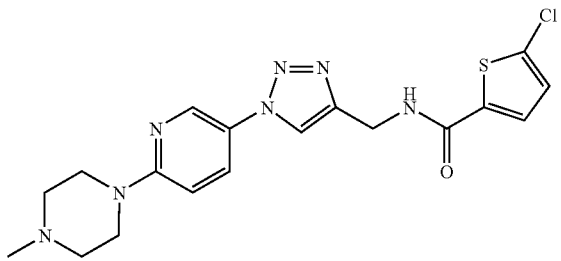

The titled compound was made by the procedure similar to that described in Example 383. MS found for $C_{18}H_{20}ClN_7OS$ as (M+H)+ 418.1, 420.1.

Example 392

5-Chloro-N-((1-(6-(piperidin-1-yl)pyridin-3-yl)-1H-1,2,3-triazol-4-yl)methyl)thiophene-2-carboxamide

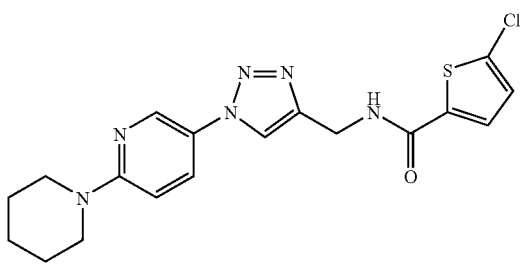

The titled compound was made by the procedure similar to that described in Example 383. MS found for $C_{18}H_{19}ClN_6OS$ as (M+H)+ 403.1, 405.1.

Example 393

5-Chloro-N-((3-(4-(8-(trifluoromethyl)quinolin-4-ylamino)phenyl)-4,5-dihydroisoxazol-5-yl)methyl)thiophene-2-carboxamide

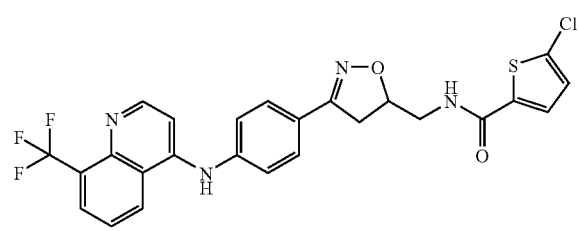

The titled compound was made by the procedure similar to that described in Example 222. MS found for $C_{25}H_{18}ClF_3N_4O_2S$ as (M+H)+ 531.0, 533.0.

Example 394

5-Chloro-N-((3-(4-(7-(trifluoromethyl)quinolin-4-ylamino)phenyl)-4,5-dihydroisoxazol-5-yl)methyl)thiophene-2-carboxamide

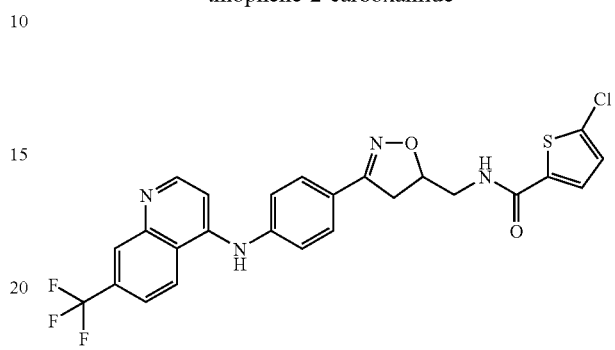

The titled compound was made by the procedure similar to that described in Example 222. MS found for $C_{25}H_{18}ClF_3N_4O_2S$ as (M+H)+ 531.0, 533.0.

Example 395

5-Chloro-N-((3-(4-(6-(trifluoromethyl)quinolin-4-ylamino)phenyl)-4,5-dihydroisoxazol-5-yl)methyl)thiophene-2-carboxamide

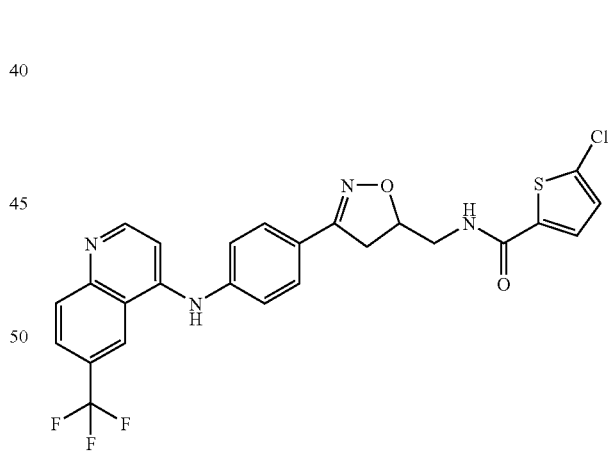

The titled compound was made by the procedure similar to that described in Example 222. MS found for $C_{25}H_{18}ClF_3N_4O_2S$ as (M+H)+ 531.0, 533.0.

Example 396

5-Chloro-N-((3-(4-(quinolin-6-ylamino)phenyl)-4,5-dihydroisoxazol-5-yl)methyl)thiophene-2-carboxamide

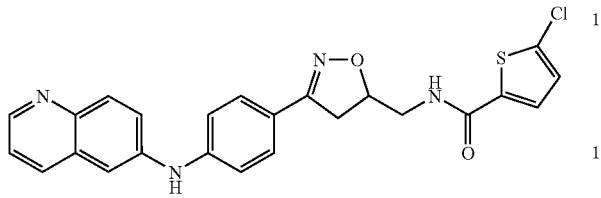

The titled compound was made by the procedure similar to that described in Example 222. MS found for $C_{24}H_{19}ClN_4O_2S$ as (M+H)$^+$ 463.1, 465.1.

Example 397

5-Chloro-N-((3-(4-(2,5-dihydro-1H-pyrrole-1-carbonyl)phenyl)-4,5-dihydroisoxazol-5-yl)methyl)thiophene-2-carboxamide

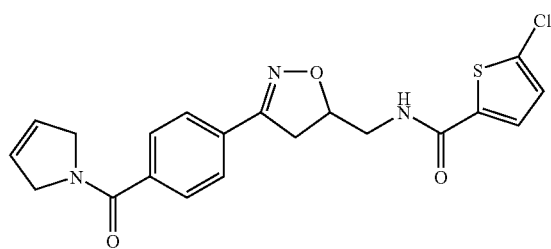

The titled compound was made by the procedure similar to that described in Example 162. MS found for $C_{20}H_{18}ClN_3O_3S$ as (M+H)$^+$ 416.0, 418.0.

Example 398

5-Chloro-N-((3-(4-(2,5-dihydro-1H-pyrrole-1-carbonyl)phenyl)-4,5-dihydroisoxazol-5-yl)methyl)thiophene-2-carboxamide

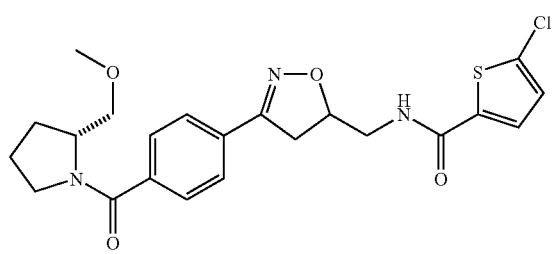

The titled compound was made by the procedure similar to that described in Example 162. MS found for $C_{22}H_{24}ClN_3O_4S$ as (M+H)$^+$ 462.0, 464.0.

Example 399

N-((3-(4-((2-Hydroxypropyl)carbamoyl)phenyl)-4,5-dihydroisoxazol-5-yl)methyl)-5-chlorothiophene-2-carboxamide

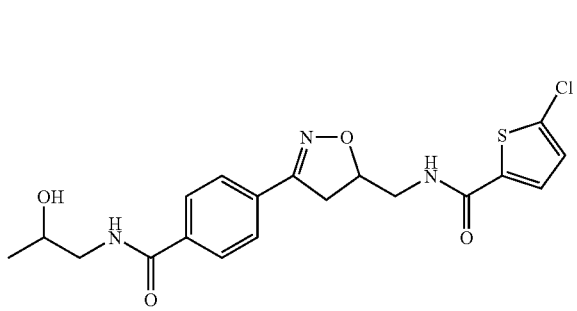

The titled compound was made by the procedure similar to that described in Example 162. MS found for $C_{19}H_{20}ClN_3O_4S$ as (M+H)$^+$ 422.0, 424.0.

Example 400

5-Chloro-N-((3-(4-(3-methylpyridin-4-ylamino)phenyl)-4,5-dihydroisoxazol-5-yl)methyl)thiophene-2-carboxamide

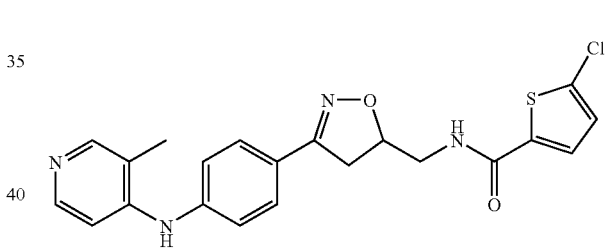

The titled compound was made by the procedure similar to that described in Example 222. MS found for $C_{21}H_{19}ClN_4O_2S$ as (M+H)$^+$ 427.0, 429.0.

Example 401

5-Chloro-N-((3-(4-(2-ethoxypyridin-4-ylamino)phenyl)-4,5-dihydroisoxazol-5-yl)methyl)thiophene-2-carboxamide

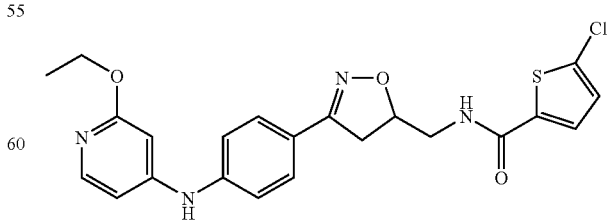

The titled compound was made by the procedure similar to that described in Example 222. MS found for $C_{22}H_{21}ClN_4O_3S$ as (M+H)$^+$ 457.1, 459.1.

Example 402

5-Chloro-N-((3-(4-(3,5-dichloropyridin-4-ylamino) phenyl)-4,5-dihydroisoxazol-5-yl)methyl)thiophene-2-carboxamide

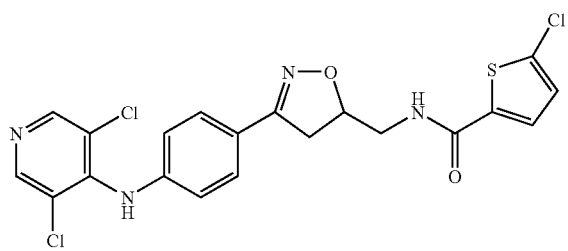

The titled compound was made by the procedure similar to that described in Example 222. MS found for $C_{20}H_{15}C_{l3}N_4O_2S$ as $(M+H)^+$ 481.0, 483.0.

Example 403

5-Chloro-N-((3-(4-(3-(trifluoromethyl)pyridin-4-ylamino)phenyl)-4,5-dihydroisoxazol-5-yl)methyl) thiophene-2-carboxamide

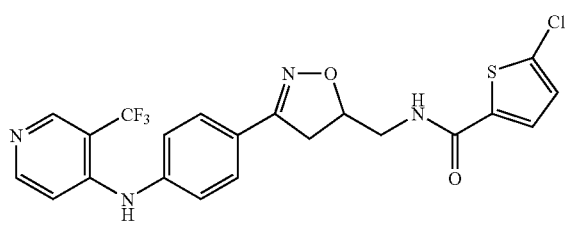

The titled compound was made by the procedure similar to that described in Example 222. MS found for $C_{21}H_{16}ClF_3N_4O_2S$ as $(M+H)^+$ 481.1, 483.1.

Example 404

This example illustrates methods for evaluating the compounds of the invention, along with results obtained for such assays. The in vitro and in vivo Factor Xa isoform activities of the inventive compounds can be determined by various procedures known in the art, such as a test for their ability to inhibit the activity of the Factor Xa isoform. The potent affinities for Factor Xa isoform exhibited by the inventive compounds can be measured by an $IC_{50}$ value (in nM). The $IC_{50}$ value is the concentration (in nM) of the compound required to provide 50% inhibition of Factor Xa isoform. The smaller the $IC_{50}$ value, the more active (potent) is a compound for inhibiting Factor Xa isoform.

An in vitro assay for detecting and measuring inhibition activity against Factor Xa is as follows:

$IC_{50}$ and $K_i$ Determinations:

Substrate:

The substrate S-2765 (Z-D-Arg-Gly-Arg-pNA.HCl) was obtained from Diapharma (West Chester, Ohio).

Enzyme:

The human plasma protein factor Xa was purchased from Haematologic Technologies (Essex Junction, Vt.).

Methods $IC_{50}$ Determinations

All assays, which are performed in 96-well microtiter plates, measure proteolytic activity of the enzyme (factor Xa) by following cleavage of paranitroanilide substrate. The assay buffer used for proteolytic assays was Tris buffered saline (20 mM Tris, 150 mM NaCl, 5 mM $CaCl_2$, 0.1% Bovine serum albumin (BSA), 5% Dimethly Sulfoxide (DMSO) pH 7.4). In a 96-well microtiter plate, inhibitor was serially diluted to give a range of concentrations from 0.01 nM to 10 µM (final). Duplicate sets of wells were assayed and control wells without inhibitor were included. Enzyme was added to each well,(fXa concentration=1 nM), the plate was shaken for 5 seconds and then incubated for 5 minutes at room temperature. S2765 was added (100 µM final) and the plate was shaken for 5 seconds (final liquid volume in each well was 200 µl). The degree of substrate hydrolysis was measured at 405 nm on a Thermomax plate reader (Molecular Devices, Sunnyvale, Calif.) for 2 minutes. The initial velocities (mOD/min), for each range of inhibitor concentrations, were fitted to a four parameter equation using Softmax data analysis software. The parameter C, derived from the resulting curve-fit, corresponded to the concentration for half maximal inhibition ($IC_{50}$).

$K_i$ Determination

The assay buffer for this series of assays was Hepes buffered saline (20 mM Hepes, 150 mM NaCl, 5 mM $CaCl_2$, 0.1% PEG-8000, pH 7.4). In a 96-well microtiter plate, inhibitor was serially diluted in a duplicate set of wells to give a range of final concentrations from 5 pM to 3 µM final. Controls without inhibitor (8 wells) were included. The enzyme, fXa (1 nM final) was added to the wells. The substrate S-2765 (200 µM final) was added and the degree of substrate hydrolysis was measured at 405 nm on a Thermomax plate reader for 5 minutes, using Softmax software. Initial velocities (mOD/min) were analyzed by non-linear least squares regression in the Plate Ki software (BioKin Ltd, Pullman, Wash.)(Literature reference: Kusmic P, Sideris S, Cregar L M, Elrod K C, Rice K D, Janc J. High-throughput screening of enzyme inhibitors: Automatic determination of tight-binding inhibition constants. *Anal. Biochemistry* 2000, 281:62-67). The model used for fitting the inhibitor dose-response curves was the Morrison equation. An apparent $K_i$($Ki^*$) was determined. The overall $K_i$ was calculated using the following equation:

$$Ki = \frac{Ki^*}{1 + \frac{[S]}{Km}}$$

where [S] is substrate concentration (200 µM) and $K_m$, the Michaelis constant for S2765.

The hERG (Human Ether-a-Go-Go Related Gene Protein) Membrane Binding Assay

Human embryonic kidney (HEK293) cells stably transfected with hERG cDNA were used for preparation of membranes (Literature reference: Zhou, Z., Gong, Q., Ye, B., Fan, Z., Makielski, C., Robertson, G., January, C T., Properties of HERG stably expressed in HEK293 cells studied at physiological temperature. *Biophys. J,* 1998, 74:230-241). The assay buffer was comprised of 50 mM Tris, 10 mM KCl, 1 mM $MgCl_2$, pH 7.4. Competition assays for hERG binding were performed, in a 96 well plate, with 50 μL $^3$H-dofetilide, at a concentration of 3.5 nM (final concentration of 0.01% ethanol). Test compound was added at final concentrations of 100 μM, 33.33 μM, 11.11 μM, 3.70 μM, 1.23 μM, 0.41 μM, 0.14 μM, 0.046 μM, 0.015 μM, and 0.005 μM (1.0% DMSO). Each compound was run in duplicate on each of two plates. Total binding was determined by addition of 50 μL of assay buffer in place of compound. Non-specific binding was determined by addition of 50 μL of 50 μM terfenadine in place of test compound. All assays were initiated by addition of 150 μL of membrane homogenates (15 ug protein/well as final concentration) to the wells (total volume=250 μL per well), and the plates were incubated at room temperature for 80 minutes on a shaking platform. All assays were terminated by vacuum filtration on to glass fiber filters, followed by two washes with cold assay buffer. The filter plates were dried at 55° C. for 90 minutes, after which, Microscint 0 (50 μL) was added to each well of the dried filter plate. The plates were counted on a Packard Topcount (Perkin Elmer, Boston, Mass.) using a one minute protocol. Scintillation reading (counts per minute, CPM) data generated by the Packard TopCount was used to calculate the percent inhibition of $^3$H-dofetilide binding, for each compound at each concentration, using the total binding control value corrected for non-specific binding. The IC$_{50}$ value was calculated from the percent inhibition curve generated using Excel XL Fit software (Microsoft). The equilibrium dissociation constant (K$_i$) was calculated using the equation of Cheng and Prusoff (see "Relationship between the inhibition constant (K$_i$) and the concentration of inhibitor which causes 50 percent inhibition (I$_{50}$) of an enzymatic reaction," *Biochem Pharmacol.*, 1973, 22(23):3099-108.

$$K_i = IC_{50}/[1+([L]/K_D)].$$

A compound can be run through this assay and its corresponding IC$_{50}$ inhibition value can be calculated from the assay data.

The following examples exhibited Factor Xa IC$_{50}$ values less than or equal to 100 nM:

7-10, 16-18, 20-32, 48-51, 56-65, 67, 69-72, 77, 82, 86, 91-142, 161-164, 166, 193-200, 203-205, 208, 209, 216-219, 225-227, 239, 240, 242, 243, 245-248, 253, 254, 269, 278-286, 289-303, 305-341, 352, 364-377, 379-384, 387-389, 394, 395, 397, 400, 401, 403.

The following examples exhibited Factor Xa IC$_{50}$ values greater than 100 nM and less than 500 nM:

11-15, 33, 66, 68, 73-76, 78-80, 83-85, 87-90, 165, 167, 186-190, 206, 210, 211, 229, 230, 233, 235, 237, 238, 241, 244, 342-347, 349-351, 353, 354, 359, 378, 385, 386, 390-392, 398.

The following examples exhibited Factor Xa IC$_{50}$ values greater than or equal to 500 nM:

1, 4, 5, 34-47, 52-55, 81, 143-160, 168-181, 183-185, 191, 192, 201, 202, 207, 212-215, 220-224, 228, 231, 232, 234, 236, 249-252, 255-268, 270-276, 288, 304, 348, 355-358, 360-363, 393, 396, 399, 402.

The present invention provides a number of embodiments. It is apparent that the examples may be altered to provide other embodiments of this invention. Therefore, it will be appreciated that the scope of this invention is to be defined by the appended claims rather than by the specific embodiments, which have been represented by way of example.

What is claimed is:

1. A compound having the formula:

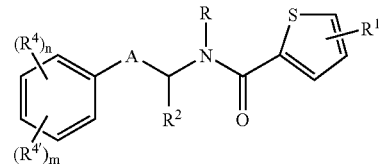

and pharmaceutically acceptable salts thereof, wherein

A represents a five-membered heterocycle containing 1-4 nitrogen atoms; with 0-4 substituents selected from halogen, R$^A$, —OR$^A$, N(R$^A$)$_2$, CO$_2$R$^A$, CON(R$^A$)$_2$, S(O)$_2$ R$^A$, S(O)$_2$N(R$^A$)$_2$, X$^1$OR$^A$, X$^1$CO$_2$R$^A$, X$^1$CON (R$^A$)$_2$, X$^1$N(R$^A$)$_2$, wherein each R$^A$ is independently selected from H, C$_{1-8}$alkyl, C$_{2-8}$alkenyl, C$_{2-8}$alkynyl, or optionally two R$^A$ attached to the same atom are combined to form a 3-, 4-, 5-, 6- or 7-membered ring;

R is a member selected from the group consisting of H and C$_{1-4}$alkyl;

R$^1$ is a member selected from the group consisting of halogen, C$_{1-8}$alkyl, C$_{2-8}$alkenyl and C$_{2-8}$alkynyl;

R$^2$ is a member selected from the group consisting of H, and C$_{1-8}$alkyl, the subscript n is an integer of from 0 to 3 and the subscript m is an integer of from 0 to 1;

R$^4$ is a member selected from the group consisting of halogen, —OR$^{4a}$, —OC(O)R$^{4a}$, —NR$^{4a}$R$^{4b}$, —SR$^{4a}$, S(O)R$^{4a}$, S(O)$_2$R$^{4a}$, S(O)$_2$NR$^{4a}$R$^{4b}$, —R$^{4c}$, —CN, —NO$_2$, —CO$_2$R$^{4a}$, —CONR$^{4a}$R$^{4b}$, —C(O)R$^{4a}$, —OC(O) NR$^{4a}$R$^{4b}$, —NR$^{4b}$C(O)R$^{4a}$, —NR$^{4b}$C(O)$_2$R$^{4c}$, —NR$^{4a}$—C(O)NR$^{4a}$R$^{4b}$, —X$^1$OR$^{4a}$, —X$^1$OC(O)R$^{4a}$, —X$^1$NR$^{4a}$R$^{4b}$, —X$^1$SR$^{4a}$, —X$^1$S(O)R$^{4a}$, —X$^1$S(O)$_2$ R$^{4a}$, —X$^1$CN, —X$^1$NO$_2$, —X$^1$CO$_2$R$^{4a}$—O— X$^1$CO$_2$R$^{4a}$, —X$^1$CONR$^{4a}$R$^{4b}$, —O—X$^1$ CONR$^{4a}$R$^{4b}$, —X$^1$C(O)R$^{4a}$, —O—X$^1$NR$^{4a}$R$^{4b}$, —S(O)X$^1$NR$^{4a}$R$^{4b}$, —S(O)$_2$X$^1$NR$^{4a}$R$^{4b}$, —X$^1$OC(O)NR$^{4a}$R$^{4b}$, —X$^1$NR$^{4a}$C(O)R$^{4a}$, —X$^1$NR$^{4b}$C(O)$_2$R$^{4c}$, —X$^1$NR$^{4a}$C (O)NR$^{4a}$R$^{4b}$, —Y, —X$^1$—Y, —O—Y, —NR$^{4a}$Y,—SY, —S(O)Y and —S(O)$_2$Y;

R$^{4'}$ is a member selected from the group consisting of —C(=NH)R$^{4a}$, —C(=NR$^{4c}$)R$^{4a}$, —C(=NH)NR$^{4a}$R$^{4b}$, —C(=NR$^{4c}$)NR$^{4a}$R$^{4b}$, —C(=N$^+$R$^{4c}$R$^{4c}$)NR$^{4a}$R$^{4b}$, —X$^2$—C(=NH)NR$^{4a}$R$^{4b}$, —X$^2$—C(=NR$^{4c}$)NR$^{4a}$R$^{4b}$, —X$^2$—C(=NR$^+$R$^{4c}$R$^{4c}$)NR$^{4a}$R$^{4b}$ and —C(=NR$^{4a}$) NR$^{4a}$—Y, wherein Y is a five or six-membered aryl, heterocyclyl or aryl-C$_{1-2}$ alkyl, optionally substituted with from one to three substitutents selected from the group consisting of halogen, oxo, —OR$^{4a}$,—OC(O)R$^{4a}$, —NR$^{4a}$R$^{4b}$, —R$^{4c}$, —SR$^{4a}$, S(O)R$^{4a}$, S(O)$_2$R$^{4a}$, S(O)$_2$NR$^{4a}$R$^{4b}$, —CN, —NO$_2$, —CO$_2$R$^{4a}$, —CONR$^{4a}$R$^{4b}$, —C(O)R$^{4a}$, —NR$^{4b}$C(O)R$^{4a}$, —NR$^{4b}$C(O)$_2$R$^{4c}$, —X$^1$R$^{4a}$, —X$^1$OR$^{4a}$, —X$^1$SR$^{4a}$, —X$^1$S(O)R$^{4a}$, —X$^1$S(O)$_2$R$^{4a}$, —X$^1$CN, —X$^1$NO$_2$, —X$^1$CO$_2$R$^{4a}$—X$^1$CONR$^{4a}$R$^{4b}$, —X$^1$C(O)R$^{4a}$, —O—X$^1$NR$^{4a}$R$^{4b}$, —S(O)X$^1$NR$^{4a}$R$^{4b}$, —S(O)$_2$X$^1$NR$^{4a}$R$^{4b}$, —X$^1$OC(O)NR$^{4a}$R$^{4b}$, —X$^1$NR$^{4b}$C(O)R$^{4a}$,—X$^1$NR$^{4b}$C(O)$_2$R$^{4c}$, —X$^1$NR$^{4a}$—C(O)NR$^{4a}$R$^{4b}$, —X$^1$OC(O)R$^{4a}$, —X$^1$NR$^{4a}$R$^{4b}$, —O—X$^1$OR$^{4a}$, —O—X$^1$NR$^{4a}$R$^{4b}$, —O—X$^1$CO$_2$R$^{4a}$, —O—X$^1$CONR$^{4a}$R$^{4b}$, —NR$^{4b}$—X$^1$OR$^{4a}$, —NR$^{4b}$—X$^1$NR$^{4a}$R$^{4b}$, —NR$^{4b}$—X$^1$CO$_2$R$^{4a}$, and —NR$^{4b}$—X$^1$CONR$^{4a}$R$^{4b}$, each $X^1$ and $X^2$ are members independently selected from the group consisting of $C_{1-4}$alkylene, $C_{2-4}$alkenylene and $C_{2-4}$alkynylene;

each $R^{4a}$ and $R^{4b}$ are independently selected from the group consisting of hydrogen, $C_{1-8}$alkyl, $C_{1-8}$haloalkyl, $C_{3-6}$cycloalkyl, $C_{3-6}$heterocycloalkyl, $C_{2-8}$alkenyl, $C_{2-8}$alkynyl, aryl, heteroaryl, aryl-$C_{1-4}$alkyl, and aryloxy-$C_{1-4}$alkyl, each $R^{4c}$ is independently selected from the group consisting of $C_{1-8}$alkyl, $C_{1-8}$haloalkyl, $C_{3-6}$cycloalkyl, $C_{3-6}$heterocycloalkyl, $C_{2-8}$alkenyl, $C_{2-8}$alkynyl, aryl, heteroaryl, aryl-$C_{1-4}$alkyl, and aryloxy-$C_{1-4}$alkyl, optionally any two of $R^{4a}$, $R^{4b}$ and $R^{4c}$ when part of a common $R^4$ or $R^{4'}$ substituent can be combined with the atoms to which each is attached to form a saturated or unsaturated, four to nine-membered mono- or bicyclic ring having from 0 to 2 additional heteroatoms as ring members; and each of $R^{4a}$, $R^{4b}$ and $R^{4c}$ is optionally further substituted with from one to three members selected from the group consisting of —OH, oxo, —$R^m$, —$OR^m$, —OC(O)NHR$^m$, —OC(O)N(R$^m$)$_2$, —SH, —SR$^m$, —S(O)R$^m$, —S(O)$_2$R$^m$, —SO$_2$NH$_2$, —S(O)$_2$NHR$^m$, —S(O)$_2$N(R$^m$)$_2$, —NHS(O)$_2$R$^m$, —NR$^m$S(O)$_2$R$^m$, —C(O)NH$_2$, —C(O)NHR$^m$, —C(O)N(R$^m$)$_2$, —C(O)R$^m$, —NHC(O)R$^m$, —NR$^m$C(O)R$^m$, —NHC(O)NH$_2$, —NR$^m$C(O)NH$_2$, —NR$^m$C(O)NHR$^m$, —NHC(O)NHR$^m$, —NR$^m$C(O)N(R$^m$)$_2$, —NHC(O)N(R$^m$)$_2$, —CO$_2$H, —CO$_2$R$^m$, —NHCO$_2$R$^m$, —NR$^m$CO$_2$R$^m$, —CN, —NO$_2$, —NH$_2$, —NHR$^m$, —N(R$^m$)$_2$, —NR$^m$S(O)NH$_2$ and —NR$^m$S(O)$_2$NHR$^m$, wherein each R$^m$ is independently an unsubstituted $C_{1-6}$alkyl, benzyl or combined with the atoms to which each is attached to form a saturated four-, five-, six- or seven-membered ring having from 0 to 2 additional heteroatoms as ring members.

2. The compound of claim 1, wherein m is 1 and $R^{4'}$ is selected from the group consisting of:

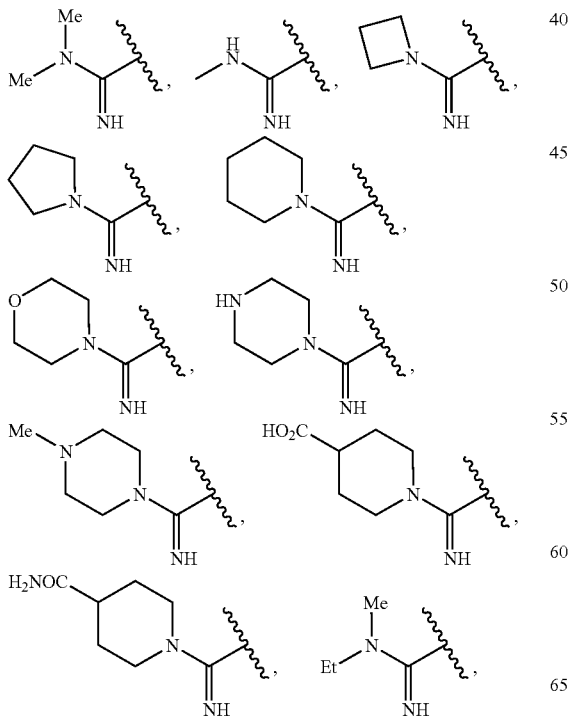

-continued

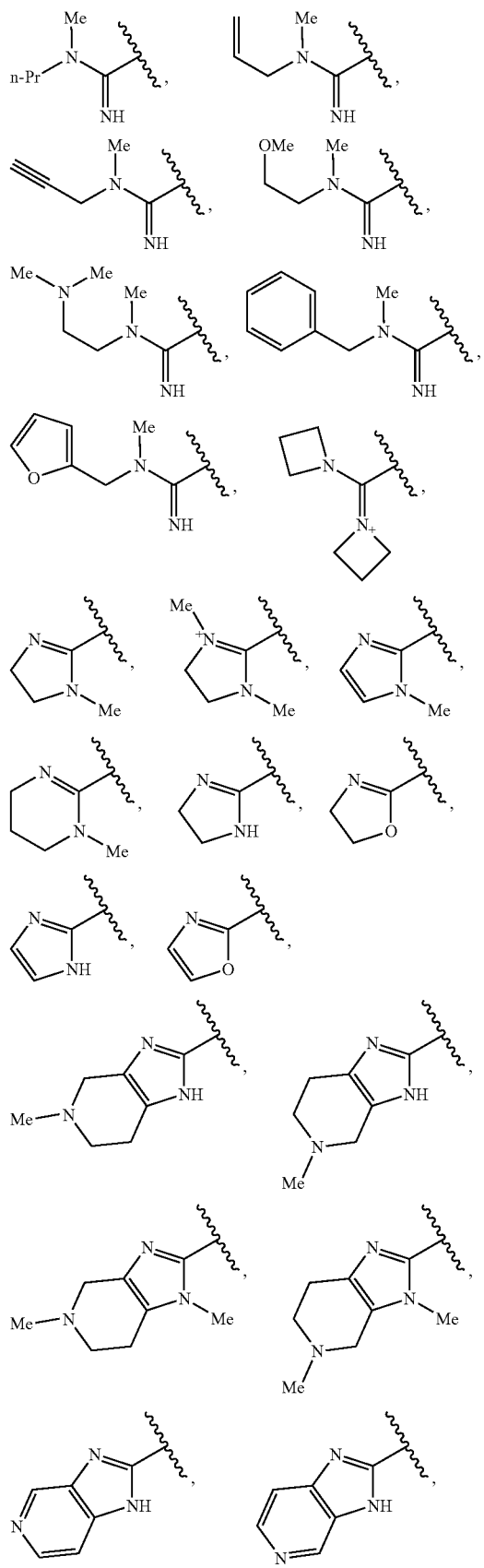

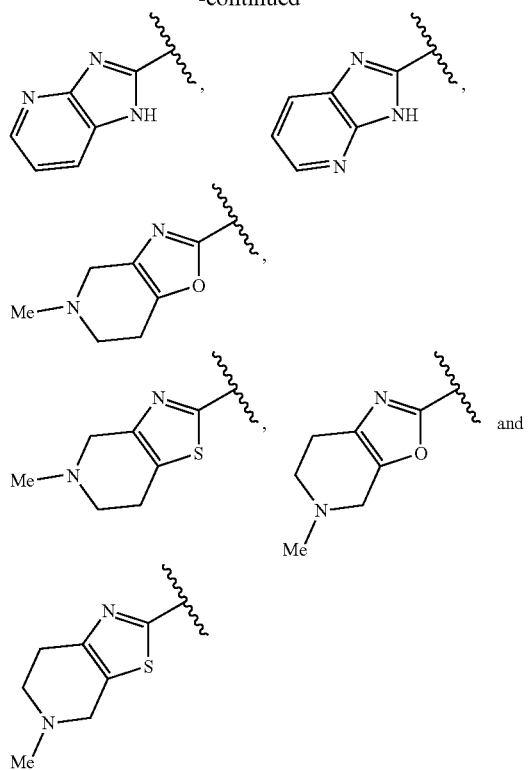

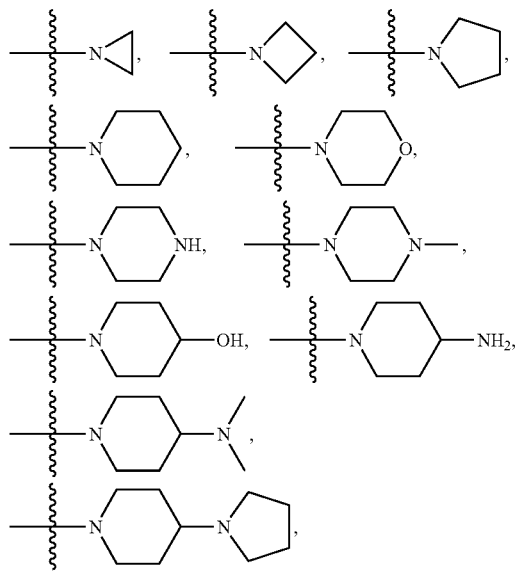

and the wavy line indicates the point of attachment to the rest of the molecule.

3. The compound of claim 1 wherein n is 1 and $R^4$ is selected from the group consisting of H, halogen, $OR^{4a}$, $C_{1-4}$alkyl, $SR^{4a}$, $S(O)R^{4a}$, $S(O)_2R^{4a}$, $S(O)_2N(R^{4a}R^{4b})$, $NR^{4a}R^{4b}$, $C_{1-4}$alkyl$OR^{4a}$, $C_{1-4}$alkyl$NR^{4a}R^{4b}$, $C_{1-4}$alkyl$CO_2R^{4a}$, $OC_{1-4}$alkyl$OR^{4a}$, $OC_{1-4}$alkyl$N(R^{4a}N^{4b})$, $N(R^{4a})C_{1-4}$alkyl$OR_{4b}$, $N(R^{4a})C_{1-4}$alkyl$N(R^{4a}R^{4b})$, $S(O)_2 C_{1-4}$ alkyl$N(R^{4a}R^{4b})$,

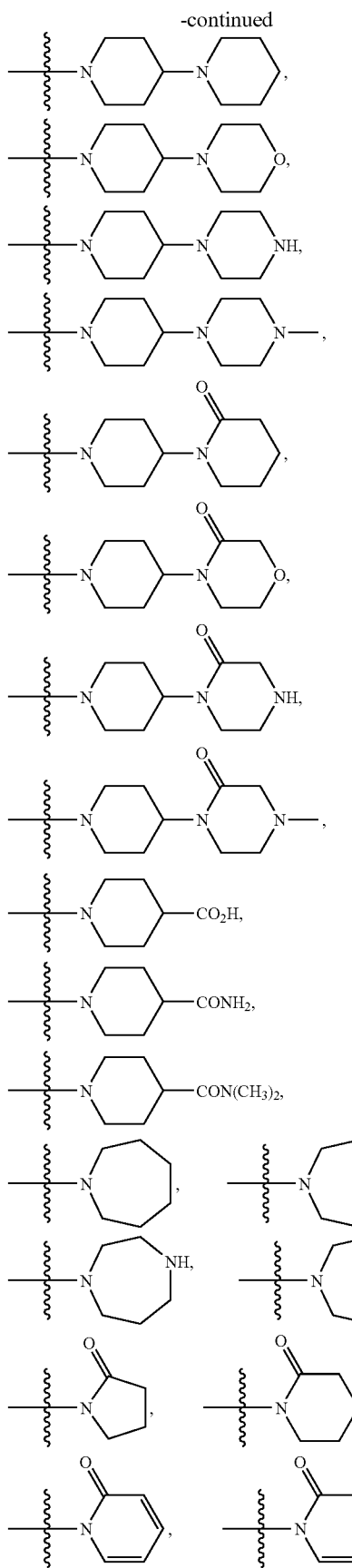

-continued
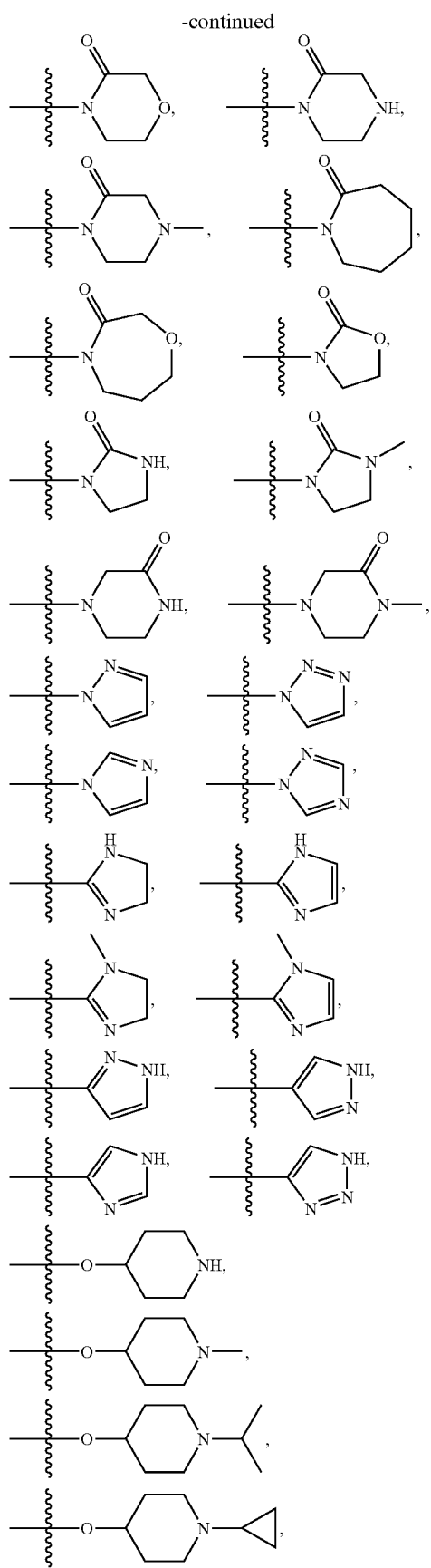
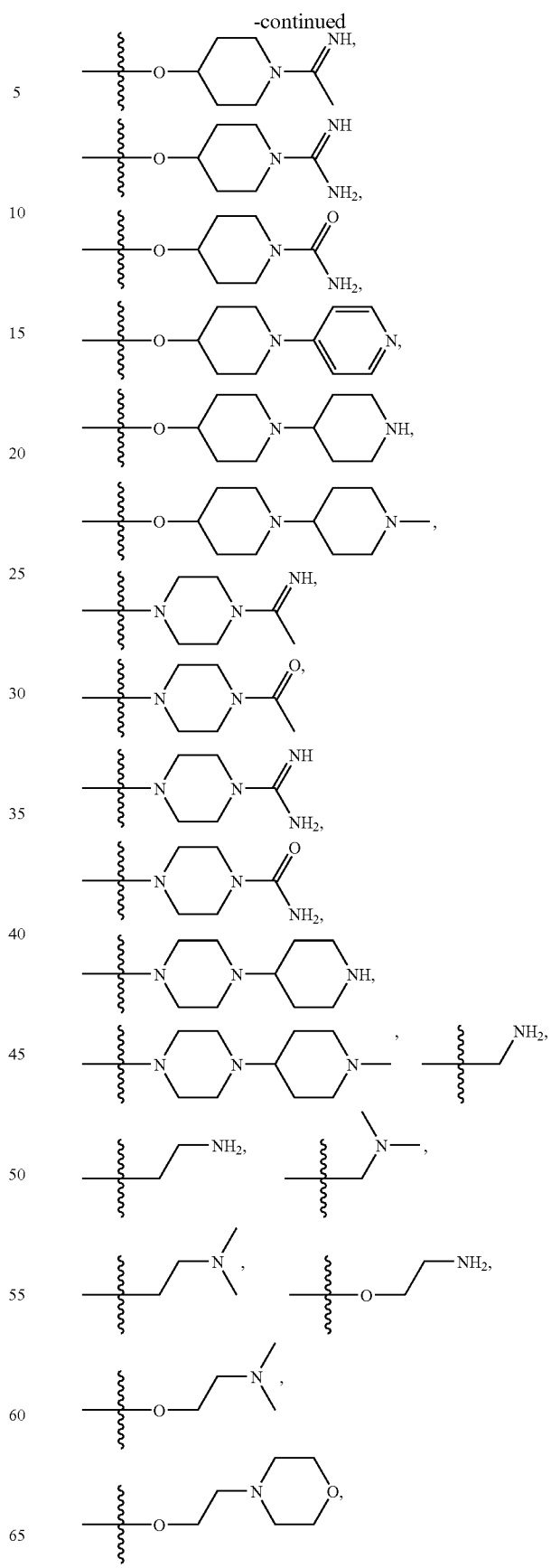

-continued
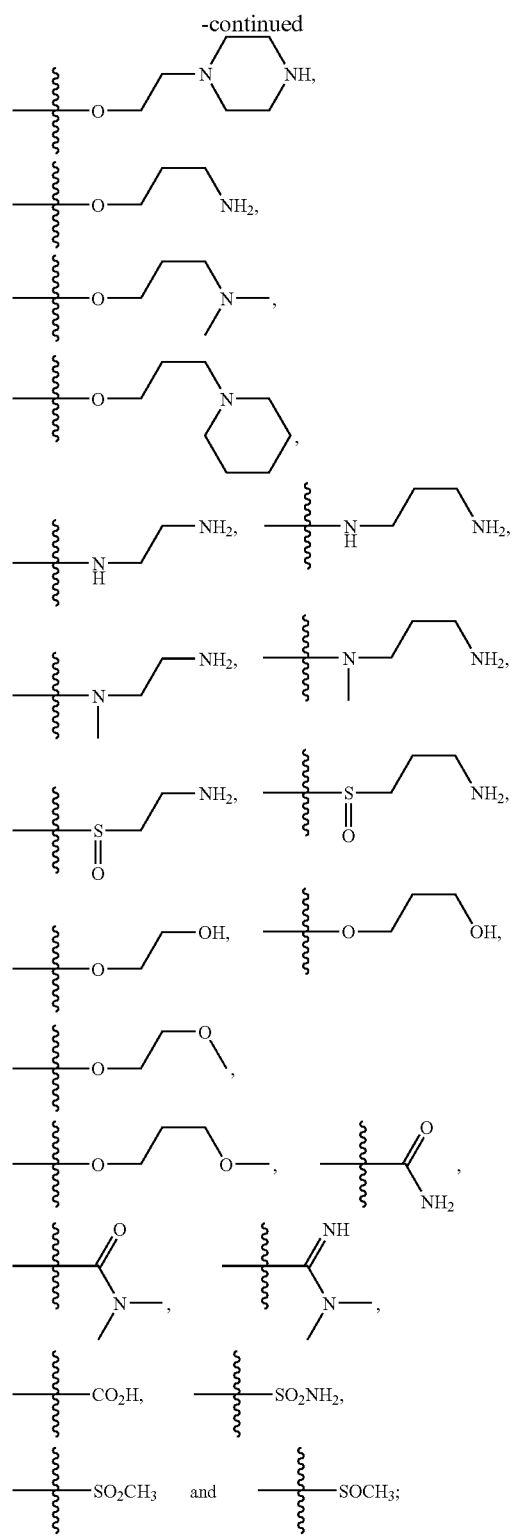
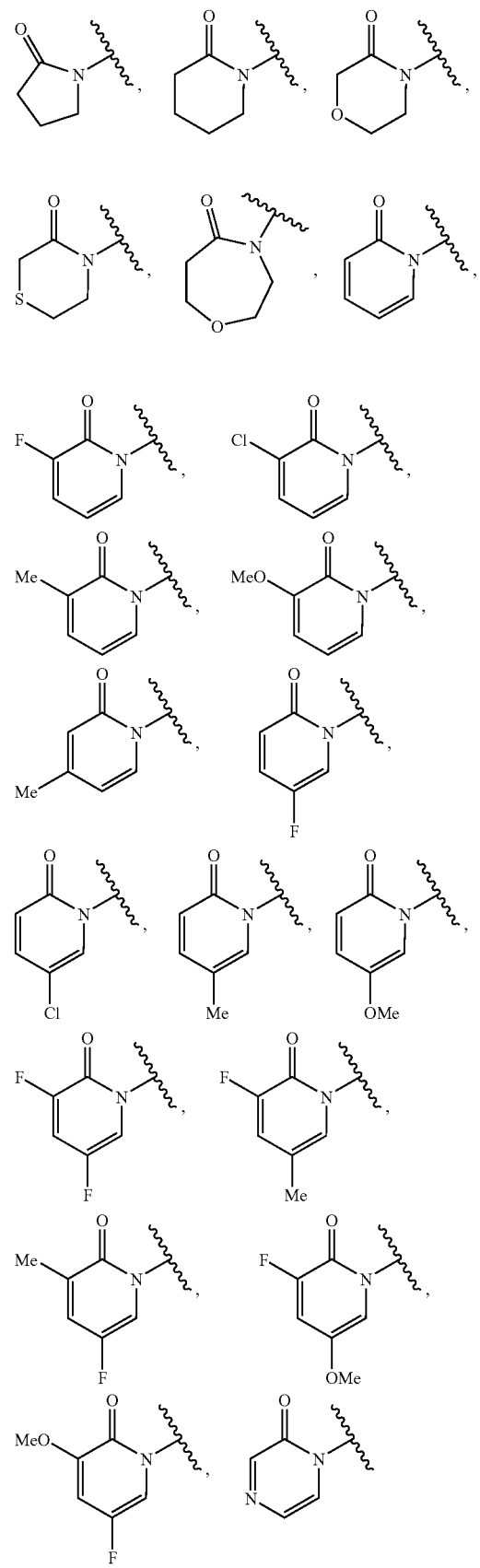
each $R^{4a}$ is independently H or $C_{1-4}$alkyl; each $R^{4d}$ is independently selected from the group consisting of H, OH, $NH_2$, $N(CH_3)_2$, $CONH_2$ and $CON(CH_3)_2$; and the wavy line indicates the point of attachment to the rest of the molecule.
4. The compound of claim 1, wherein n is 1 and $R^4$ is selected from the group consisting of:

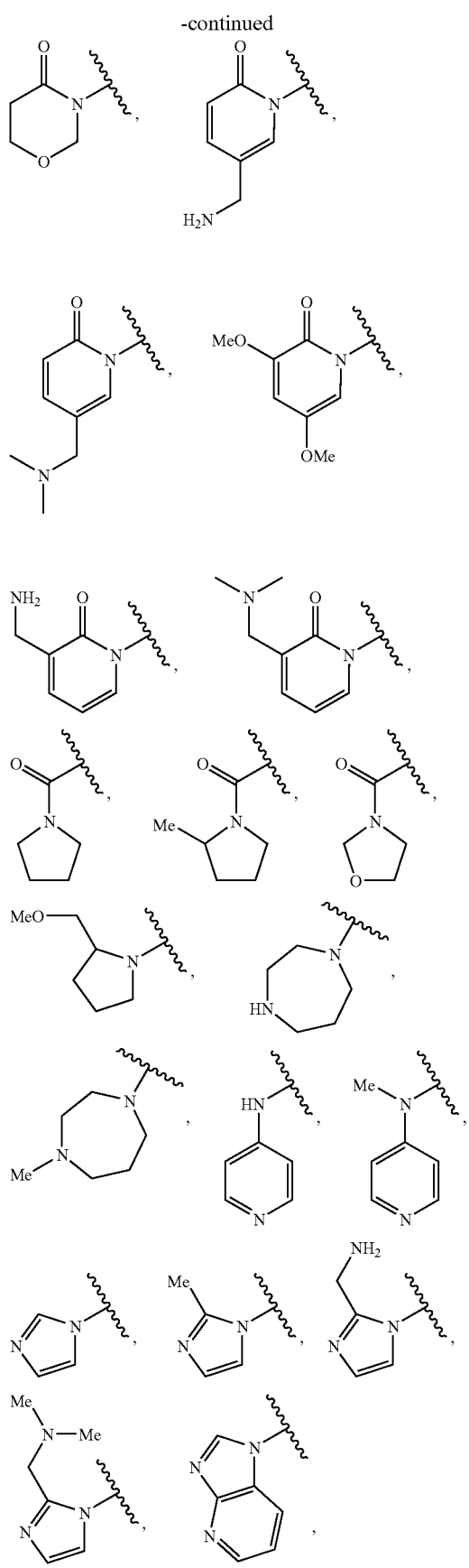

and the wavy line indicates the point of attachment to the rest of the molecule.

5. The compound of any one of claims 1, and 2 to 4, wherein $R^{4'}$ is attached to the ring at a position para to A.

6. The compound of any of claims 1, and 2 to 4, wherein $R^4$ is attached to the ring at a position ortho to A.

7. The compound of any of claims 1, and 2 to 4, wherein Y is an optionally substituted member selected from the group consisting of phenyl, benzyl, pyridyl, pyridylmethyl, pyrimidinyl, pyrazolyl, triazolyl and imidazolyl.

8. The compound of any of claims 1, 3 and 4, wherein m is 1.

9. The compound of claim 1, wherein $R^4$ is selected from the group consisting of:

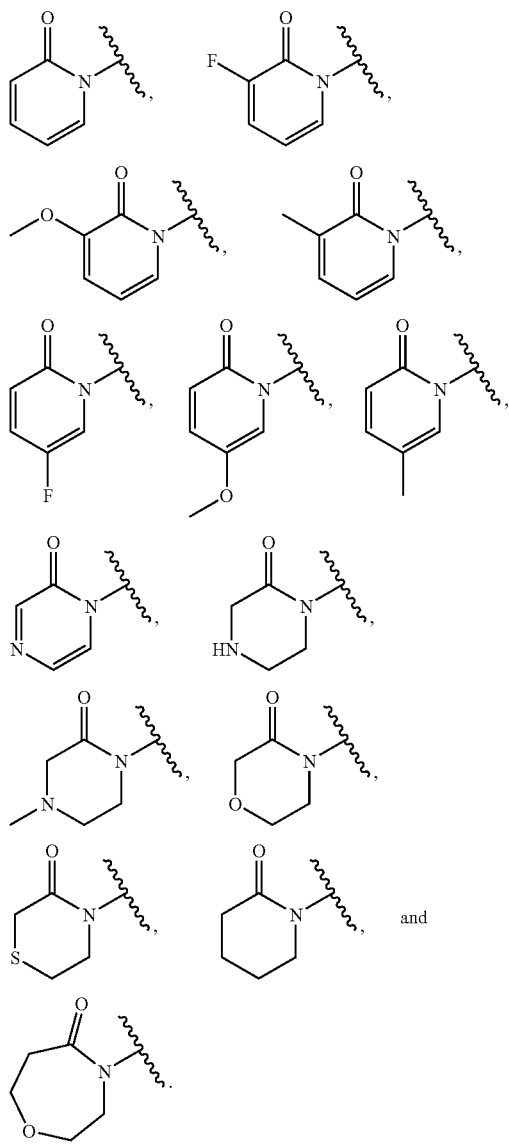
10. The compound of claim 8, wherein $R^{4'}$ is attached to the phenyl ring at a position para to the ring A.
11. The compound of claim 1, wherein A is a member selected from the group consisting of pyrazole, imidazole, pyrazoline, imidazoline, 1,2,3-triazole, 1,2,4-triazole, pyrrolidine, and pyrrole.
12. The compound of claim 11, wherein A is selected from the group consisting of:
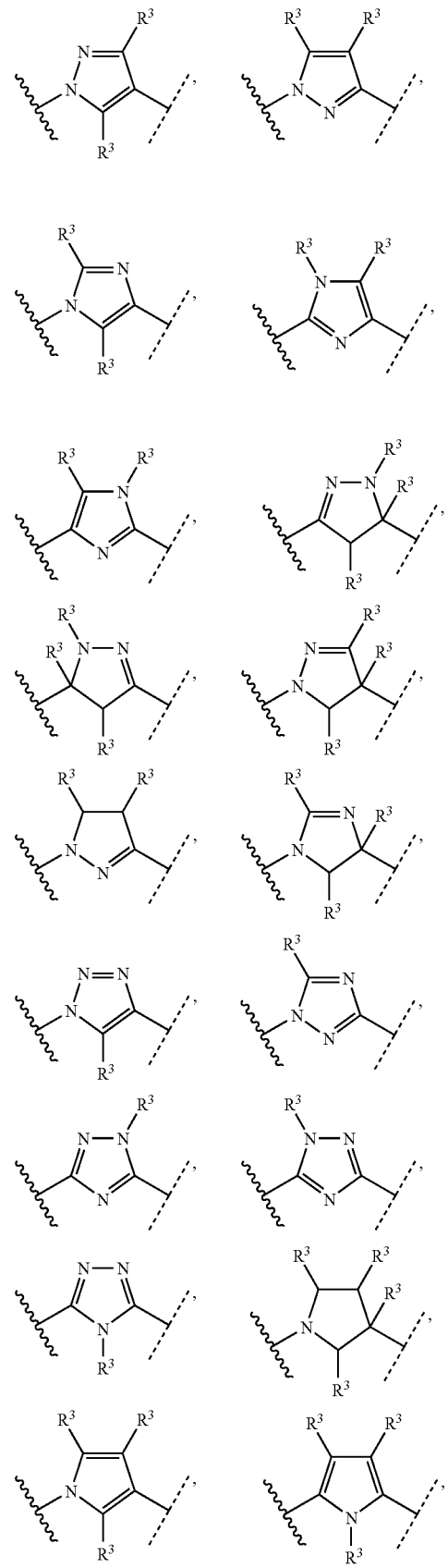

-continued

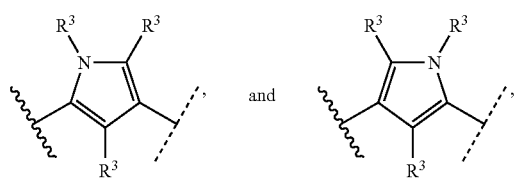

each R³ is independently selected from the group consisting of halogen, $C_{1-8}$alkyl, $C_{2-8}$alkenyl, $C_{2-8}$alkynyl, $OR^{3a}$, $N(R^{3a})_2$, $X^0CO_2R^{3a}$, $X^0CON(R^{3a})_2$, $SO_2C_{1-4}$alkyl, $SO_2N(R^{3a})_2$; each $R^{3a}$ is independently selected from the group consisting of H, $C_{1-8}$alkyl, $C_{2-8}$alkenyl and $C_{2-8}$alkynyl; and $X^0$ is a bond or $C_{1-8}$alkylene; and the wavy line indicates the point of attachment to the phenyl ring, and the dashed line indicates the point of attachment to the rest of the molecule.

13. The compound of claim 11 or claim 12, wherein m is 1.

14. The compound of claim 13, wherein $R^4$ is selected from the group consisting of:

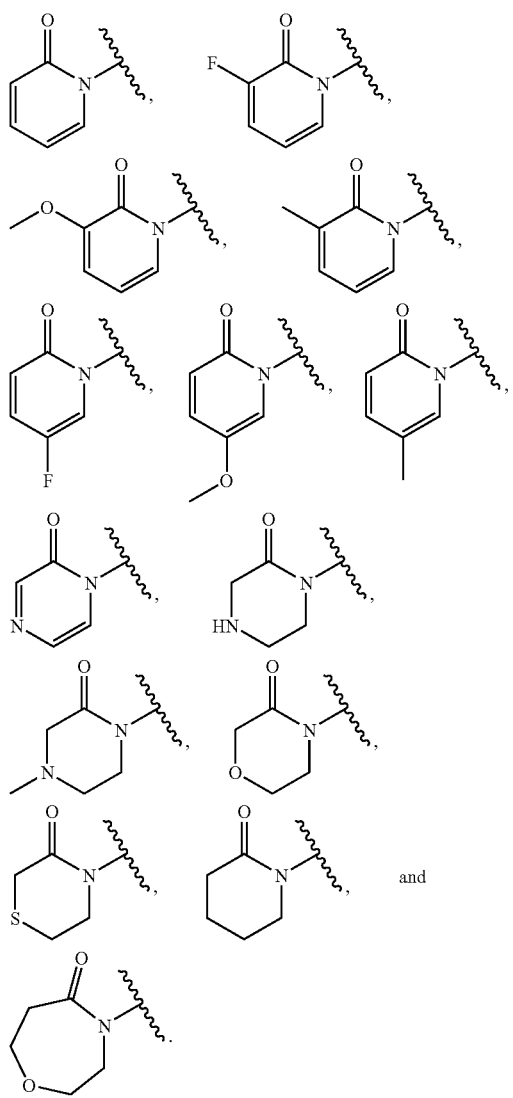

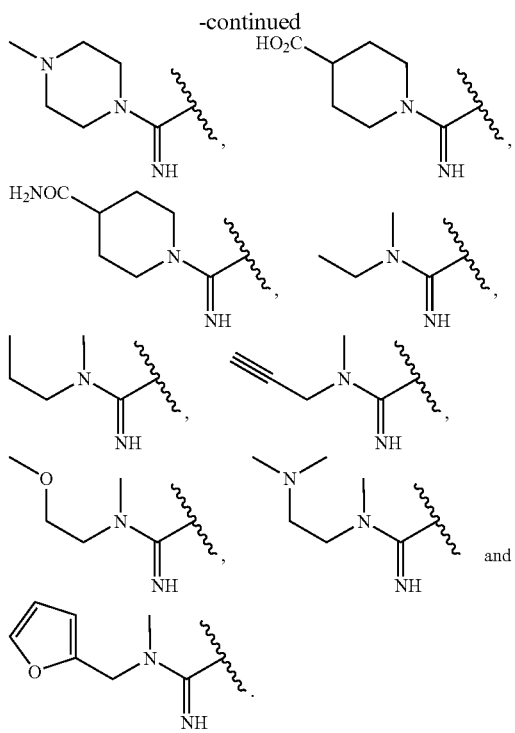

15. The compound of claim 11 or claim 12, wherein $R^{4'}$ is attached to the phenyl ring at a position para to A.

16. The compound of claim 11 or claim 12 wherein the subscript n is an integer of from 0 to 1.

17. The compound of claim 11 or claim 12, wherein the subscript n is 1; $R^4$ is attached to the phenyl ring at a position ortho to A and $R^{4'}$ is attached to the phenyl ring at a position para to A.

18. The compound of claim 11 or claim 12, wherein $R^4$ is selected from the group consisting of halogen, —$OR^{4a}$, —$NR^{4a}R^{4b}$, —$SR^{4a}$, —Y, —$X^1$—Y, —O—Y, —$NR^{4a}$Y and —SY.

19. The compound of claim 11 or claim 12, wherein n is 0, 1 or 2, and $R^4$ is independently selected from the group consisting of H, halogen, $OR^{4a}$, $C_{1-4}$ alkyl, $SR^{4a}$, $S(O)R^{4a}$, $S(O)_2R^{4a}$, $S(O)_2N(R^{4a}R^{4b})$, $NR^{4a}R^{4b}$, $C_{1-4}$alkyl$OR^{4a}$, $C_{1-4}$alkyl$NR^{4a}R^{4b}$, $C_{1-4}$alkyl$CO_2R^{4a}$, $OC_{1-4}$alkyl$OR^{4a}$, $OC_{1-4}$alkyl$N(R^{4a}N^{4b})$, $N(R^{4a})C_{1-4}$alkyl$OR^{4b}$, $N(R^{4a})C_{1-4}$alkyl$N(R^{4a}R^{4b})$, $S(O)_2C_{1-4}$alkyl$N(R^{4a}R^{4b})$, -continued
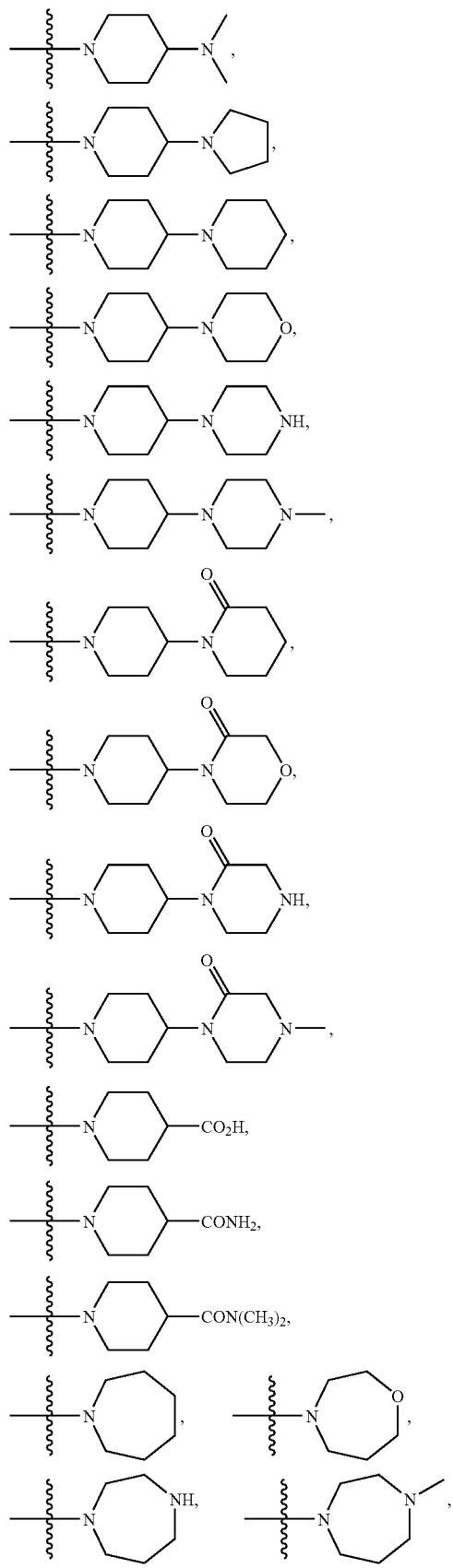
-continued
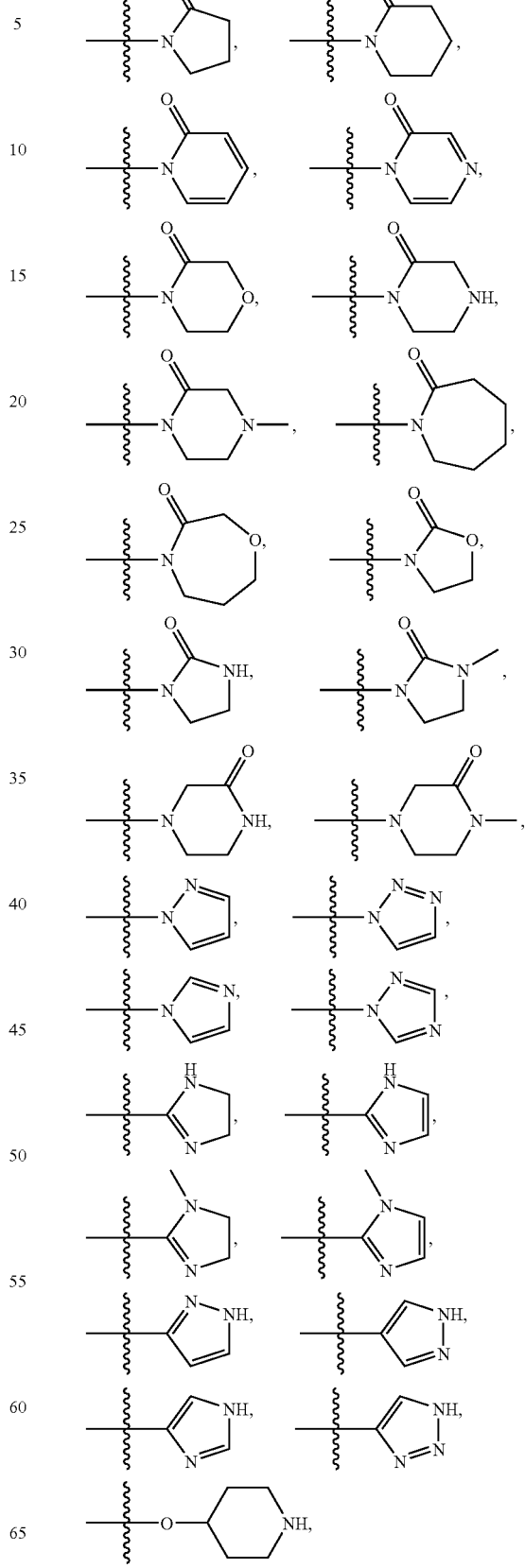

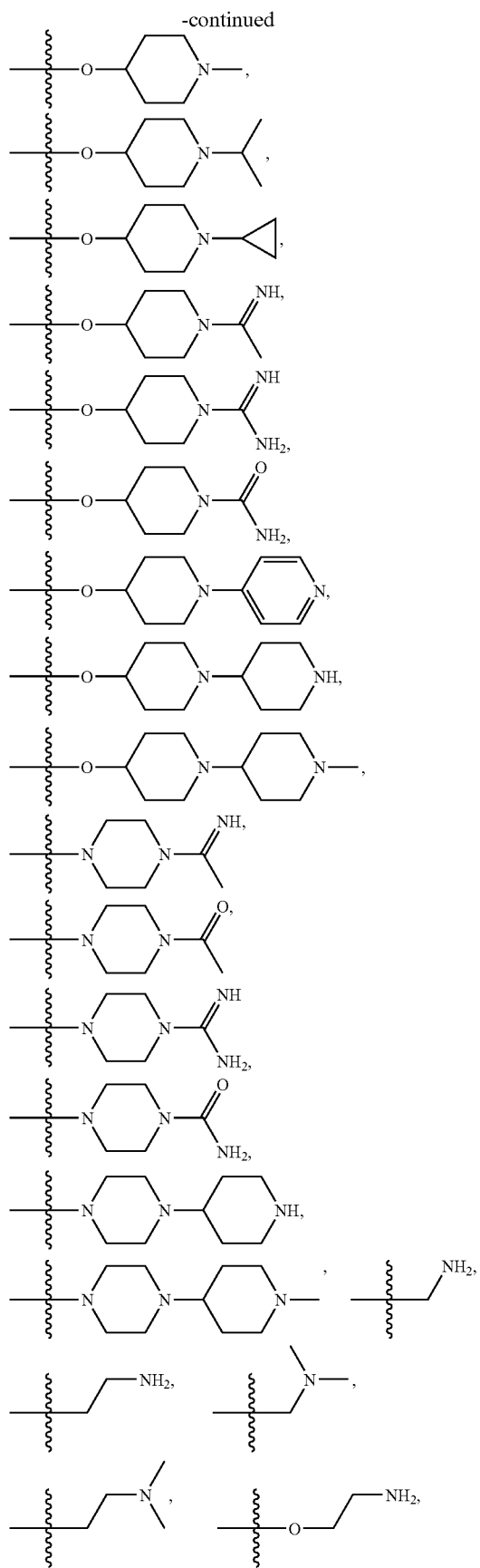
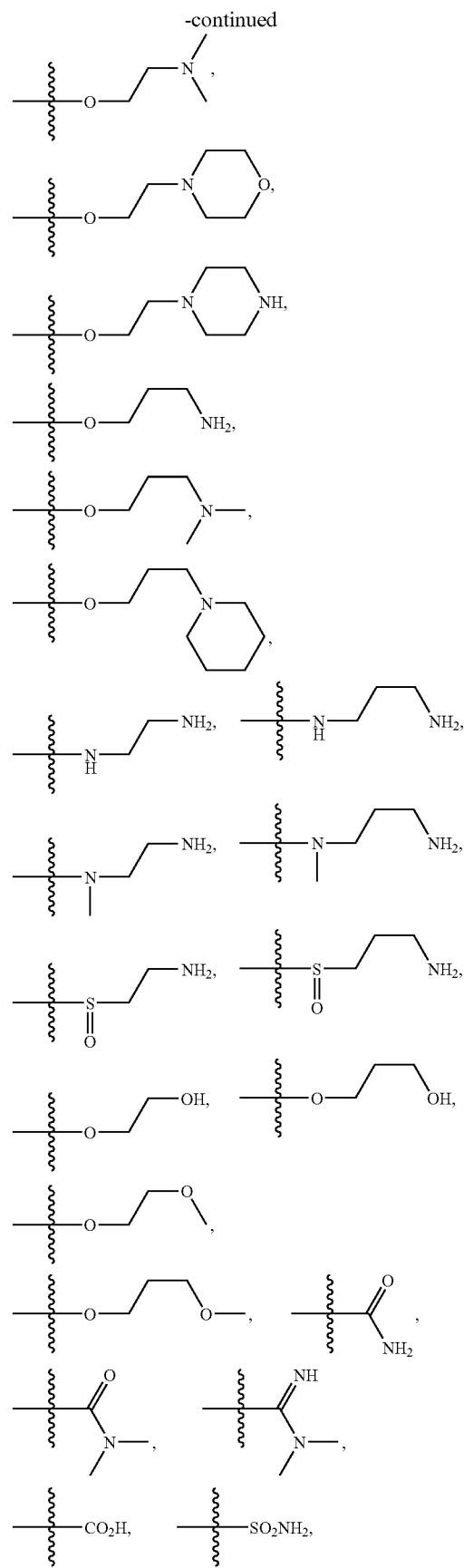

-continued

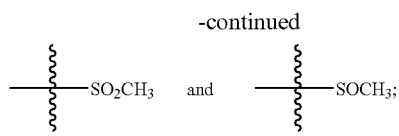

each $R^{4a}$ is independently H or $C_{1-4}$alkyl; each $R^{4d}$ is independently selected from the group consisting of H, OH, $NH_2$, $N(CH_3)_2$, $CONH_2$ and $CON(CH_3)_2$; and the wavy line indicates the point of attachment to the rest of the molecule, and wherein m is 0 or 1, and $R^{4'}$ is selected from the group consisting of

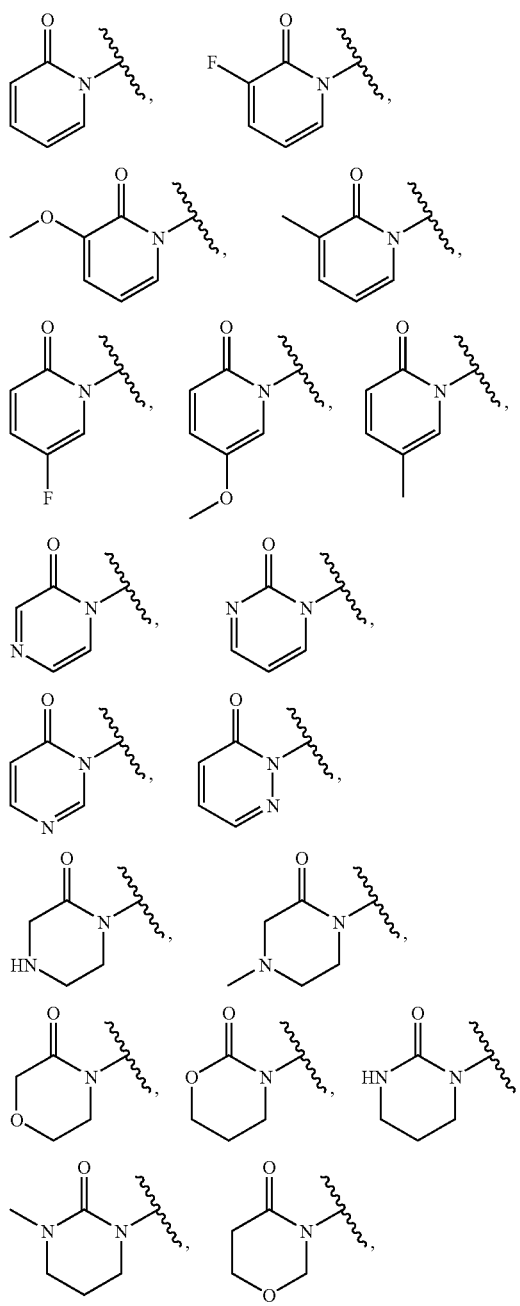

-continued

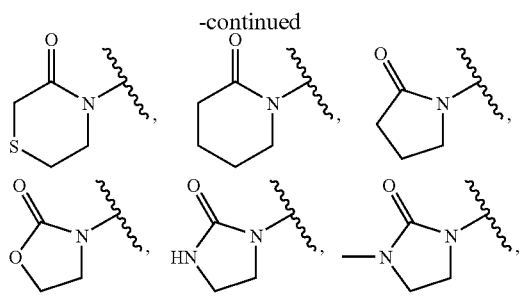

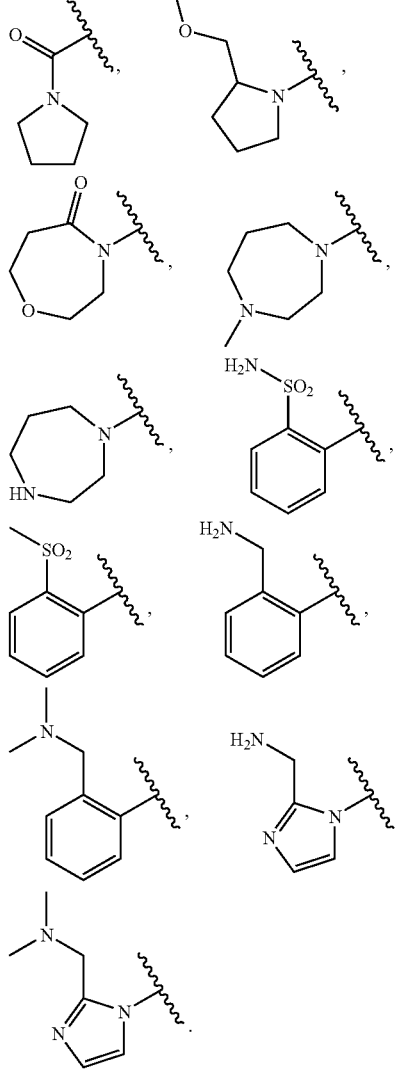

20. The compound of claim 11 or claim 12, wherein m is 0 or 1; n is 0, 1 or 2; and at least one $R^4$ is selected from the group consisting of —Y, —$X^1$—Y, —O—Y, —$NR^{4a}$Y, —SY, —S(O)Y and —S(O)$_2$Y, wherein Y is an optionally substituted member selected from the group consisting of phenyl, benzyl, pyridyl, pyridylmethyl, pyrimidinyl and pyrazolyl.

21. The compound of claim 20, wherein $R^4$ is selected from the group consisting of —Y, —$X^1$—Y, —O—Y and —$NR^{4a}$Y, wherein Y is an optionally substituted member selected from the group consisting of phenyl, benzyl, pyridyl and pyridylmethyl.

22. The compound of claim 21, wherein the optional substituents are selected from the group consisting of halogen, —OR$^{4a}$, —NR$^{4a}$R$^{4b}$, —R$^{4c}$, —SR$^{4a}$, —CO$_2$R$^{4a}$, —CONR$^{4a}$R$^{4b}$, —C(O)R$^{4a}$, —X$^1$OR$^{4a}$ and —X$^1$NR$^{4a}$R$^{4b}$.

23. The compound of claim 11 or claim 12, wherein when R$^2$ is present the carbon attached to R$^2$ has the R-configuration.

24. The compound of claim 12, wherein when R$^3$ is other than H the carbon attached to R$^3$ has the R-configuration.

25. A compound selected from the group consisting of: 5-Chloro-N-((1-(4-(2-oxopyridin-1(2H)-yl)phenyl)-1H-1,2,3-triazol-4-yl)methyl)thiophene-2-carboxamide; 5-Chloro-N-((1-(4-(3-fluoro-2-oxopyridin-1(2H)-yl)phenyl)-1H-1,2,3-triazol-4-yl)methyl)thiophene-2-carboxamide; 5-Chloro-N-((1-(4-(3-chloro-2-oxopyridin-1(2H)-yl)phenyl)-1H-1,2,3-triazol-4-yl)methyl)thiophene-2-carboxamide; 5-Chloro-N-((1-(4-(3-methyl-2-oxopyridin-1(2H)-yl)phenyl)-1H-1,2,3-triazol-4-yl)methyl)thiophene-2-carboxamide; 5-Chloro-N-((1-(4-(3-methoxy-2-oxopyridin-1(2H)-yl)phenyl)-1H-1,2,3-triazol-4-yl)methyl)thiophene-2-carboxamide; 5-Chloro-N-((1-(4-(4-methyl-2-oxopyridin-1(2H)-yl)phenyl)-1H-1,2,3-triazol-4-yl)methyl)thiophene-2-carboxamide; 5-Chloro-N-((1-(4-(5-methyl-2-oxopyridin-1(2H)-yl)phenyl)-1H-i,2,3-triazol-4-yl)methyl)thiophene-2-carboxamide; 5-Chloro-N-((1-(4-(5-methoxy-2-oxopyridin-1(2H)-yl)phenyl)-1H-1,2,3-triazol-4-yl)methyl)thiophene-2-carboxamide; 5-Chloro-N-((1-(4-(5-fluoro-2-oxopyridin-1(2H)-yl)phenyl)-1H-1,2,3-triazol-4-yl)methyl)thiophene-2-carboxamide; 5-Chloro-N-((1-(4-(5-chloro-2-oxopyridin-1(2H)-yl)phenyl)-1H-1,2,3-triazol-4-yl)methyl)thiophene-2-carboxamide; 5-Chloro-N-((1-(4-(2-oxopiperidin-1-yl)phenyl)-1H-1,2,3-triazol-4-yl)methyl)thiophene-2-carboxamide; 5-Chloro-N-((1-(4-(3-oxomorpholino)phenyl)-1H-1,2,3-triazol-4-yl)methyl)thiophene-2-carboxamide; 5-Chloro-N-((1-(4-(3-oxothiomorpholino)phenyl)-1H-1,2,3-triazol-4-yl)methyl)thiophene-2-carboxamide; 5-Chloro-N-((1-(4-(5-oxo-1,4-oxazepan-4-yl)phenyl)-1H-1,2,3-triazol-4-yl)methyl)thiophene-2-carboxamide; 5-Chloro-N-((1-(2-fluoro-4-jodophenyl)-1H-1,2,3-triazol-4-yl)methyl)thiophene-2-carboxamide; 5-Chloro-N-((1-(2-fluoro-4-(2-oxopyridin-1(2H)-yl)phenyl)-1H-1,2,3-triazol-4-yl)methyl)thiophene-2-carboxamide; 5-Chloro-N-((1-(2-fluoro-4-(3-oxomorpholino)phenyl)-111-1,2,3-triazol-4-yl)methyl)thiophene-2-carboxamide; 5-Chloro-N-((1-(2-hyroxy-4-(2-oxopyridin-1(2H)-yl)phenyl)-111-1,2,3-triazol-4-yl)methyl)thiophene-2-carboxamide; 5-Chloro-N-(( 1-(2-(4-methylpiperazin- 1-yl)-4-(2-oxopyridin-1(2H)-yl)phenyl)-111-1,2,3-triazol-4-yl)methyl)thiophene-2-carboxamide; 5-Chioro-N-(( 1-(5-(2-oxopyridin-1(211)-yl)pyridin-2-yl)-111-1,2,3-triazol-4-yl)methyl)thiophene-2-carboxamide; 5-Chloro-N-(( 1-(4-( 1-methyl-4,5-dihydro-1H-imidazol-2-yl)phenyl)-111-1,2,3-triazol-4-yl)methyl)thiophene-2-carboxamide; N-(( 1-(4-(N,N-Dimethylcarbamimidoyl)phenyl) -111-1,2,3-triazol-4-yl)methyl)-5-chlorothiophene-2-carboxamide; N-(( 1-(4-(N-Ethyl-N -methylcarbamimidoyl)phenyl)-111-1,2,3-triazol-4-yl)methyl)-5-chlorothiophene-2-carboxamide; N-(( 1-(4-(N-Methyl-N-propylcarbamimidoyl)phenyl)-1H-1,2,3-triazol-4-yl)methyl)-5-chlorothiophene-2-carboxamide; N-(( 1-(4-(N-(2-Methoxyethyl)-N -methylcarbamimidoyl)phenyl)-111-1,2,3-triazol-4-yl)methyl)-5-chlorothiophene-2-carboxamide; N-(( I -(4-(Azetidin-1-yl(imino)methyl)phenyl)-111-1,2,3-triazol-4-yl)methyl)-5-chiorothiophene-2-carboxamide; 5-Chloro-N-(( 1-(4-(imino(pyrrolidin-1-yl)methyl)phenyl)-111-1,2,3-triazol-4-yl)methyl)thiophene-2-carboxamide; 5-Chloro-N-(( 1-(4-(imino(piperidin-1-yl)methyl)phenyl) -111-1,2,3-triazol-4-yl)methyl)thiophene-2-carboxamide; N-(( 1-(4-(N,N -Dimethylcarbamimidoyl)-2-fluorophenyl)-111-1,2,3-triazol-4-yl)methyl)-5-chlorothiophene-2-carboxamide; N-(( 1-(4-(Azetidin-1-yl(imino)methyl)-2-fluorophenyl)-111-1,2,3-triazol-4-yl)methyl)-5-chlorothiophene-2-carboxamide; 5-Chloro-N-(( 1-(2-fluoro-4-(imino(pyrrolidin-1-yl)methyl)phenyl)-111-1,2,3-triazol-4-yl)methyl)thiophene-2-carboxamide; 5-Chloro-N-(( 1-(2-fluoro-4-(imino(piperidin-1-yl)methyl)phenyl)-111-1,2,3-triazol-4-yl)methyl)thiophene-2-carboxamide; 5-Chloro-N-(( 1-(2-fluoro-4-( 1-methyl-4,5-dihydro-1H-imidazol-2-yl)phenyl)-111-1,2,3-triazol-4-yl)methyl)thiophene-2-carboxamide; N-(( 1-(4-(N,N -Dimethylcarbamimidoyl)phenyl)-1H-pyrazol-4-yl)methyl)-5-chlorothiophene-2-carboxamide; 5-Chloro-N-(( 1-(4-( 1-methyl-4,5-dihydro-1H-imidazol-2-yl)phenyl)-1H-pyrazol-4-yl)methyl)thiophene-2-carboxamide; N-(( 1-(4-(Azetidin-1-yl(imino)methyl)phenyl)-1H-pyrazol -4-yl)methyl)-5-chlorothiophene-2-carboxamide; 5-Chloro-N-(( 1-(4-(imino(pyrrolidin-1-yl)methyl)phenyl)-1H-pyrazol-4-yl)methyl)thiophene-2-carboxamide; 5-Chloro-N-(( 1-(4-(imino(piperidin-1-yl)methyl)phenyl)-1H-pyrazol-4-yl)methyl)thiophene-2-carboxamide; Chloro-N-(( 1-(4-( 1-methyl-4,5-dihydro-1H-imidazol-2-yl)phenyl)-1H-imidazol-4-yl)methyl)thiophene-2-carboxamide; N-(( 1-(4-(Azetidin-1-yl(imino)methyl)phenyl)-1H -imidazol-4-yl)methyl)-5-chlorothiophene-2-carboxamide; 5-Chloro-N-(( 1-(4-(imino(pyrrolidin -1-yl)methyl)phenyl)-1H-imidazol-4-yl)methyl)thiophene-2-carboxamide; and 5-Chloro-N-(( 1-(4-(imino(piperidin-1-yl)methyl)phenyl)-1H-imidazol-4-yl)methyl)thiophene-2-carboxamide.

26. A composition comprising a pharmaceutically acceptable excipient and a compound of any of claims 1, 2-4, 9, 11, 12, and 25.

27. A method for lipreventing oril treating a condition in a mammal characterized by undesired thrombosis comprising the step of administering to said mammal a therapeutically effective amount of a compound of any of claims 1, 2-4, 9, 11, 12, and 25.

28. The method in accordance with claim 27, wherein the condition is selected from the group consisting of acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient isehemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, and conditions requiring the fitting of prosthetic devices.

29. The method for inhibiting the coagulation of a blood sample in vitro comprising contacting said sample with a compound of any of claims 1, 2- 4, 9, 11, 12, and 25.

* * * * *

UNITED STATES PATENT AND TRADEMARK OFFICE
CERTIFICATE OF CORRECTION

| | |
|---|---|
| PATENT NO. | : 7,521,470 B2 |
| APPLICATION NO. | : 11/158274 |
| DATED | : April 21, 2009 |
| INVENTOR(S) | : Zhu et al. |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 297 days Delete the phrase "by 297 days" and insert -- by 483 days --

Signed and Sealed this

Fourth Day of May, 2010

David J. Kappos
*Director of the United States Patent and Trademark Office*

UNITED STATES PATENT AND TRADEMARK OFFICE
CERTIFICATE OF CORRECTION

PATENT NO.      : 7,521,470 B2
APPLICATION NO. : 11/158274
DATED           : April 21, 2009
INVENTOR(S)     : Bing-Yan Zhu et al.

It is certified that error appears in the above-identified patent and that said Letters Patent is hereby corrected as shown below:

IN THE CLAIMS:

In Column 244, Claim 1, Line 48, please replace, "-$X^2$-C(=NR$^+$R$^{4c}$R$^{4c}$)NR$^{4a}$R$^{4b}$" with -- -$X^2$-C(=N$^+$R$^{4c}$R$^{4c}$)NR$^{4a}$R$^{4b}$ --.

In Column 246, Claim 2, Line 35, please remove structure,

In Column 246, Claim 2, Line 40, please remove structure,

In Column 247, Claim 2, Lines 10 through 30, please remove structures,

Signed and Sealed this

Sixteenth Day of November, 2010

David J. Kappos
*Director of the United States Patent and Trademark Office*

CERTIFICATE OF CORRECTION (continued)
U.S. Pat. No. 7,521,470 B2

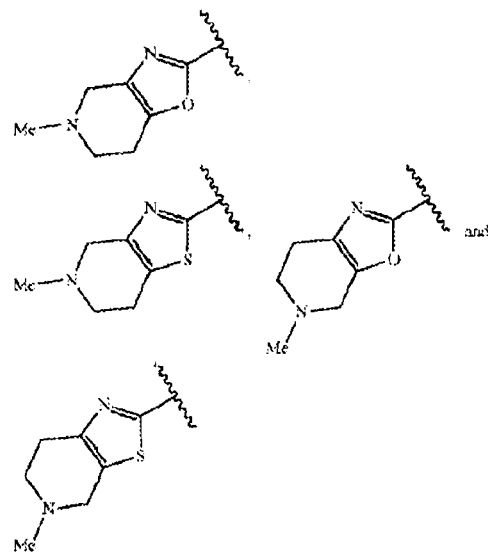

In Column 258, Claim 14, Lines 1 through 30, please remove structures,

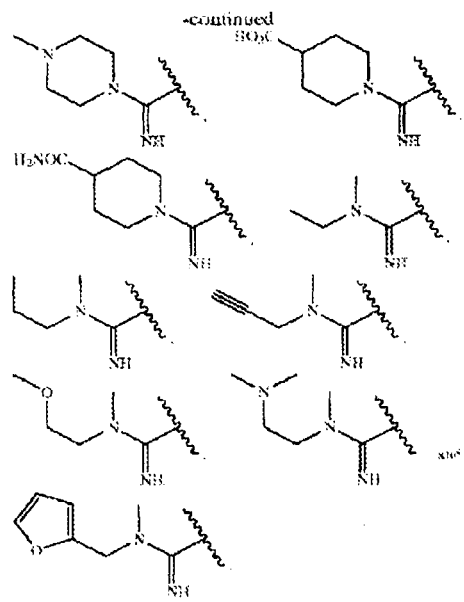

In Column 265, Claim 25, Line 24, please replace "phenyl)-1H-i" with -- phenyl)-1H-1 --.

In Column 265, Claim 25, Line 39, please replace "5-Chloro-N-((1-(2-fluoro-4-jodophenyl)-1H-1,2,3-triazol-4-yl)methyl)thiophene-2-carboxamide;" with -- 5-Chloro-N-((1-(2-fluoro-4-iodophenyl)-1H-1,2,3-triazol-4-yl)methyl)thiophene-2-carboxamide; --.

In Column 265, Claim 25, Line 44, please replace "111-1,2,3-triazol-4-yl)methyl)thiophene-2-carboxamide;" with -- -1H-1,2,3-triazol-4-yl)methyl)thiophene-2-carboxamide; --.

In Column 265, Claim 25, Line 46, please replace "nyl)-111-1,2,3-triazol-4-yl)methyl)thiophene-2 carboxamide;" with -- nyl)-1H-1,2,3-triazol-4-yl)methyl)thiophene-2-carboxamide; --.

In Column 265, Claim 25, Line 48, please replace "opyridin-1 (2H)-yl)phenyl)-111-1,2,3,-triazol-4-yl)methyl)" with -- opyridin-1 (2H)-yl)phenyl)-1H-1,2,3,-triazol-4-yl)methyl) --.

In Column 265, Claim 25, Line 50, please replace "oxopyridin-1(211)-yl)pyridin-2-yl)-111-1,2,3-triazol-4-yl)" with -- oxopyridin-1(2H)-yl)pyridin-2-yl)-1H-1,2,3-triazol-4-yl) --.

In Column 265, Claim 25, Line 52, please replace "1-methyl-4,5-dihydro-1H-imidazol-2-yl)phenyl)-111-1,2,3" with -- 1-methyl-4,5-dihydro-1H-imidazol-2-yl)phenyl)-1H-1,2,3 --.

In Column 265, Claim 25, Line 54, please replace "(N,N-Dimethylcarbamimidoyl)phenyl) -111-1,2,3-triazol-4-" with -- (N,N-Dimethylcarbamimidoyl)phenyl)-1H-1,2,3-triazol-4- --.

In Column 265, Claim 25, Line 56, please replace "Ethyl-N –methylcarbamimidoyl)phenyl)-111-1,2,3-triazol-" with -- Ethyl-N –methylcarbamimidoyl)phenyl)-1H-1,2,3-triazol- --.

In Column 265, Claim 25, Line 61, please replace "phenyl)-111-1,2,3-triazol-4-yl)methyl)-5-chlorothiophene-" with -- phenyl)-1H-1,2,3-triazol-4-yl)methyl)-5-chlorothiophene- --.

In Column 265, Claim 25, Line 63, please replace "nyl)-111-1,2,3-triazol-4-yl)methyl)-5-chiorothiophene" with -- nyl)-1H-1,2,3-triazol-4-yl)methyl)-5-chlorothiophene --.

In Column 266, Claim 25, Line 2, please replace "methyl)phenyl)-111-1,2,3-triazol-4-yl)methyl)thiophene-2-" with -- methyl)phenyl)-1H-1,2,3-triazol-4-yl)methyl)thiophene-2- --.

In Column 266, Claim 25, Line 4, please replace "thyl)phenyl-111-1,2,3-triazol-4-yl)methyl)thiophene-2-" with -- thyl)phenyl-1H-1,2,3-triazol-4-yl)methyl)thiophene-2- --.

In Column 266, Claim 25, Line 6, please replace "fluorophenyl)-111-1,2,3-triazol-4-yl)methyl)-5-" with -- fluorophenyl)-1H-1,2,3-triazol-4-yl)methyl)-5- --.

In Column 266, Claim 25, Line 8, please replace "(imino)methyl)-2-fluorophenyl)-111-1,2,3-triazol-4-yl)" with -- (imino)methyl)-2-fluorophenyl)-1H-1,2,3-triazol-4-yl) --.

In Column 266, Claim 25, Line 10, please replace "1-(2-fluoro-4-(imino(pyrrolidin-1-yl)methyl)phenyl)-111-1," with -- 1-(2-fluoro-4-(imino(pyrrolidin-1-yl)methyl)phenyl)-1H-1, --.

In Column 266, Claim 25, Line 13, please replace "phenyl)-111-1,2,3-triazol-4-yl)methyl)thiophene-2-car-" with -- phenyl)-1H-1,2,3-triazol-4-yl)methyl)thiophene-2-car- --.

CERTIFICATE OF CORRECTION (continued)
U.S. Pat. No. 7,521,470 B2

In Column 266, Claim 25, Line 15, please replace "dro-1H-imidazol-2-yl)phenyl)-111-1,2,3-triazol-4-yl)" with -- dro-1H-imidazol-2-yl)phenyl)-1H-1,2,3-triazol-4-yl) --.

In Column 266, Claim 27, Line 38, please replace "A method for lipreventing oril treating a condition in a" with -- A method for treating a condition in a --.